(12) United States Patent
Liao et al.

(10) Patent No.: US 10,312,459 B2
(45) Date of Patent: Jun. 4, 2019

(54) COMPOUND AND ORGANIC ELECTRONIC DEVICE USING THE SAME

(71) Applicant: NICHEM FINE TECHNOLOGY CO., LTD., Hsinchu County (TW)

(72) Inventors: Liang-Di Liao, Hsinchu County (TW); Hui-Ling Wu, Hsinchu County (TW); Shwu-Ju Shieh, Hsinchu County (TW); Chi-Chung Chen, Hsinchu County (TW)

(73) Assignee: NICHEM FINE TECHNOLOGY CO., LTD., Hsinchu County (TW)

( * ) Notice: Subject to any disclaimer, the term of this patent is extended or adjusted under 35 U.S.C. 154(b) by 223 days.

(21) Appl. No.: 15/412,834

(22) Filed: Jan. 23, 2017

(65) Prior Publication Data

US 2017/0213978 A1 Jul. 27, 2017

Related U.S. Application Data

(60) Provisional application No. 62/287,724, filed on Jan. 27, 2016.

(51) Int. Cl.
*H01L 51/50* (2006.01)
*H01L 51/00* (2006.01)
(Continued)

(52) U.S. Cl.
CPC ........ *H01L 51/0085* (2013.01); *C07C 211/61* (2013.01); *C07C 255/51* (2013.01);
(Continued)

(58) Field of Classification Search
None
See application file for complete search history.

(56) References Cited

U.S. PATENT DOCUMENTS

| 9,209,413 | B1 | 12/2015 | Chen et al. |
| 2016/0111648 | A1 | 4/2016 | Chen et al. |
| 2017/0317283 | A1* | 11/2017 | Mujica-Fernaud ......................... H01L 51/006 |

FOREIGN PATENT DOCUMENTS

| CN | 106432107 A | † | 2/2017 |
| CN | 106467469 | | 3/2017 |

(Continued)

OTHER PUBLICATIONS

Evidence-10: Switching of non-helical overcrowded tetrabenzoheptafulvalene derivatives, pp. 2029-2034, by Jiye Luo et al., Chemical Science, Publication Date: Jul. 21, 2011. Pages/Lines Cited: p. 2031 printed on bottom right corner, left col.†

(Continued)

*Primary Examiner* — Gregory D Clark
(74) *Attorney, Agent, or Firm* — Ming Chow; Sinorica, LLC

(57) ABSTRACT

Provided are a novel compound and an organic electronic device using the same. The novel compound is represented by the following Formula (I):

(Continued)

Formula (I)

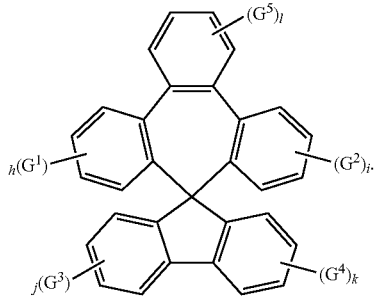

20 Claims, 15 Drawing Sheets

(51) Int. Cl.
| | |
|---|---|
| C07F 15/00 | (2006.01) |
| C09K 11/06 | (2006.01) |
| C07C 255/51 | (2006.01) |
| C07D 213/06 | (2006.01) |
| C07D 213/22 | (2006.01) |
| C07D 213/57 | (2006.01) |
| C07D 235/18 | (2006.01) |
| C07D 239/26 | (2006.01) |
| C07D 239/74 | (2006.01) |
| C07D 251/24 | (2006.01) |
| C07C 211/61 | (2006.01) |
| C07D 223/14 | (2006.01) |
| C07D 307/91 | (2006.01) |
| C07D 313/06 | (2006.01) |
| C07D 213/38 | (2006.01) |
| H01L 51/42 | (2006.01) |

(52) U.S. Cl.
CPC ......... *C07D 213/06* (2013.01); *C07D 213/22* (2013.01); *C07D 213/38* (2013.01); *C07D 213/57* (2013.01); *C07D 223/14* (2013.01); *C07D 235/18* (2013.01); *C07D 239/26* (2013.01); *C07D 239/74* (2013.01); *C07D 251/24* (2013.01); *C07D 307/91* (2013.01); *C07D 313/06* (2013.01); *C07F 15/0033* (2013.01); *C09K 11/06* (2013.01); *H01L 51/006* (2013.01); *H01L 51/0056* (2013.01); *H01L 51/0057* (2013.01); *H01L 51/0061* (2013.01); *H01L 51/0067* (2013.01); *H01L 51/0072* (2013.01); *H01L 51/5016* (2013.01); *C07C 2603/18* (2017.05); *C07C 2603/98* (2017.05); *C07C 2603/99* (2017.05); *C09K 2211/1007* (2013.01); *C09K 2211/1029* (2013.01); *C09K 2211/1033* (2013.01); *C09K 2211/185* (2013.01); *H01L 51/0058* (2013.01); *H01L 51/0073* (2013.01); *H01L 51/42* (2013.01); *H01L 51/5056* (2013.01); *H01L 51/5072* (2013.01); *H01L 51/5088* (2013.01); *H01L 51/5096* (2013.01); *Y02E 10/549* (2013.01)

(56) References Cited

FOREIGN PATENT DOCUMENTS

| | | |
|---|---|---|
| JP | 2010/024149 | 2/2010 |
| KR | 2011-0041730 | 4/2011 |
| KR | 2012-0093076 | 4/2012 |
| TW | 201634441 A | 10/2016 |
| WO | 2016/087017 | 6/2016 |

OTHER PUBLICATIONS

Evidence-9: Doubly Ortho-linked cis-4,4'-Bis(diarylamino)stilbene/Fluorene Hybrids as Efficient Non-doped, Sky-blue Fluorescent Materials for Optoelectronic Applications, pp. S1-S22, by Yi Wei et al., 2007, which is 1H NMR spectrum (p. S16) in Supporting Information from Evidence-8. Pages/Lines Cited: S16 printed on top right corner.†
Evidence-8: Doubly Ortho-Linked cis-4,4'-Bis(diarylamino)stilbene/Fluorene Hybrids as Efficient Nondoped, Sky-Blue Fluorescent Materials for Optoelectronic Applications, pp. 7478-7479, by Yi Wei et al., J. Am. Chem. Soc., Publication Date: May 25, 2007. Pages/Lines Cited: p. 7478 printed on bottom left corner, right col.†
Evidence-7: Doubly Ortho-linked Quinoxaline/Diphenylfluorene Hybrids as Bipolar, Fluorescent Chameleons for Optoelectronic Applications, pp. S1-S23, by Chien-Tien Chen et al., Publication Date: 2006, which is 1H NMR spectrum (p. S20) in Supporting Information from Evidence-6. Pages/Lines Cited: S20 printed on top right corner.†
Evidence-6: Doubly Ortho-Linked Quinoxaline/Diphenylfluorene Hybrids as Bipolar, Fluorescent Chameleons for Optoelectronic Applications, pp. 10992-10993, Chien-Tien Chen et al., J. Am. Chem. Soc., Publication Date: Aug. 8, 2006. Pages/Lines Cited: p. 10992 printed on bottom left corner, right col.†
Evidence-5: hint of step 4 "Check that the integration of the peak matches the number of hydrogens in the molecule", webpage of Golden Rules to Nuclear Magnetic Resonance Spectroscopy (NMR) Analysis, 1 page, by Dr. Madalee Gassaway, Publication Date: Oct. 23, 2017 (from http://blog.cambridgecoaching.com/golden-rules-to-nuclear-magnetic-resonance-spectroscopy-nmr-analysis-part-1-0); Pages/Lines Cited : hint of step 4, webpage of Golden Rules to Nuclear Magnetic Resonance Spectroscopy (NMR) Analysis.†
Evidence-4: Proton Nuclear Magnetic Resonance Spectroscopy, Lecture of Structure Determination Using Spectroscopic Methods at University of Wisconsin, pp. 1-38, by Dr. Hans J. Reich, 2017 (from https://www.chem.wisc.edu/areas/reich/nmr/Notes-05-Hmr-v26-part1.pdf); Pages/Lines Cited: p. 8, lines 3-4, Proton Nuclear Magnetic Resonance Spectroscopy.†
Evidence-3: Real-Time Enzyme Kinetics by Quantitative NMR Spectroscopy and Determination of the Michaelis−Menten Constant Using the Lambert‑W Function, pp. 1943-1948, by Cheenou Her et al., J. Chem. Educ., 2015; Pages/Lines Cited: p. 1946 printed on bottom, right col., lines 13-17.†
Evidence-2: Integration of 1H NMR spectra (proton) from NMR theory of Spectroscopy of Organic Chemistry Lecture Website at University of Colorado Boulder, which was built by Dr. Patty Feist et al. (from < http://www.orgchemboulder.com:80/Spectroscopy/nmrtheory/NMRtutorial.shtml> 1 page, Dec. 14, 2016, retrieved from Internet Wayback Machine < http://web.archive.org/web/20161214110543/http://www.orgchemboulder.com:80/Spectroscopy/nmrtheory/ NMRtutorial.shtml> on Feb. 7, 2018); Pages/Lines Cited: lines 2-3 & 4-5.†
Evidence-1: Organic Chemistry (eighth edition), Paula Yurkanis Bruice, Global Edition, pp. 660, 661, 668, 678, Publication Date: Jan. 15, 2016, Pearson Education, Inc., NJ, USA; Pages/Lines Cited: pp. 660, 661, 668, 678.†
Evidence-16: Doubly Ortho-linked Quinoxaline/Triarylamine Hybrid as a Bifunctional, Dipolar Electroluminescent Template for Optoelectronic Applications, pp. 1-12, by Chien-Tien Chen et al., Publication Date: 2005, which is 1H NMR spectroscopic data (pp. 5 and 6) in Supporting Information from Evidence-15. Pages/Lines Cited: p. 5 and 6.†
Evidence-15: Doubly ortho-linked quinoxaline/triarylamine hybrid as a bifunctional, dipolar electroluminescent template for optoelectronic applications, pp. 3980-3982, Chien-Tien Chen et al., Chem. Commun, Publication Date: Jul. 8, 2005. Pages/Lines Cited: p. 3980 printed on bottom left corner.†

(56) References Cited

OTHER PUBLICATIONS

Evidence-14: Supplementary Information—Polycationic ligands in gold catalysis: Synthesis and applications of extremely π-acidic catalysts, pp. S1-S231, by Javier Carreras et al., Publication Date: 2013, which is 1H NMR spectrum (p. S200) in Supporting Information from Evidence-13. Pages/Lines Cited: S200 printed on bottom right corner.†

Evidence-13: Polycationic Ligands in Gold Catalysis: Synthesis and Applications of Extremely π‑Acidic Catalysts, pp. 18815-18823, by Javier Carreras et al., Journal of the American Chemical Society, Publication Date: Dec. 5, 2013. Pages/Lines Cited: p. 18817 printed on bottom.†

Evidence-12: The Synthesis of Novel p-Quinone Methides: O-Dealkylation of 5-(p-Alkyloxyaryl)-10,11-dihydrodibenzo[a,d]cyclohepten-5-ols and Related Compounds, pp. 2607-2619, by Benjamin Taljaard et al., Eur. J. Org. Chem., Publication Date: Dec. 31, 2005. Pages/Lines Cited: p. 2612 printed on bottom left corner, right col.†

Evidence-11: Supporting Information for: Switching of Non-Helical Overcrowded Heptafulvalene Derivatives, pp. 1-59, by Jiye Luo et al., Publication Date: 2011, which is 1H NMR spectrum (p. 30) in Supporting Information from Evidence-10. Pages/Lines Cited: p. 30.†

\* cited by examiner
† cited by third party

FIG.5

COMPOUND AND ORGANIC ELECTRONIC DEVICE USING THE SAME

CROSS-REFERENCE TO RELATED APPLICATION

Pursuant to 35 U.S.C. § 119(e), this application claims the benefit of the priority to U.S. Provisional Patent Application No. 62/287,724, filed Jan. 27, 2016. The content of the prior application is incorporated herein by its entirety.

BACKGROUND OF THE INVENTION

1. Field of the Invention

The present invention relates to a novel compound and an organic electronic device using the same, more particularly to a novel compound as electron-transporters and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching Tang and Steven VanSlyke of Kodak Company deposited an electron transport material such as tris(8-hydroxyquinoline)aluminum(III) (abbreviated as Alq$_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 moves to the EL via HIL and HTL and the electrons injected from the cathode 18 moves to the EL via EIL and ETL. Recombination of the electrons and the holes occurs in the EL to generate excitons, thereby emitting a light when the excitons decay from excited state to ground state.

Another approach is to modify the materials of ETL for OLEDs to render the electron transport materials to exhibit hole-blocking ability. Examples of conventional electron transport materials include 3,3'-[5'-[3-(3-pyridinyl)phenyl] [1,1':3',1''-terphenyl]-3,3''-diyl]bispyridine (TmPyPb), 1,3,5-tris(1-phenyl-1H-benzimidazol-2-yl)benzene (TPBi), tris (2,4,6-trimethyl-3-(pyridin-3-yl)phenyl)borane (3TPYMB), 1,3-bis(3,5-dipyrid-3-yl-phenyl)benzene (BmPyPb), and 9,10-bis(3-(pyridin-3-yl)phenyl)anthracene (DPyPA).

However, even using the foresaid electron transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to reduce the driving voltage of the organic electronic device.

Further another objective of the present invention is to provide an organic electronic device using the novel compound, so as to improve the efficiency of the organic electronic device.

To achieve the foresaid objectives, the present invention provides a novel compound represented by the following Formula (I):

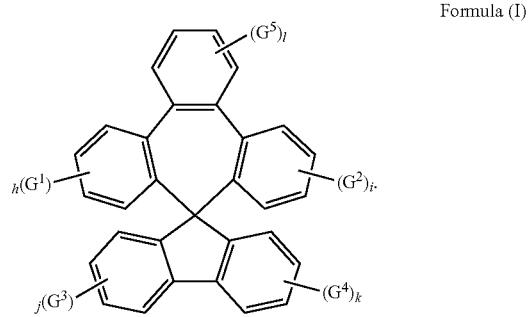

Formula (I)

In the Formula (I), one of $G^1$ to $G^4$ is selected from the group consisting of: an heteroaryl group having 3 to 60 carbon atoms and containing at least one nitrogen atom, an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 carbon atoms and substituted with at least one functional group, a heterocycloalkyl group having 3 to 60 carbon atoms and substituted with at least one functional group, an alkoxy group having 1 to 40 carbon atoms and substituted with at least one functional group, an aryl group having 6 to 60 carbon atoms and substituted with at least one functional group, an aryloxy group having 6 to 60 carbon atoms and substituted with at least one functional group, an alkylsilyl group having 1 to 40 carbon atoms and substituted with at least one functional group, an arylsilyl group having 6 to 60 carbon atoms and substituted with at least one functional group, an alkylboron group having 1 to 40 carbon atoms and substituted with at least one functional group, an arylboron group having 6 to 60 carbon atoms and substituted with at least one functional group, a phosphine group having 1 to 40 carbon atoms and substituted with at least one functional group, and a phosphine oxide group having 1 to 40 carbon atoms and substituted with at least one functional group, wherein said functional group is selected from the group consisting of: a cyano group, a nitro group, a trifluoromethyl group, a fluoro group, and a chloro group; and the others of $G^1$ to $G^4$ and $G^5$ are each independently selected from the group consisting of: a hydrogen atom, a deuterium atom, a halogen group, a cyano group, a nitro group, a trifluoromethyl group, a substituted or nonsubstituted alkyl group having 1 to 40 carbon atoms, a substituted or nonsubstituted alkenyl group having 2 to 40 carbon atoms, a substituted or nonsubstituted alkynyl group having 2 to 40 carbon atoms, a substituted or nonsubstituted cycloalkyl group having 3 to 60 carbon atoms, a heterocycloalkyl group having 3 to 60 carbon atoms substituted or nonsubstituted, a substituted or nonsubstituted alkoxy group having 1 to 40 carbon atoms, a substituted or nonsubstituted aryl group having 6 to 60 carbon atoms, a substituted or nonsubstituted heteroaryl group having 3 to 60 carbon atoms, a substituted or nonsubstituted aryloxy group having 6 to 60 carbon atoms, a substituted or nonsubstituted alkylsilyl group having 1 to 40 carbon atoms, a substituted or nonsubstituted arylsilyl group having 6 to 60 carbon atoms, a substituted or nonsubstituted alkylboron group having 1 to 40 carbon atoms, a substituted or nonsubstituted arylboron group having 6 to 60 carbon atoms, a substituted or nonsubstituted phosphine group having 1 to 40 carbon atoms, a substituted or nonsubstituted phosphine oxide group having 1 to 40 carbon atoms;

In the formula (I), h, i, j, k, l are each independently an integral of 1 to 4, i.e, 1, 2, 3, or 4.

More specifically, the compound may be represented by, for example, but not limited to, the following Formulae (I-I) to (I-XV):

Formula (I-I)

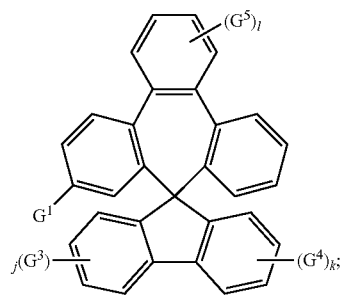

Formula (I-II)

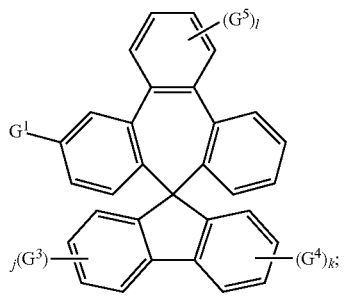

Formula (I-III)

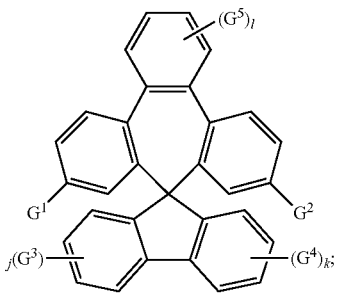

Formula (I-IV)

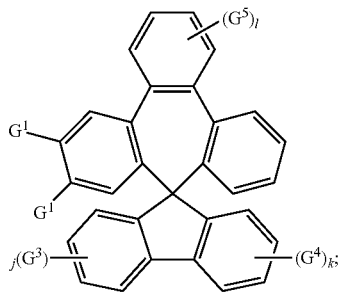

Formula (I-V)

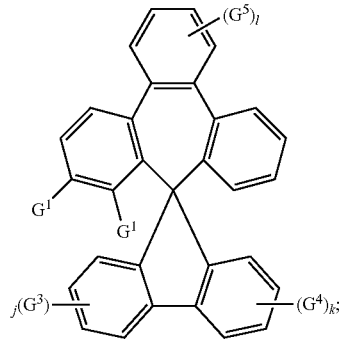

Formula (I-VI)

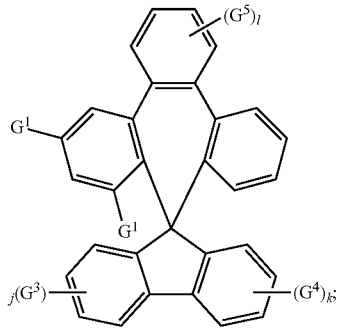

Formula (I-VII)

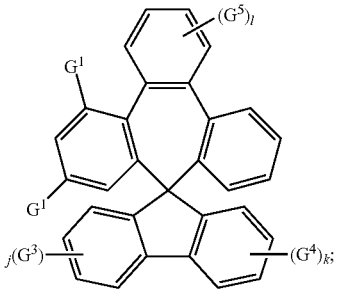

Formula (I-VIII)

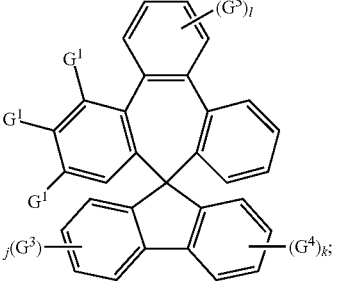

-continued

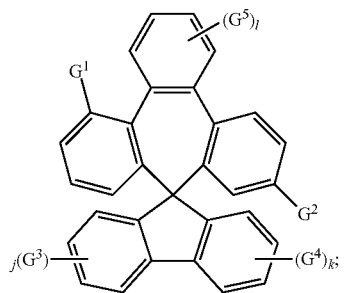
Formula (I-IX)

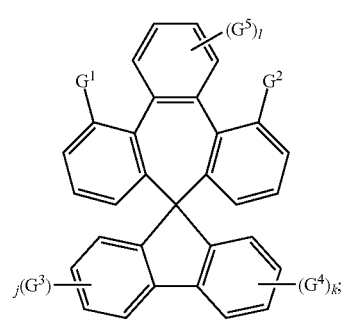
Formula (I-X)

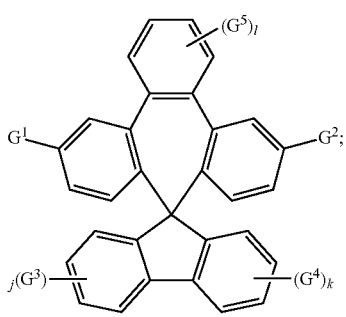
Formula (I-XI)

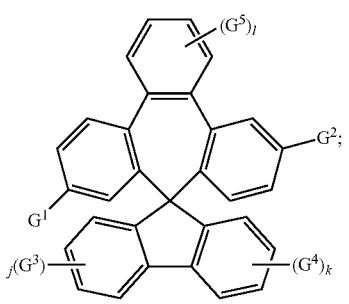
Formula (I-XII)

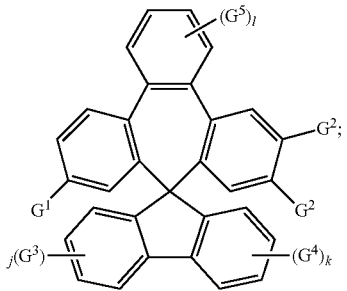
Formula (I-XIII)

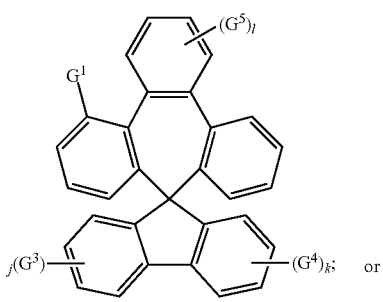
Formula (I-XIV)

or

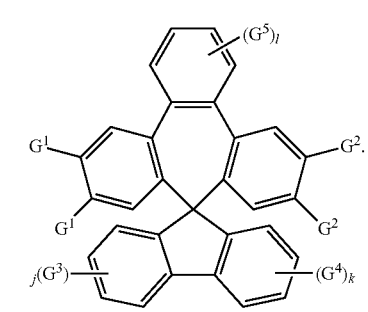
Formula (I-XV)

In the formula (I), j, k, l are each independently an integral of 1 to 3.

Preferably, h, i, j, k, l are each independently 1 or 2, and the total of h, i, j, k, and l is not more than 6.

Preferably, $G^1$ and $G^2$ may be the same or different, and $G^3$ and $G^4$ may be the same or different.

Preferably, $G^3$ to $G^5$ each may independently be selected from the group consisting of: a hydrogen atom, a deuterium atom, a halogen group, a nonsubstituted alkyl group having 1 to 12 carbon atoms, a nonsubstituted alkenyl group having 2 to 12 carbon atoms, and a nonsubstituted alkynyl group having 2 to 12 carbon atoms.

Preferably, the foresaid "heteroaryl group having 3 to 60 carbon atoms and containing the at least one nitrogen atom" may be, for example, but not limited to:

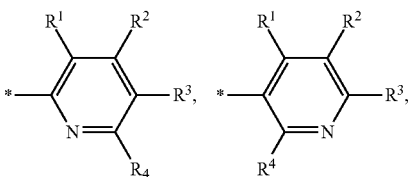

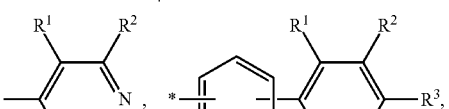

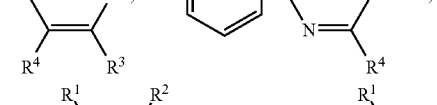

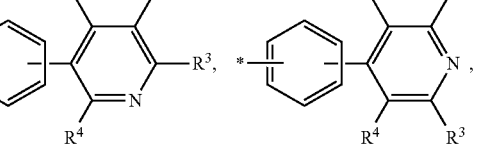

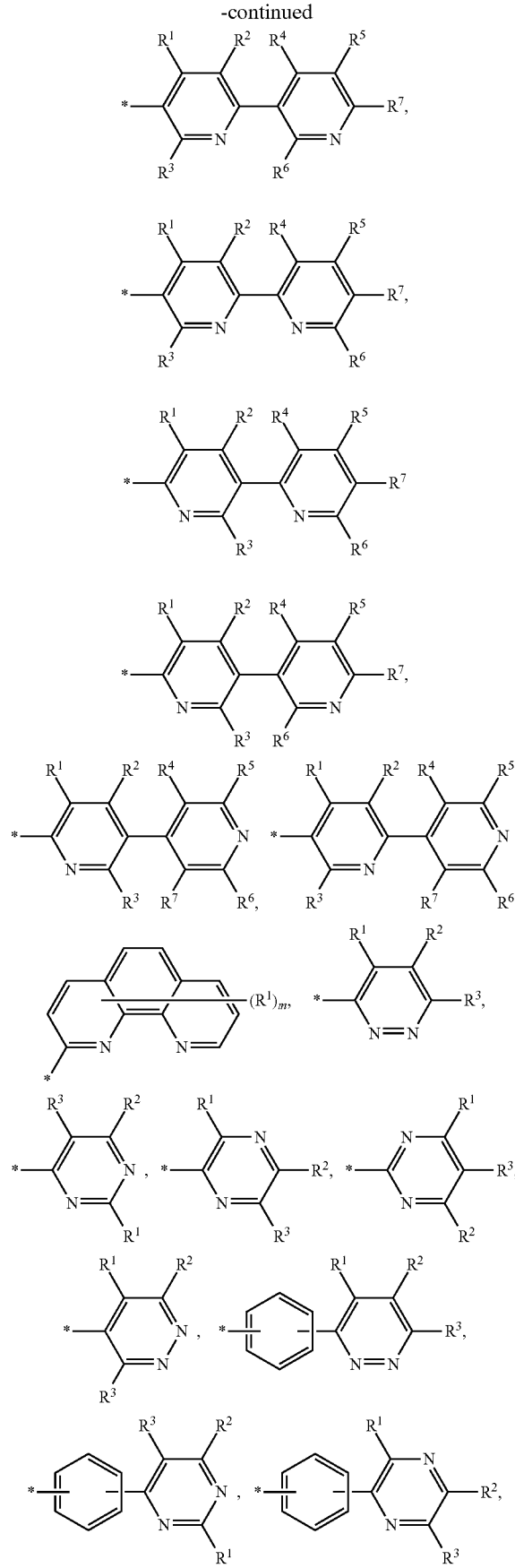
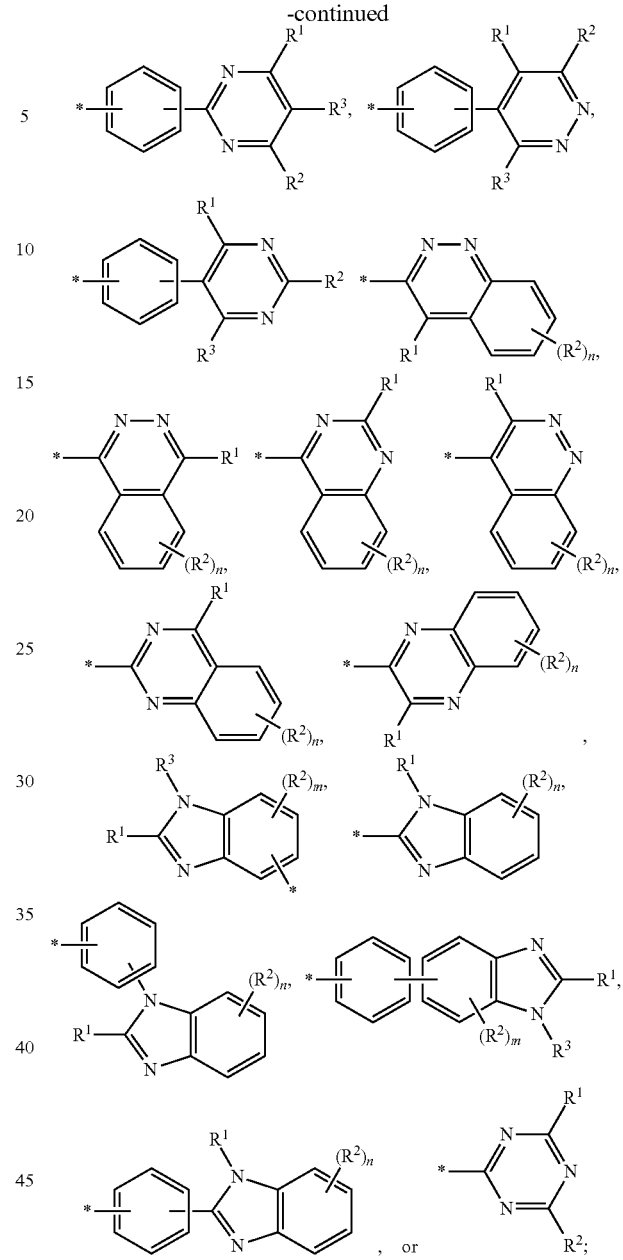

wherein $R^1$ to $R^7$ are each independently selected from the group consisting of: a hydrogen atom, a deuterium, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 20 carbon atoms, an alkoxy group having 1 to 40 carbon atoms, an aryloxy group having 6 to 30 carbon atoms, an alkylsilyl group having 1 to 40 carbon atoms, an arylsilyl group having 6 to 30 carbon atoms, an alkylboron group having 1 to 40 carbon atoms, an arylboron group having 6 to 30 carbon atoms, a phosphine group having 1 to 30 carbon atoms, and a phosphine oxide group having 1 to 30 carbon atoms; wherein n is an integral from 1 to 4, and m is an integral from 1 to 3.

Preferably, $R^1$ to $R^7$ each may independently be, for example, but not limited to, a phenyl group, a napthyl group, a pyridine group, a pyrimidine group, a pyrazine group, a pyridazine group, a cyano group, a nitro group, a trifluoromethyl group, a fluoro group, a biphenyl group, a phenylnapthyl group, a phenylpyridine group, a phenylpyrimidine group, a phenylpyrazine group, a phenylpyridazine group, a cyanophenyl group, a nitrophenyl group, or a trifluoromethylphenyl group.

Preferably, the foresaid "heteroaryl group having 3 to 60 carbon atoms and containing the at least one nitrogen atom" may be, for example, but not limited to:

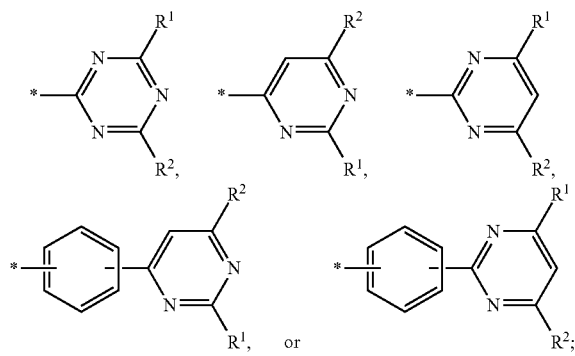

wherein $R^1$ and $R^2$ each may be a phenyl group, a napthyl group, a pyridine group, a pyrimidine group, a pyrazine group, a pyridazine group, a cyano group, a nitro group, a trifluoromethyl group, a fluoro group, a biphenyl group, a phenylnapthyl group, a phenylpyridine group, a phenylpyrimidine group, a phenylpyrazine group, a phenylpyridazine group, a cyanophenyl group, a nitrophenyl group, or a trifluoromethylphenyl group. More preferably, $R^1$ and $R^2$ each may be the pyridine group, the pyrimidine group, the pyrazine group, the pyridazine group, the cyano group, the nitro group, the trifluoromethyl group, the fluoro group, the phenylpyridine group, the phenylpyrimidine group, the phenylpyrazine group, the phenylpyridazine group, the cyanophenyl group, the nitrophenyl group, or the trifluoromethylphenyl group. In accordance with the present invention, $R^1$ and $R^2$ may be the same or different.

In an embodiment of the present invention, $G^1$ and/or $G^2$ connected to the main skeleton may be a pyridine group. For example, $G^1$ and/or $G^2$ may be, for example, but not limited to:

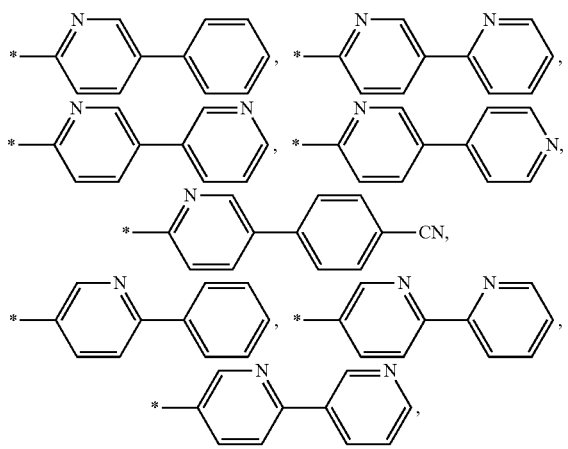

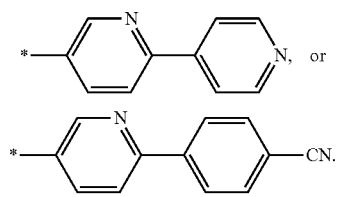

In an embodiment of the present invention, $G^1$ and/or $G^2$ connected to the main skeleton may be a pyrimidine group. For example, $G^1$ and/or $G^2$ may be, for example, but not limited to:

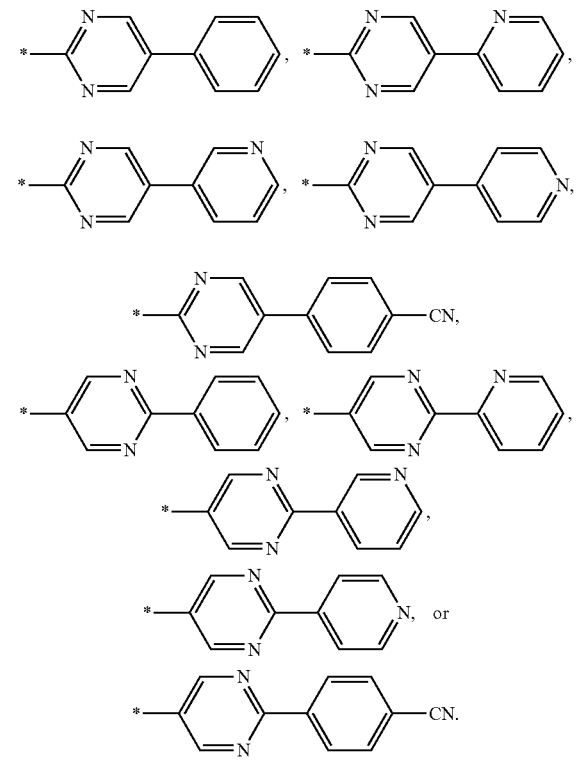

In an embodiment of the present invention, $G^1$ and/or $G^2$ connected to the main skeleton may be a benzimidazole group. For example, $G^1$ and/or $G^2$ may be, for example, but not limited to:

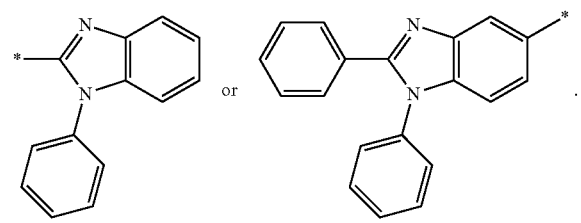 [SMILES: *c1nc2ccccc2n1-c1ccccc1 ; *c1ccc2c(c1)nc(-c1ccccc1)n2-c1ccccc1]

In an embodiment of the present invention, $G^1$ and/or $G^2$ connected to the main skeleton may be a pyrimidine group. For example, $G^1$ and/or $G^2$ may be, for example, but not limited to:

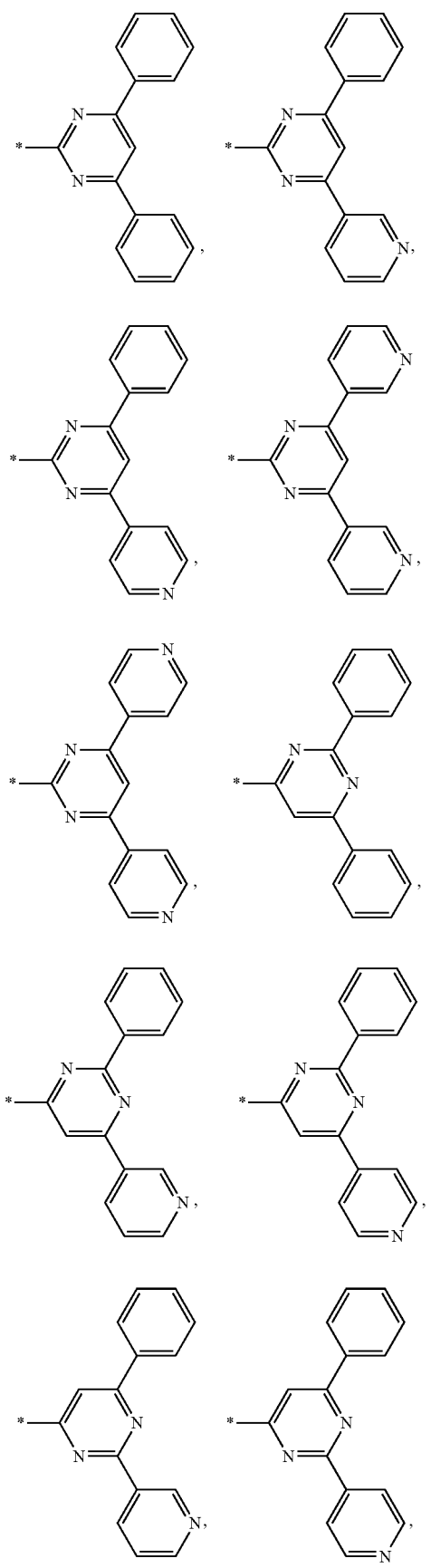
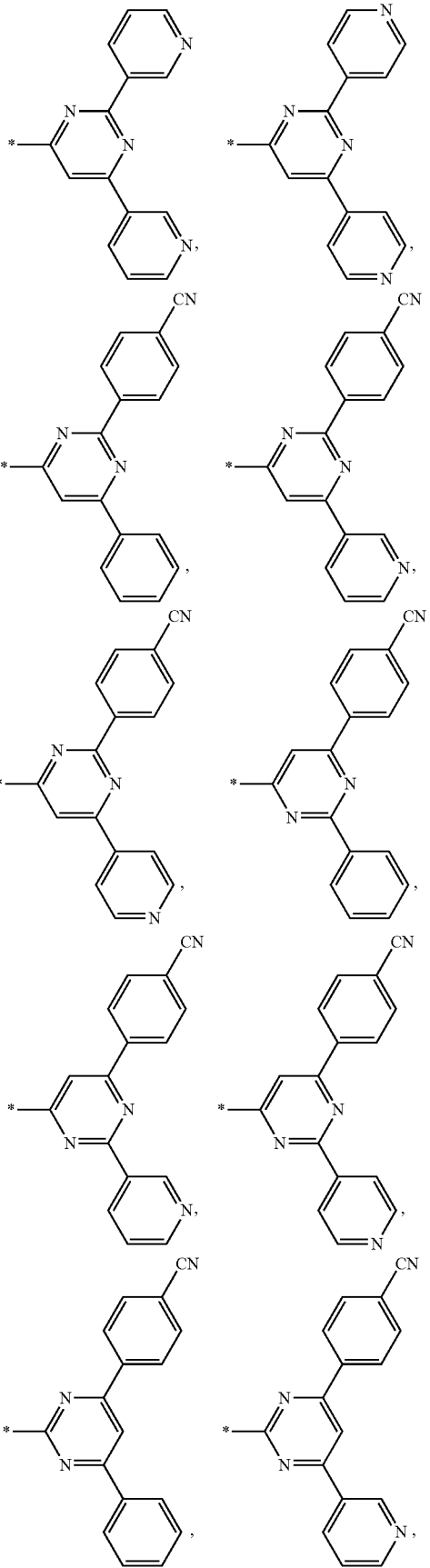

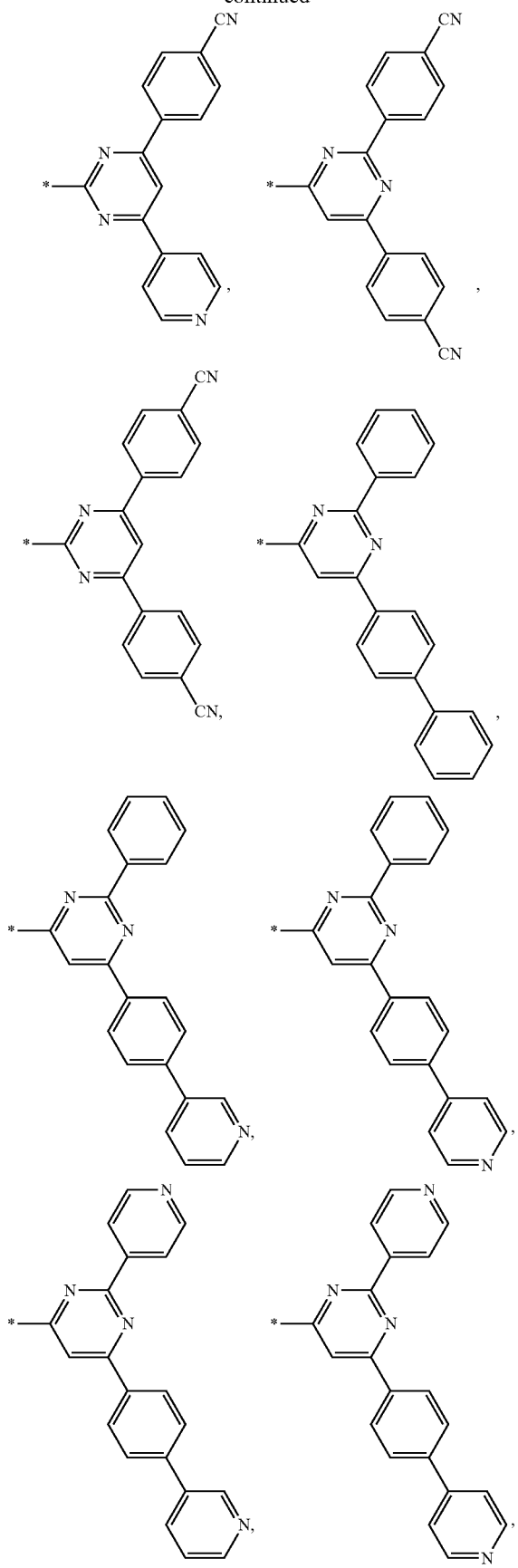

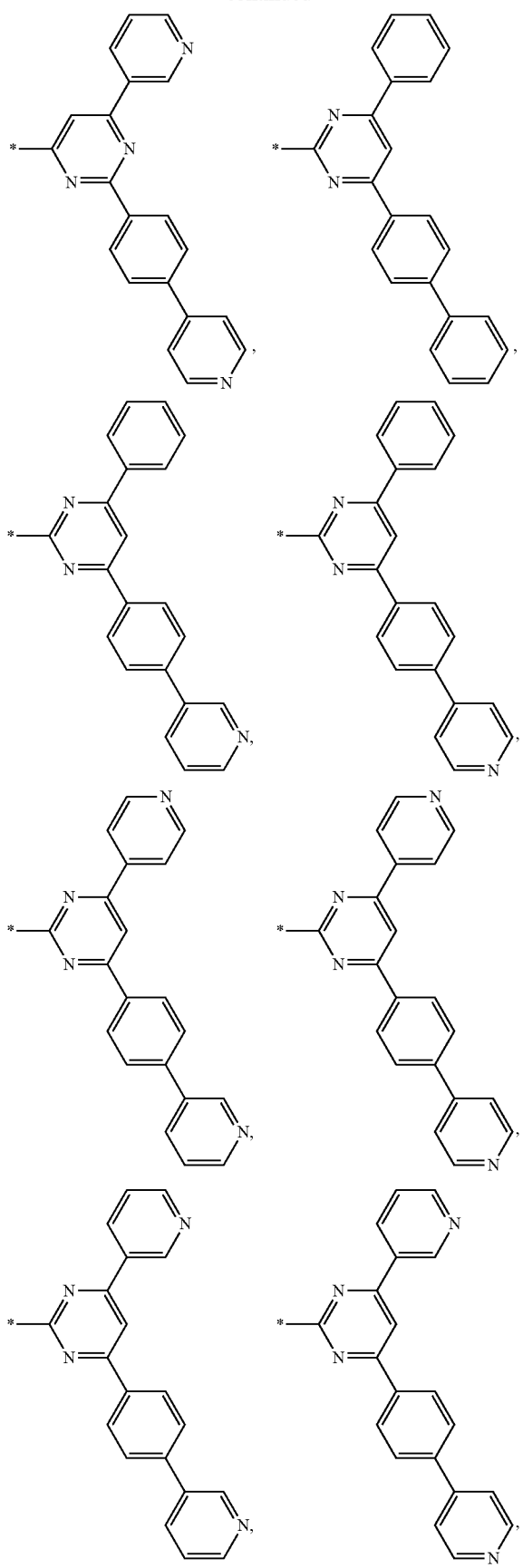
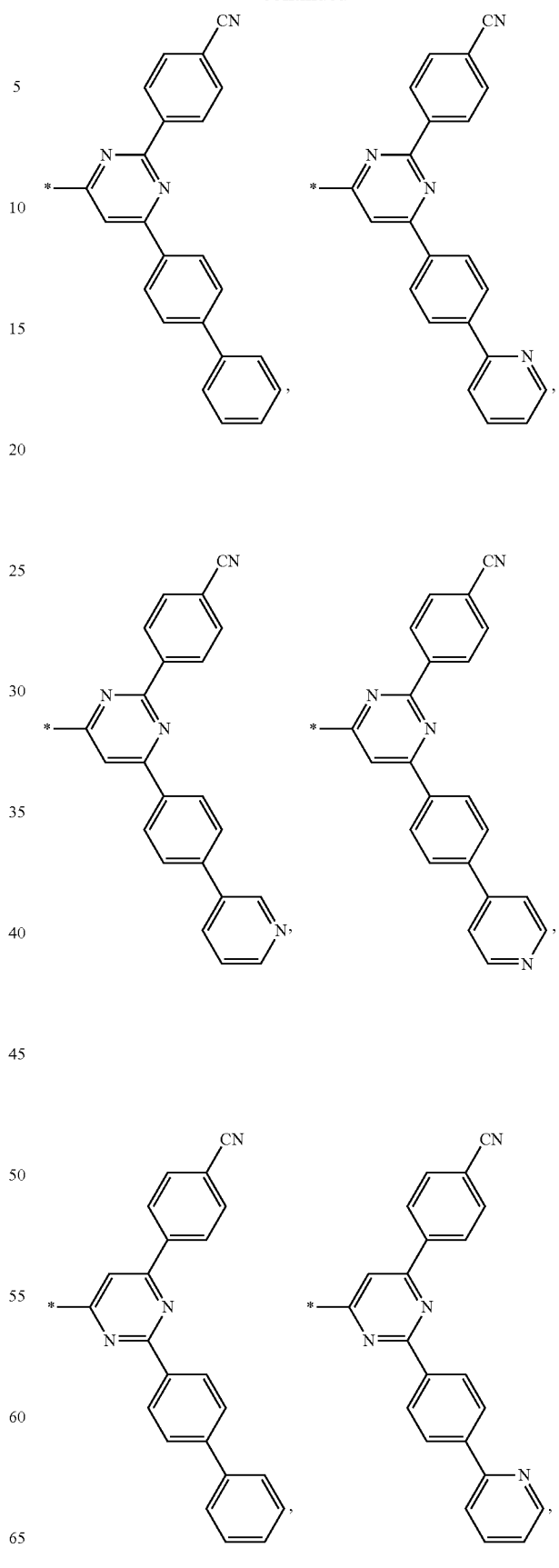

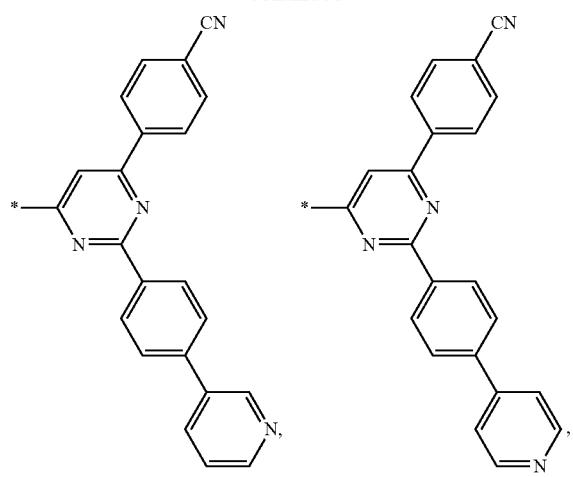
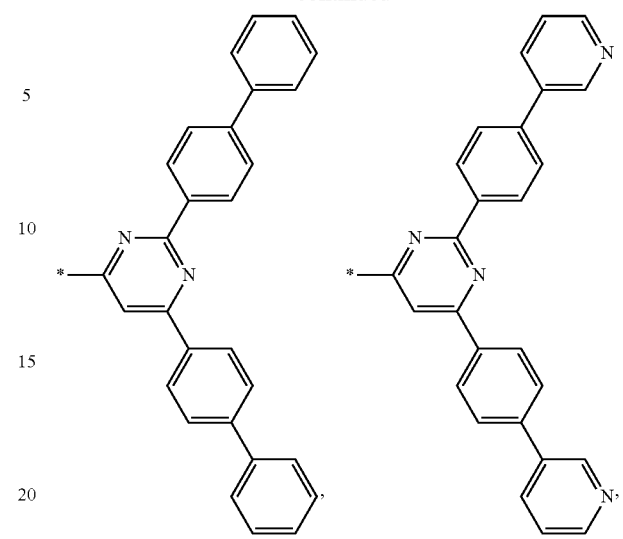
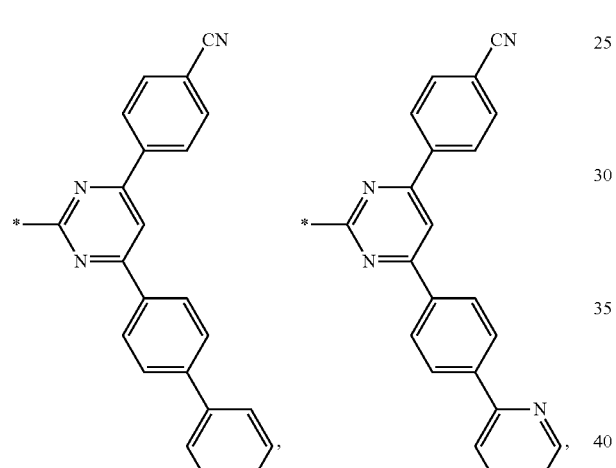
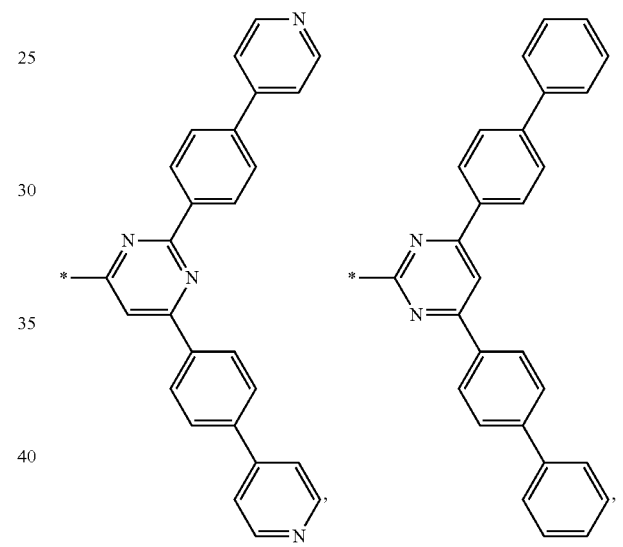
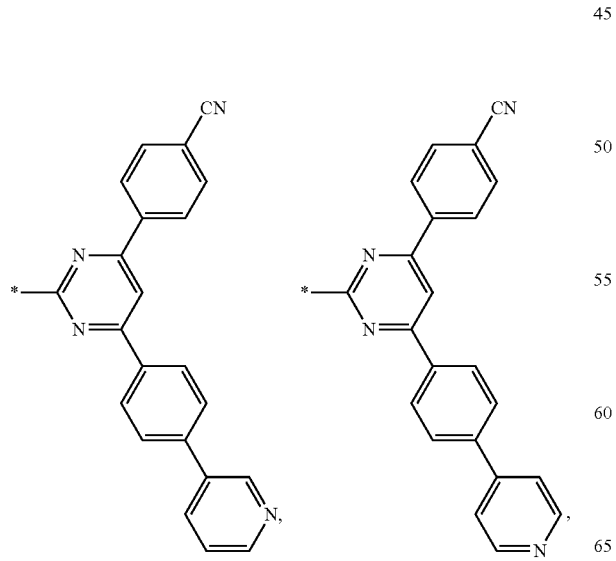
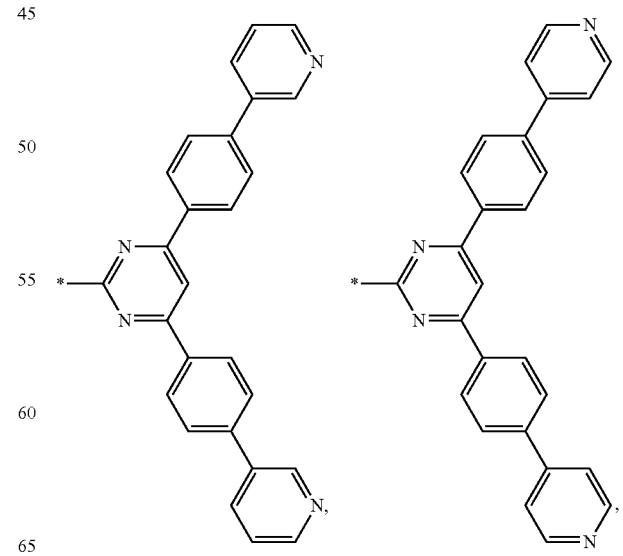

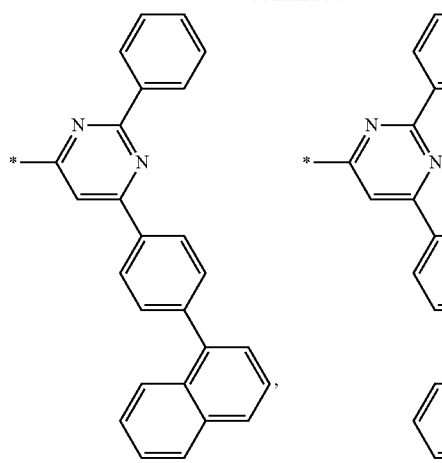 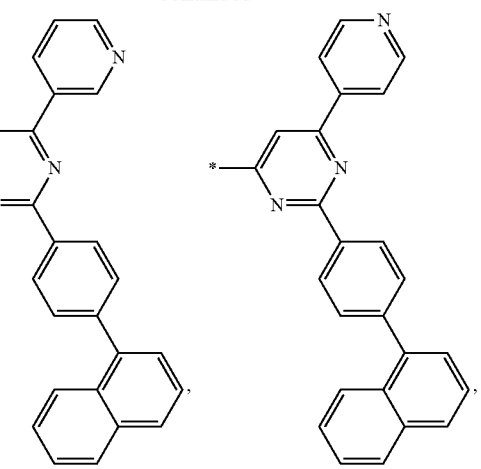
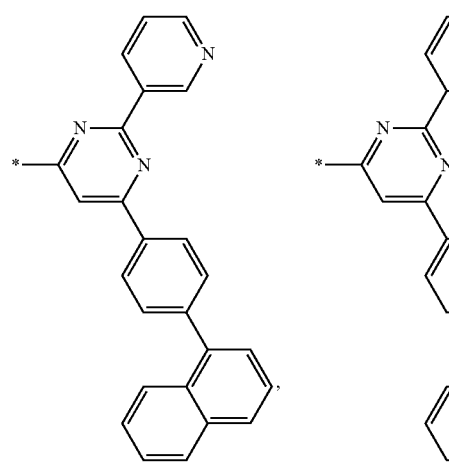 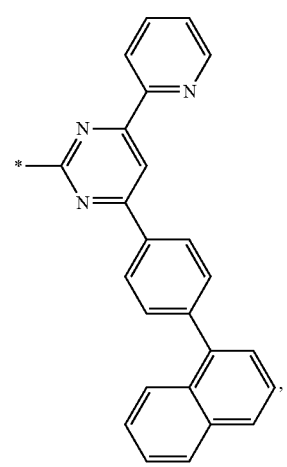
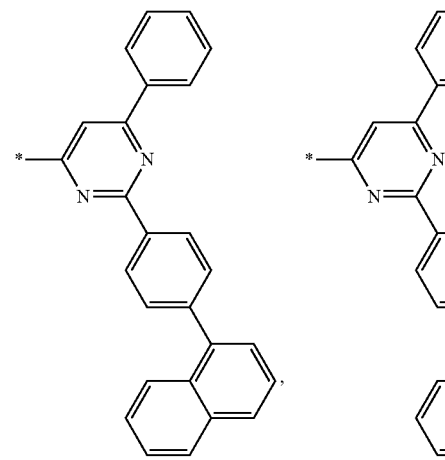 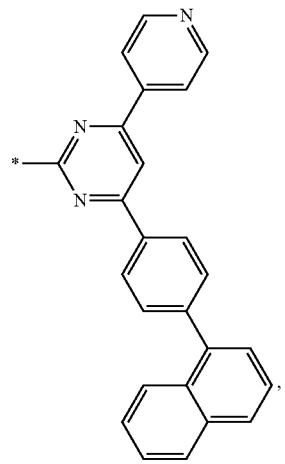

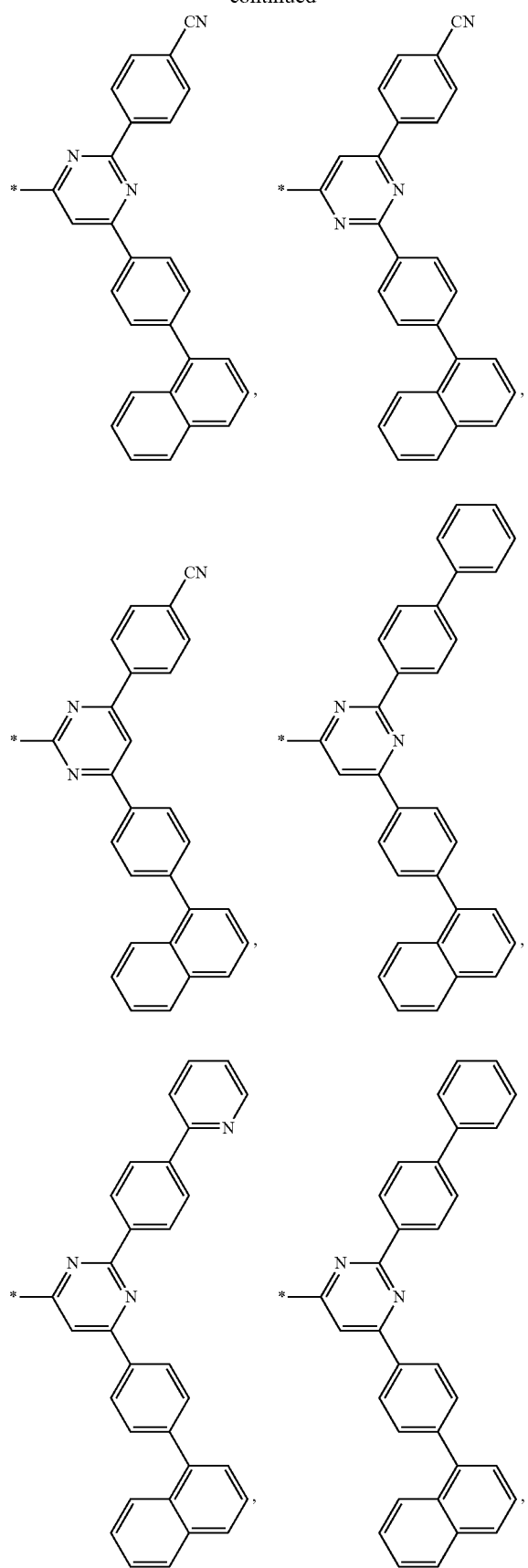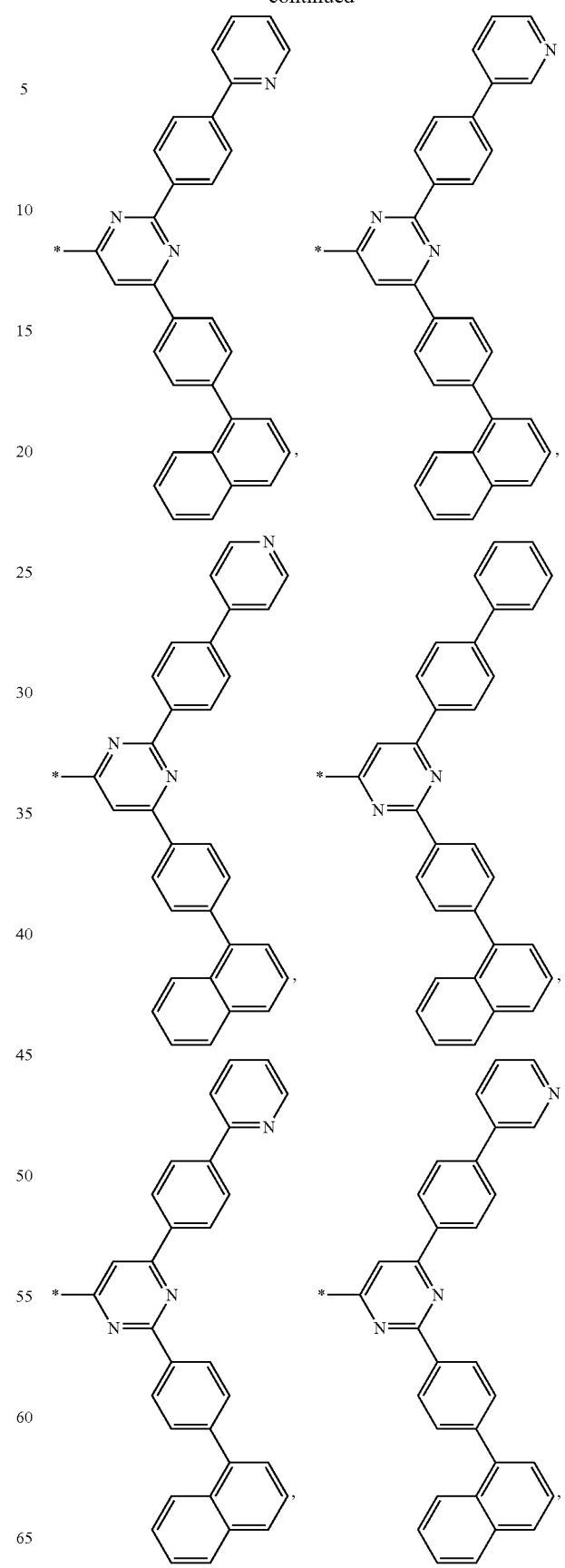

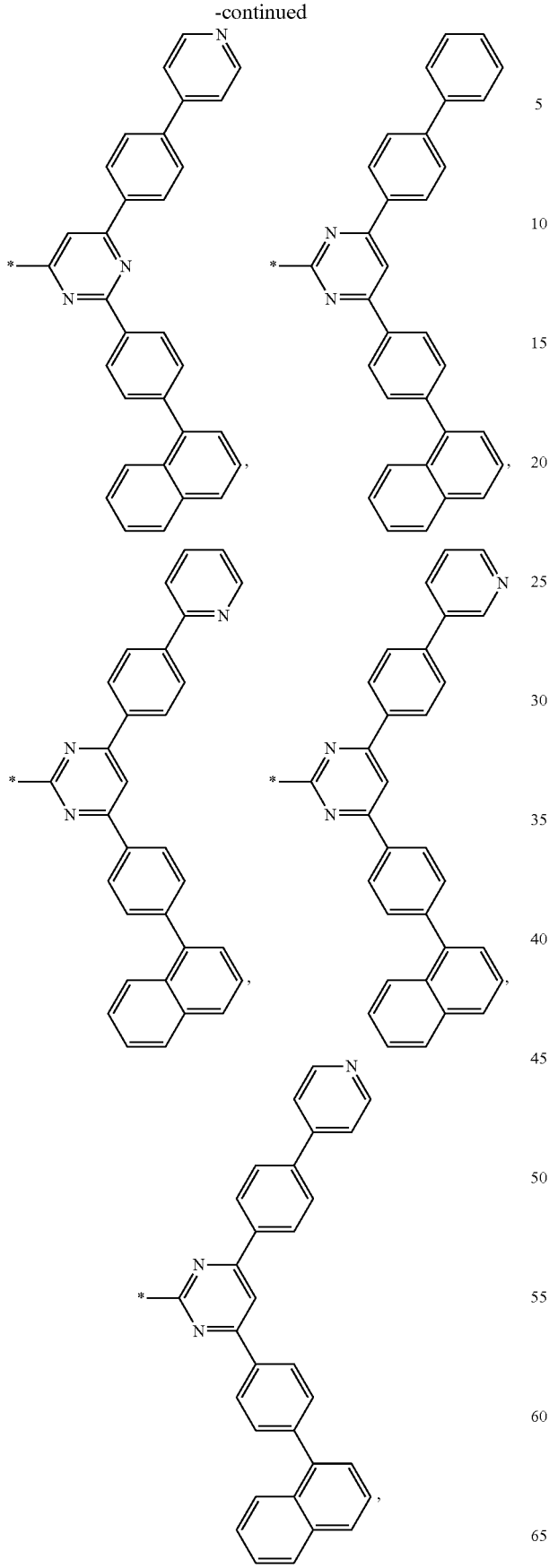
In an embodiment of the present invention, $G^1$ and/or $G^2$ connected to the main skeleton may be a triazine group. For example, $G^1$ and/or $G^2$ may be, for example, but not limited to:
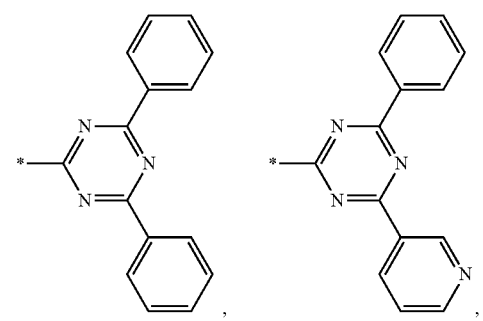

-continued
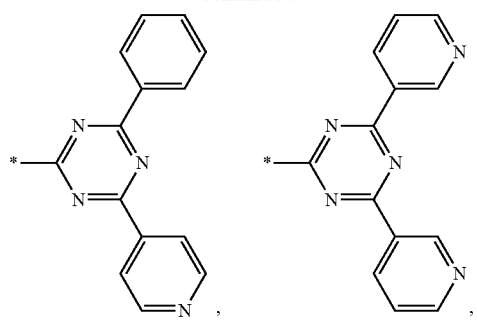
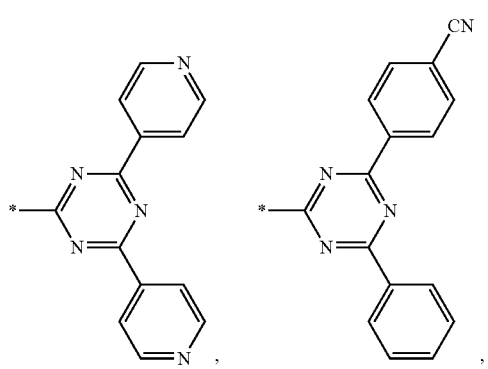
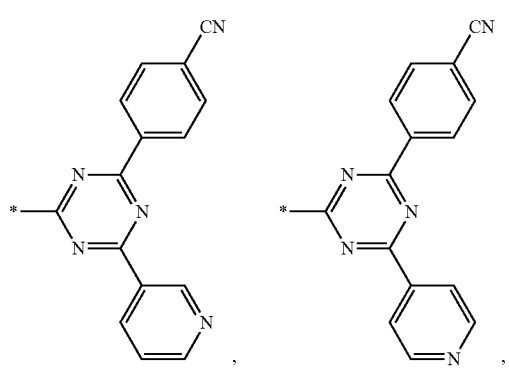
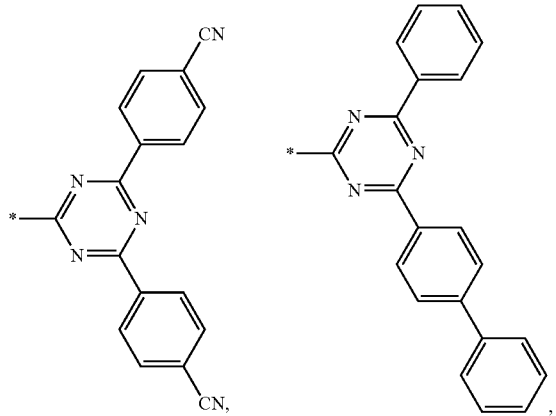
-continued
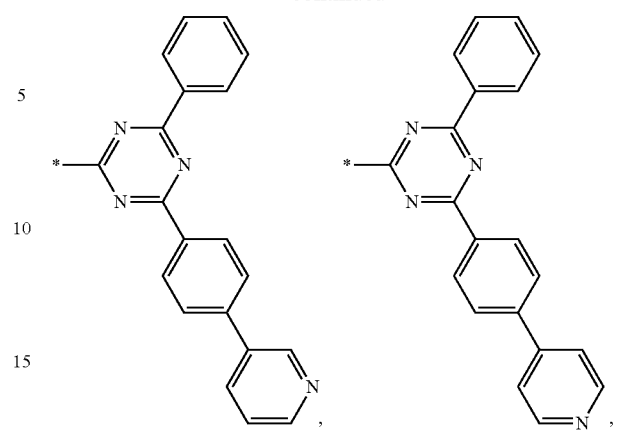
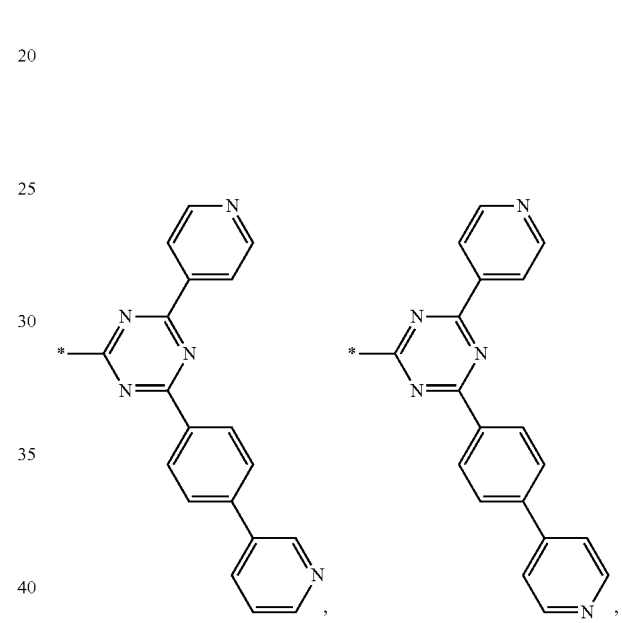
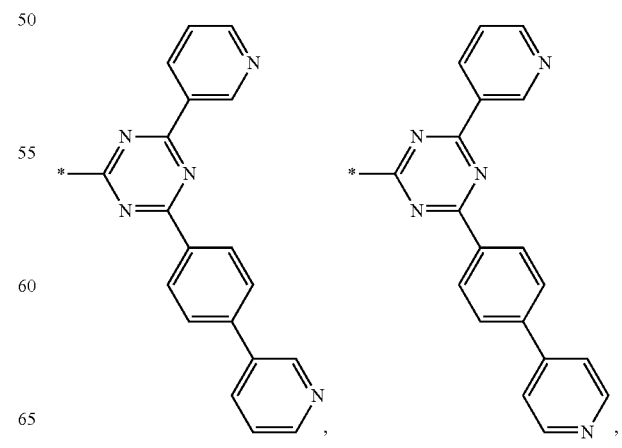

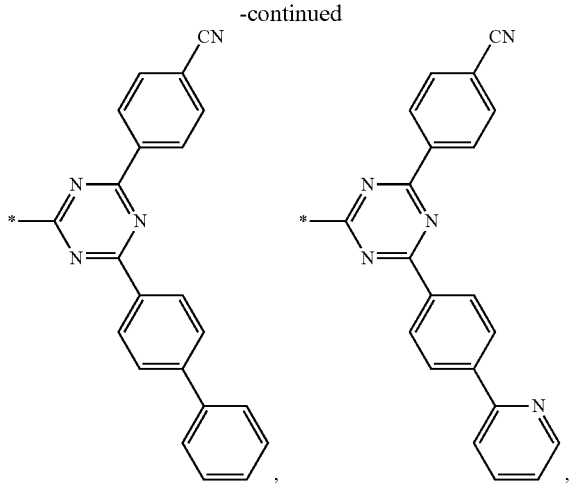
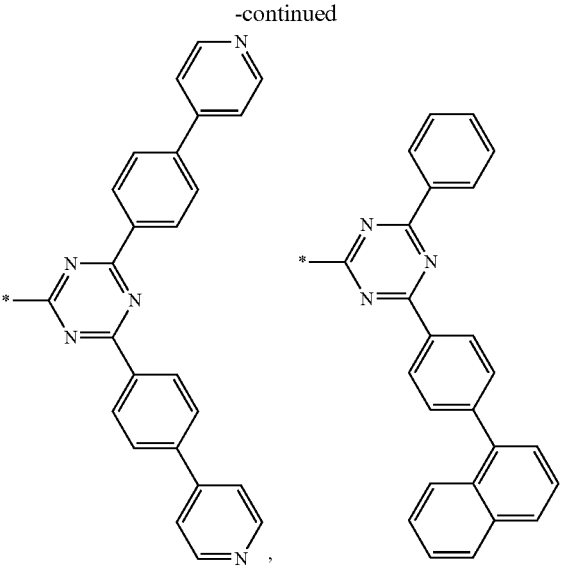
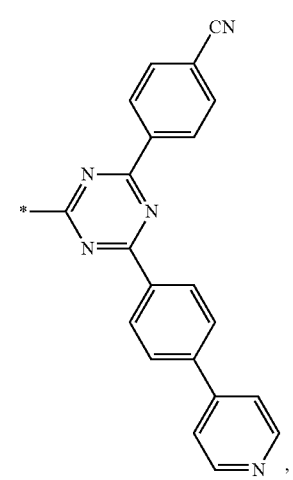
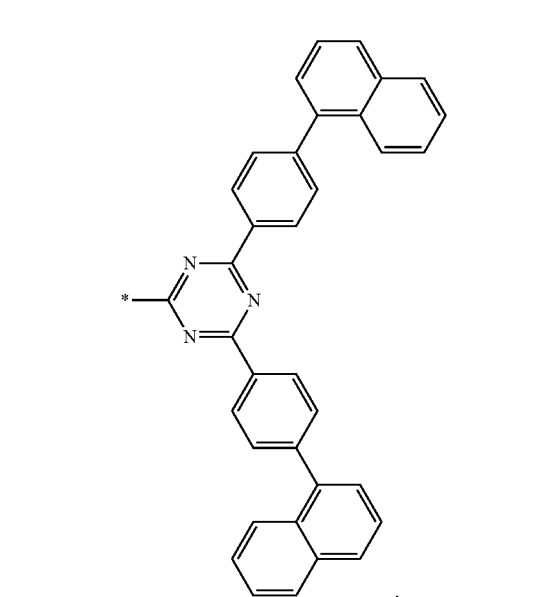
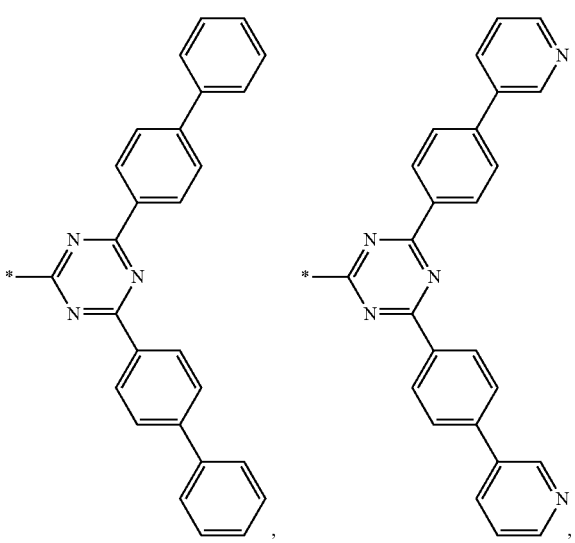
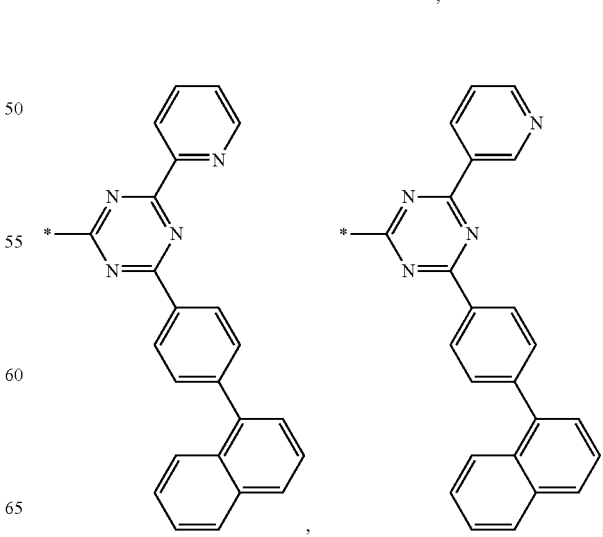

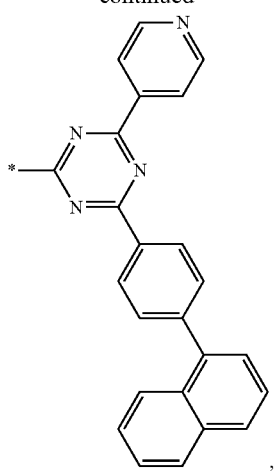
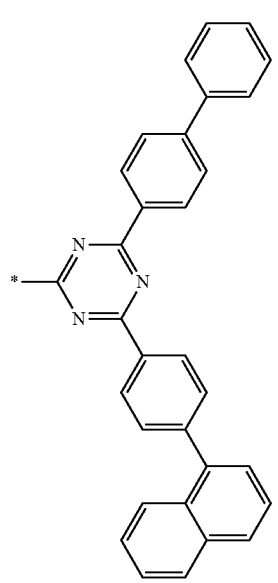
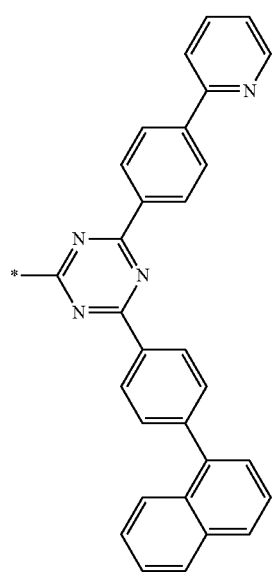
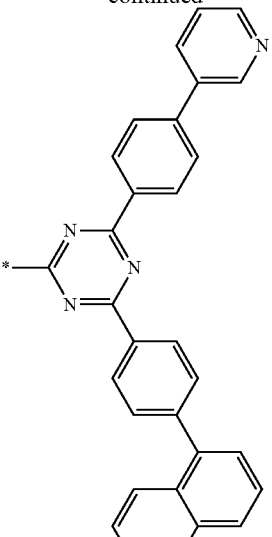
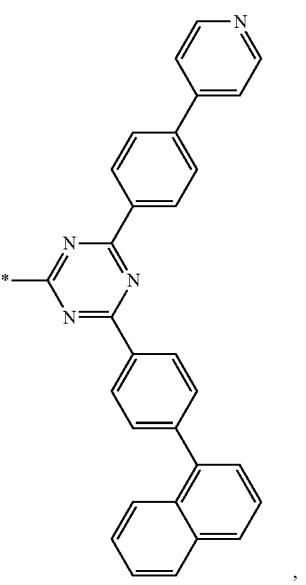
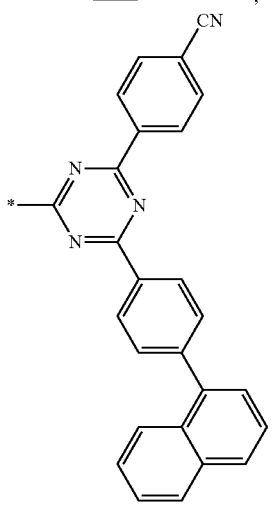
, or
Preferably, the heteroaryl group having 3 to 60 carbon atoms and containing the at least one nitrogen atom may be a substituted triazine group with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

Preferably, the foresaid "aryl group having 6 to 60 carbon atoms and substituted with the at least one functional group" may be, but not limited to:

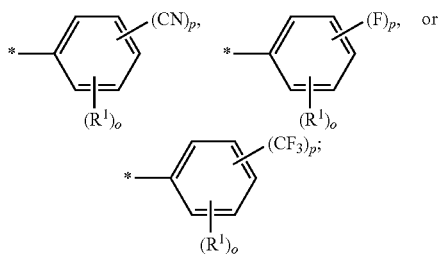

wherein $R^1$ is selected from the group consisting of: a hydrogen atom, a deuterium, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 20 carbon atoms, an alkoxy group having 1 to 40 carbon atoms, an aryloxy group having 6 to 30 carbon atoms, an alkylsilyl group having 1 to 40 carbon atoms, an arylsilyl group having 6 to 30 carbon atoms, an alkylboron group having 1 to 40 carbon atoms, an arylboron group having 6 to 30 carbon atoms, a phosphine group having 1 to 30 carbon atoms, and a phosphine oxide group having 1 to 30 carbon atoms;

wherein o is an integral from 0 to 4, p is an integral from 1 to 5, and the total of o and p is not more than 5.

Preferably, the novel compound may be, for example, but not limited to, the compounds as follows.

Compound I

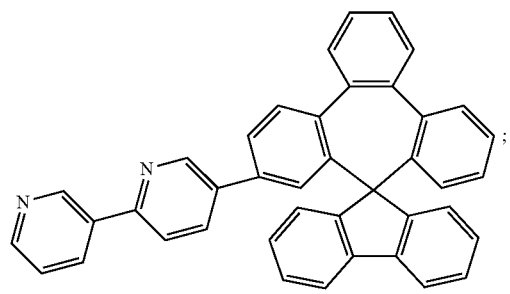

Compound II

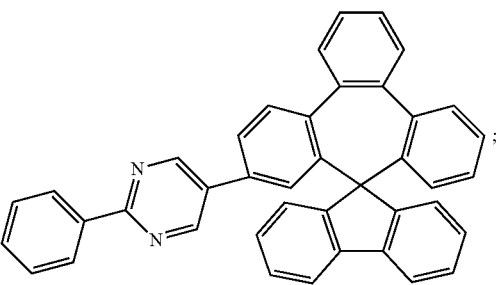

Compound III

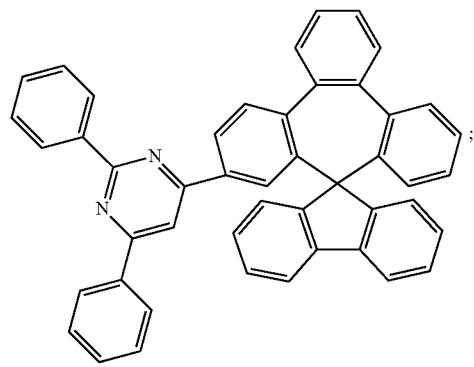

Compound IV

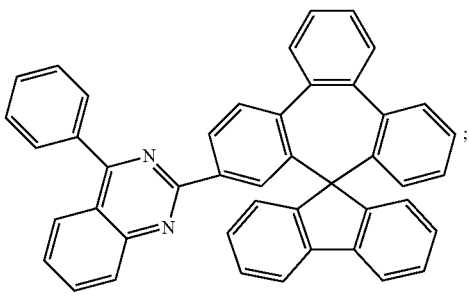

Compound V

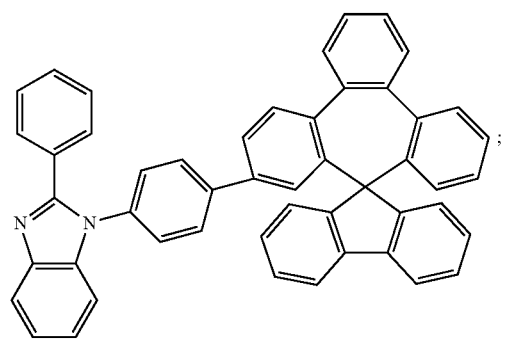

Compound VI

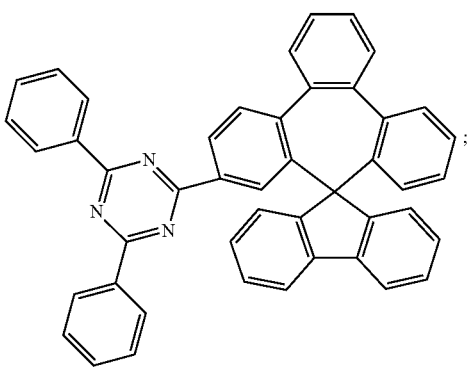

-continued
Compound VII
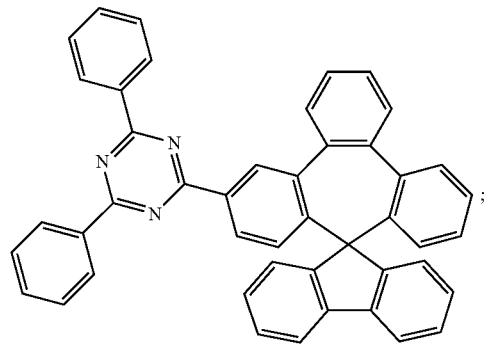
Compound VIII
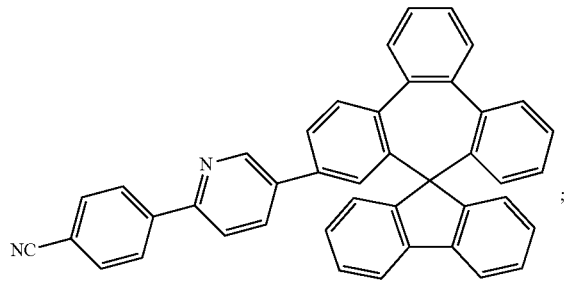
Compound IX
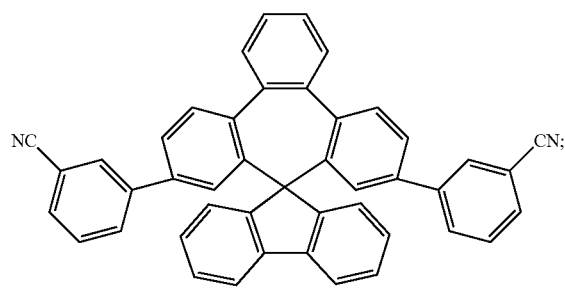
Compound X
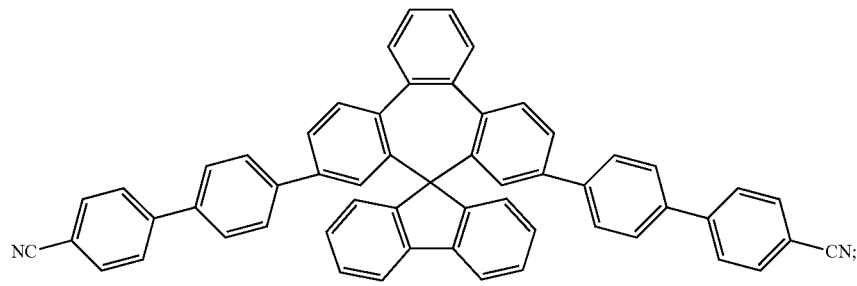
Compound XI
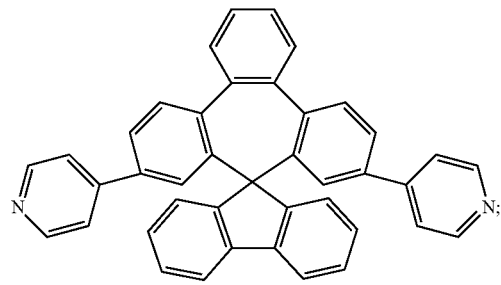
Compound XII
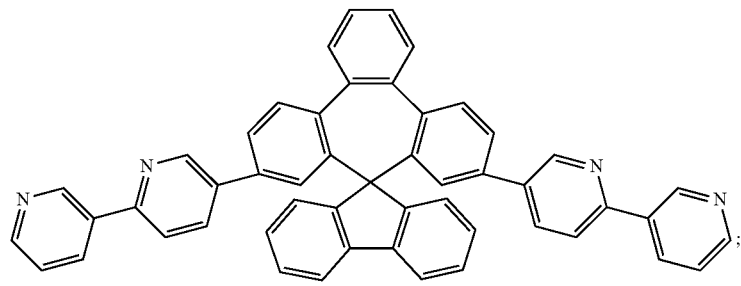

-continued
Compound XIII
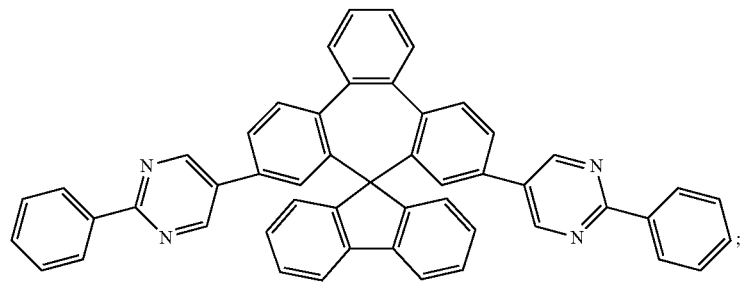
Compound XIV
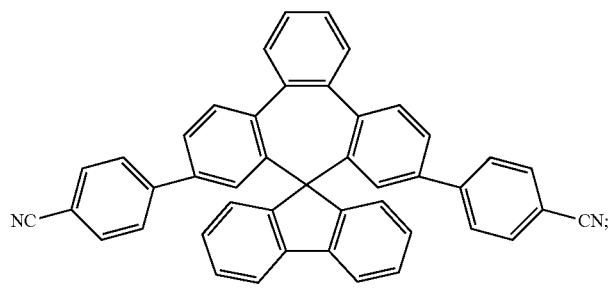
Compound XV
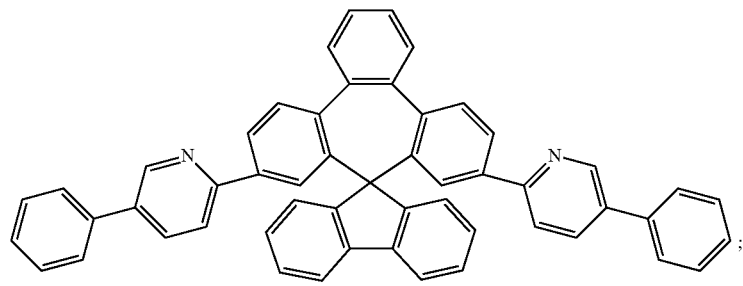
Compound XVI
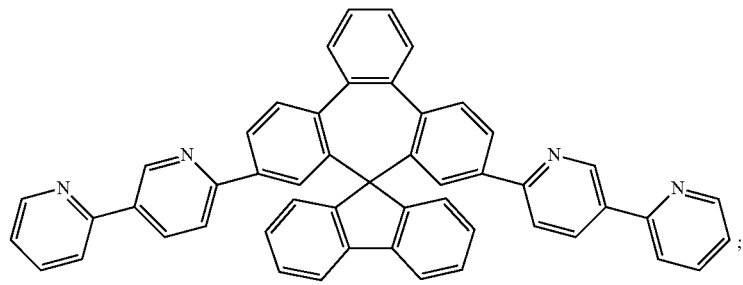
Compound XVII
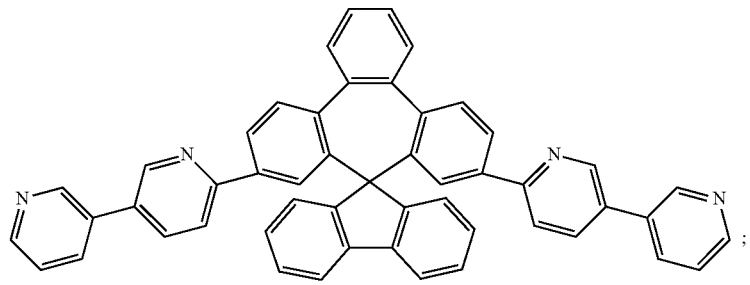

Compound XVIII
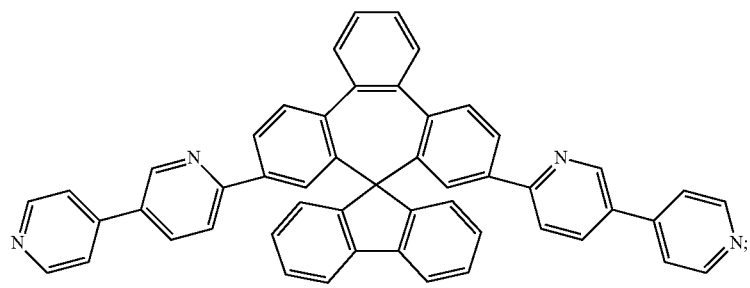
Compound XIX
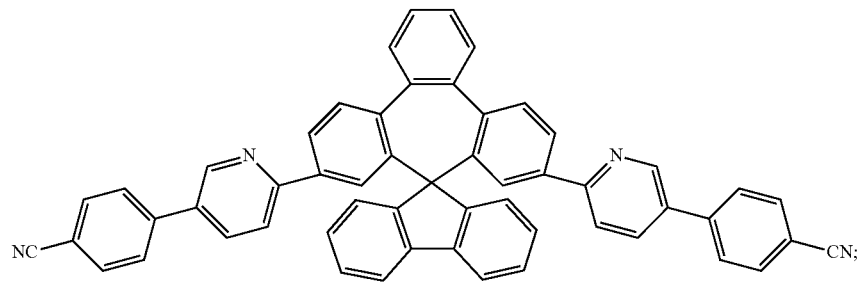
Compound XX
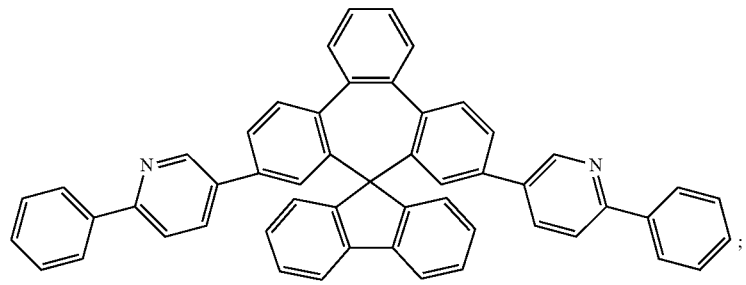
Compound XXI
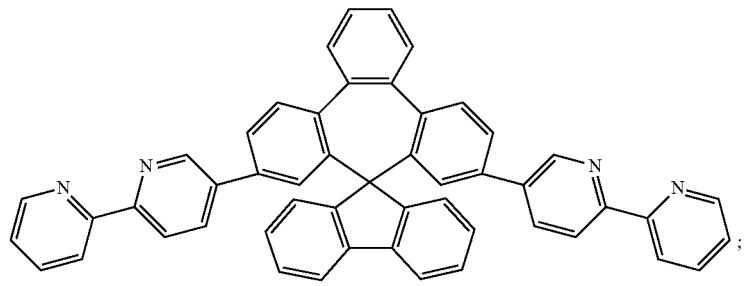
Compound XXII
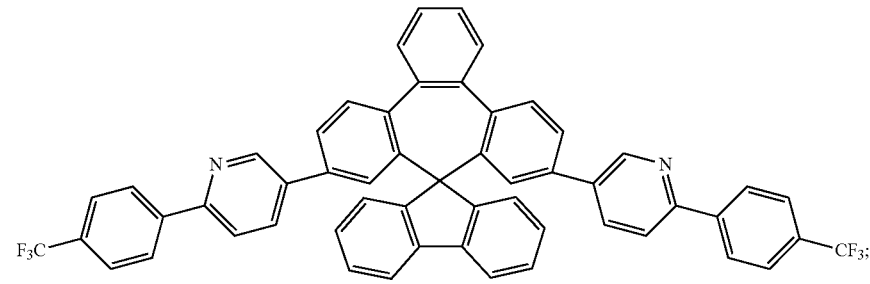

-continued
Compound XXIII
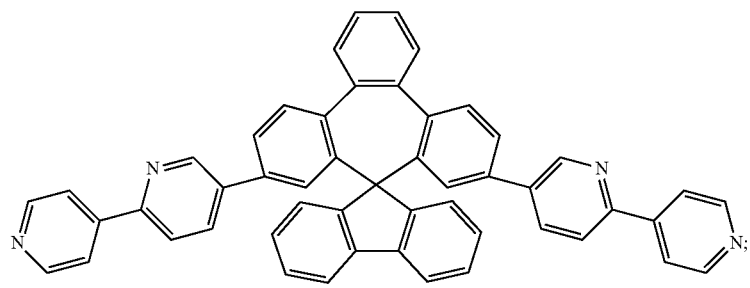
Compound XXIV
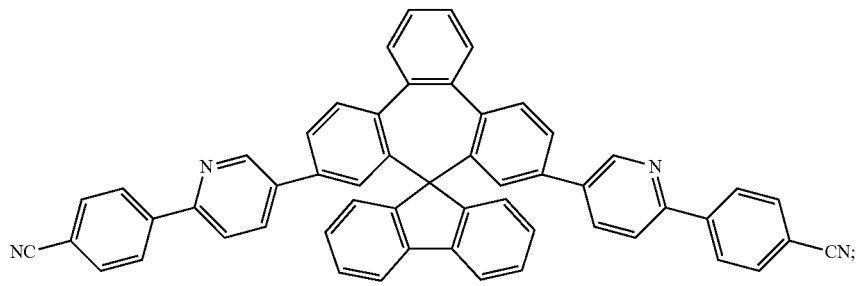
Compound XXV
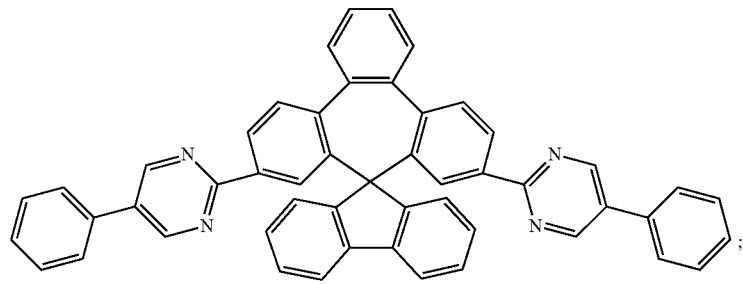
Compound XVI
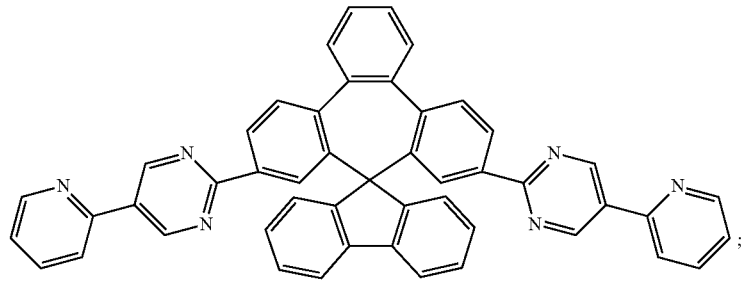
Compound XVII
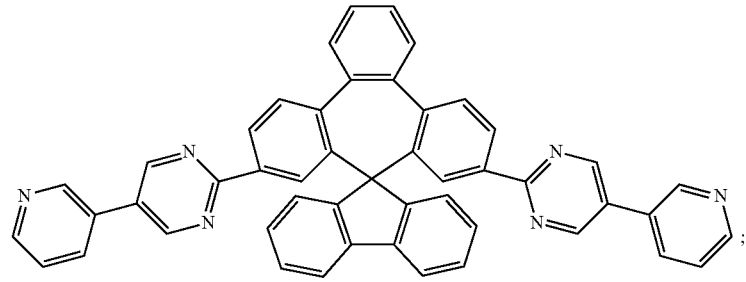

-continued
Compound XXVIII
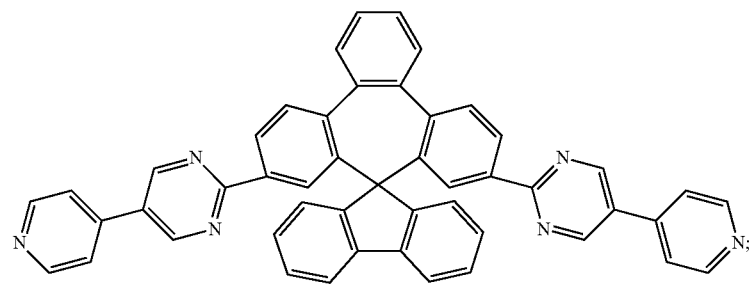
Compound XXIX
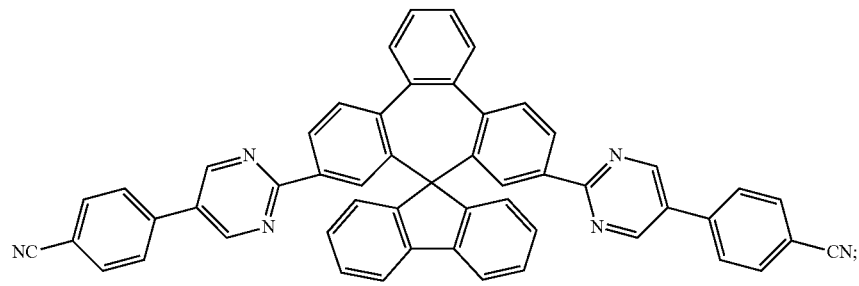
Compound XXX
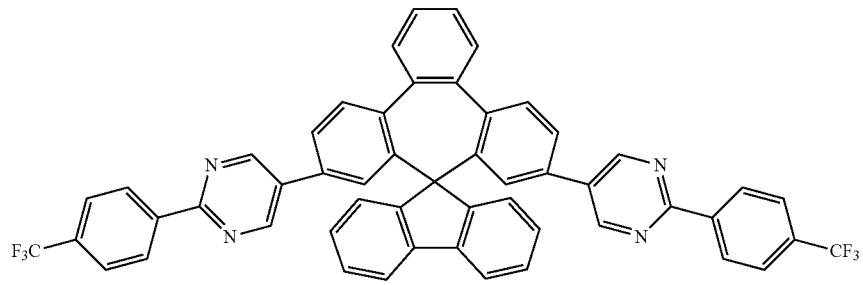
Compound XXXI
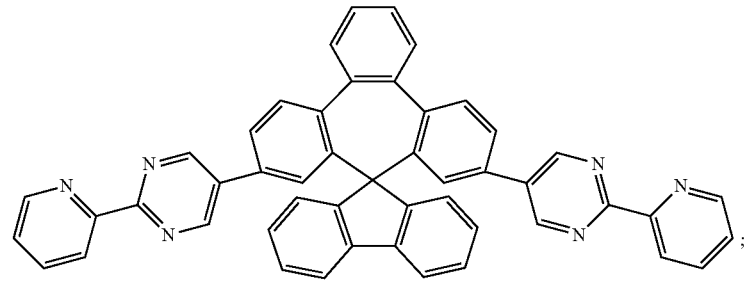
Compound XXXII
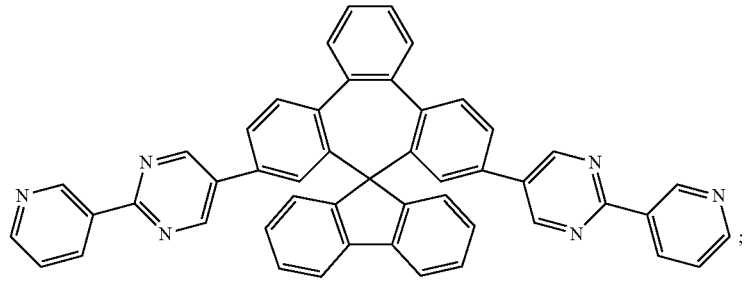

-continued
Compound XXXIII
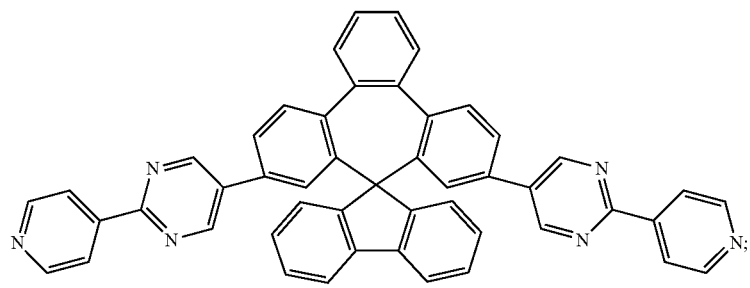
Compound XXXIV
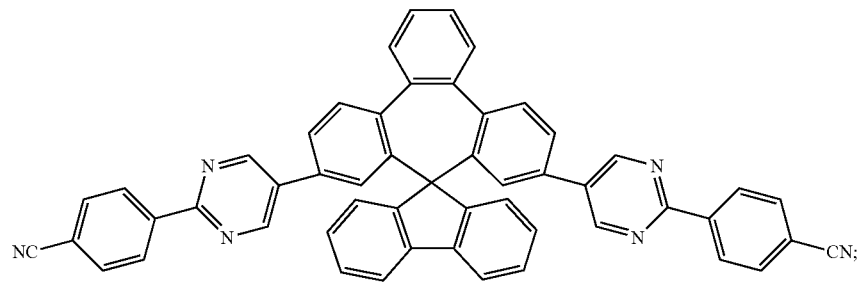
Compound XXXV
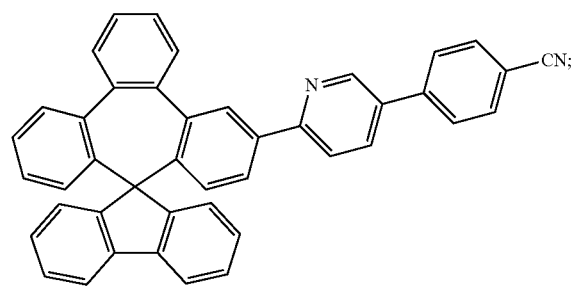
Compound XXXVI
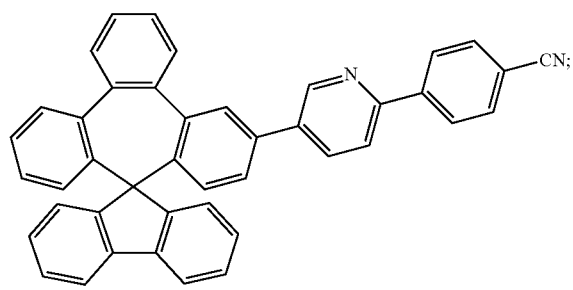
Compound XXXVII
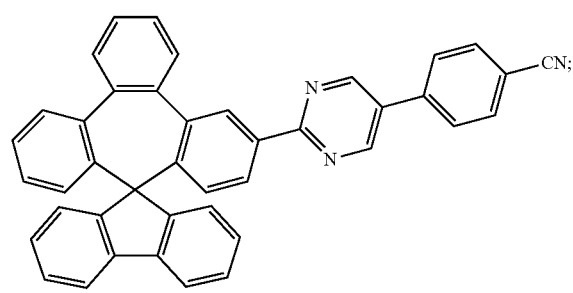
Compound XXXVIII
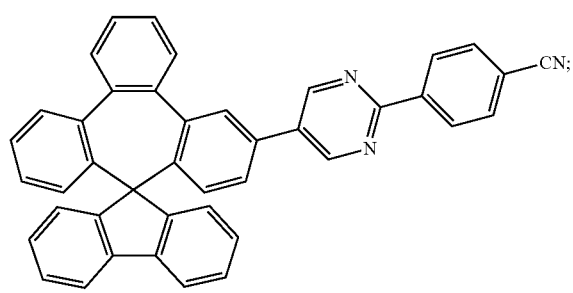
Compound XXXIX
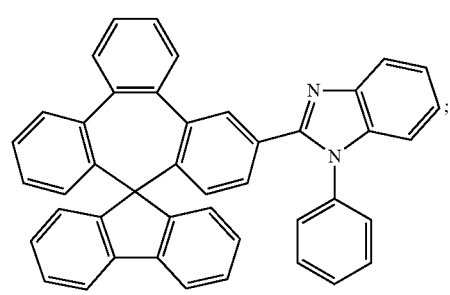
Compound XL
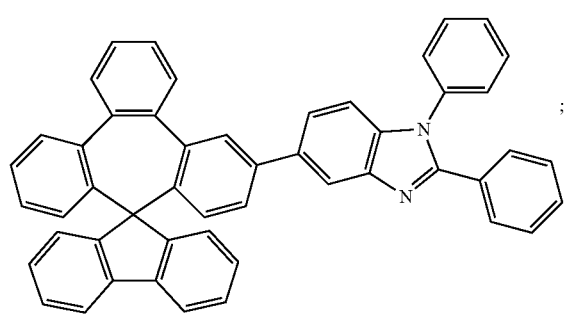

-continued
Compound XLI
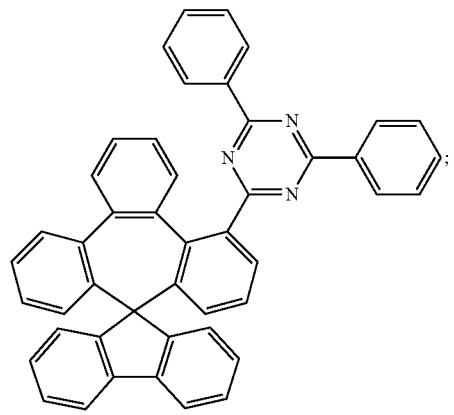
Compound XLII
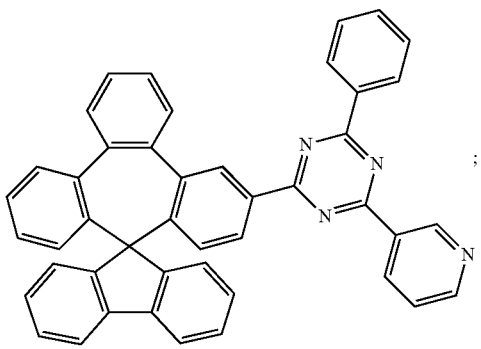
Compound XLIII
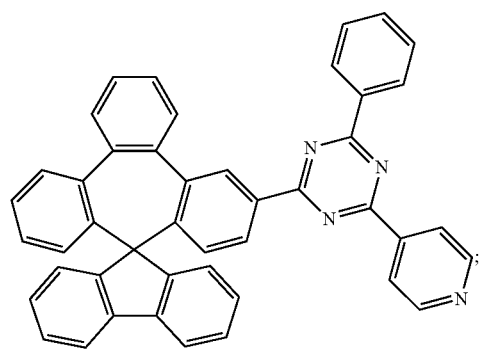
Compound XLIV
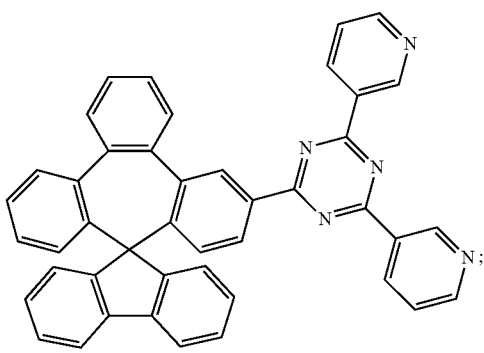
Compound XLV
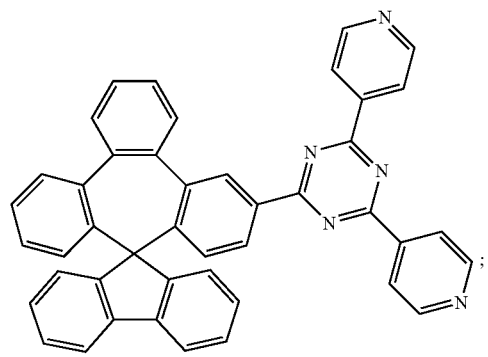
Compound XLVI
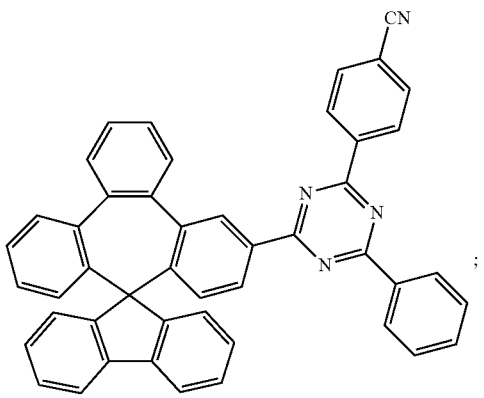
Compound XLVII
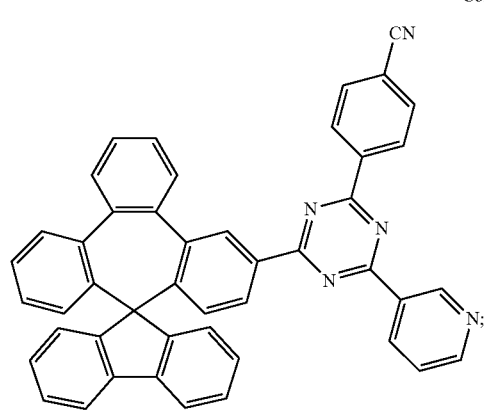
Compound XLVIII
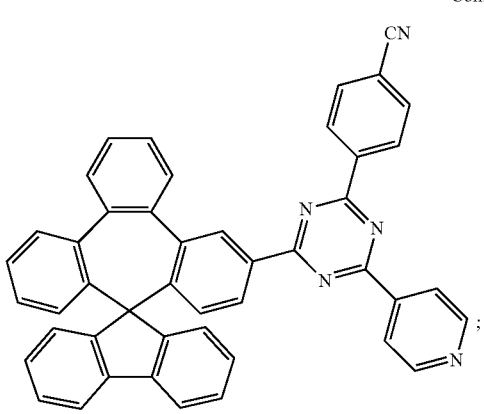

Compound IL
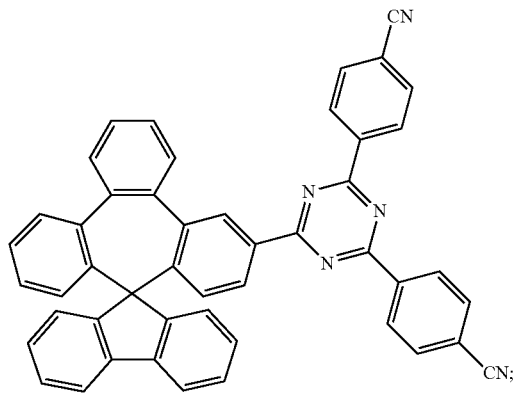
Compound L
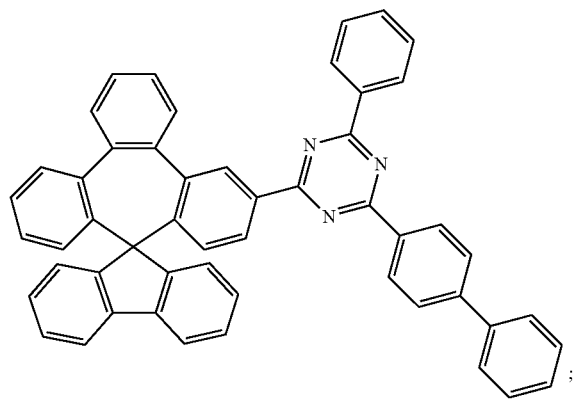
Compound LI
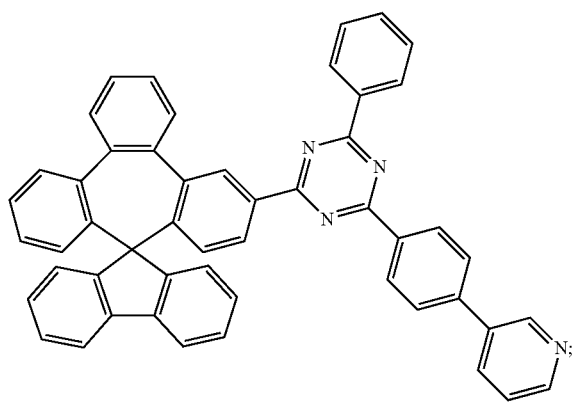
Compound LII
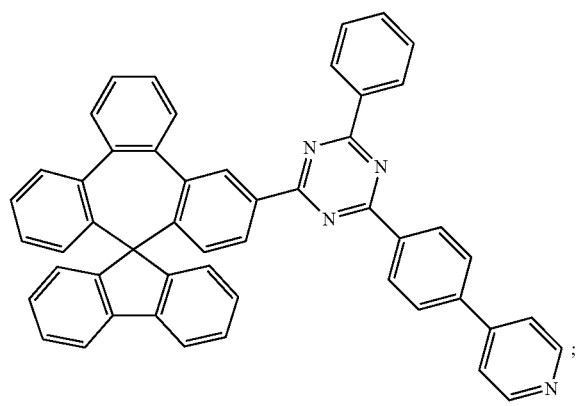
Compound LII
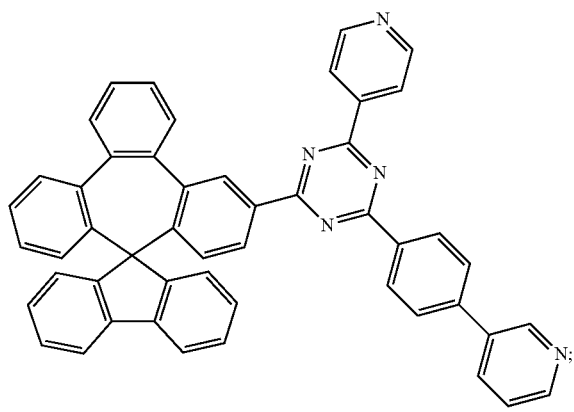
Compound LIV
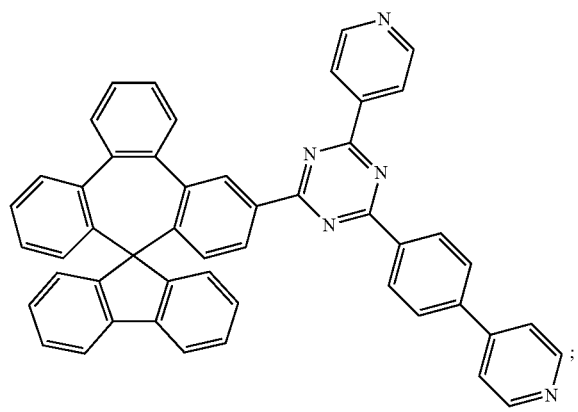

Compound LV                    Compound LVI
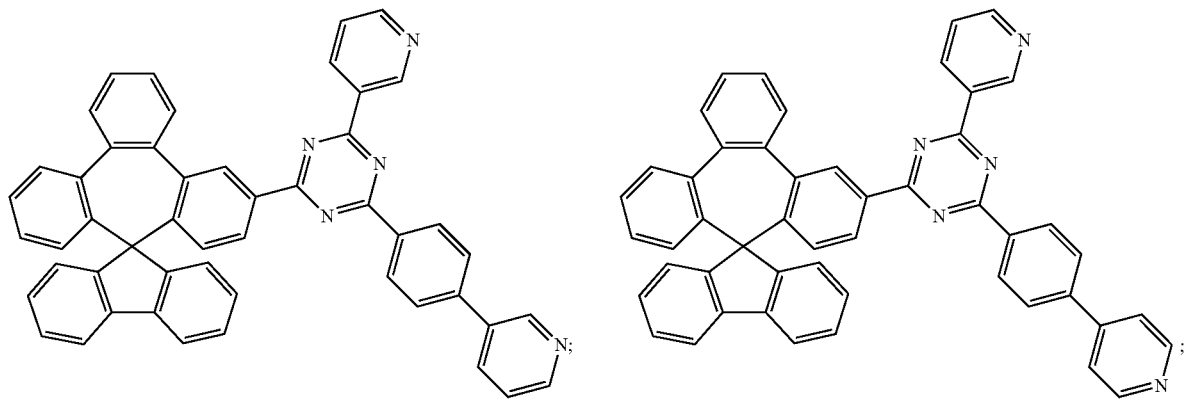
Compound LVII                  Compound LVIII
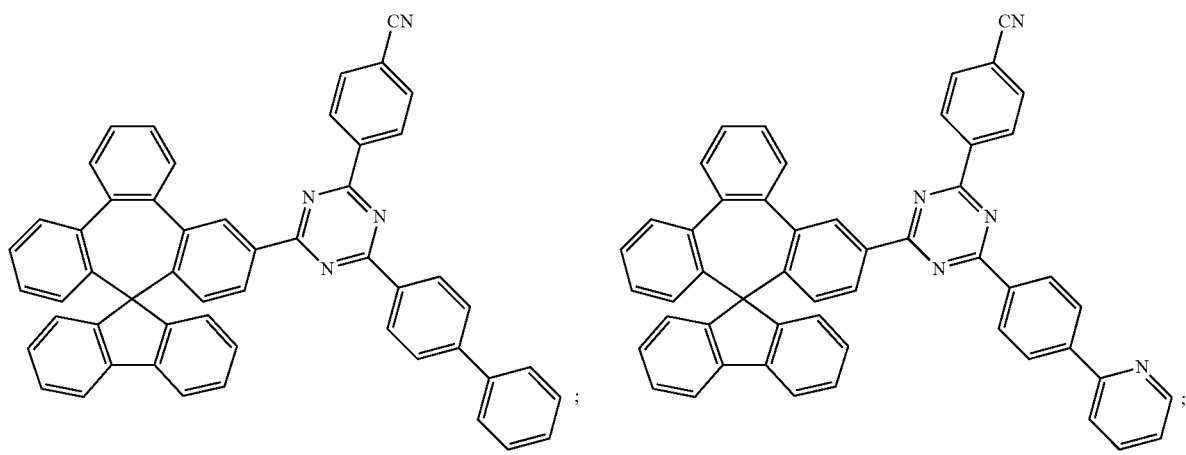
Compound LIX                   Compound LX
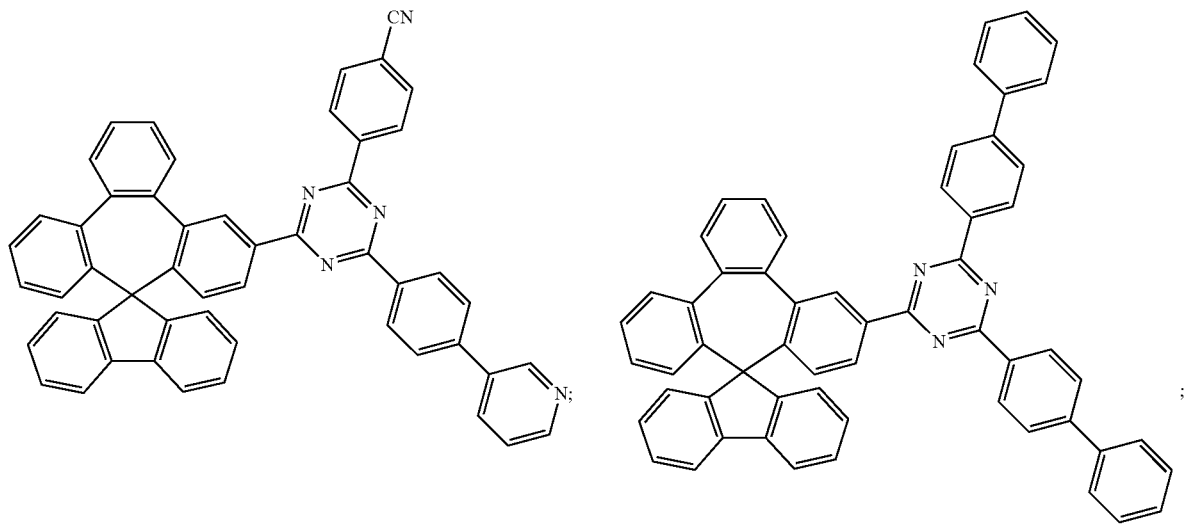

Compound LXI
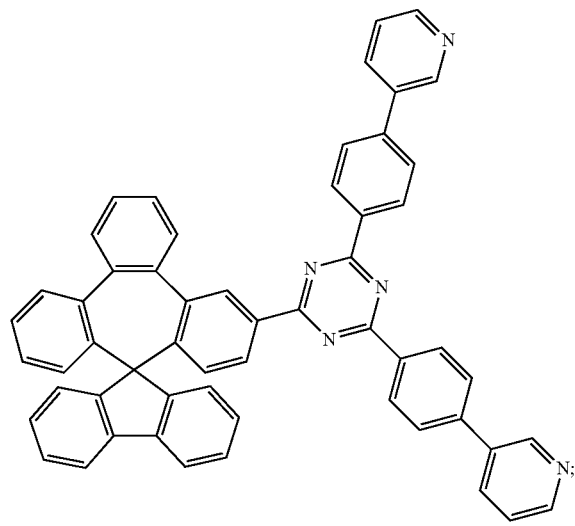
Compound LXII
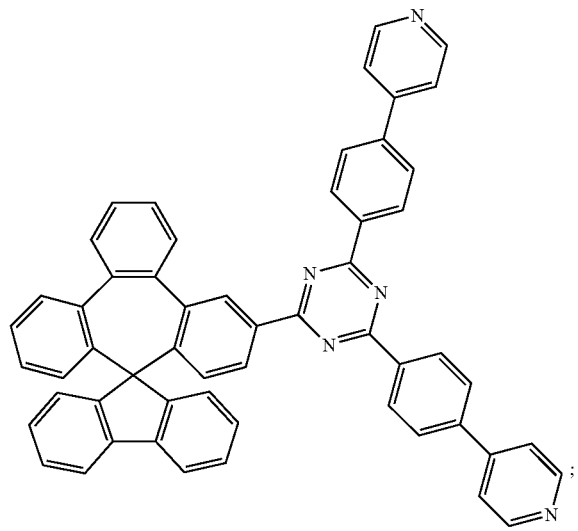
Compound LXIII
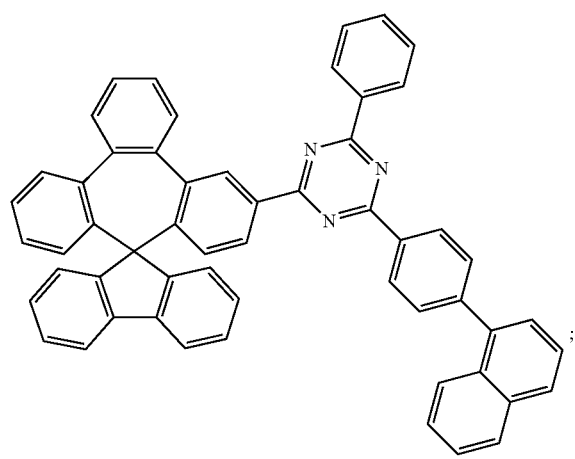
Compound LXIV
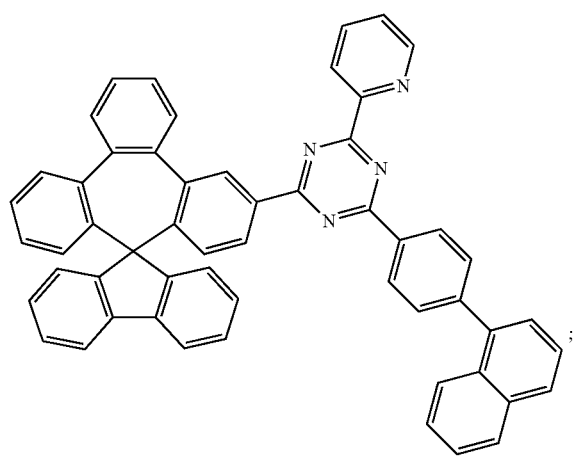
Compound LXV
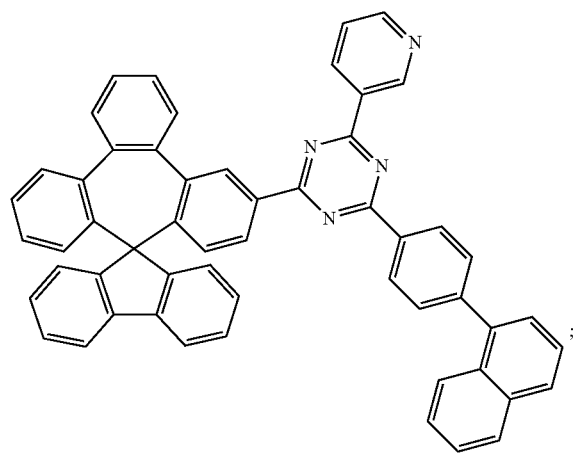
Compound LXVI
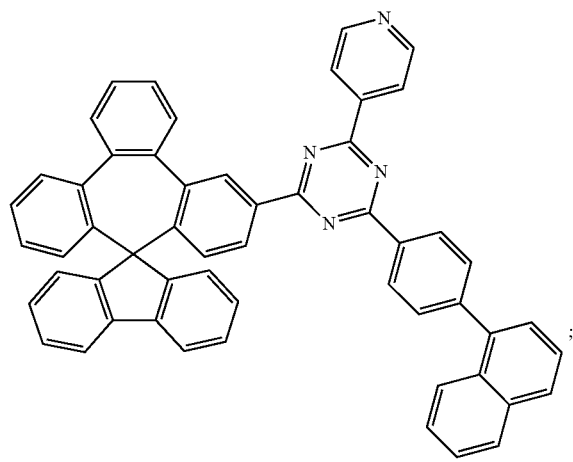

-continued
Compound LXVII
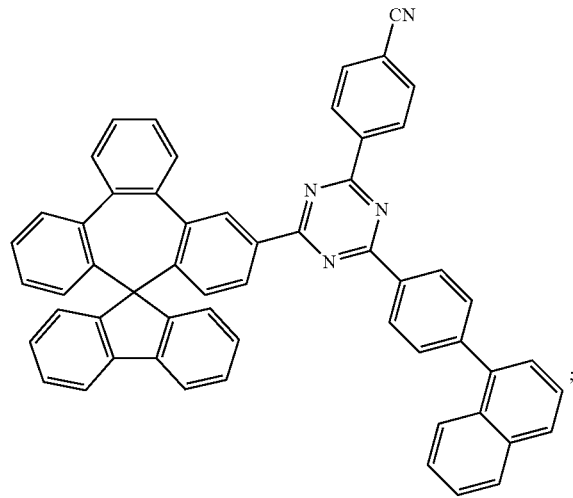
Compound LXVIII
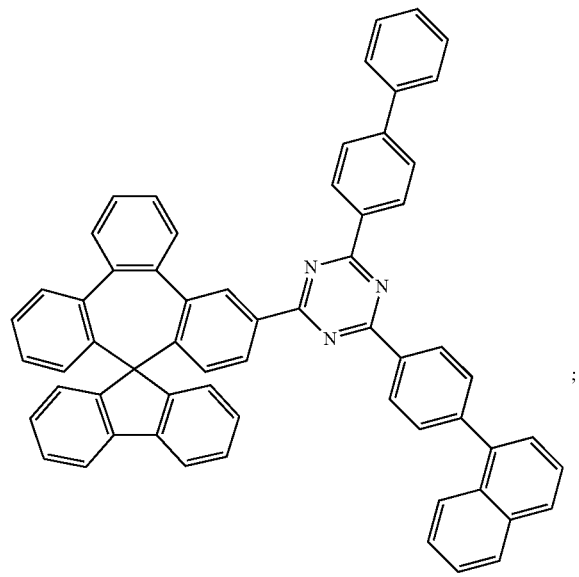
Compound LXIX
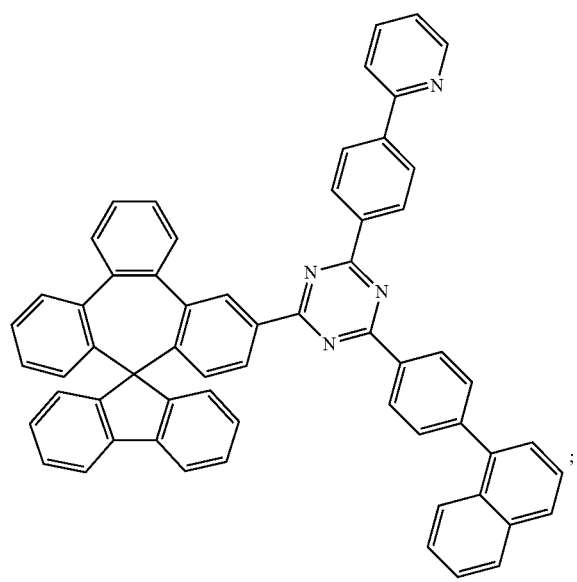
Compound LXX
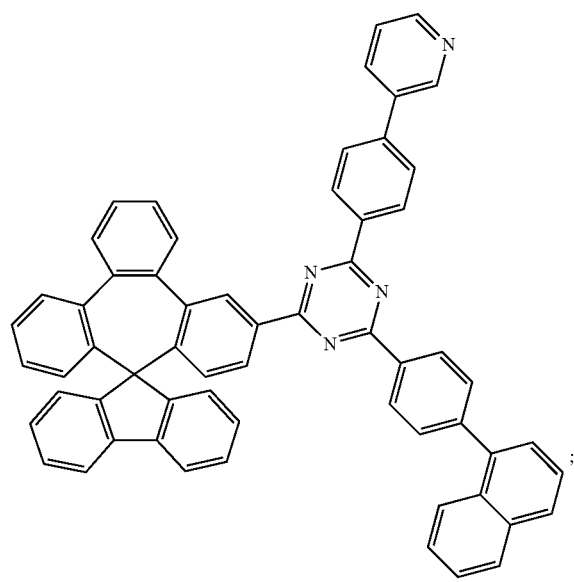

Compound LXXI
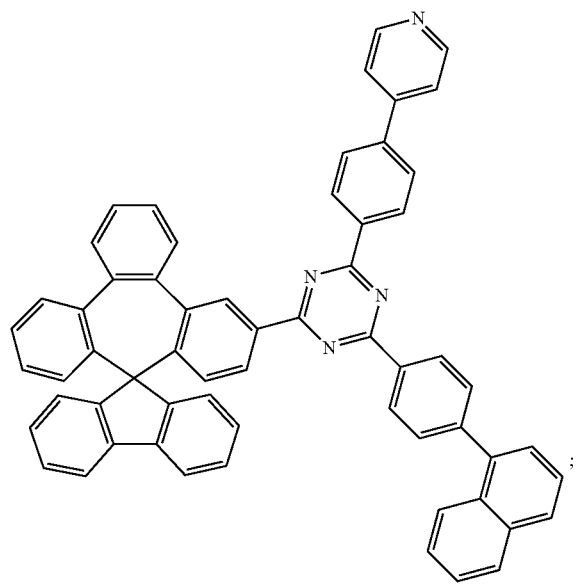
Compound LXXII
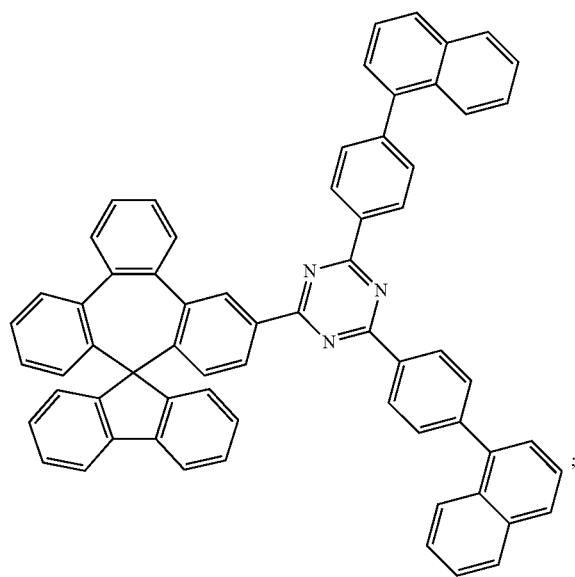
Compound LXXIII
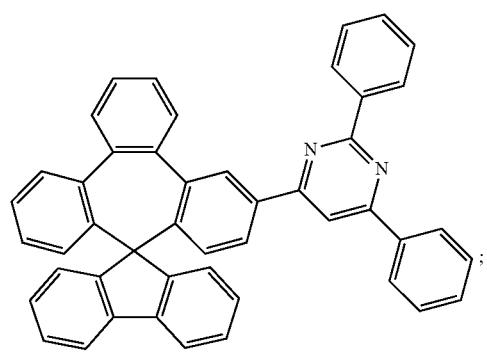
Compound LXXIV
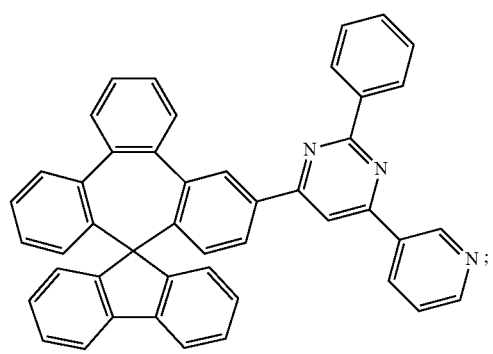
Compound LXXV
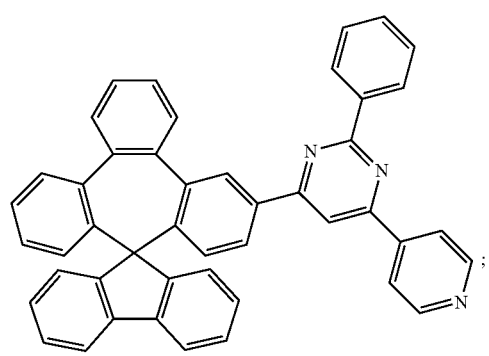
Compound LXXVI
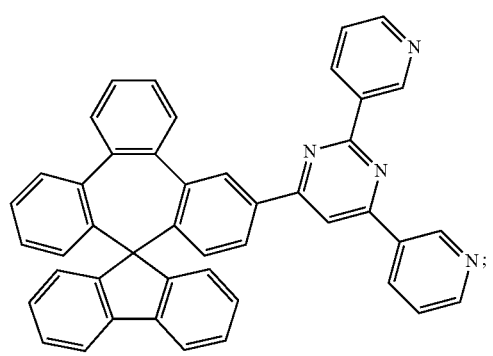

-continued
Compound LXXVII
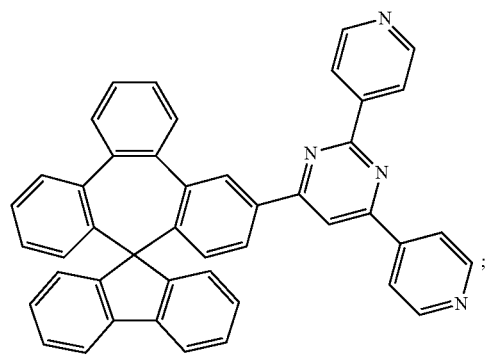
Compound LXXVIII
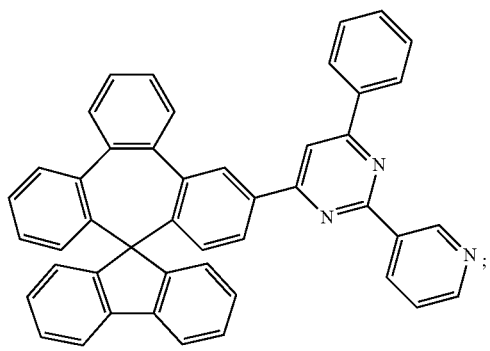
Compound LXXIX
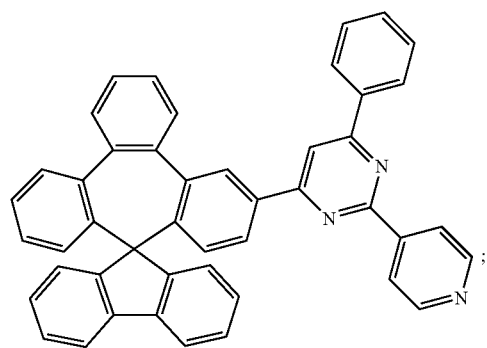
Compound LXXX
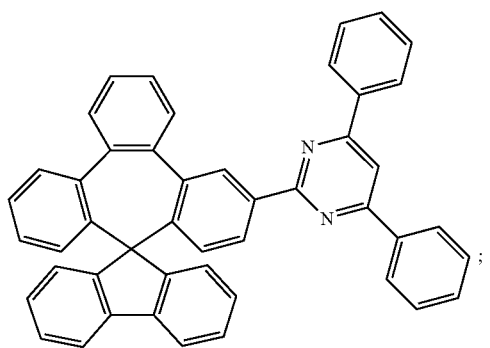
Compound LXXXI
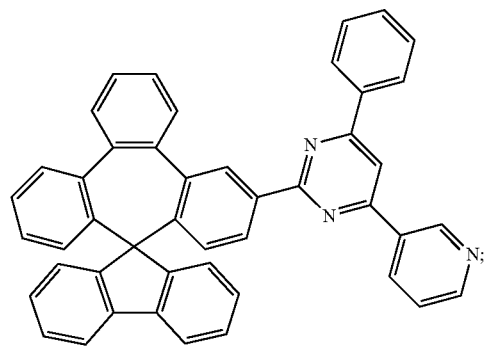
Compound LXXXII
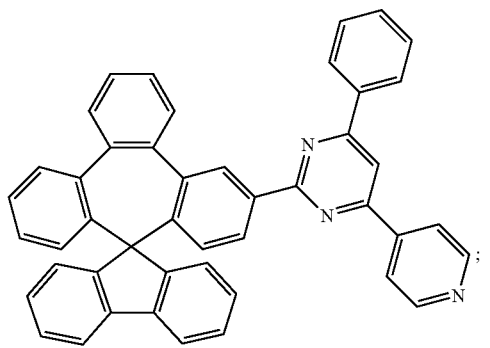
Compound LXXXII
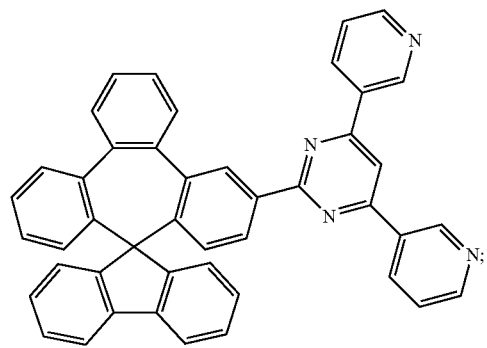
Compound LXXXIV
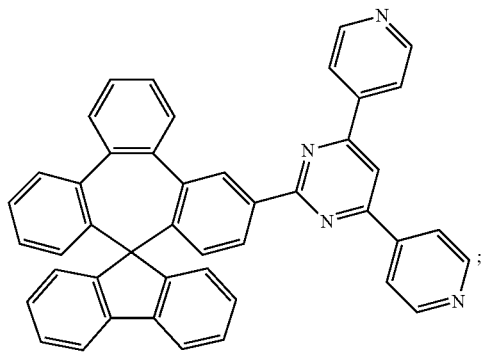

-continued
Compound LXXXV
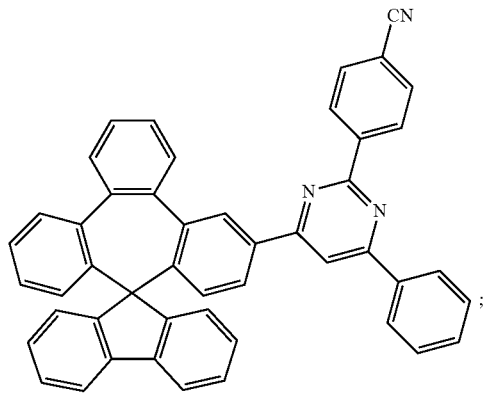
Compound LXXXVI
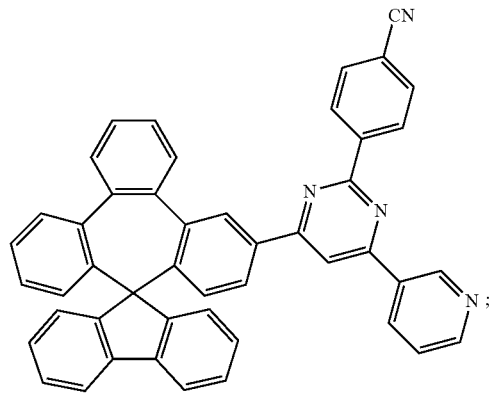
Compound LXXXVII
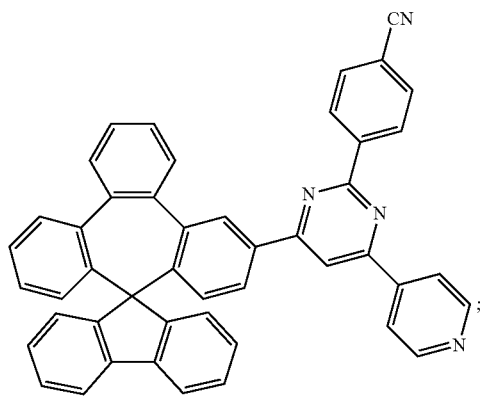
Compound LXXXVIII
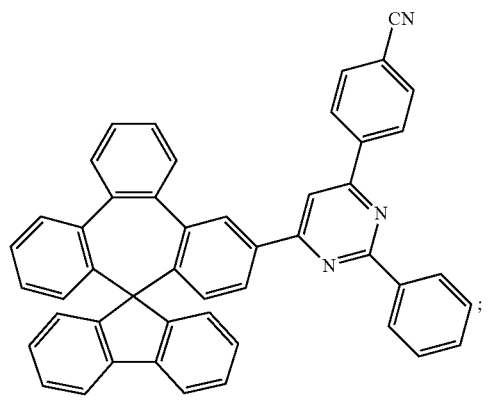
Compound LXXXIX
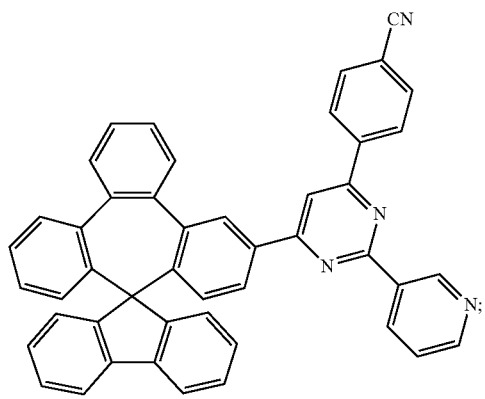
Compound XC
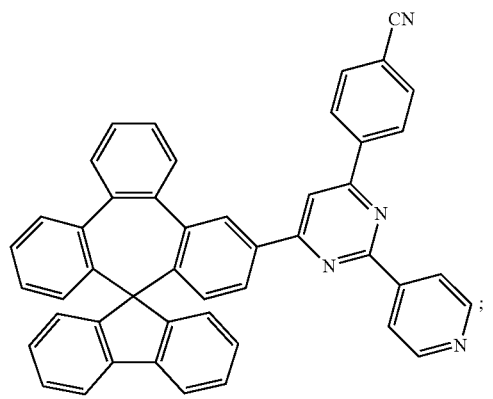
Compound XCI
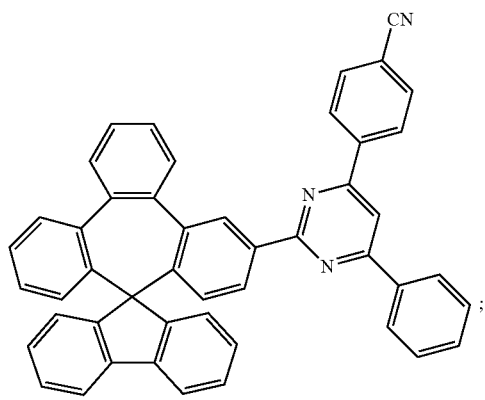
Compound XCII
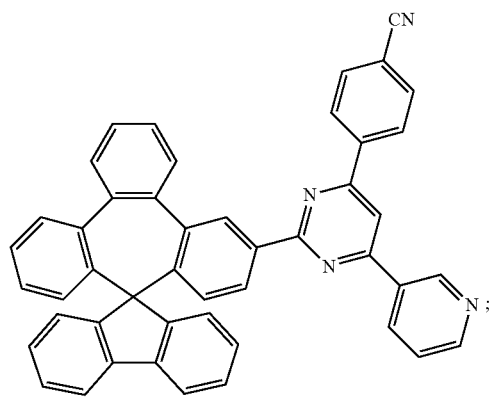

Compound XCIII
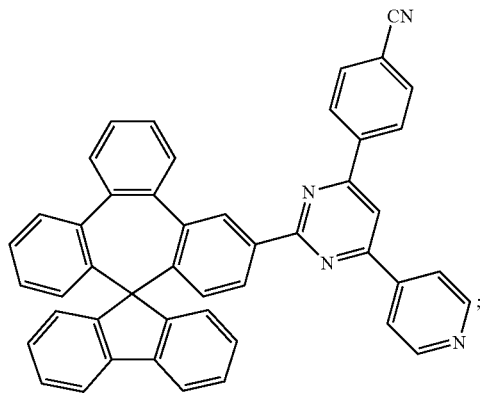
Compound XCIV
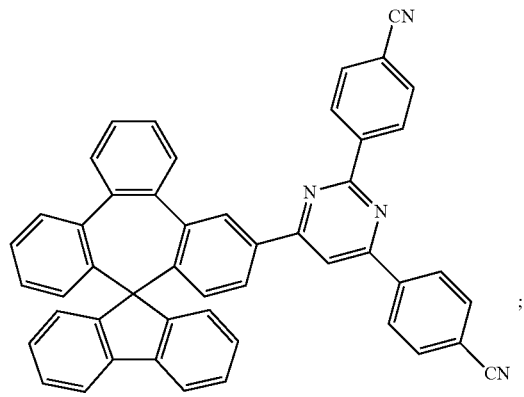
Compound XCV
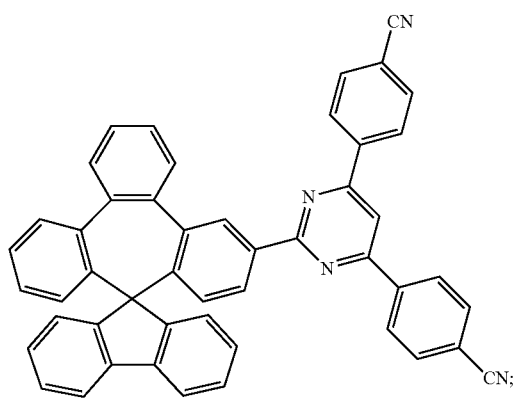
Compound XCVI
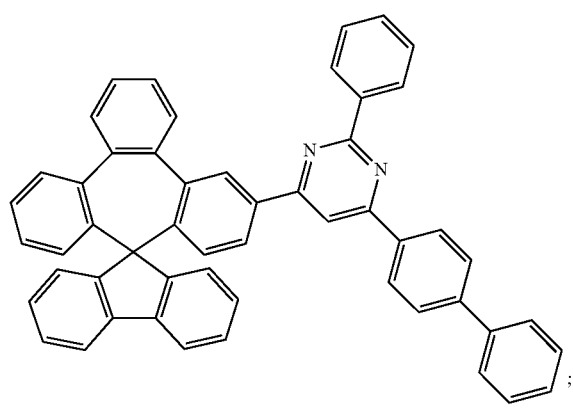
Compound XCVII
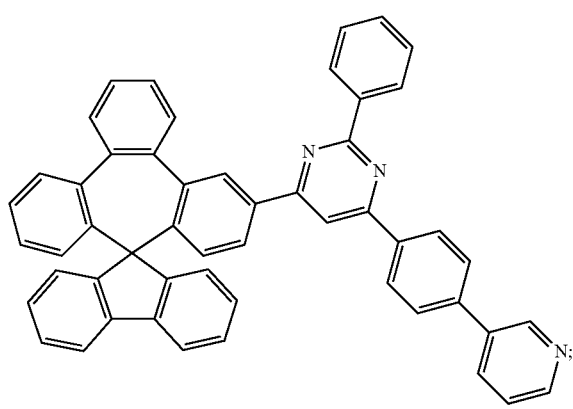
Compound XCVIII
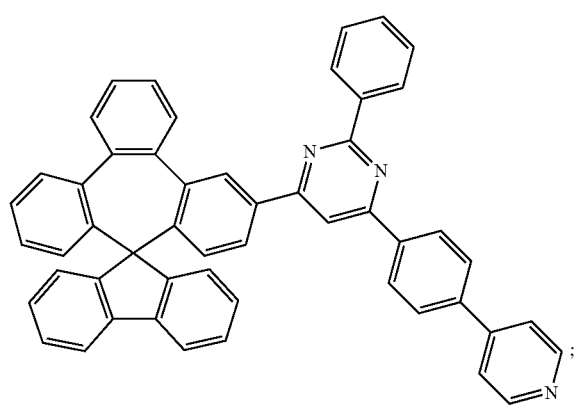

-continued
Compound XCIX
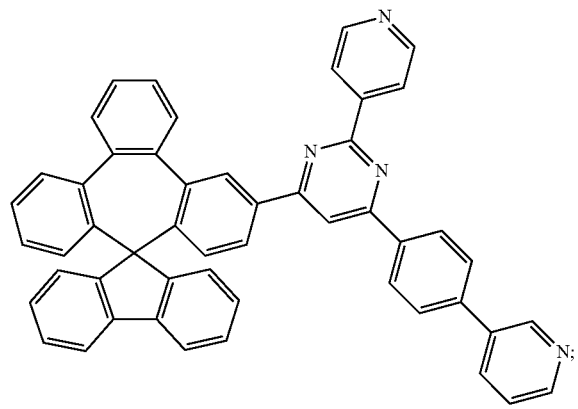
Compound C
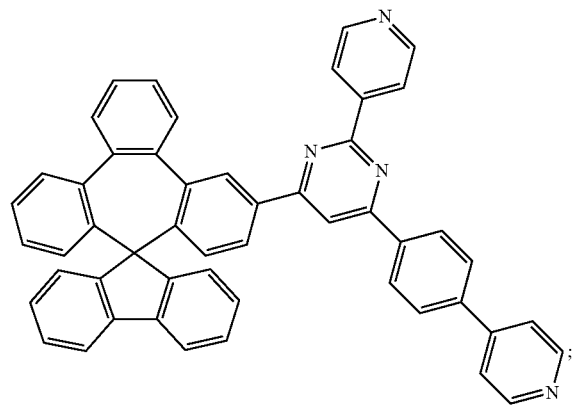
Compound CI
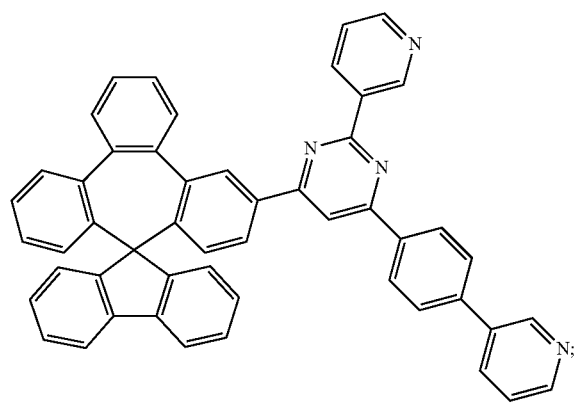
Compound CII
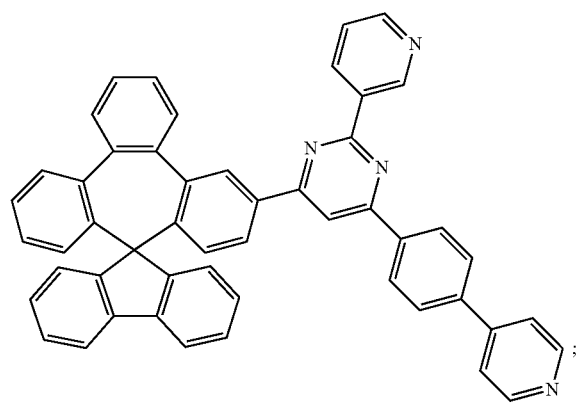
Compound CIII
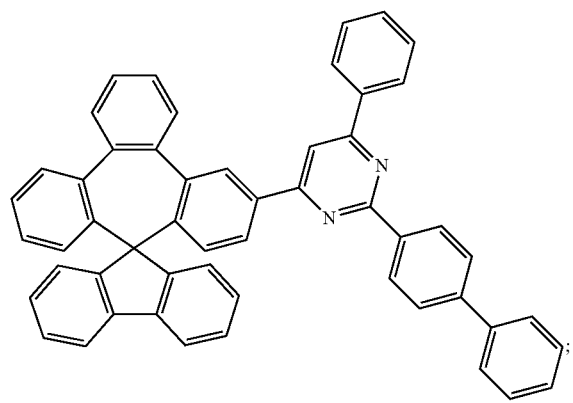
Compound CIV
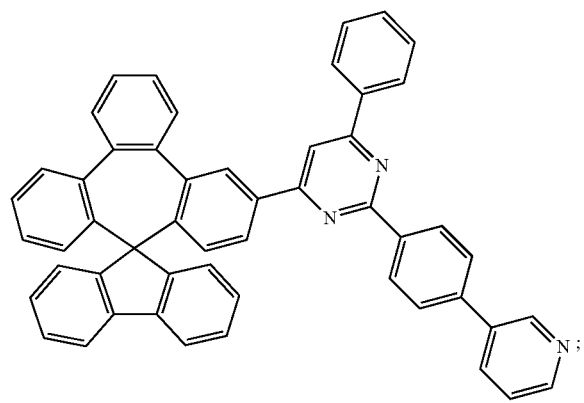

-continued
Compound CV
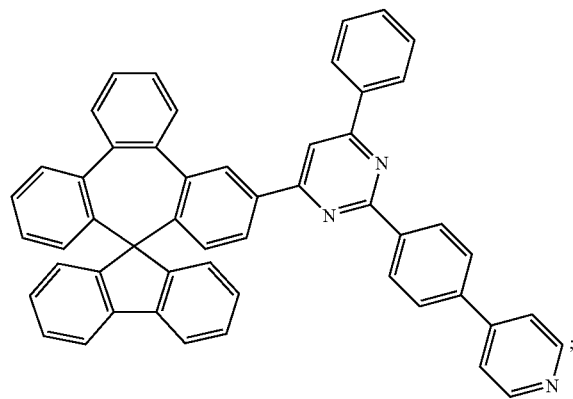
Compound CVI
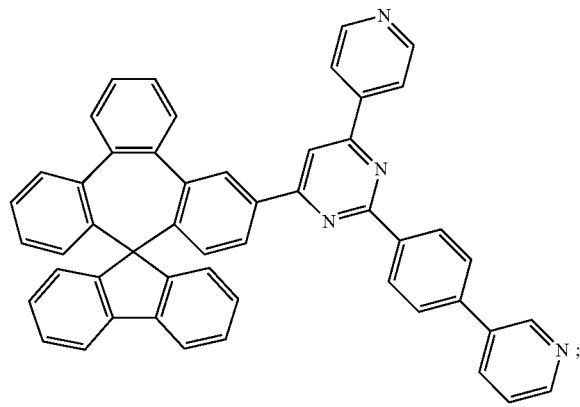
Compound CVII
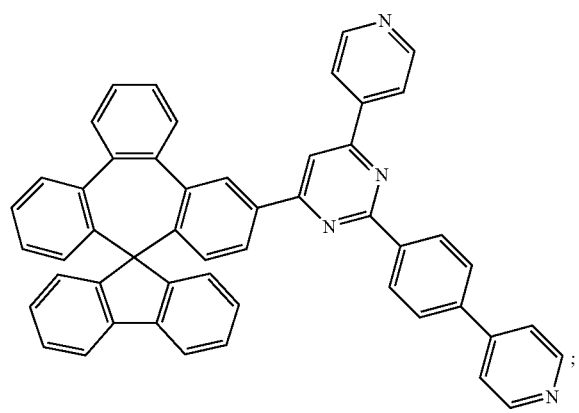
Compound CVIII
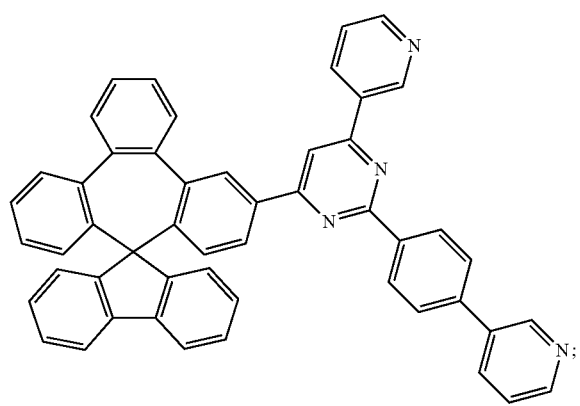
Compound CIX
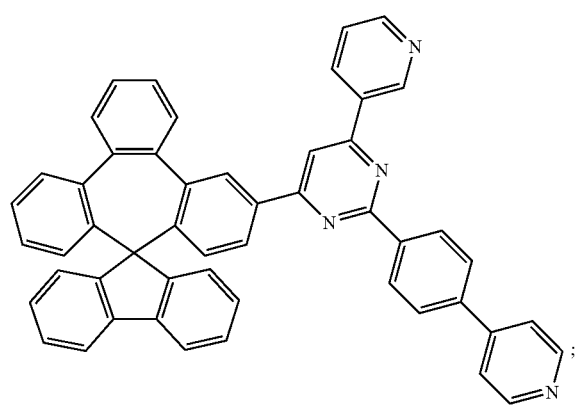
Compound CX
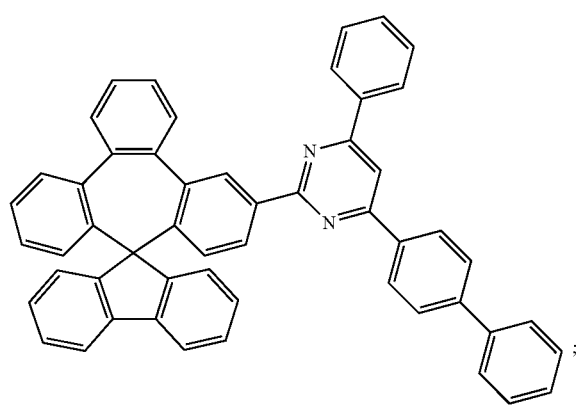

Compound CXI
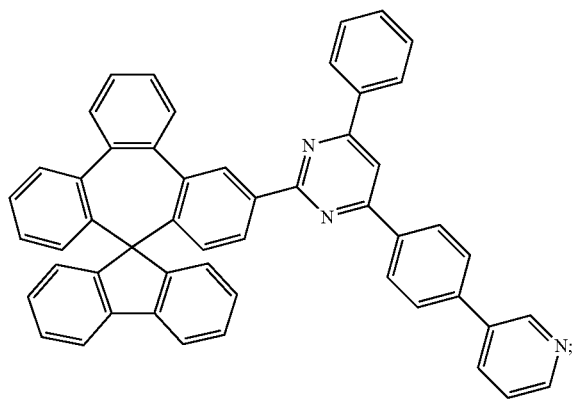
Compound CXII
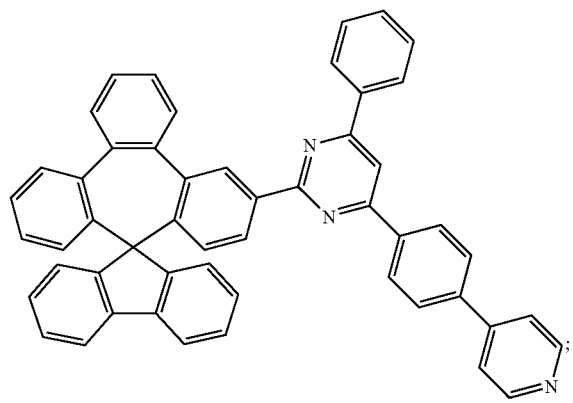
Compound CXIII
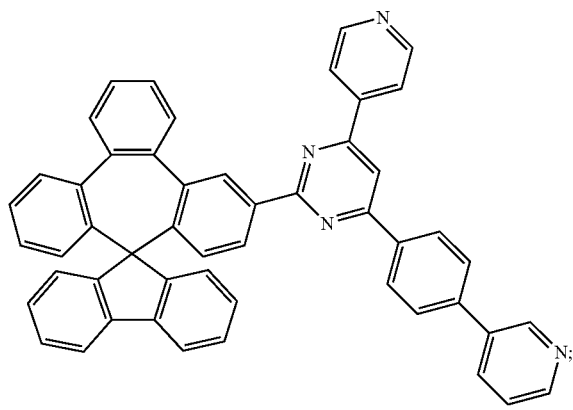
Compound CXIV
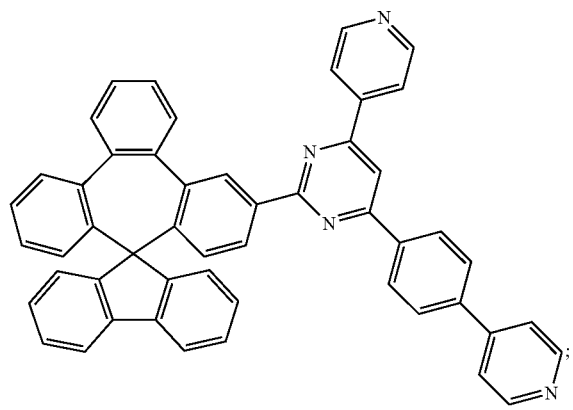
Compound CXV
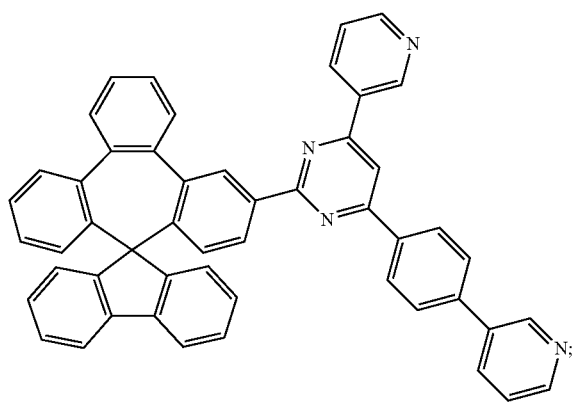
Compound CXVI
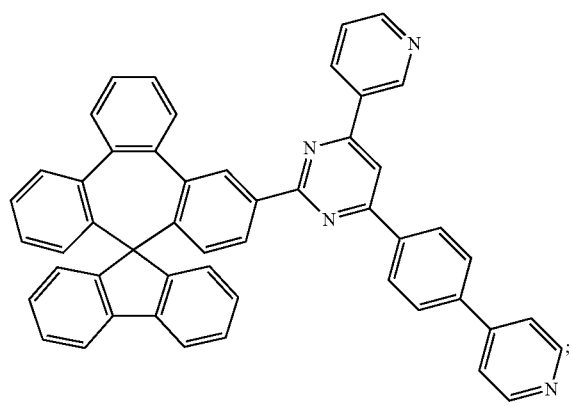

Compound CXVII
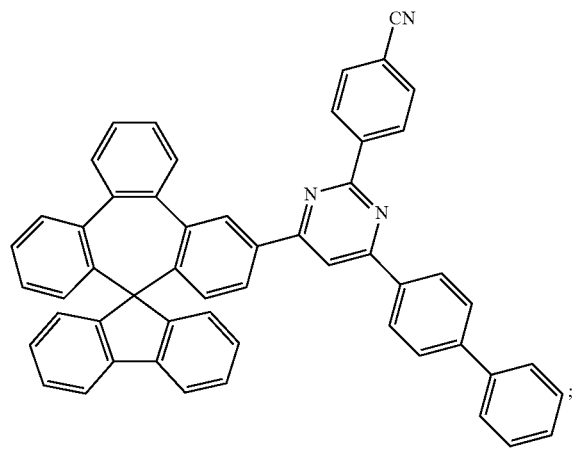
Compound CXVIII
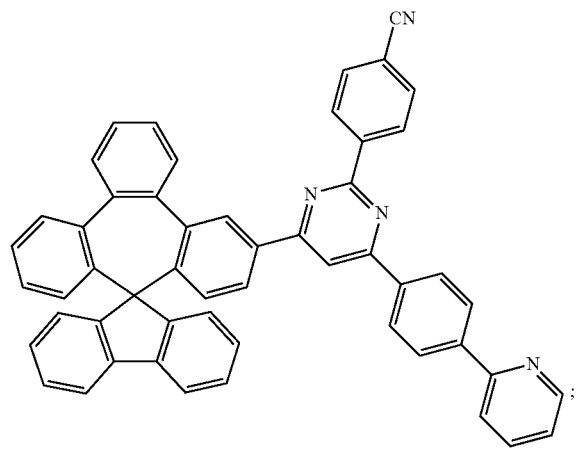
Compound CXIX
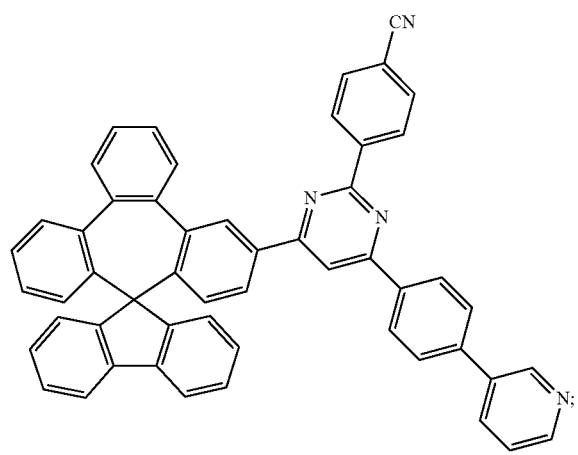
Compound CXX
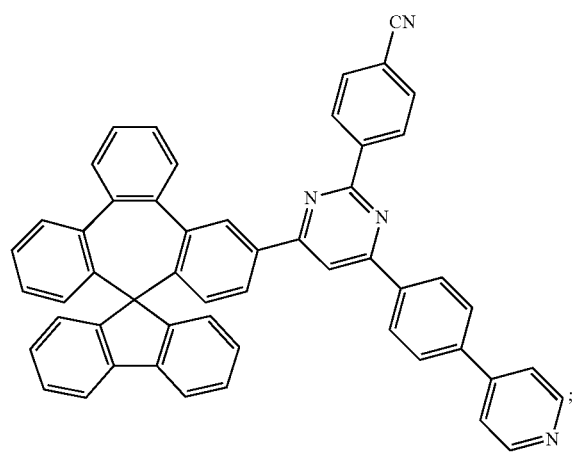
Compound CXXI
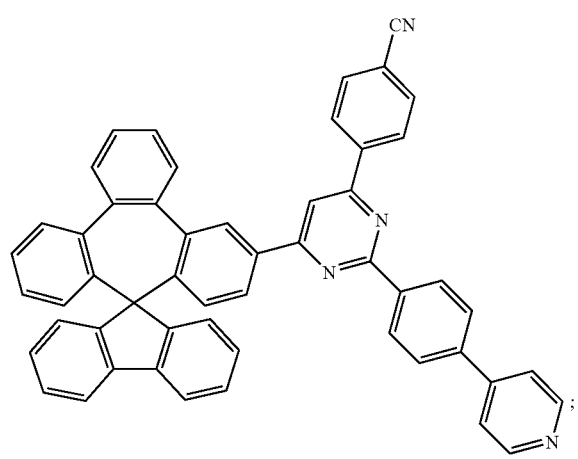
CXXII
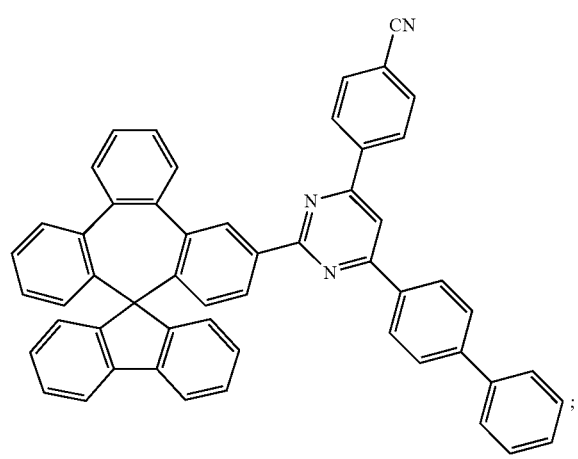

Compound CXXIII
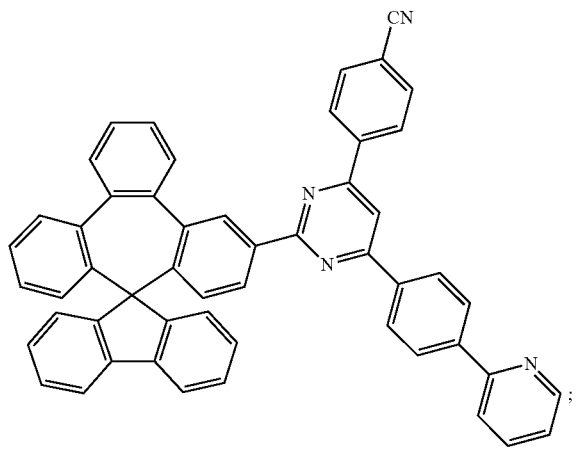
Compound CXXIV
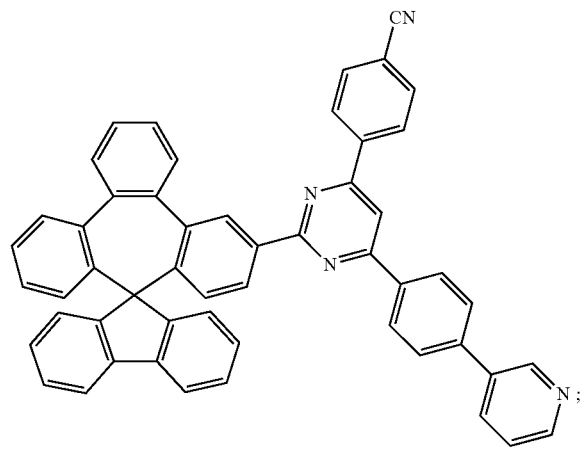
Compound CXXV
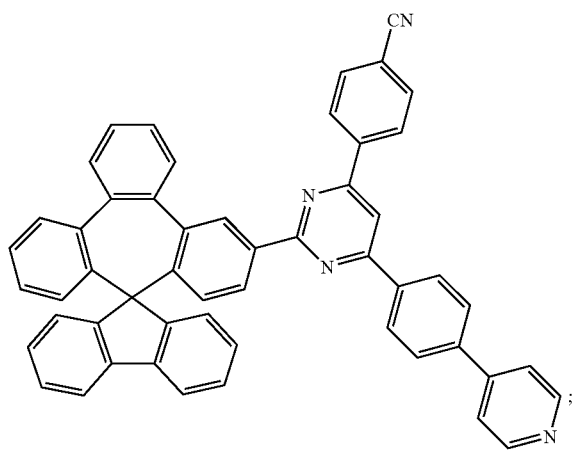
Compound CXXVI
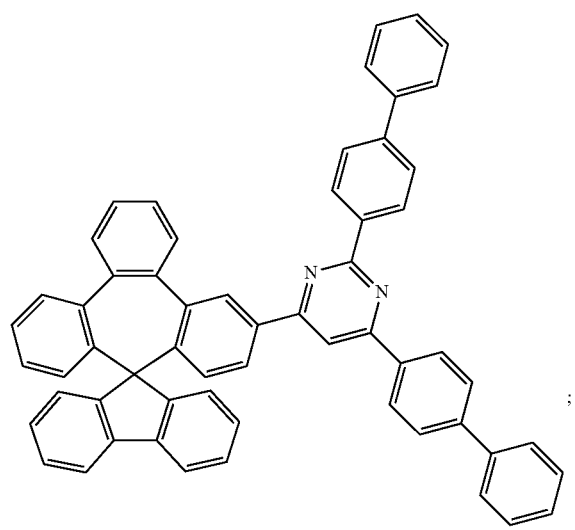
Compound CXXVII
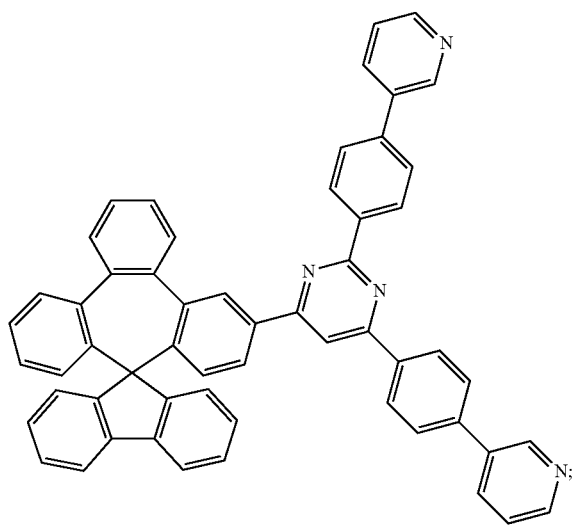
Compound CXXVIII
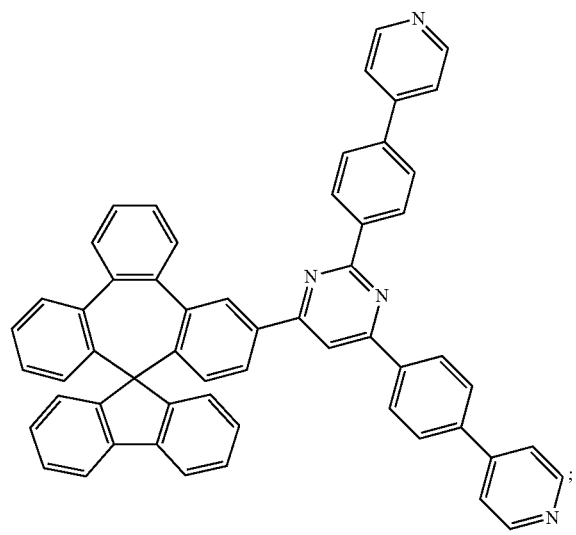

-continued
Compound CXXIX
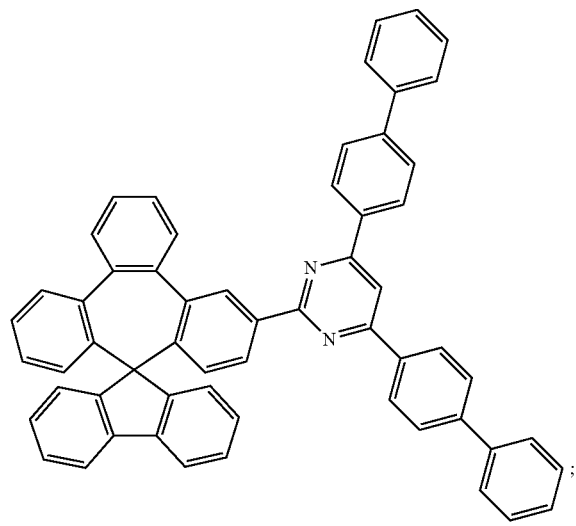
Compound CXXX
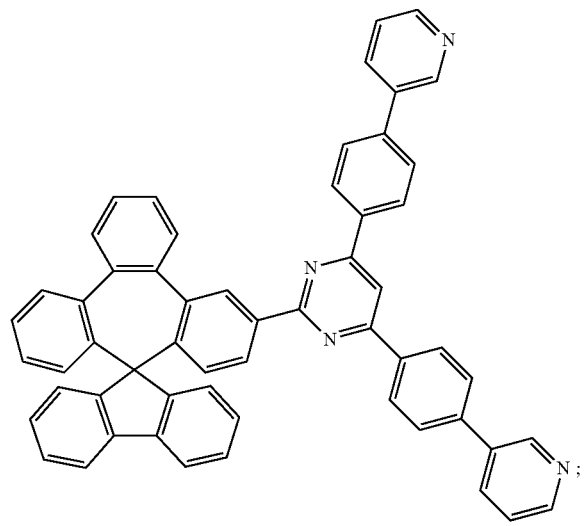
Compound CXXXI
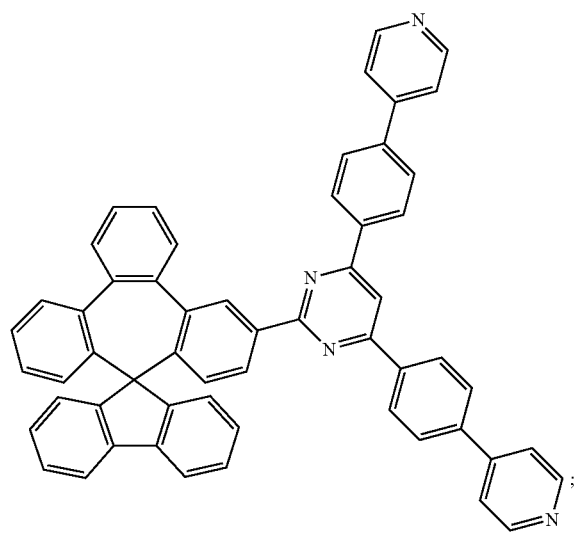
Compound CXXXII
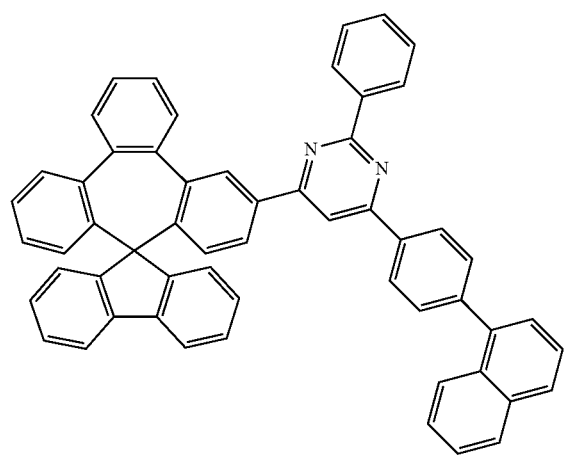
Compound CXXXIII
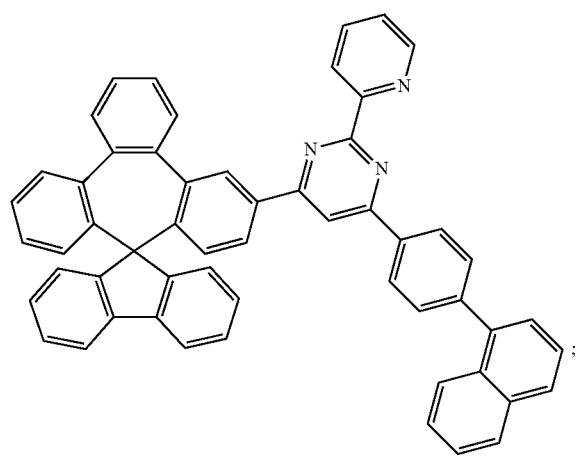
Compound CXXXIV
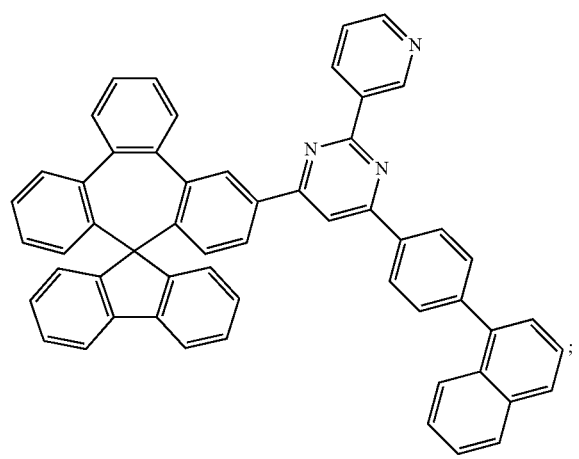

-continued
Compound CXXXV
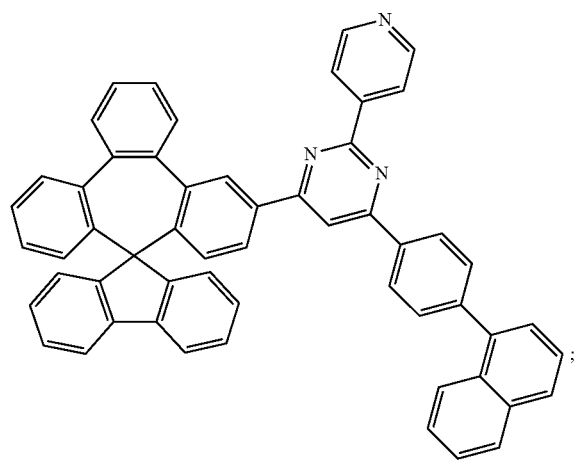
Compound CXXXVI
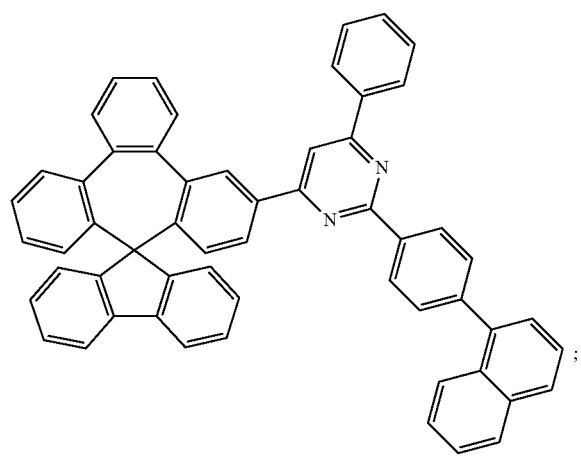
Compound CXXXVII
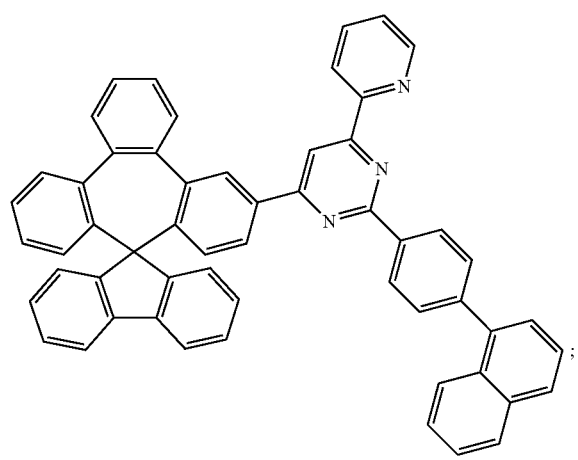
Compound CXXXVIII
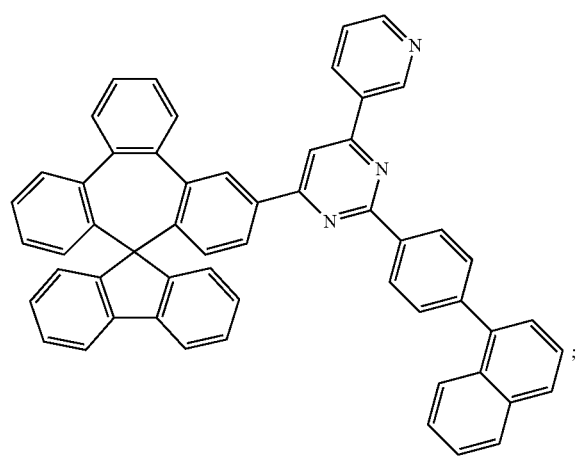
Compound CXXXIX
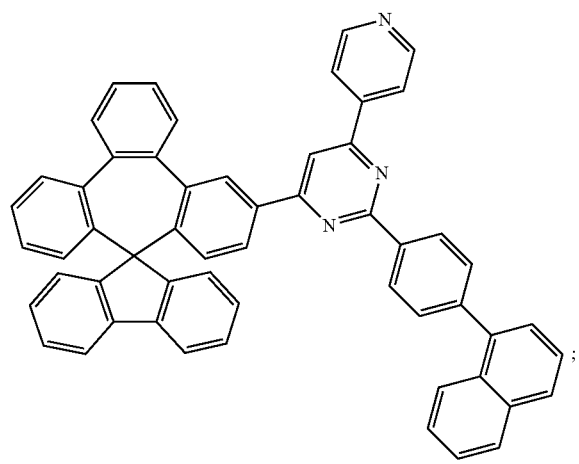
Compound CXL
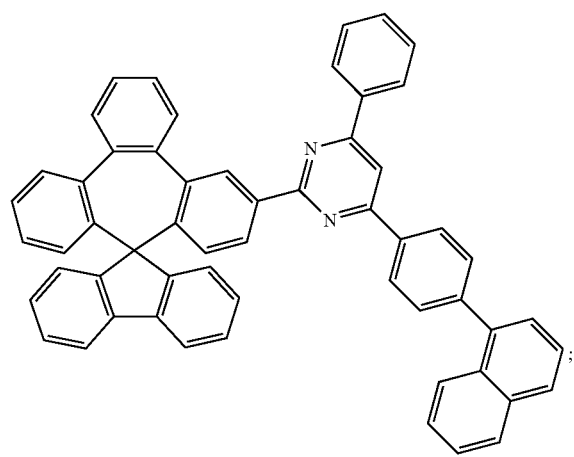

-continued
Compound CXLI
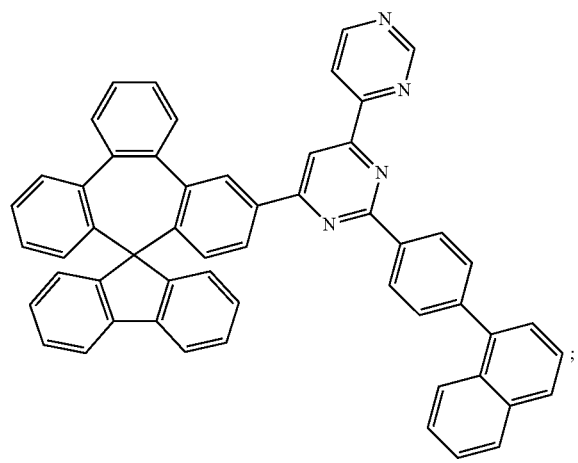
Compound CXLII
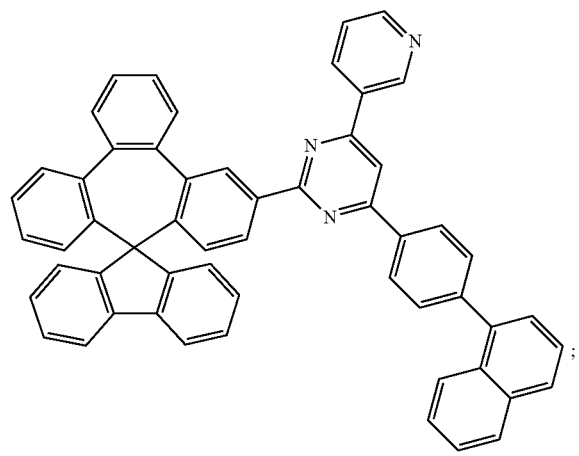
Compound CXLIII
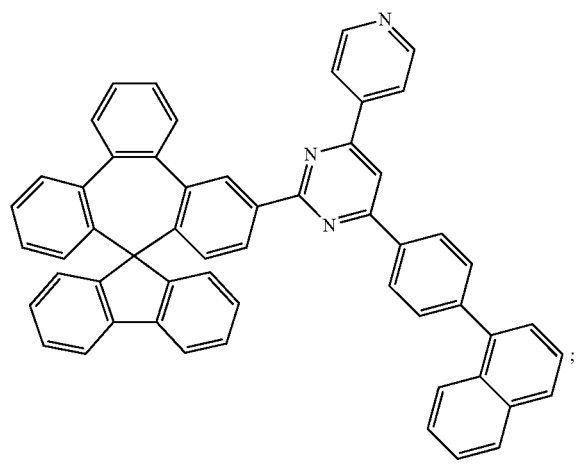
Compound CXLIV
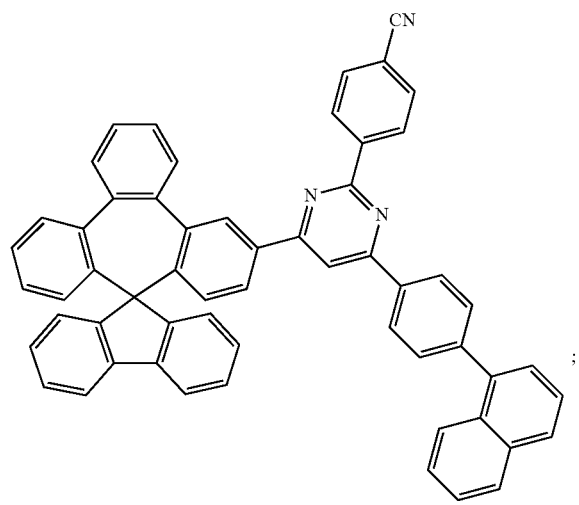
Compound CXLV
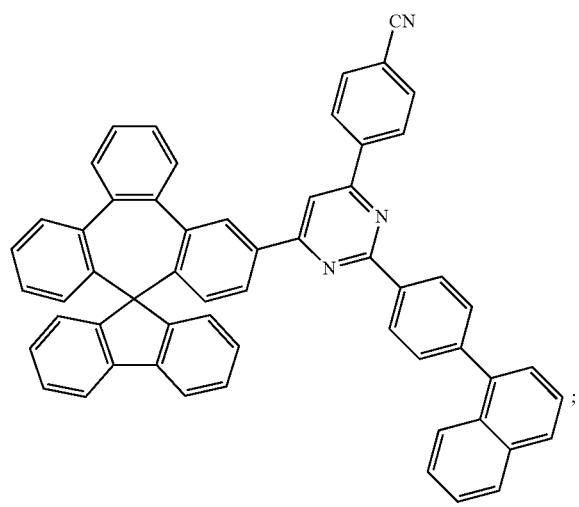
Compound CXLVI
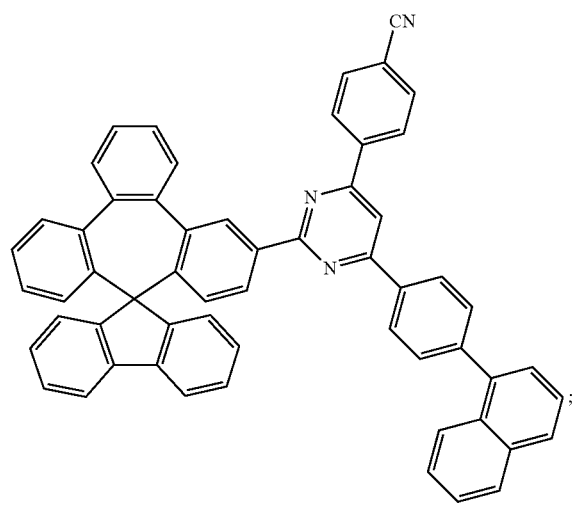

Compound CXLVII
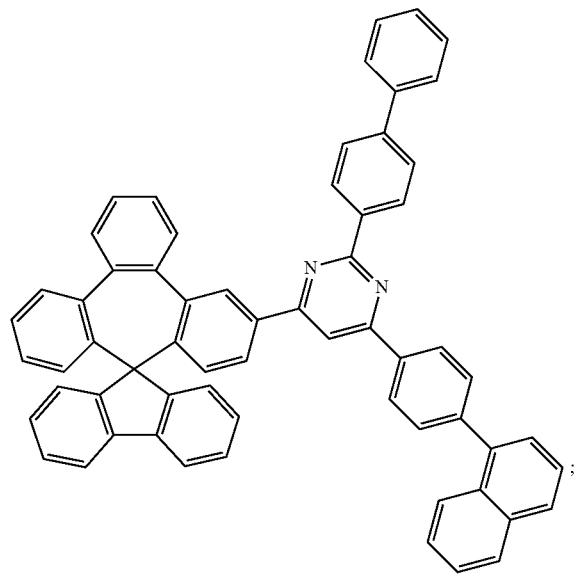
Compound CXLVIII
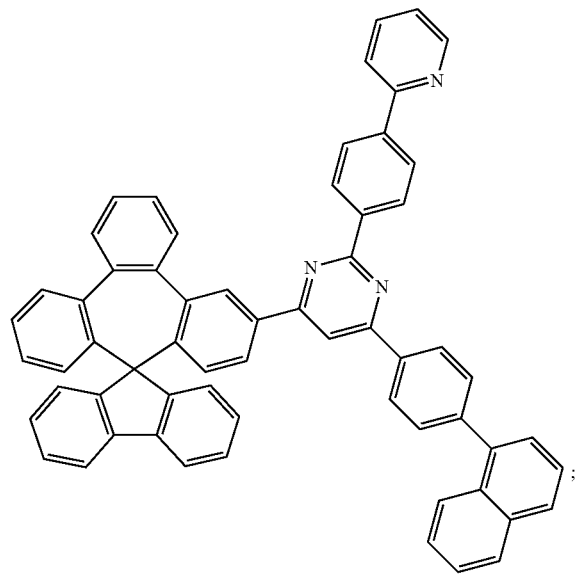
Compound CIL
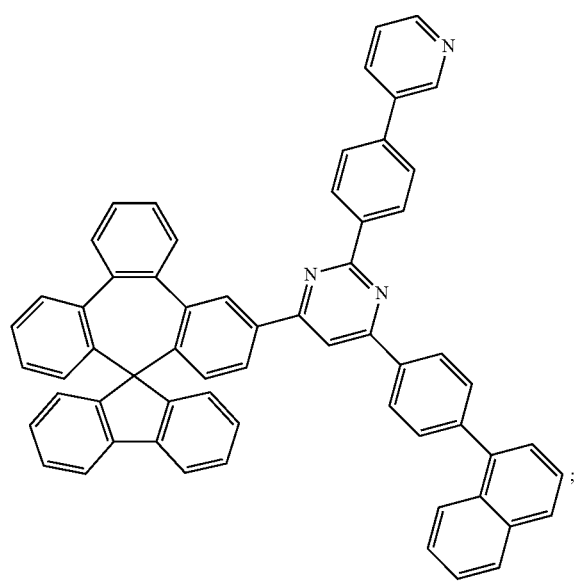
Compound CL
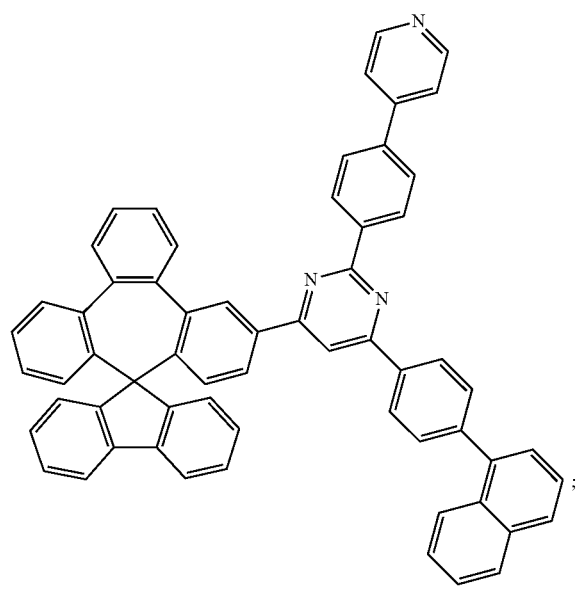

Compound CLI
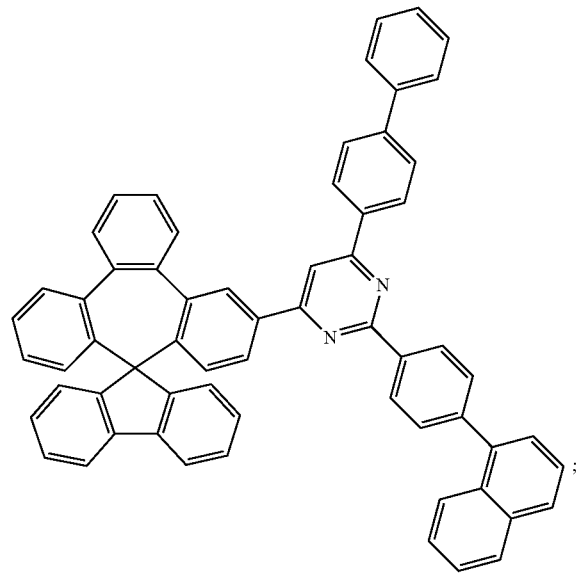
Compound CLII
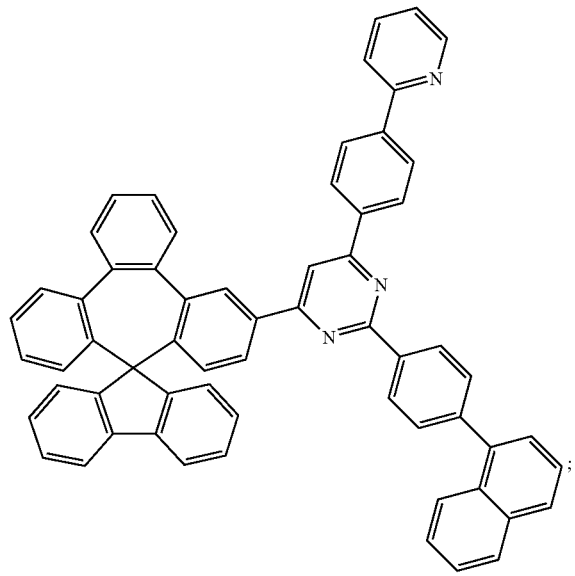
Compound CLIII
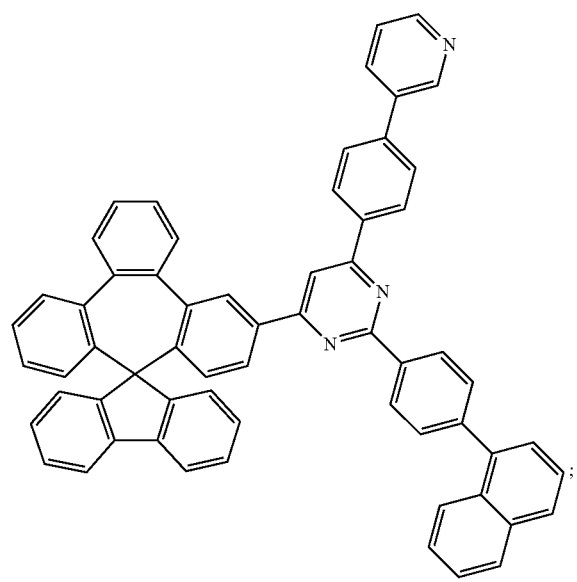
Compound CLIV
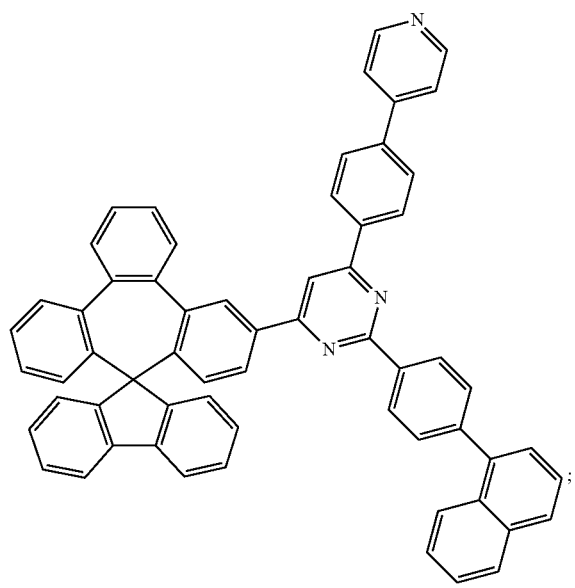

Compound CLV
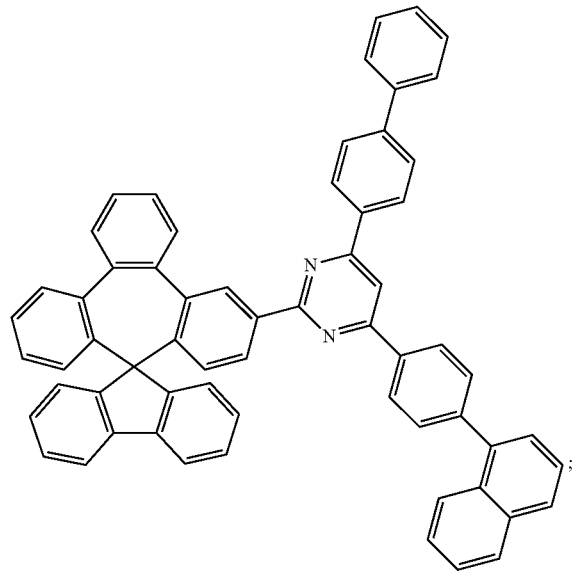
Compound CLVI
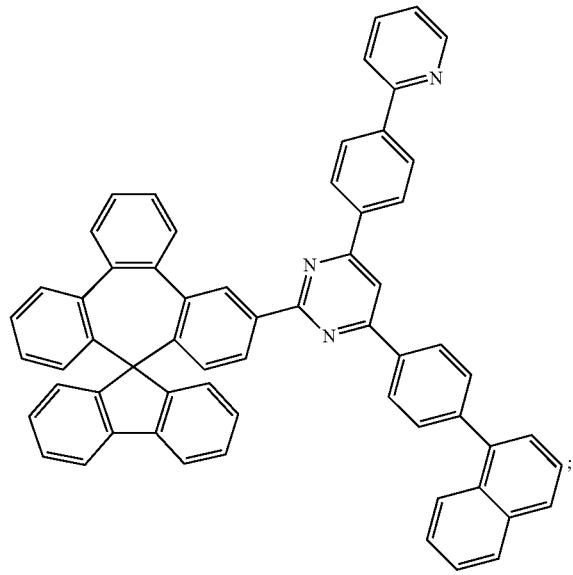
Compound CLVII
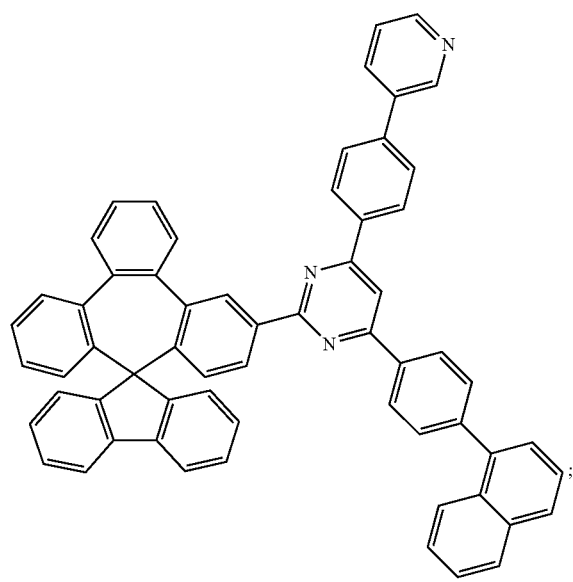
Compound CLVIII
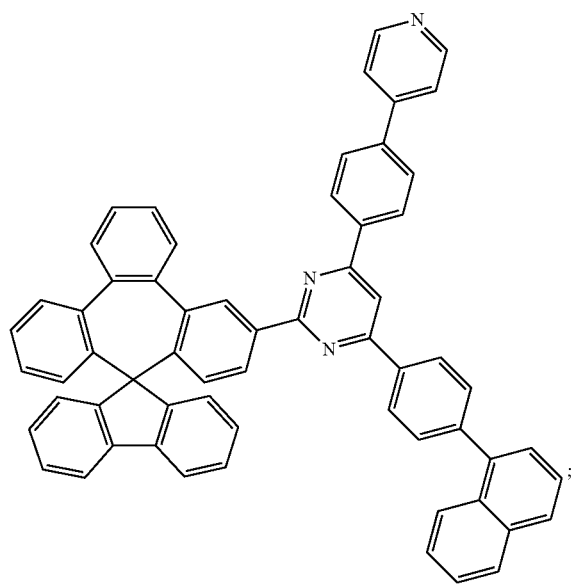

Compound CLIX
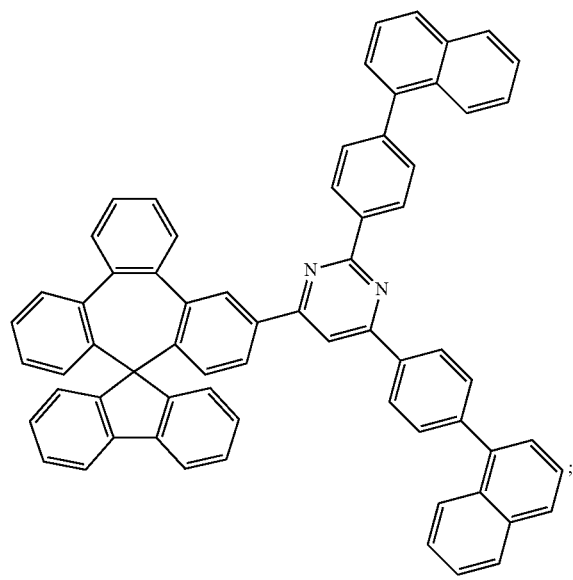
Compound CLX
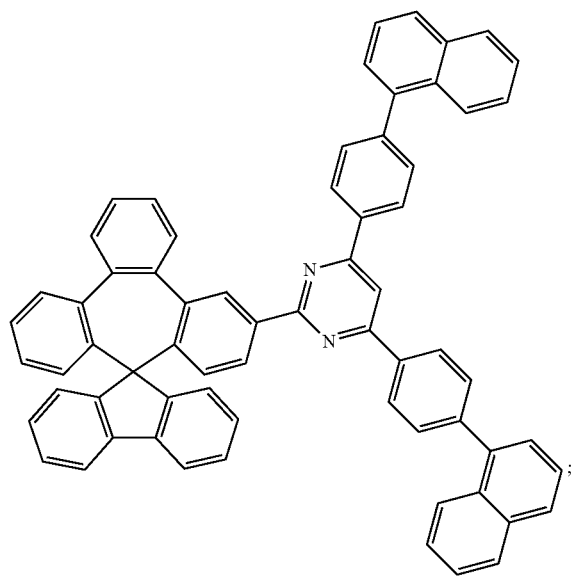
Compound CLXI
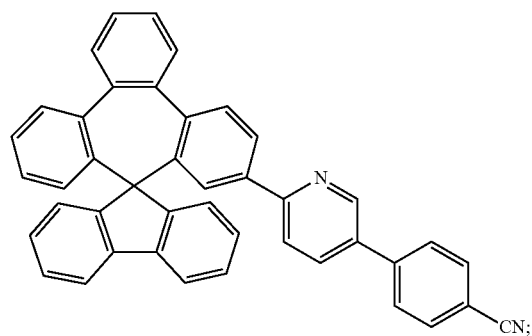
Compound CLXII
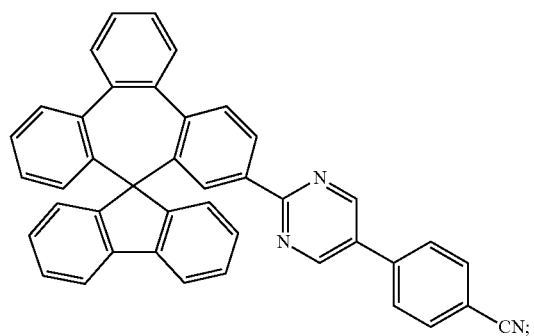
Compound CLXIII
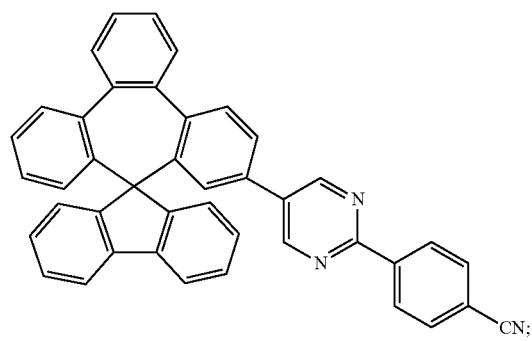
Compound CLXIV
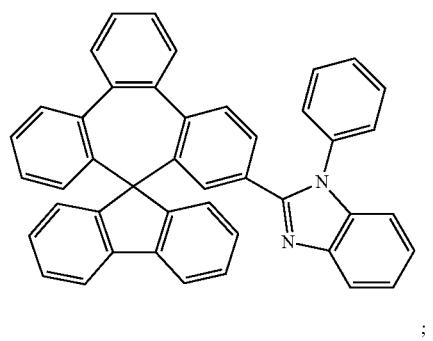

Compound CLXV
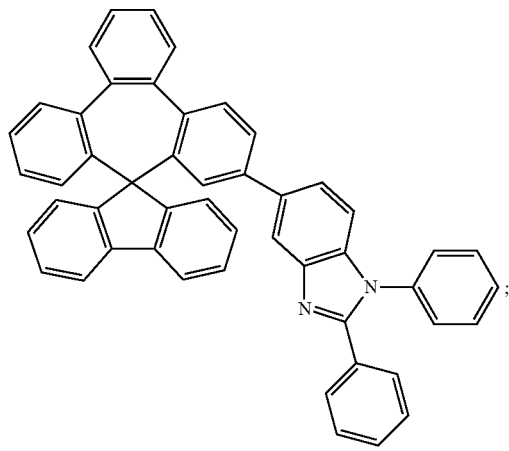
Compound CLXVI
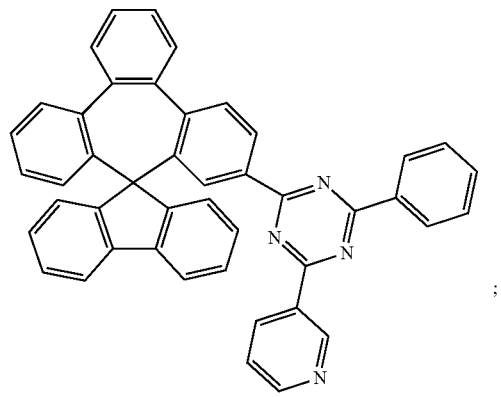
Compound CLXVII
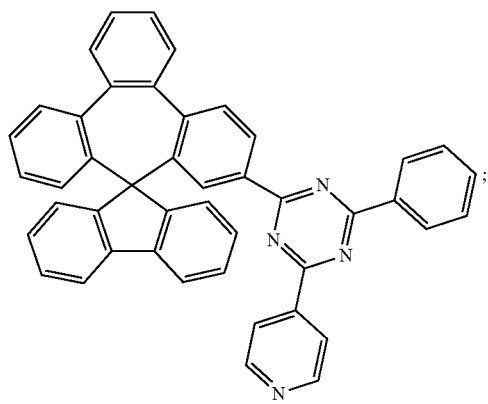
Compound CLXVIII
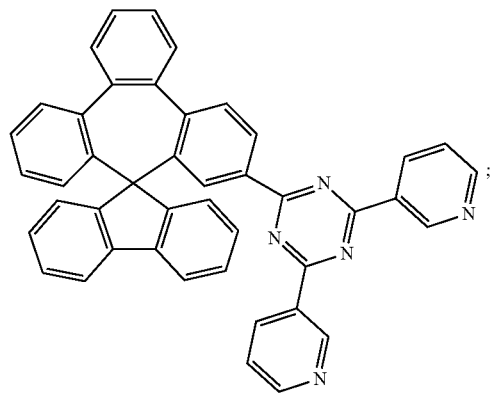
Compound CLXIX
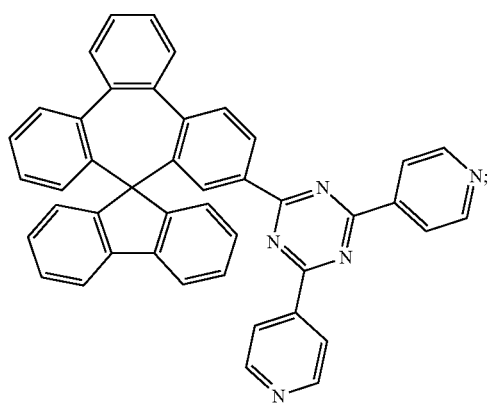
Compound CLXX
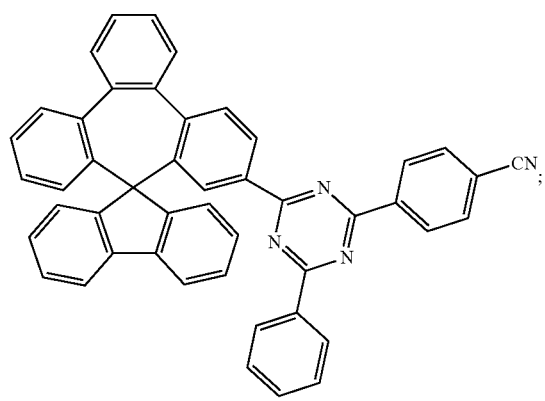

-continued
Compound CLXXI
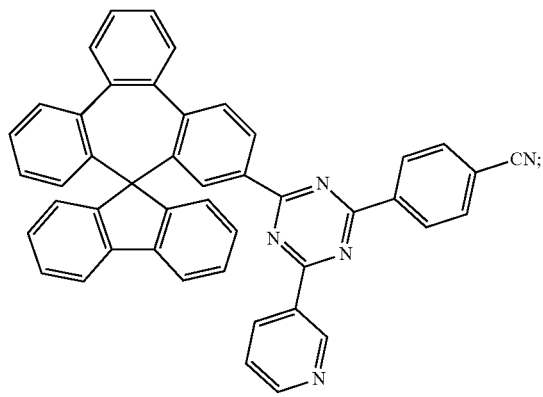
Compound CLXXII
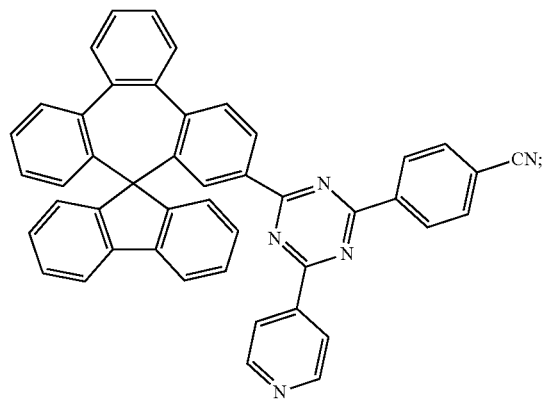
Compound CLXXIII
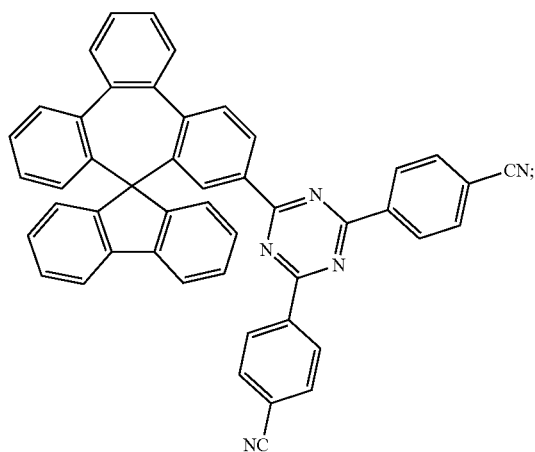
Compound CLXXIV
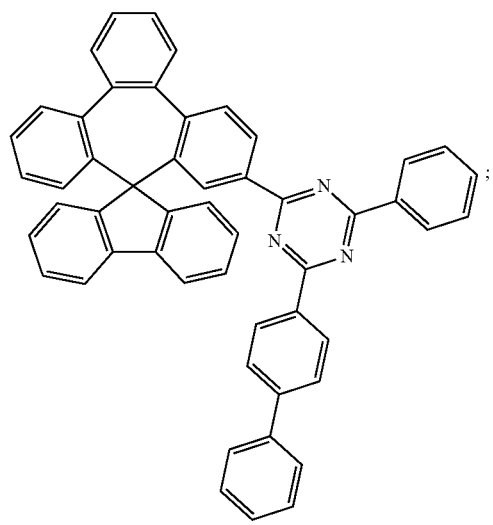
Compound CLXXV
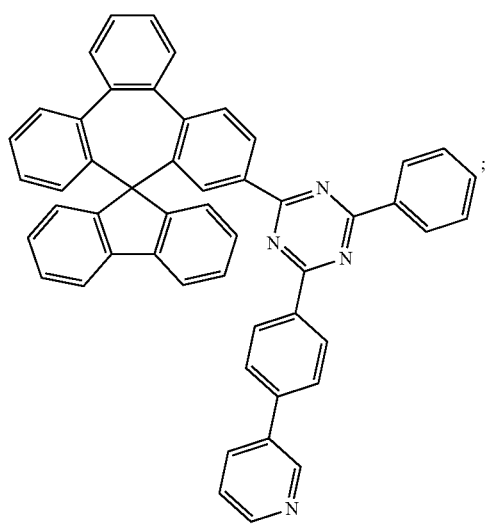
Compound CLXXVI
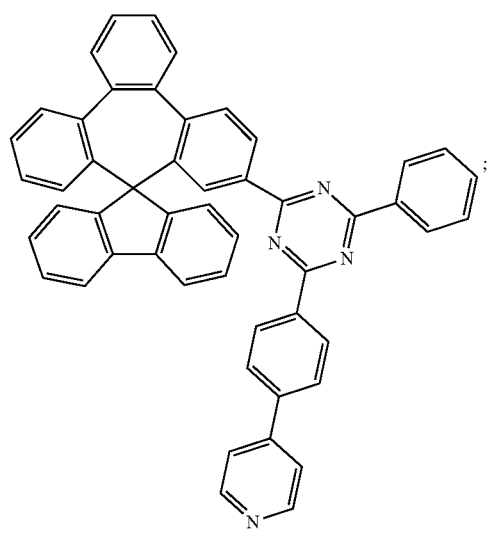

-continued
Compound CLXXVII
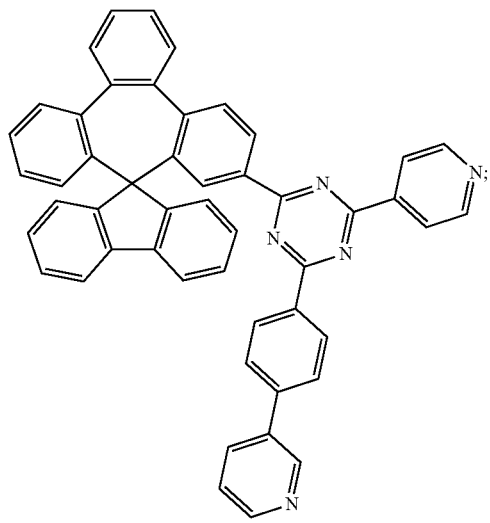
Compound CLXXVIII
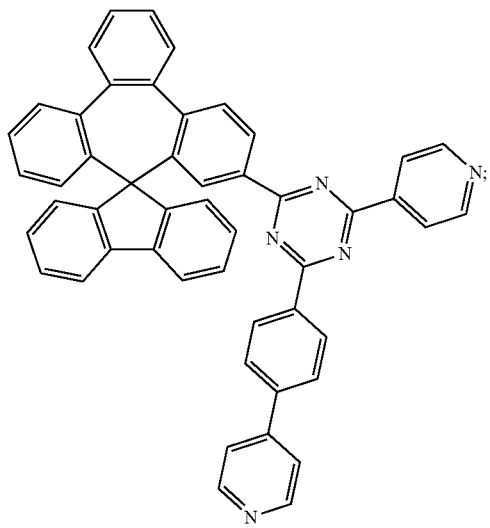
Compound CLXXIX
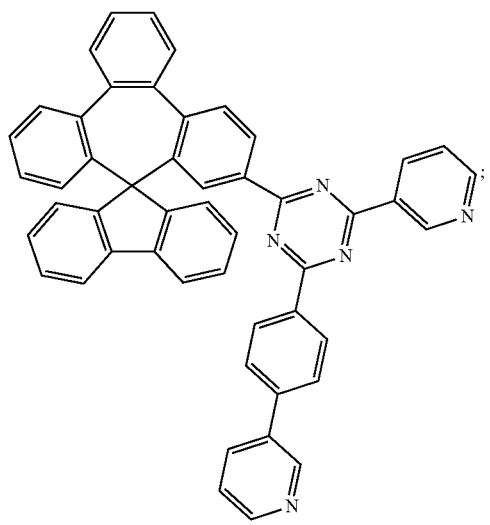
Compound CLXXX
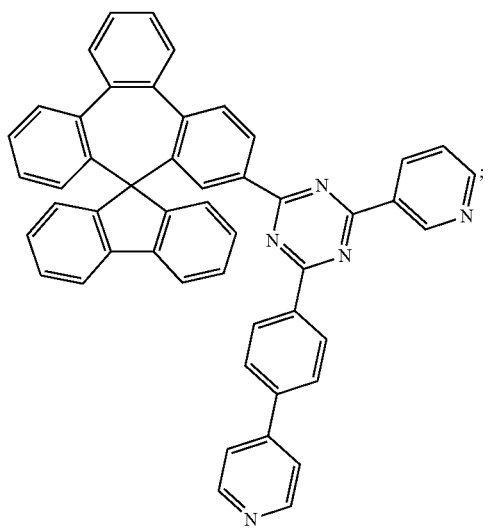
Compound CLXXXI
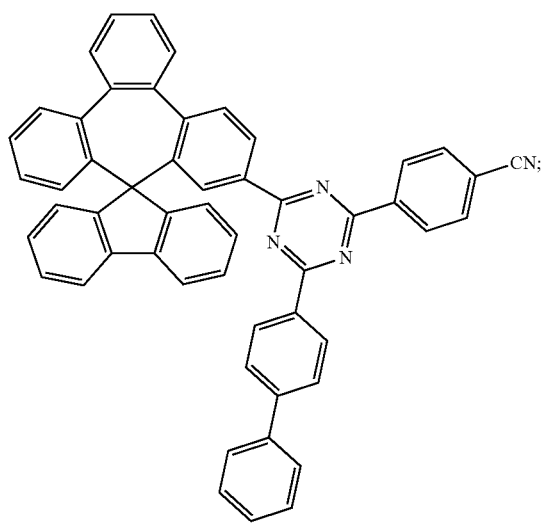
Compound CLXXXII
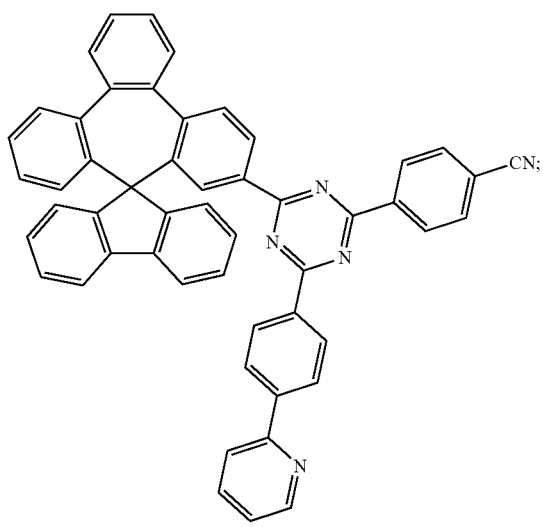

-continued
Compound CLXXXIII
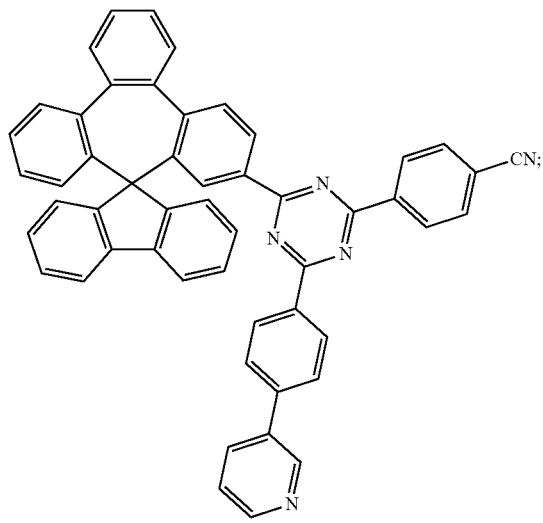
Compound CLXXXIV
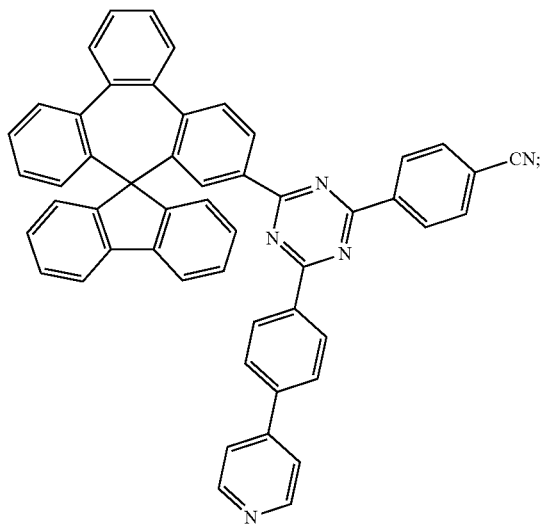
Compound CLXXXV
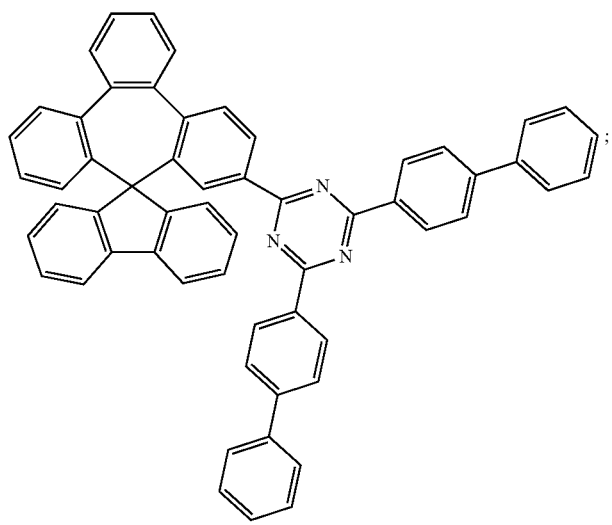
Compound CLXXXVI
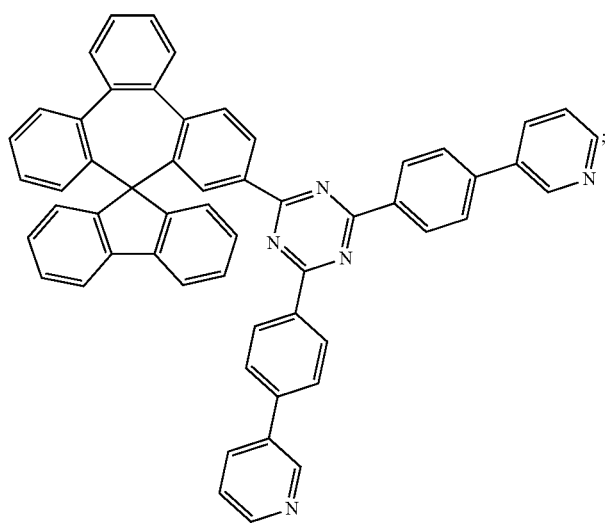

-continued
Compound CLXXXVII
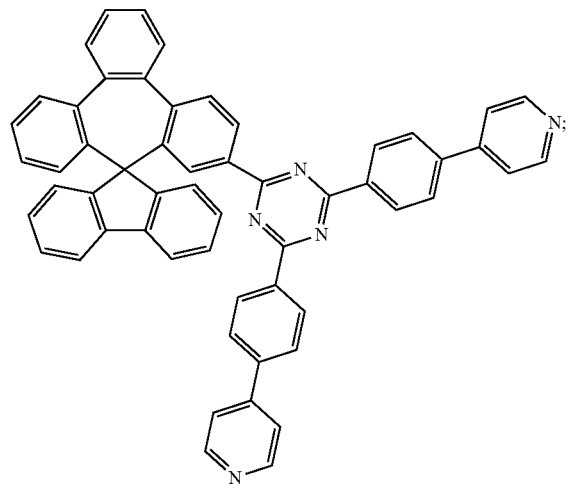
Compound CLXXXVIII
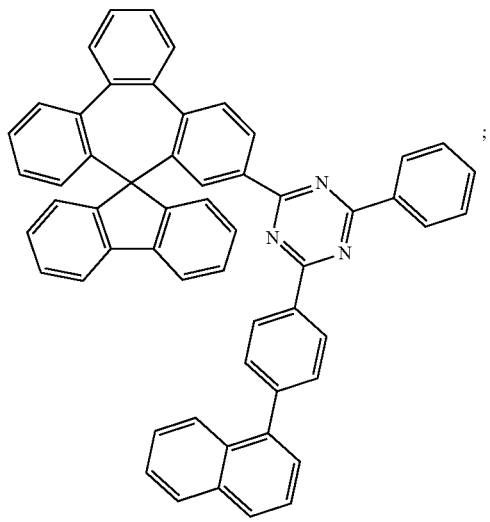
Compound CLXXXIX
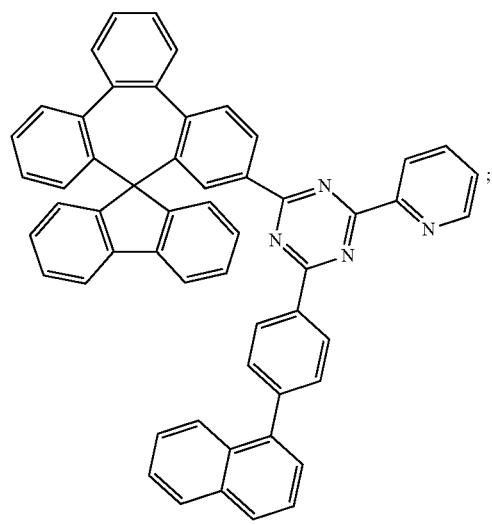
Compound CXC
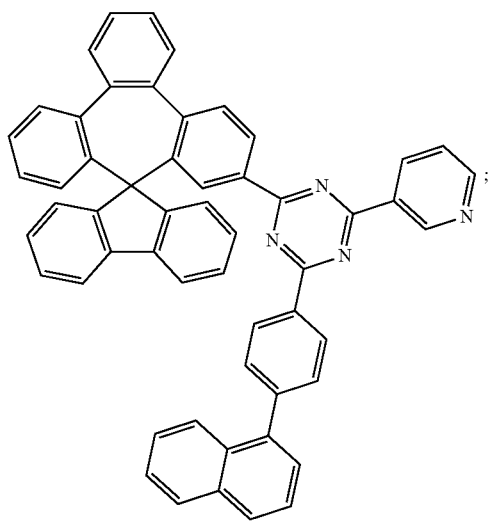
Compound CXCI
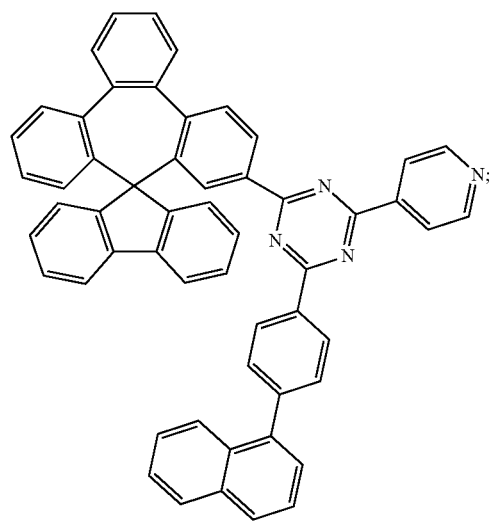
Compound CXCII
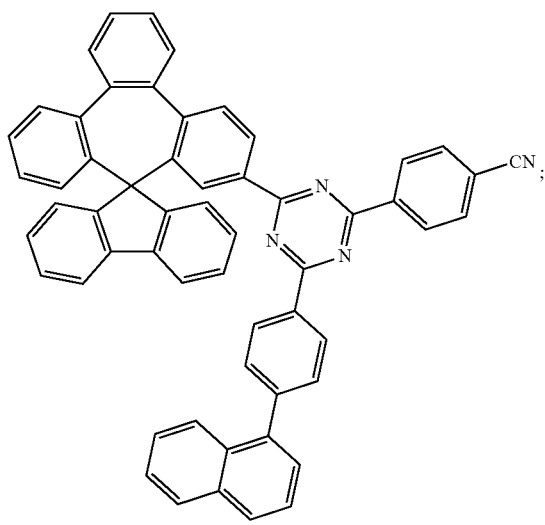

Compound CXCIII
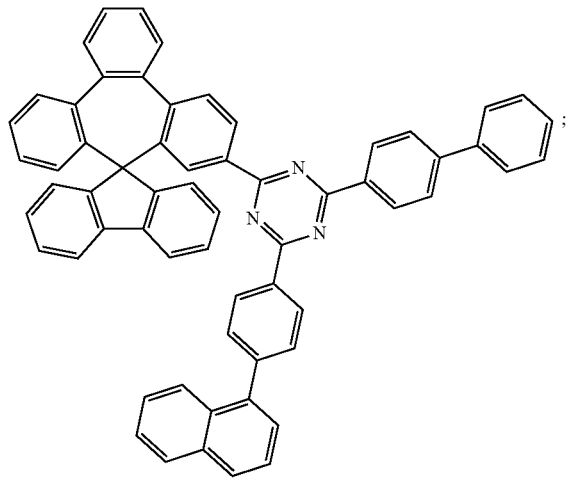
Compound CXCIV
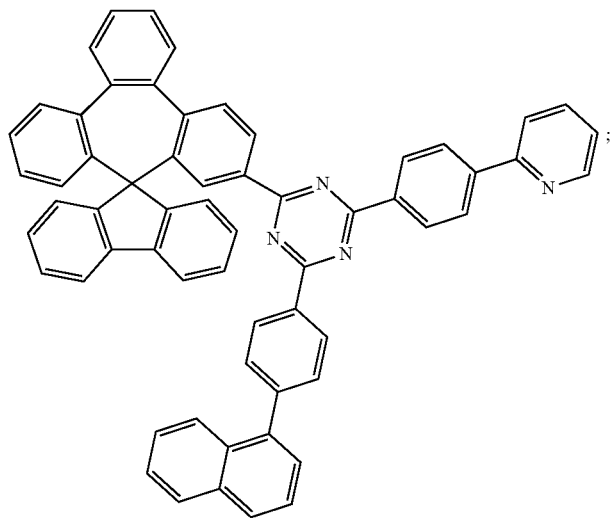
Compound CXCV
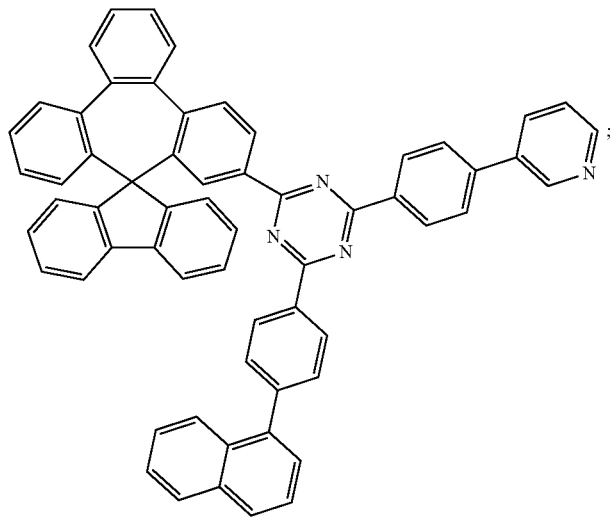

Compound CXCVI
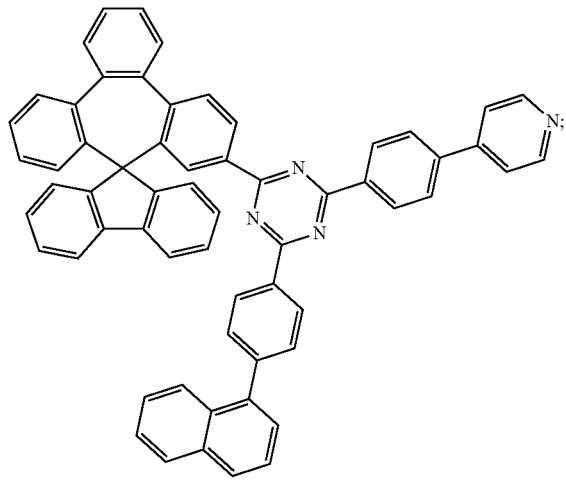
Compound CXCVII
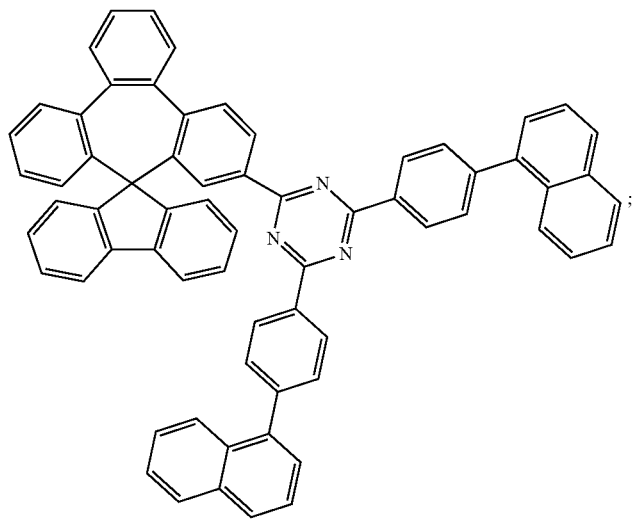
Compound CXCVIII
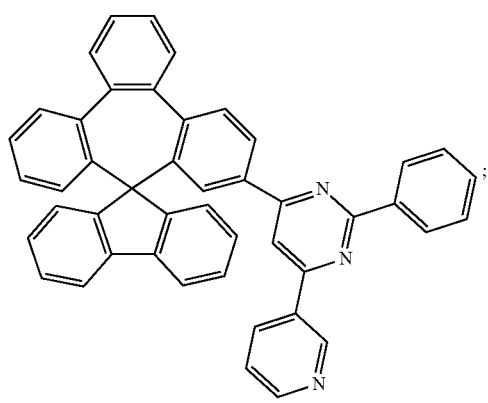
Compound CXCIX
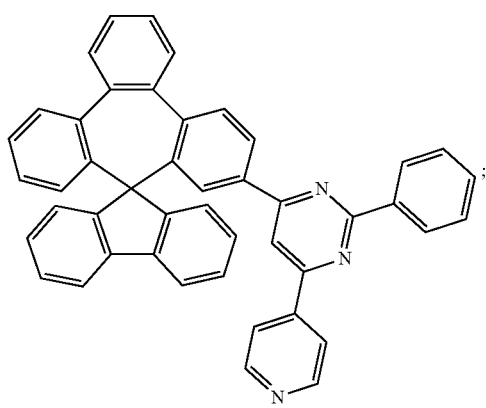

Compound CC
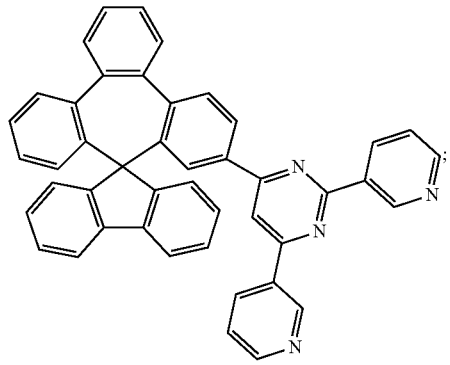
Compound CCI
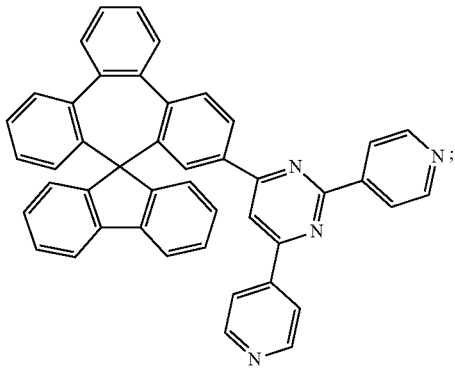
Compound CCII
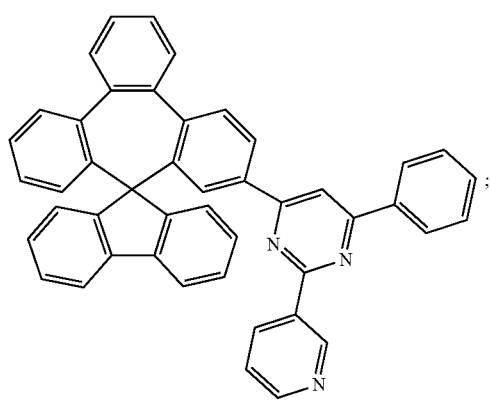
Compound CCIII
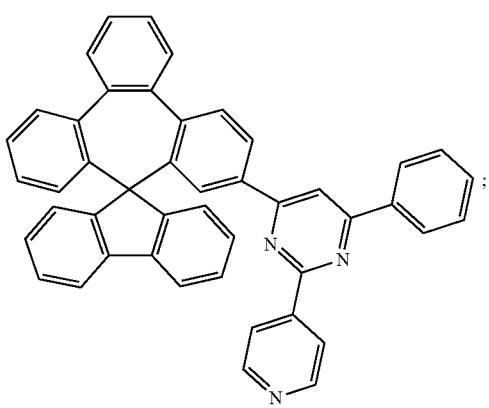
Compound CCIV
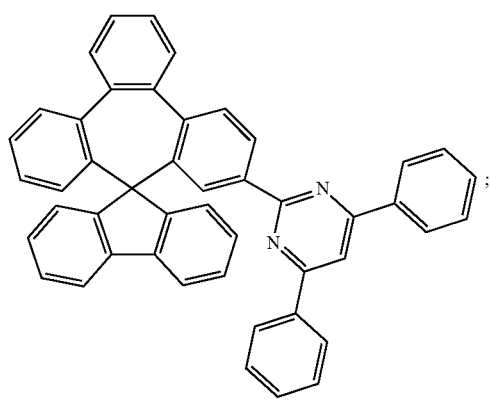
Compound CCV
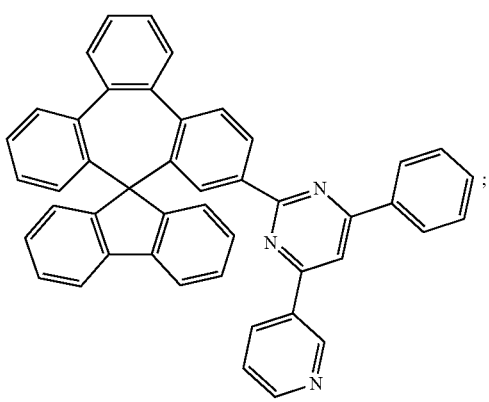
Compound CCVI
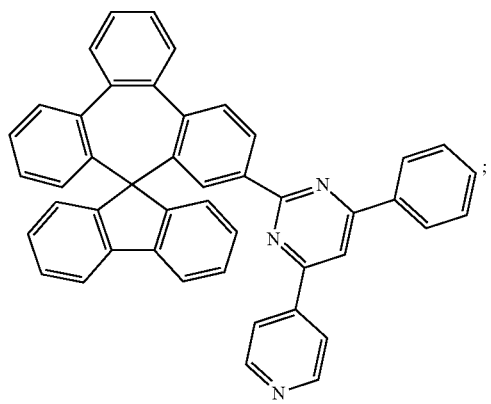
Compound CCVII
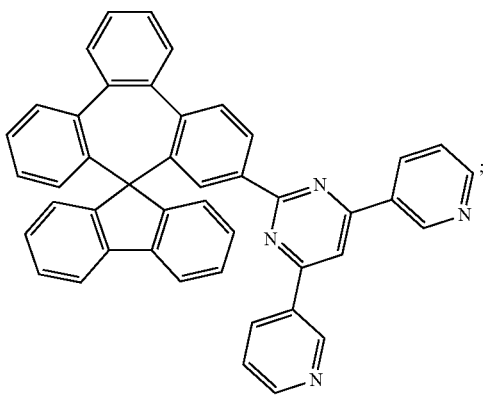

-continued
Compound CCVIII
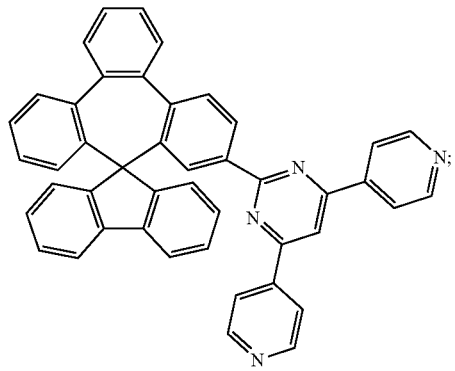
Compound CCIX
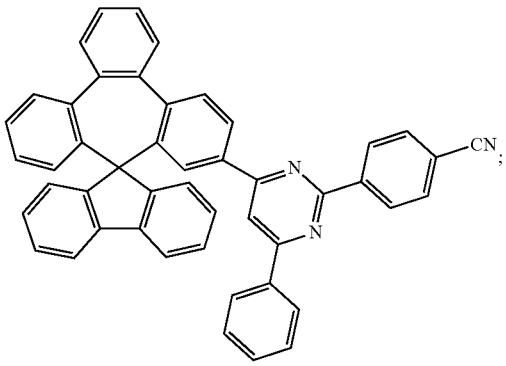
Compound CCX
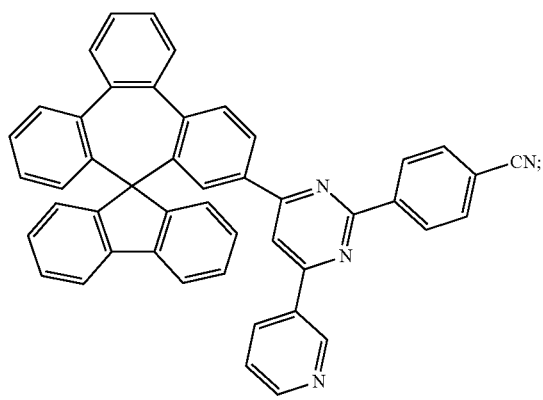
Compound CCXI
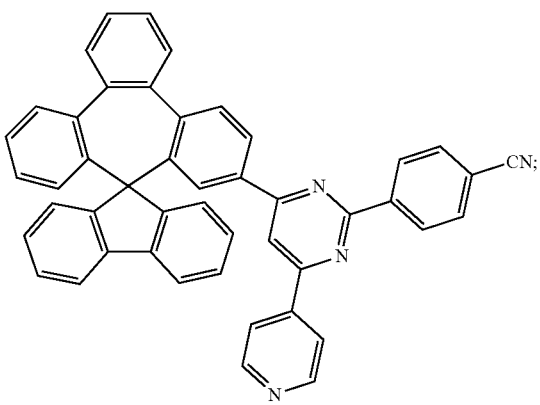
Compound CCXII
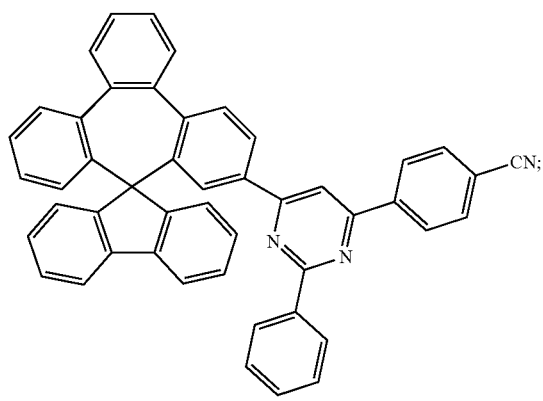
Compound CCXIII
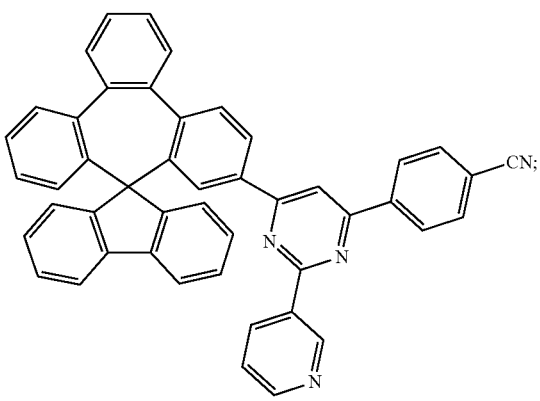
Compound CCXIV
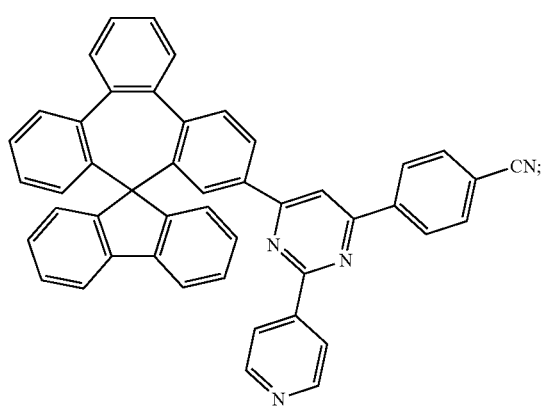
Compound CCXV
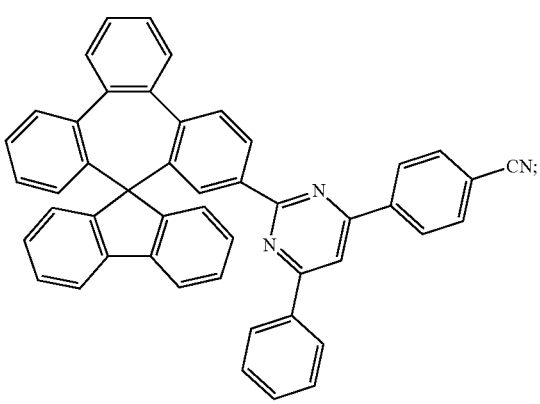

-continued
Compound CCXVI
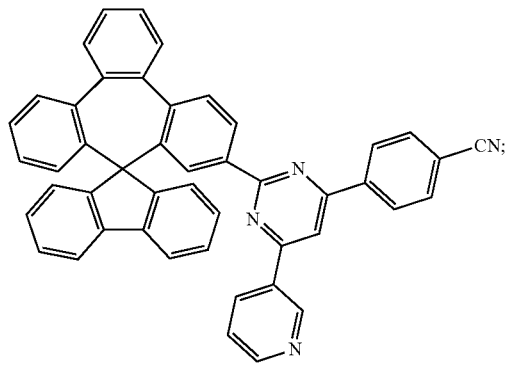
Compound CCXVII
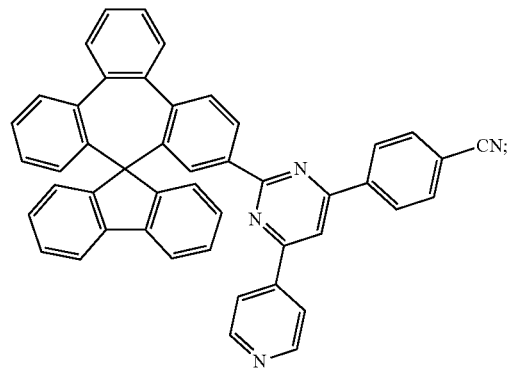
Compound CCXVIII
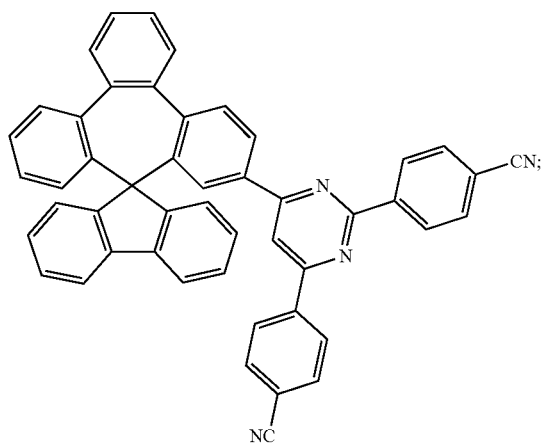
Compound CCXIX
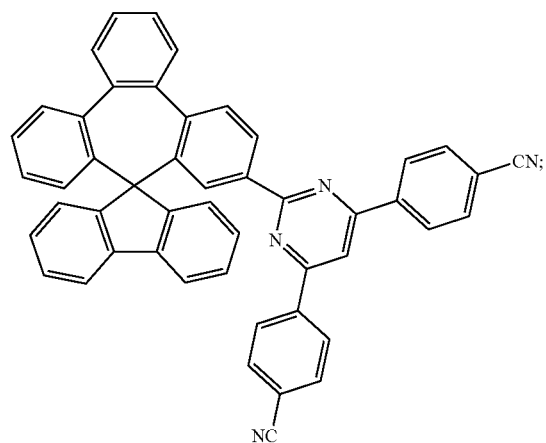
Compound CCXX
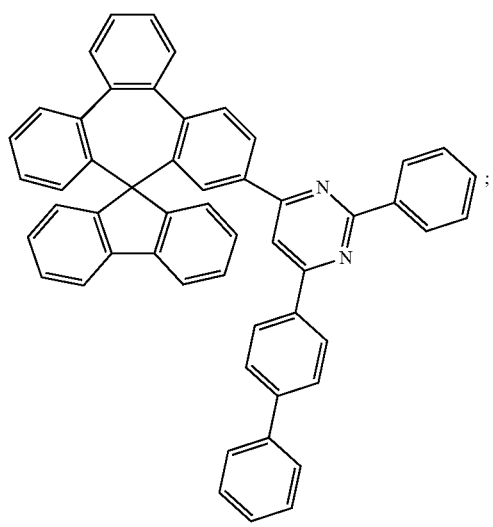
Compound CCXXI
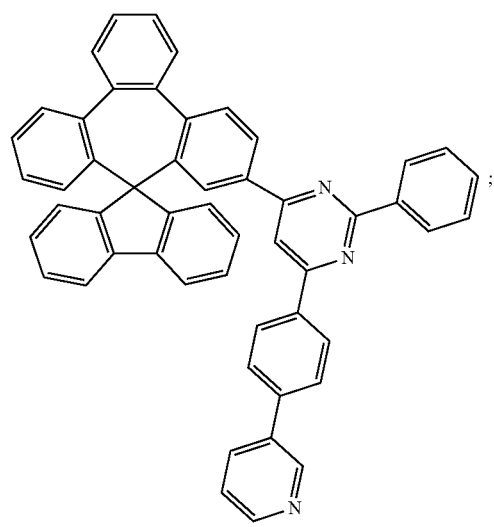

-continued
Compound CCXXII
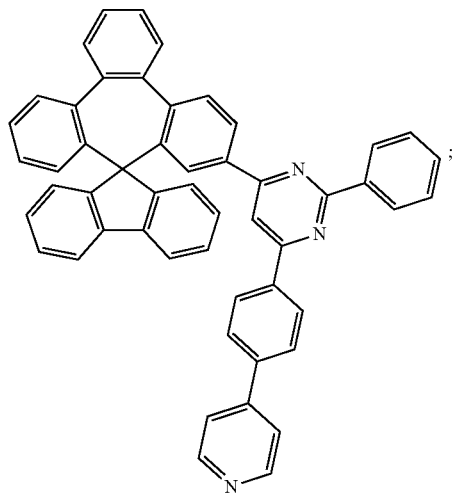
Compound CCXXIII
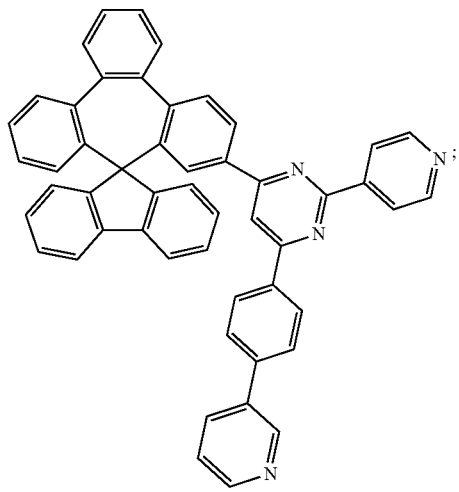
Compound CCXXIV
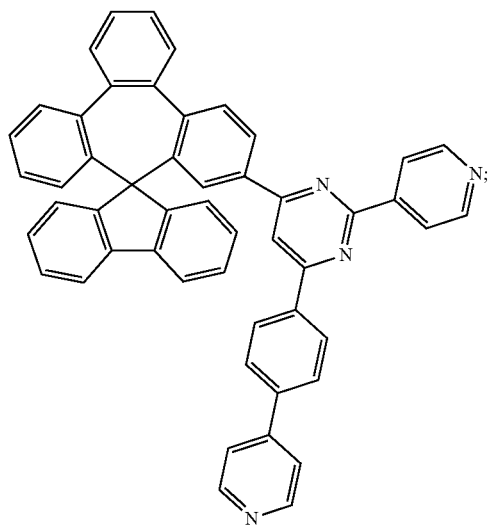
Compound CCXXV
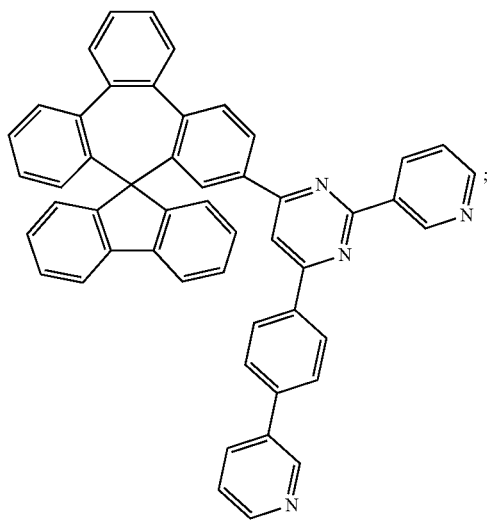
Compound CCXXVI
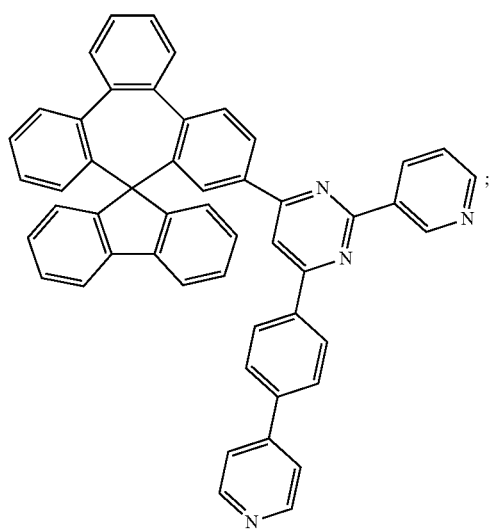
Compound CCXXVII
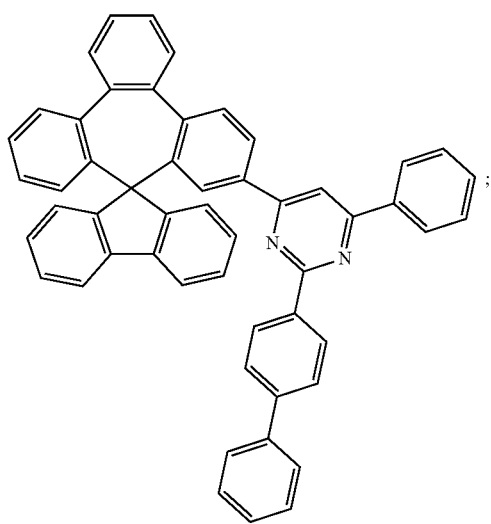

-continued
Compound CCXXVIII
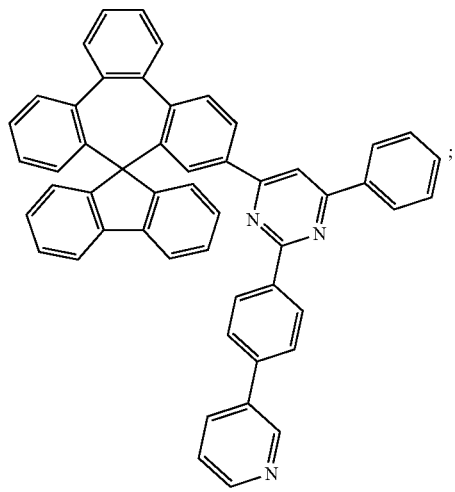
Compound CCXXIX
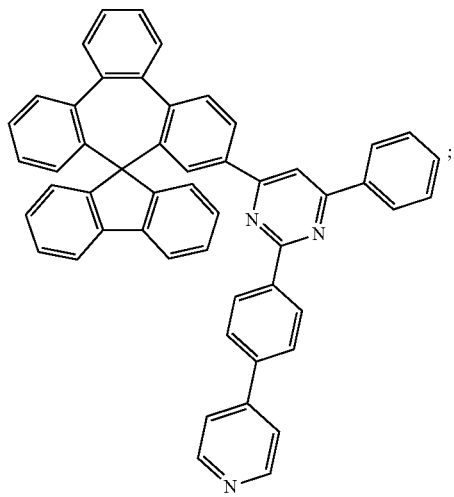
Compound CCXXX
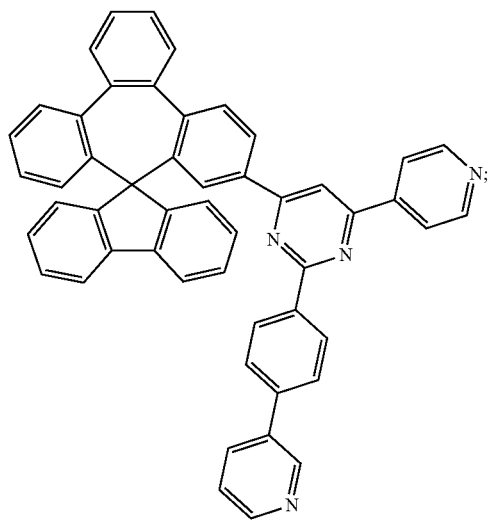
Compound CCXXXI
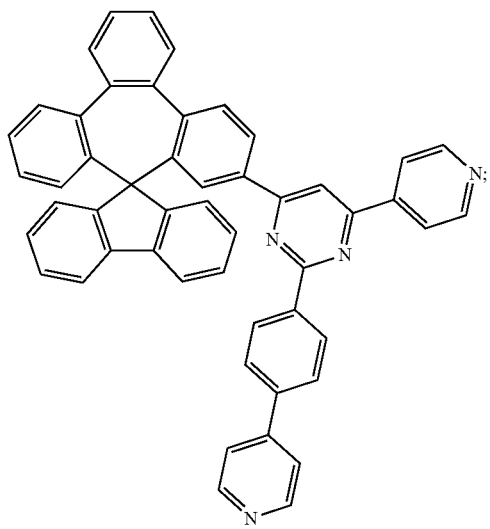
Compound CCXXXII
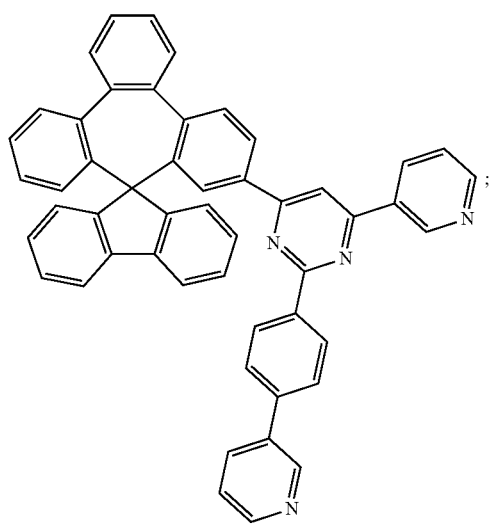
Compound CCXXXIII
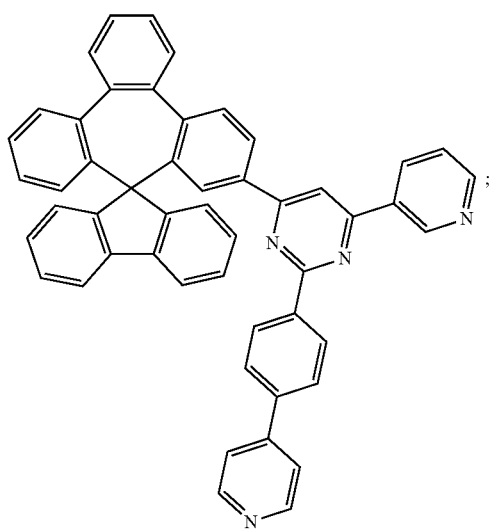

-continued
Compound CCXXXIV
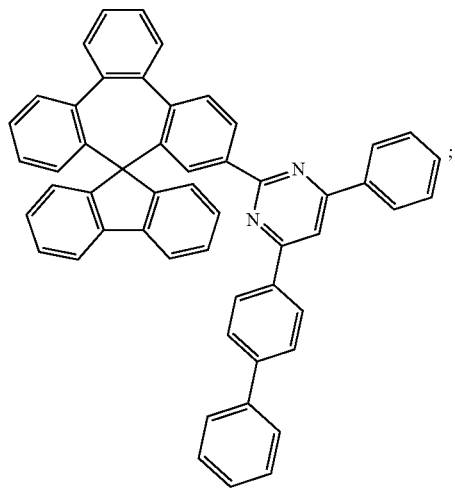
Compound CCXXXV
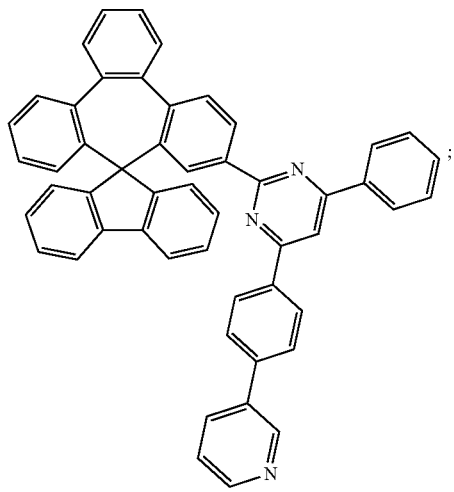
Compound CCXXXVI
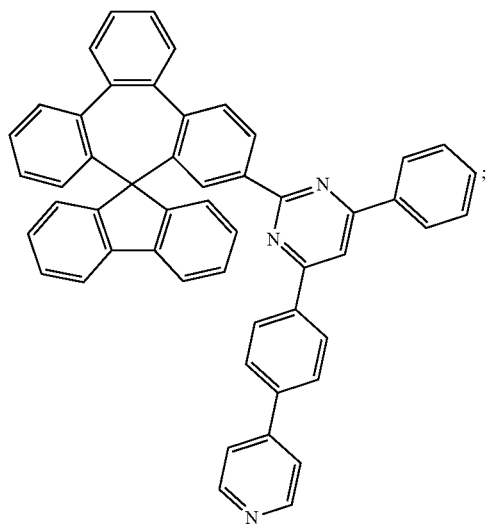
Compound CCXXXVII
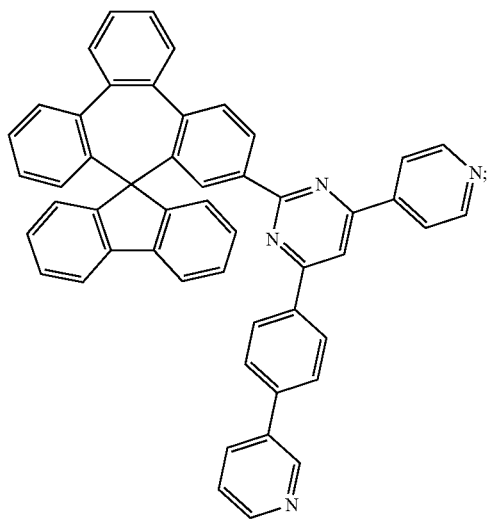
Compound CCXXXVIII
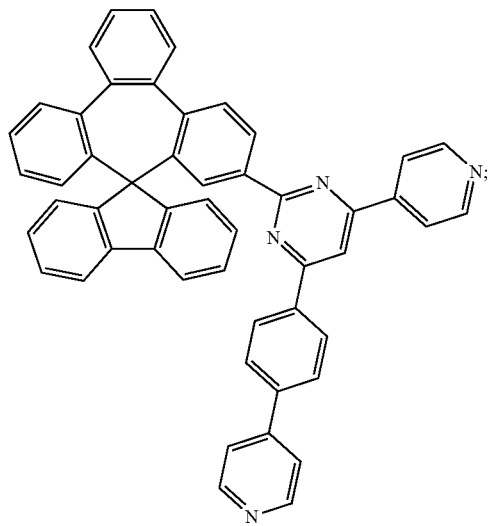
Compound CCXXXIX
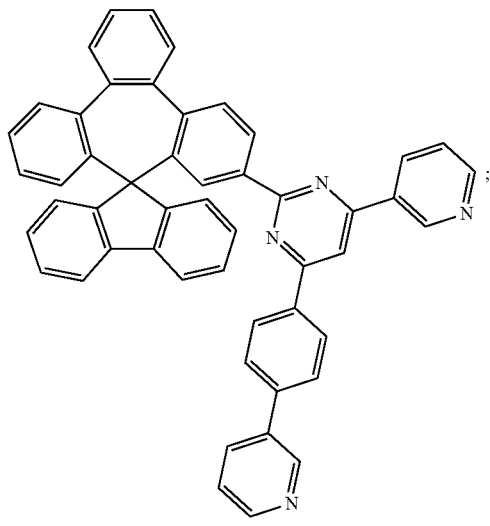

-continued
Compound CCXL
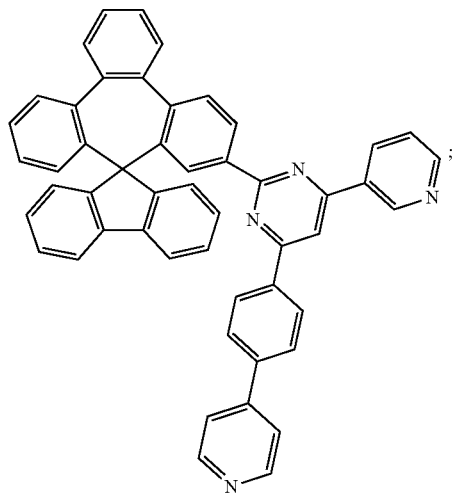
Compound CCXLI
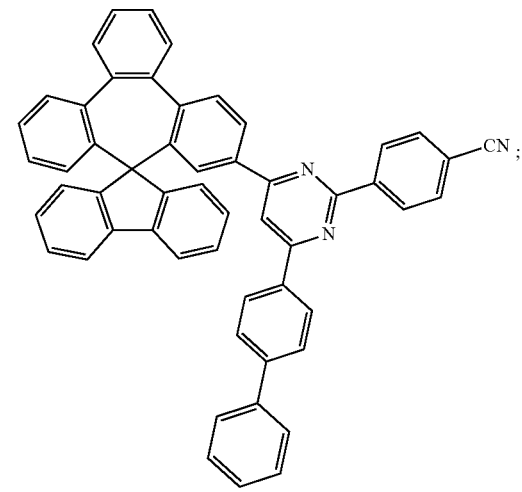
Compound CCXLII
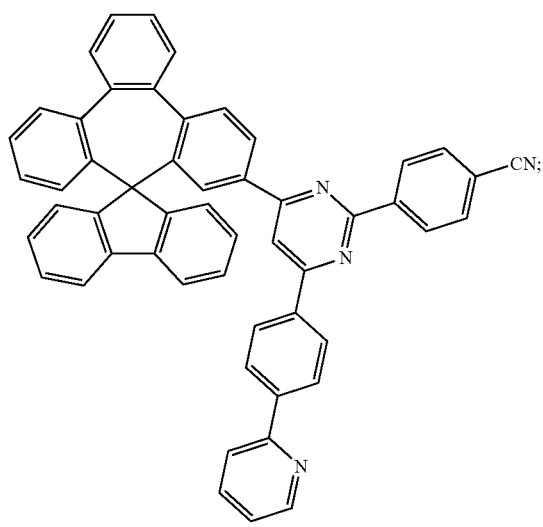
Compound CCXLIII
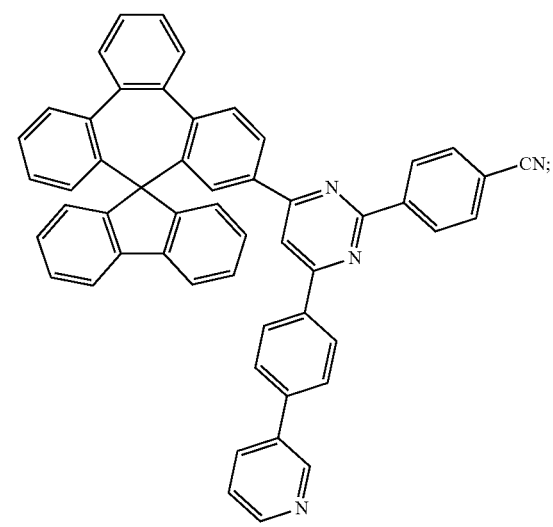
Compound CCXLIV
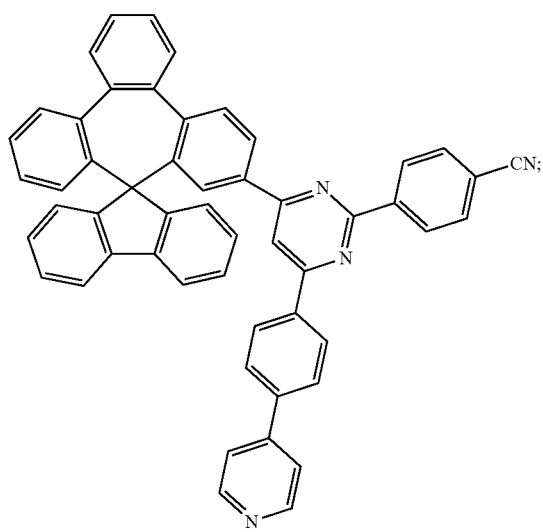
Compound CCXLV
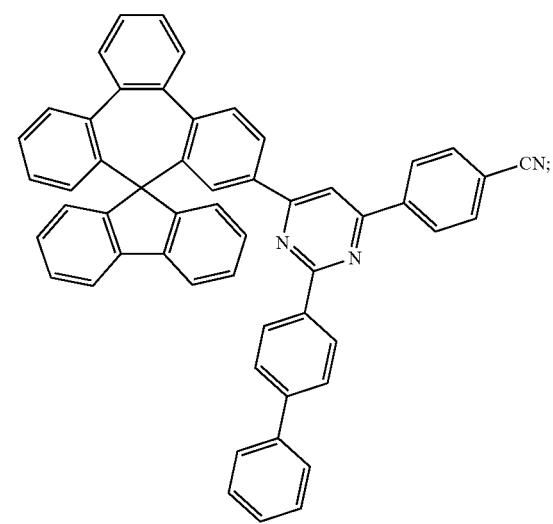

-continued
Compound CCXLVI
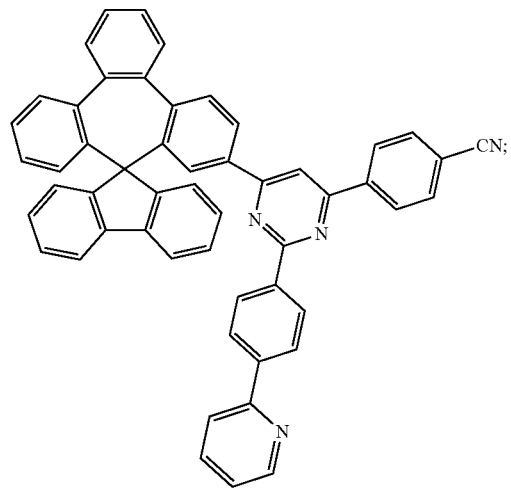
Compound CCXLVII
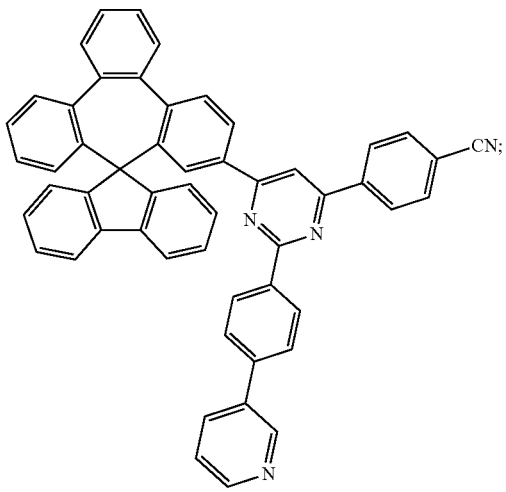
Compound CCXLVIII
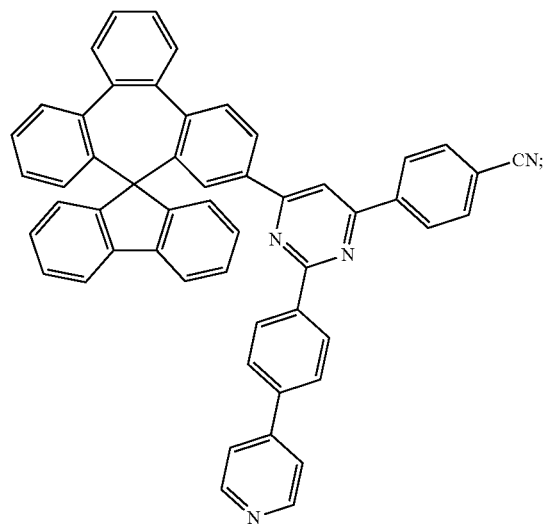
Compound CCIL
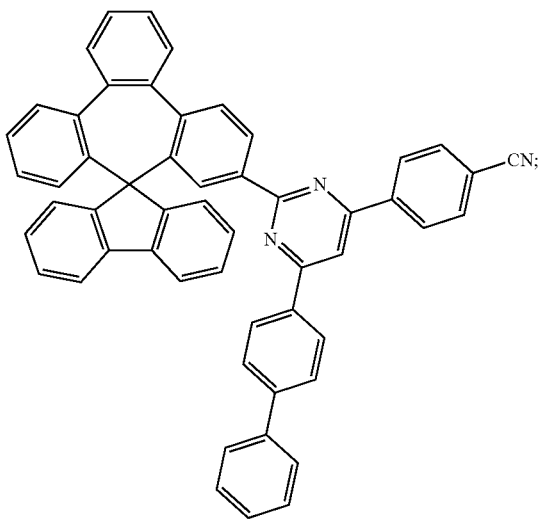
Compound CCL
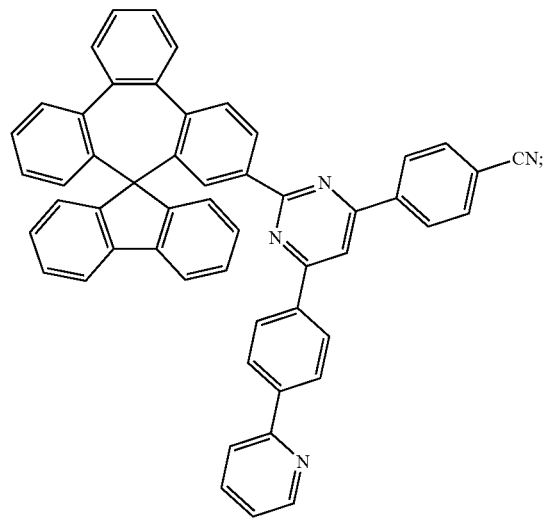
Compound CCLI
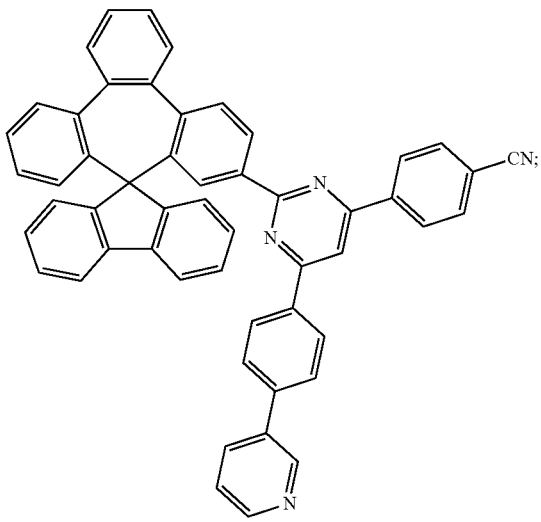

Compound CCLII
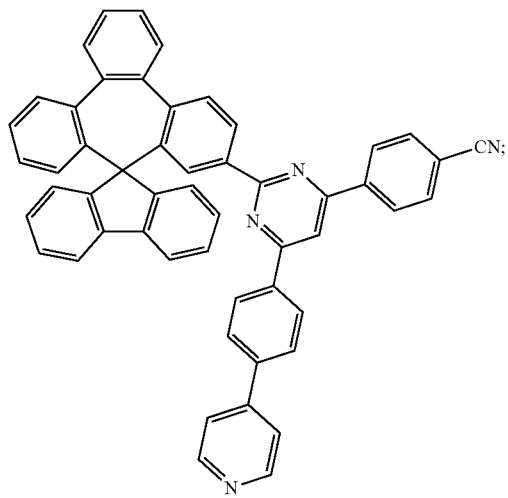
Compound CCLIII
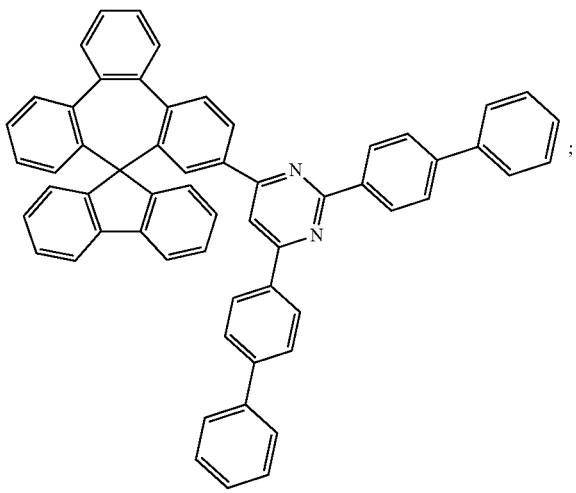
Compound CCLIV
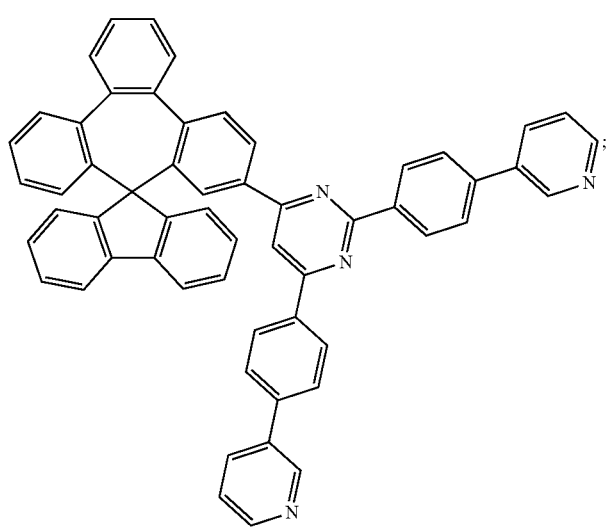
Compound CCLV
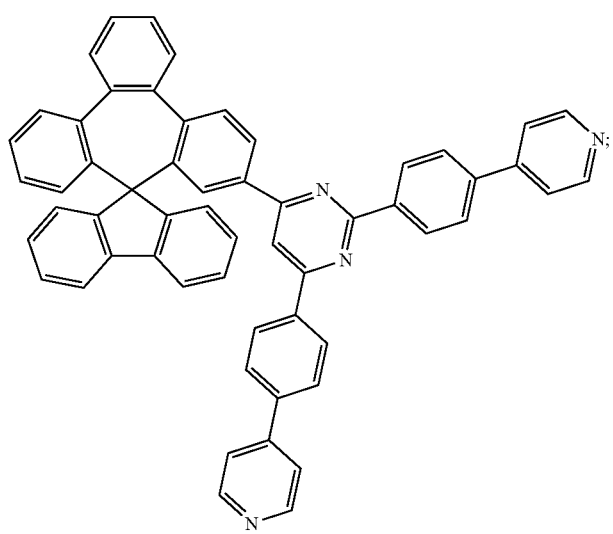

Compound CCLVI
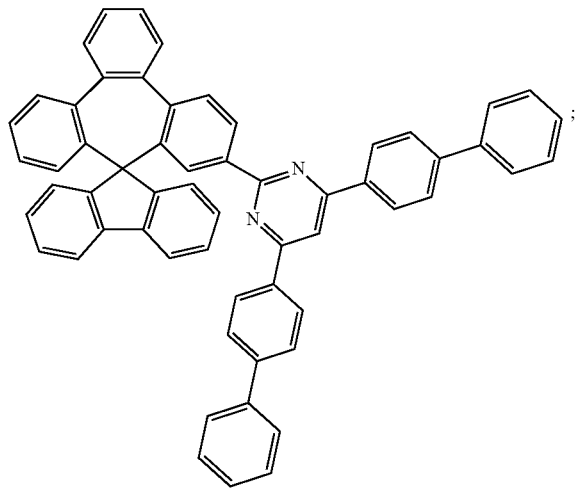
Compound CCLVII
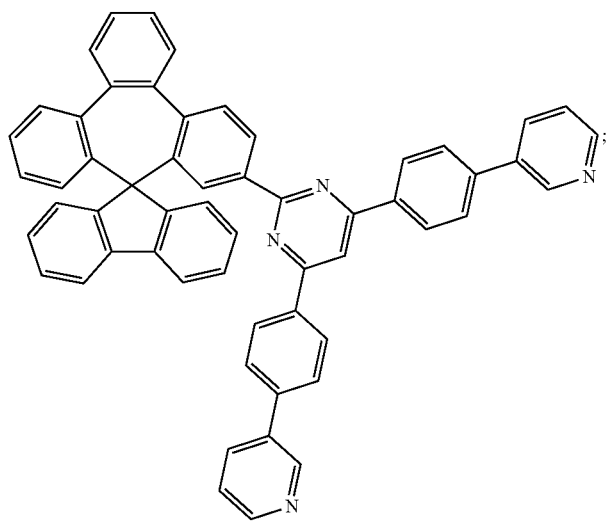
Compound CCLVIII
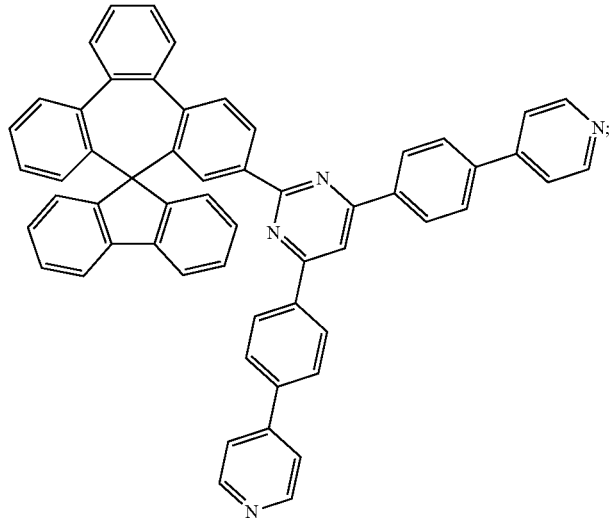

-continued
Compound CCLIX
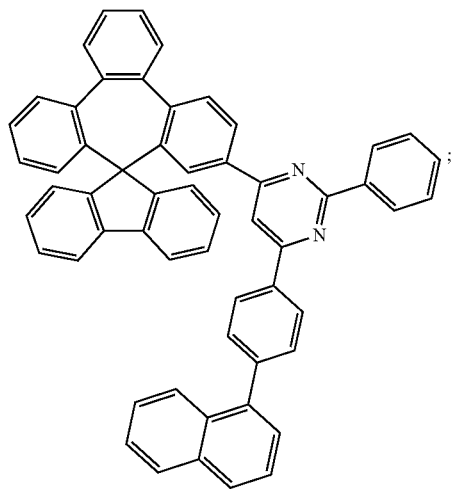
Compound CCLX
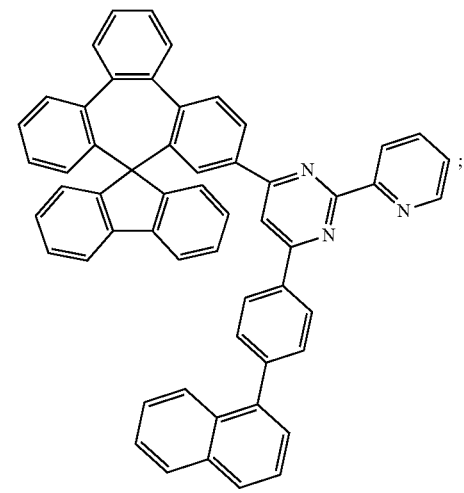
Compound CCLXI
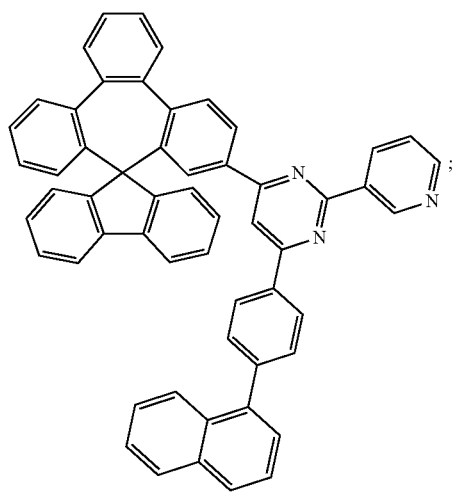
Compound CCLXII
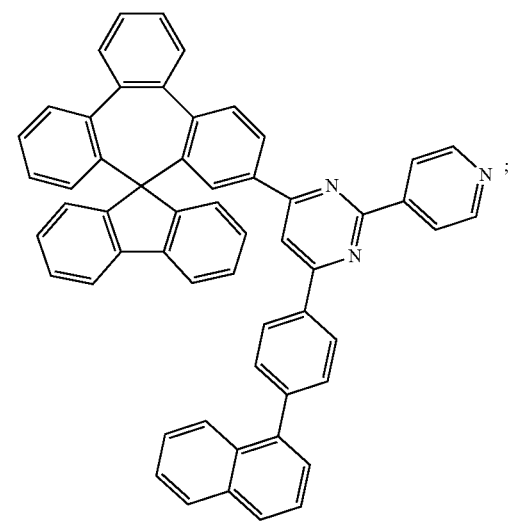
Compound CCLXIII
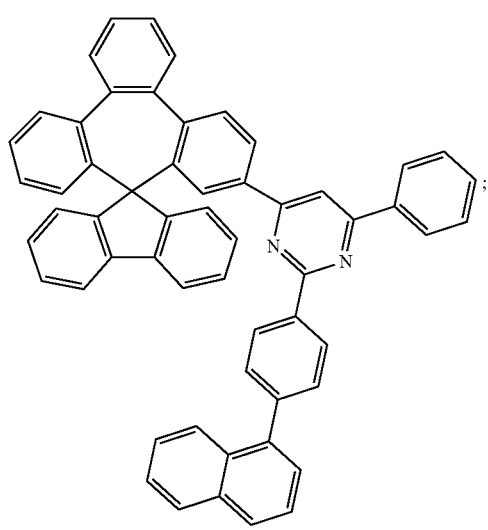
Compound CCLXIV
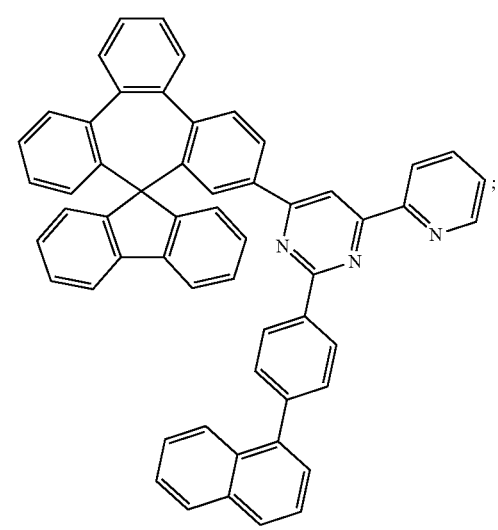

-continued
Compound CCLXV
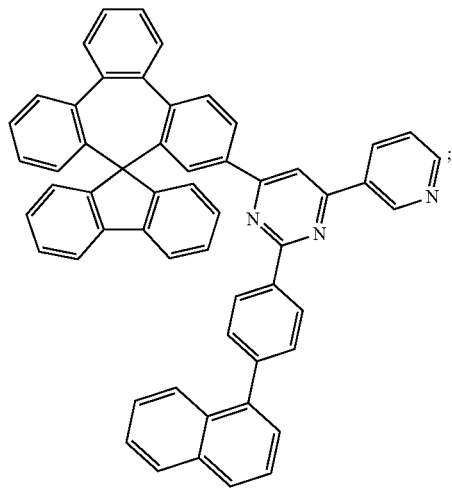
Compound CCLXVI
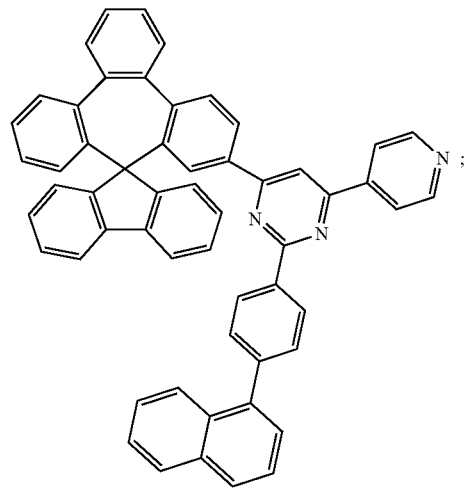
Compound CCLXVII
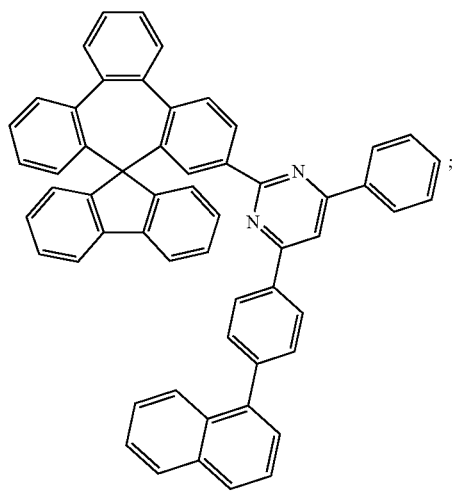
Compound CCLXVIII
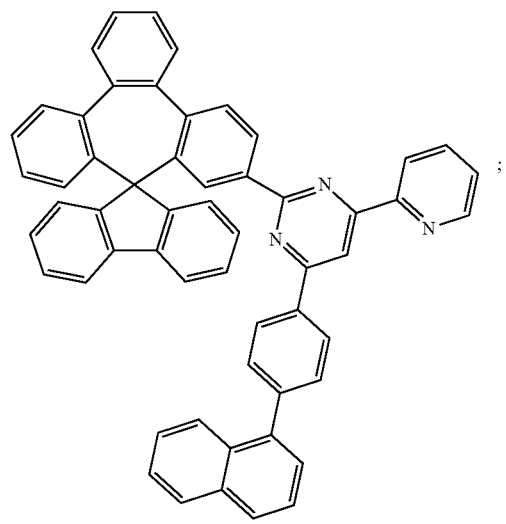
Compound CCLXIX
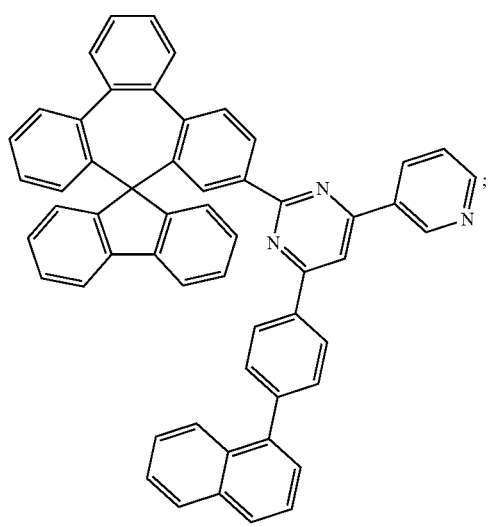
Compound CCLXX
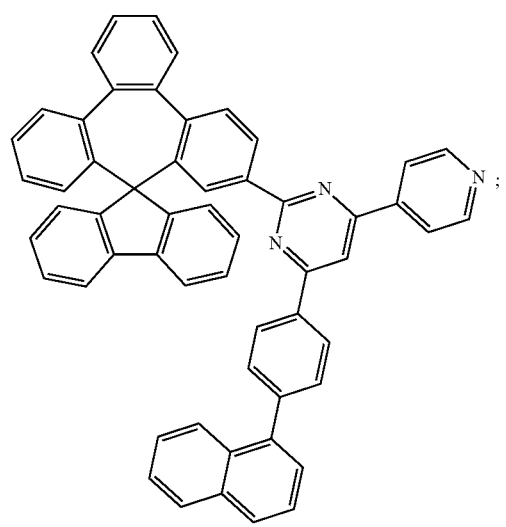

-continued
Compound CCLXXI
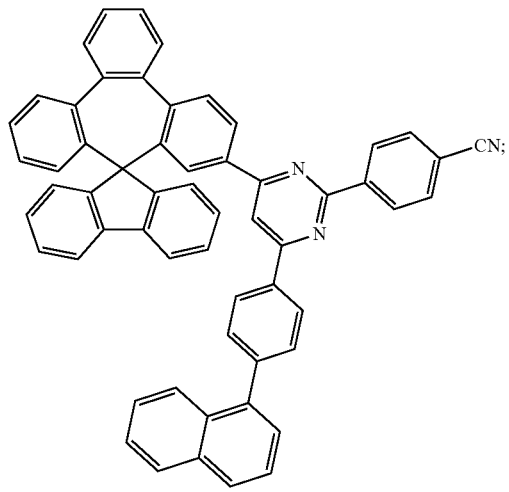
Compound CCLXXII
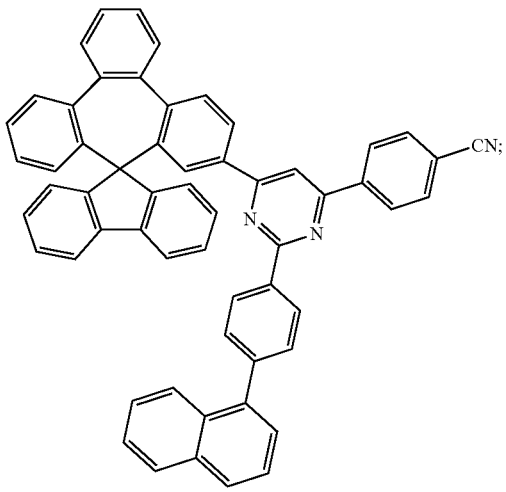
Compound CCLXXIII
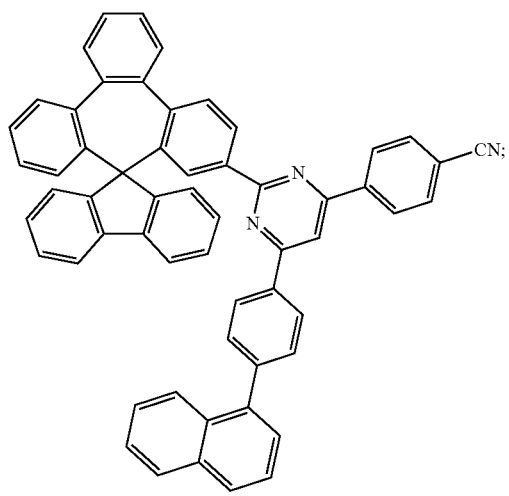
Compound CCLXXIV
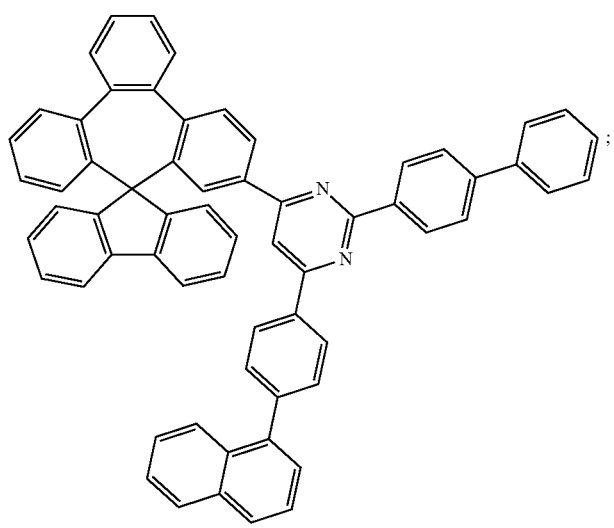

Compound CCLXXV
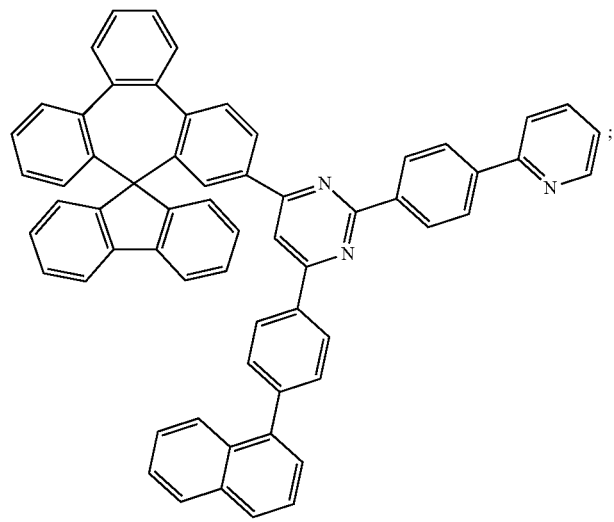
Compound CCLXXVI
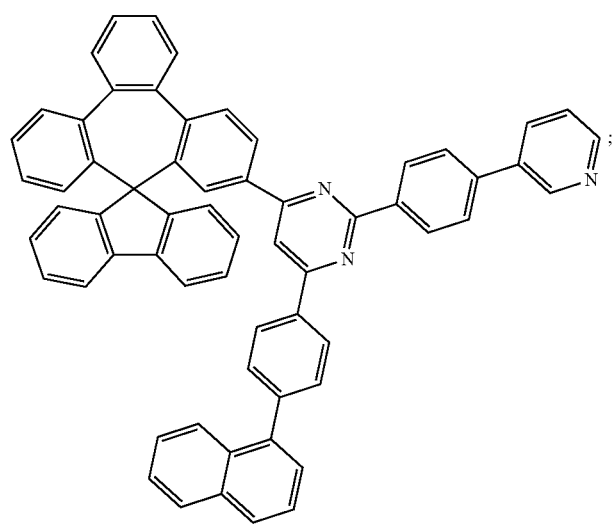
Compound CCLXXVII
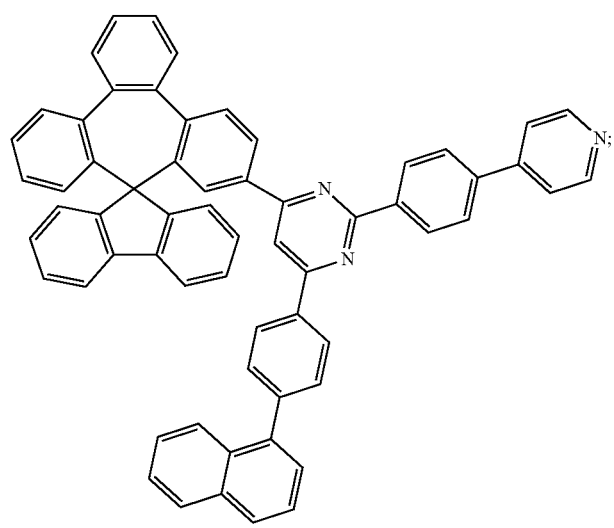

-continued
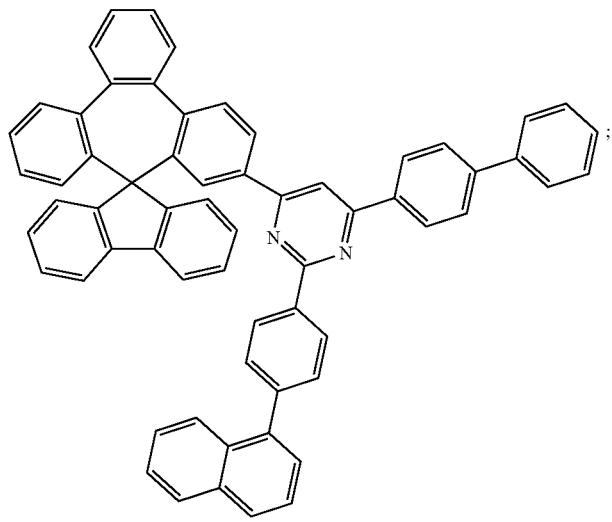
Compound CCLXXVIII
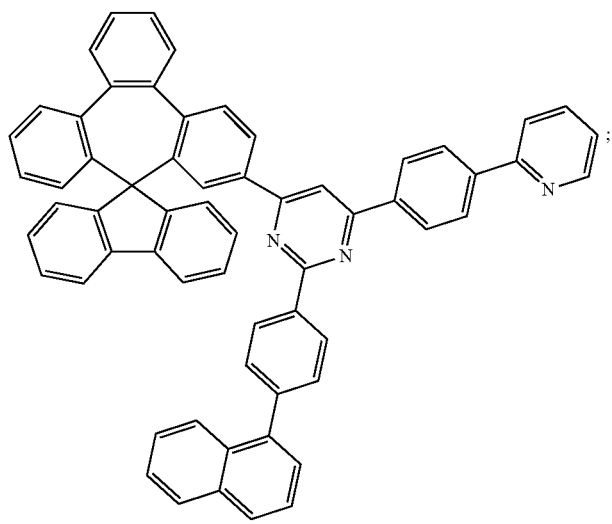
Compound CCLXXIX
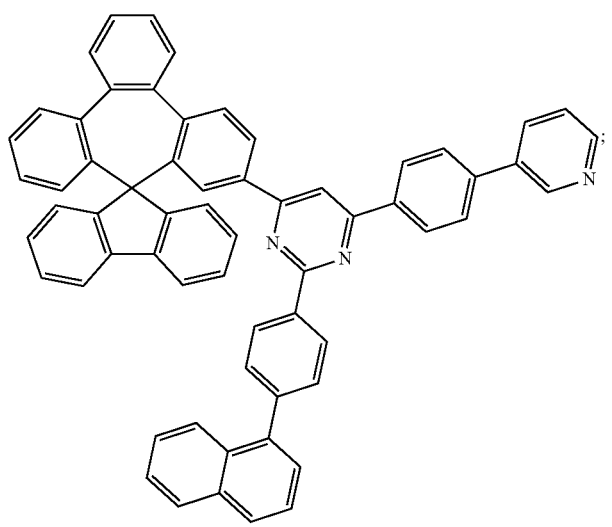
Compound CCLXXX

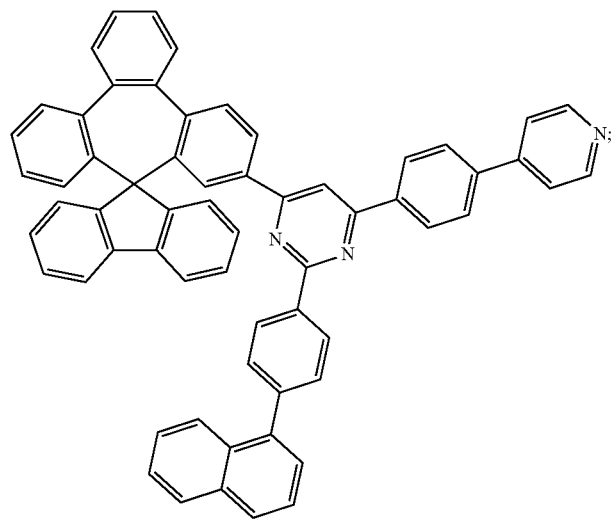
Compound CCLXXXI
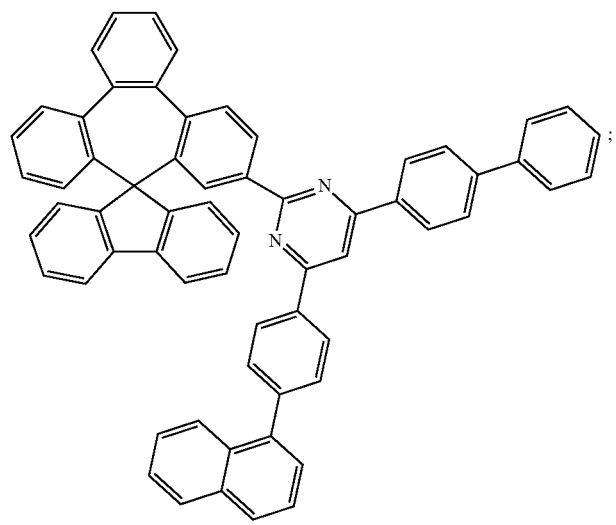
Compound CCLXXXII
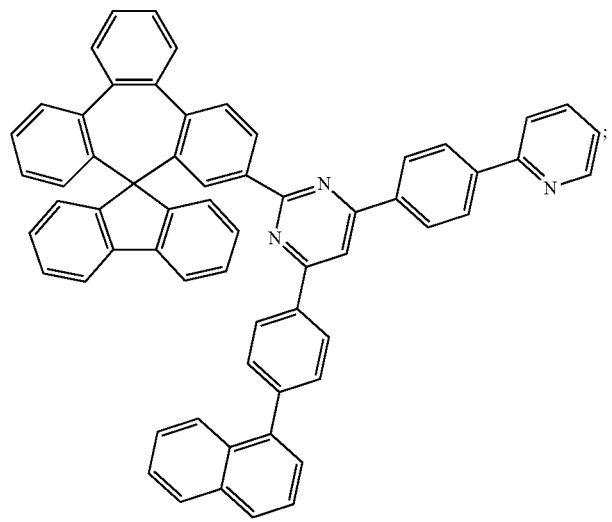
Compound CCLXXXIII -continued
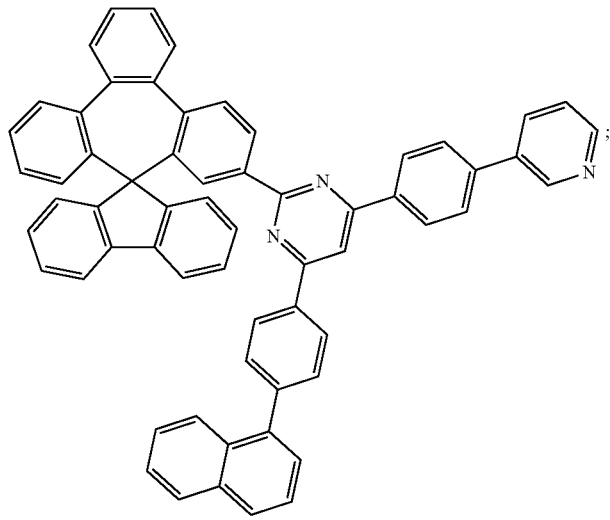
Compound CCLXXXIV
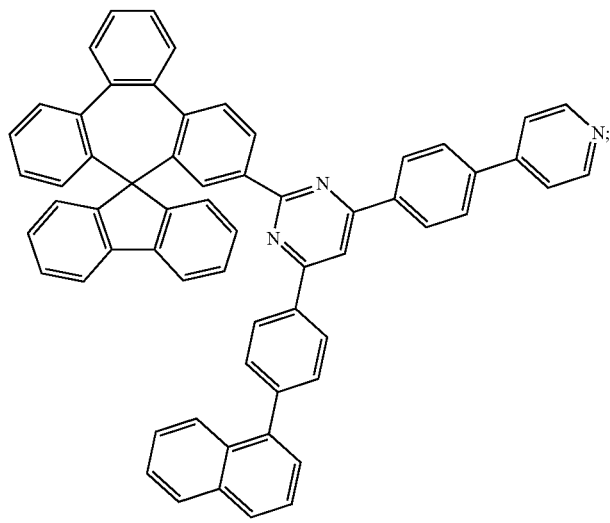
Compound CCLXXXV
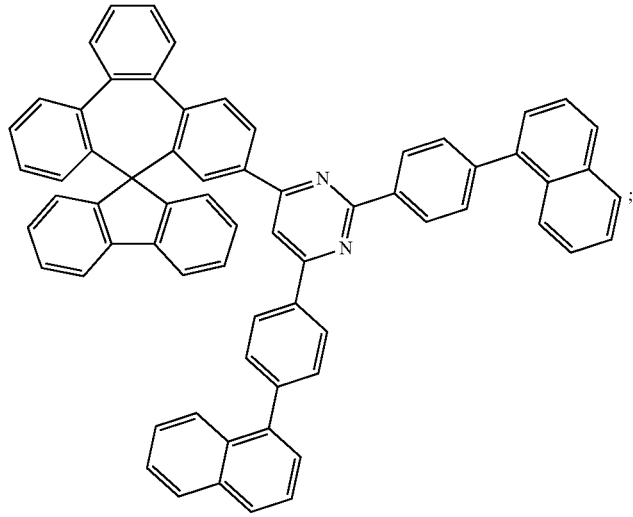
Compound CCLXXVI Compound CCLXXXVII
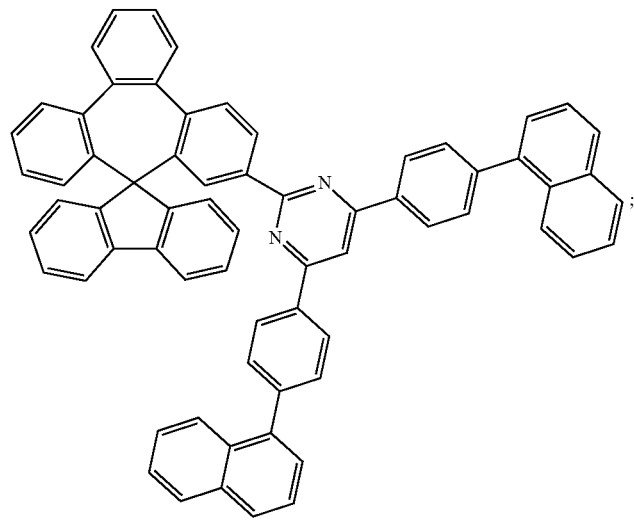
Compound CCLXXXVIII
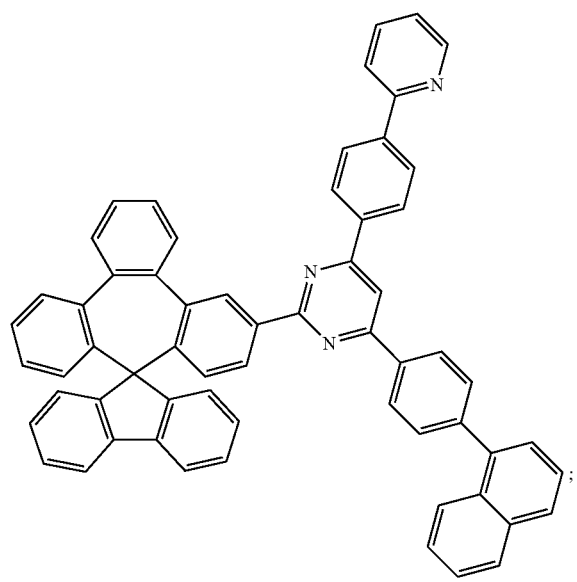
Compound CCLXXXIX
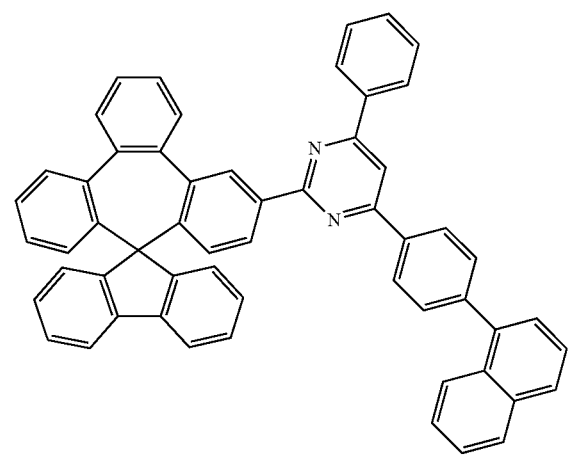
Compound CCXC
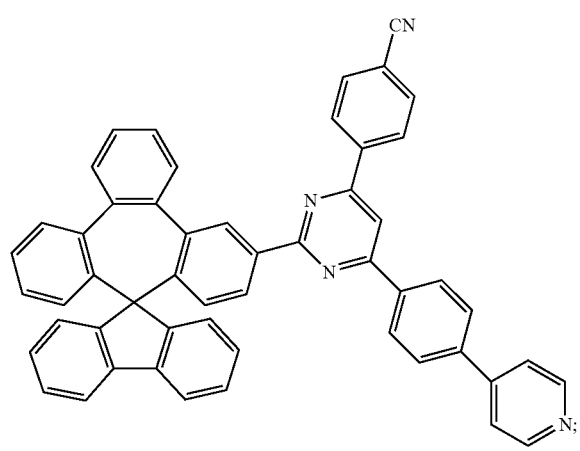
Compound CCXCI
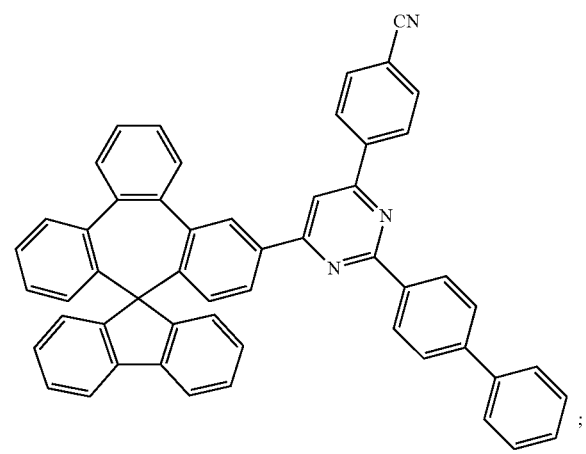

Compound CCXCII

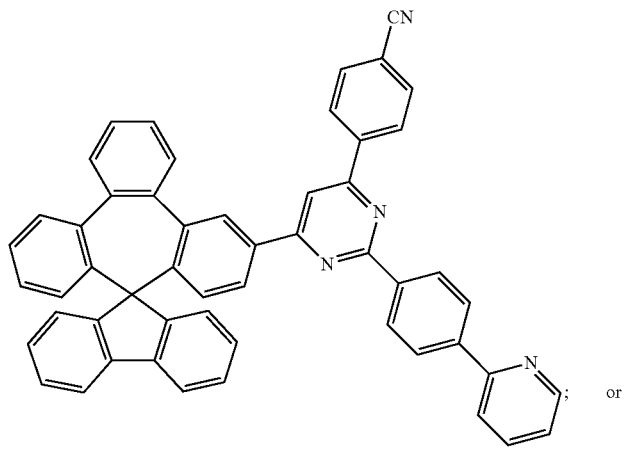

or

Compound CCXCIII

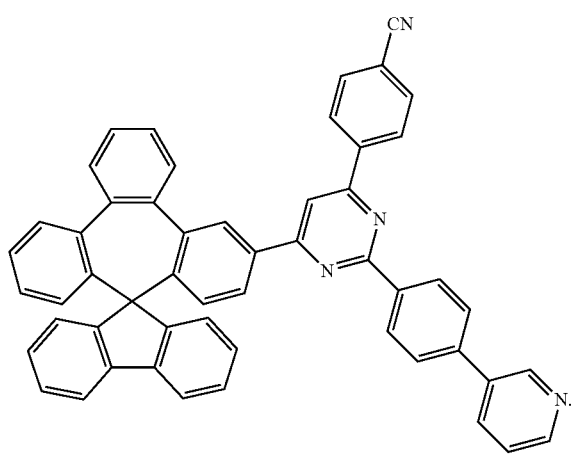

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as an electron transport material or a hole blocking material.

Specifically, the organic light emitting device may comprise:

a hole injection layer formed on the first electrode;
a hole transport layer formed on the hole injection layer;
an emission layer formed on the hole transport layer;
an electron transport layer formed on the emission layer, wherein the organic layer is the electron transport layer;
an electron injection layer formed between the electron transport layer and the second electrode.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer is made of the novel compound such as Compounds I to CCXCIII. The OLEDs using the novel compound as the electron transport material can have an improved efficiency compared to commercial OLEDs using known electron transport material, such as 2-(4-(9,10-di(naphthalen-2-yl)anthracen-2-yl)phenyl)-1-phenyl-1H-benzo[d]imidazole; bis(2-methyl-8quinolinolato)(p-phenylphenolato) aluminum; and 2-(4-biphenylyl)-5-(4-tert-butylphenyl)-1,3,4-oxadiazole (PBD), as the electron transport material.

Preferably, the OLED comprises a hole blocking layer formed between the electron transport layer and the emission layer, to block holes overflow from the emission layer to the electron transport layer. Said hole blocking layer may be made of the foresaid novel compound, 2,9-dimethyl-4,7-diphenyl-1,10-phenanthroline (BCP) or 2,3,5,6-tetramethyl-phenyl-1,4-(bis-phthalimide) (TMPP), but not limited thereto.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole (CBP) or 4,4',4''-tri(N-carbazolyl)-triphenylamine (TCTA), but not limited thereto.

In the presence of such a hole blocking layer and/or an electron blocking layer in an OLED, the OLED has a higher luminous efficiency compared to a typical OLED.

Said first and second hole transport layers may be made of, for example, but not limited to: N$^1$,N$^{1'}$-(biphenyl-4,4'-diyl)bis(N$^1$-(naphthalen-1-yl)-N$^4$, N$^{4'}$-diphenylbenzene-1,4-diamine); or N$^4$,N$^{4'}$-di(naphthalen-1-yl)-N$^4$,N$^{4'}$-diphenylbiphenyl-4,4'-diamine (NPB).

Said first and second hole injection layer may be made of, for example, but not limited to, polyaniline or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl) anthracene.

For red OLEDs, the dopant of the emission material is, for example, but not limited to: organometallic compounds of iridium (II) having perylene ligands, fluoranthene ligands or periflanthene ligands. For green OLEDs, the dopant of the emission material is, for example, but not limited to: diaminoflourenes; diaminoanthracenes; or organometallic compounds of iridium (II) having phenylpyridine ligands. For blue OLEDs, the dopant of the emission material is, for example, but not limited to: diaminoflourenes; diaminoanthracenes; diaminopyrenes; or organicmetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

BRIEF DESCRIPTION OF THE DRAWINGS

FIGS. 2 to 15 are respectively $^1$H nuclear magnetic resonance (NMR) spectra of Compounds I to XIV.

DETAILED DESCRIPTION OF THE PREFERRED EMBODIMENTS

Figure 1:
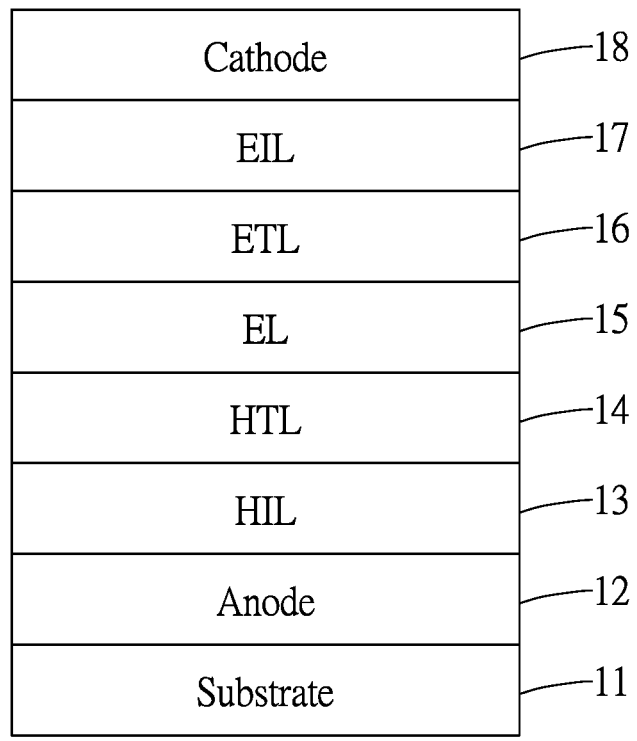
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate A1

Intermediate A1 used for preparing a novel compound was synthesized by the following steps. The synthesis pathway of the Intermediate A1 was summarized in Scheme A1.

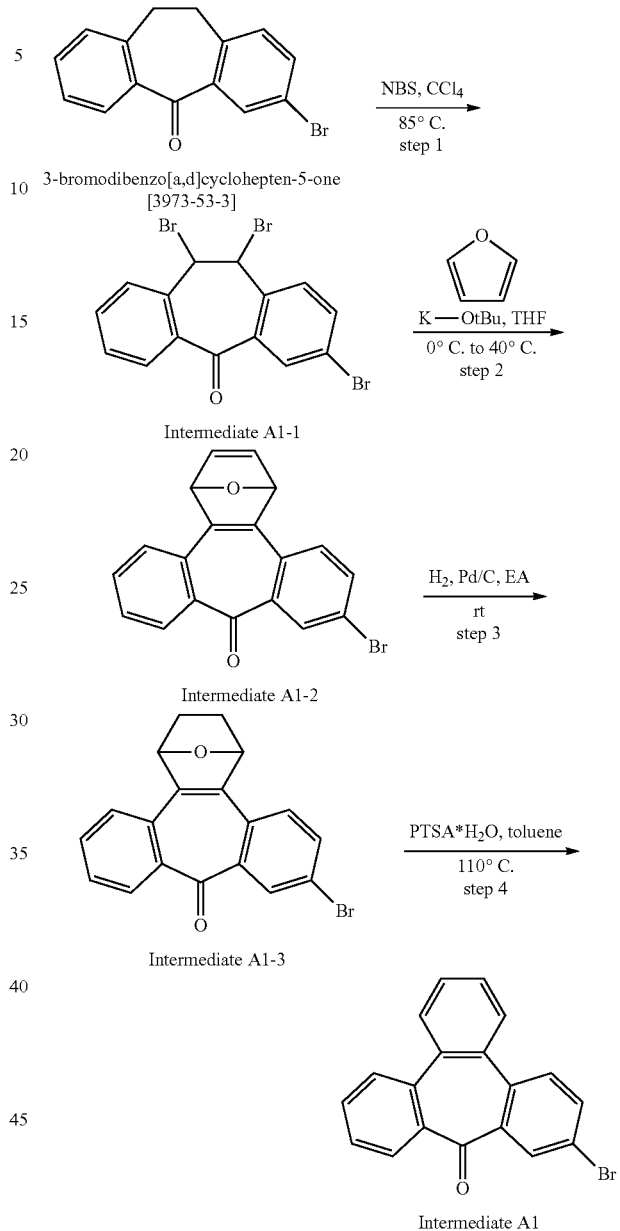

Step 1: Synthesis of Intermediate A1-1

A mixture of 3-bromodibenzo[a,d]cyclohepten-5-one (86 g, 1.0 eq), N-bromosuccinimide (NBS) (106 g, 2 eq), benzyl peroxide (0.7 g, 0.01 eq) in carbon tetrachloride (CCl$_4$) (430 ml) was heated to 85° C. The reaction progress was monitored by high performance liquid chromatography (HPLC). After completion of the reaction, the precipitate was separated by filtration and washed with CH$_3$OH, which was then purified by recrystallization. The purified product was concentrated to dryness, whereby white solids were obtained in an amount of 123 g and a yield of 92.3%.

The solid product was identified as Intermediate A1-1 by a field desorption mass spectroscopy (FD-MS) analysis. FD-MS analysis: C$_{15}$H$_9$Br$_3$O: theoretical value of 444.94 and observed value of 444.94.

Step 2: synthesis of Intermediate A1-2

The obtained Intermediate A1-1 (116.0 g, 1.0 eq) was dissolved in 960 ml of furan/THF(v/v=2/1), the reaction was cooled to 0° C. and then treated with potassium tert-butoxide (KO-t-Bu) (87.8 g, 3.0 eq). The reaction was allowed to stir at 0° C. for 1 hour, and then stirred at room temperature for another 12 hours. After completion, the reaction was quenched by DI water and the organic layer was recovered by solvent extraction operation and dried over sodium sulfate. The solvent was removed from the organic layer by distillation under reduced pressure, and the resulting residue was purified by silica gel column chromatography. The purified product was concentrated to dryness, whereby a light yellow solid product was obtained in an amount of 46.8 g and a yield of 51.1%.

The solid product was identified as Intermediate A1-2 by FD-MS analysis. FD-MS analysis $C_{19}H_{11}BrO_2$: theoretical value of 351.19 and observed value of 351.19.

Step 3: Synthesis of Intermediate A1-3

A suspension of Intermediate A1-2 (53.5 g, 1.0 eq) and 5% Pd/C (8.1 g, 0.025 eq) in 535 ml of ethyl acetate (EA) was stirred for 3 hours to 6 hours under a hydrogen atmosphere ($H_2$) provided by a balloon of hydrogen. The resulting mixture was filtered through a pad of celite and washed with EA, and the filtrate was concentrated under reduced pressure to obtain 100 g (100%) of yellow solid product.

The solid product was identified as Intermediate A1-3 by FD-MS analysis. FD-MS analysis $C_{19}H_{13}BrO_2$: theoretical value of 353.21 and observed value of 353.21. The intermediate A1-3 can be directly used in the following step without further purification.

Step 4: Synthesis of Intermediate A1-4

Intermediate A1-3 (53 g, 1.0 eq) and p-toluenesulfonic acid (PTSA) (57 g, 2.0 eq) in 530 ml of toluene was heated to reflux for 12 hours. The reaction mixture was cooled to room temperature and then quenched with a saturated aqueous solution of $NaHCO_3$ and extracted with $CH_2Cl_2$. The organic layer was washed with water, brine and dried with anhydrous $Na_2SO_4$ subsequently. Then the resulting solution was concentrated under reduced pressure and purified by column chromatography on silica gel with $CH_2Cl_2$/hexane (1:1 v/v) as eluent, whereby a light yellow solid product was obtained in a yield of 91.5%.

The solid product was identified as Intermediate A1 by FD-MS analysis. FD-MS analysis $C_{19}H_{11}BrO$: theoretical value of 335.19 and observed value of 335.19.

Synthesis of Intermediate A2

Intermediate A2 used for preparing a novel compound was synthesized in a similar manner as Intermediate A1 through steps 1 to 4, except that the starting material 3-bromodibenzo[a,d]cyclohepten-5-one was replaced by 2-bromodibenzo[a,d]cyclohepten-5-one (CAS No. 198707-82-3). The synthesis pathway of Intermediate A2 was summarized in Scheme A2. All intermediates were analyzed according to the methods as described above, and the results were listed in Table 1.

Scheme A2

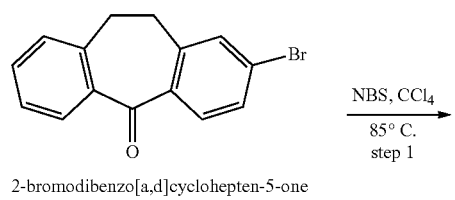

2-bromodibenzo[a,d]cyclohepten-5-one

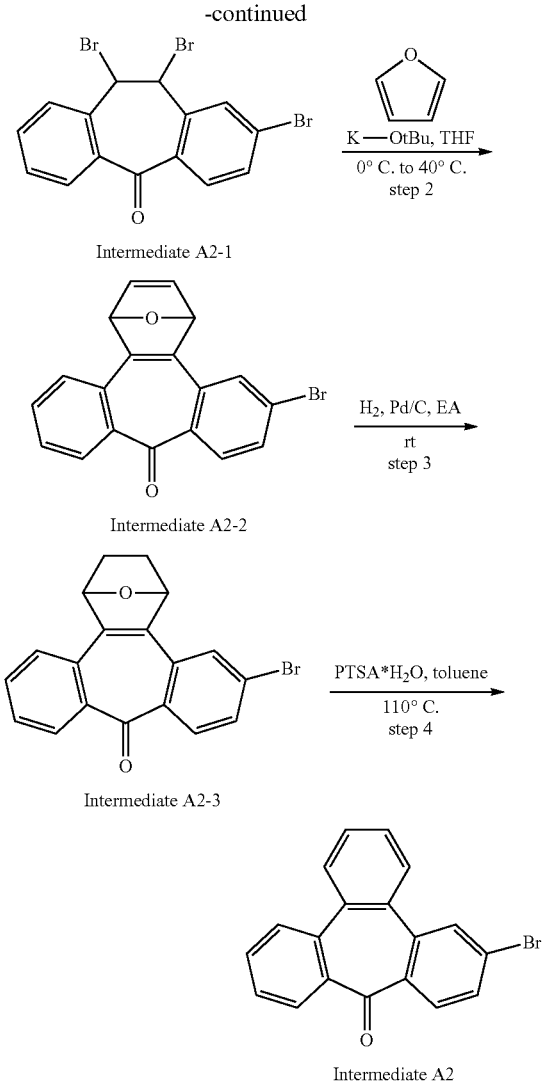

Synthesis of Intermediate A3

Intermediate A3 used for preparing a novel compound was synthesized in a similar manner as Intermediate A1 through steps 1 to 4, except that the starting material 3-bromodibenzo[a,d]cyclohepten-5-one was replaced by 3,7-dibromodibenzo[a,d]cyclohepten-5-one (CAS No. 226946-20-9). The synthesis pathway of Intermediate A3 was summarized in Scheme A3. All intermediates were analyzed as described above, and the results were listed in Table 1.

Scheme A3

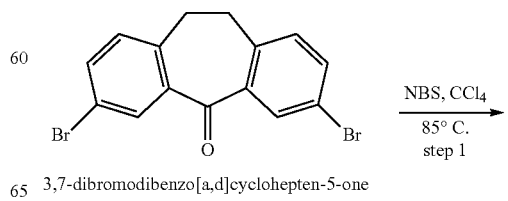

3,7-dibromodibenzo[a,d]cyclohepten-5-one

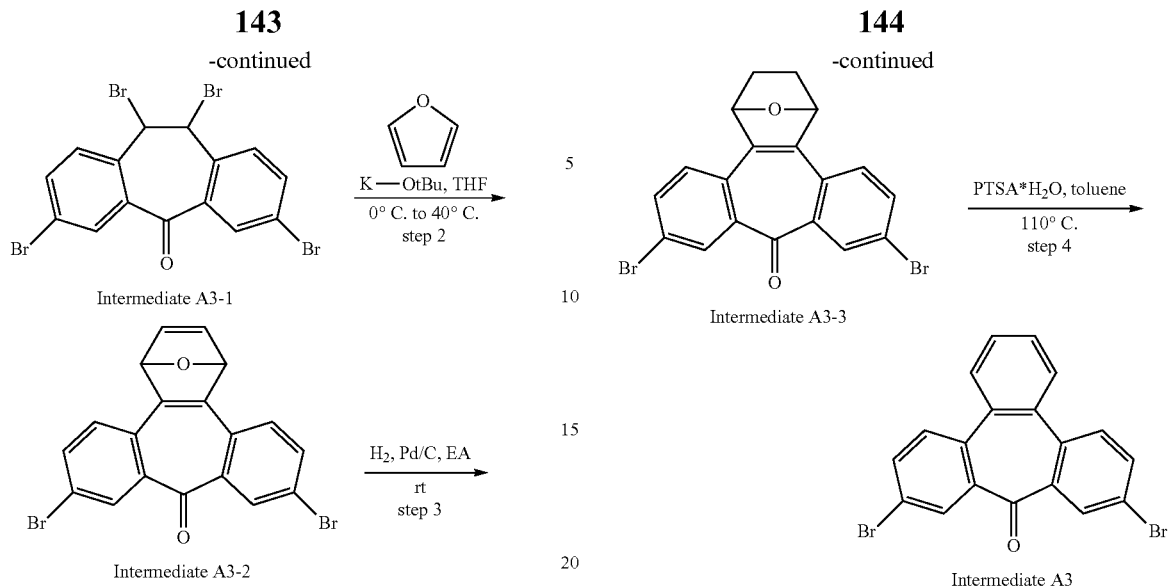

TABLE 1 chemical structures, yields, formulae, and mass (M⁺) analyzed by FD-MS of intermediates.

| Intermediate | A1-1 | A1-2 | A1-3 | A1 |
|---|---|---|---|---|
| Chemical Structure | | | | |
| Yield | 92.3% | 60.3% | NA | 91.5% |
| Formula | $C_{15}H_9Br_3O$ | $C_{19}H_{11}BrO_2$ | $C_{19}H_{13}BrO_2$ | $C_{19}H_{11}BrO$ |
| Mass (M⁺) | 444.94 | 351.19 | 353.21 | 335.19 |
| Intermediate | A2-1 | A2-2 | A2-3 | A2 |
| Chemical Structure | | | | |
| Yield | 91.5% | 58.2% | NA | 93.5% |
| Formula | $C_{15}H_9Br_3O$ | $C_{19}H_{11}BrO_2$ | $C_{19}H_{13}BrO_2$ | $C_{19}H_{11}BrO$ |
| Mass (M⁺) | 444.94 | 351.19 | 353.21 | 335.19 |
| Intermediate | A3-1 | A3-2 | A3-3 | A3 |
| Chemical Structure | | | | |
| Yield | 93.7% | 75.8% | NA | 93.0% |
| Formula | $C_{15}H_8Br_4O$ | $C_{19}H_{10}Br_2O_2$ | $C_{19}H_{12}Br_2O_2$ | $C_{19}H_{10}Br_2O$ |
| Mass (M⁺) | 523.84 | 430.09 | 432.11 | 414.09 |

Modifications of Intermediates A1 to A3

In addition to the Intermediates A1 to A3, one person skilled in the art can adopt other starting materials and successfully synthesize other desired intermediates through a reaction mechanism similar to Scheme A1 to A3. Applicable modifications of Intermediates A1 to A3 may be, for example, but not limited to, Intermediates A4 to A15 as follows.

Intermediate A4

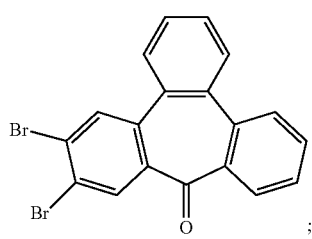

Intermediate A5

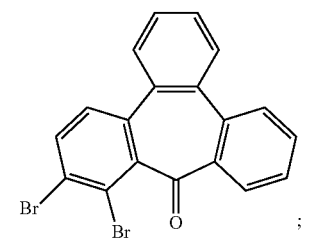

Intermediate A6

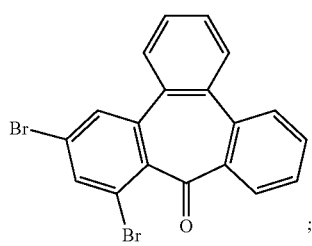

Intermediate A7

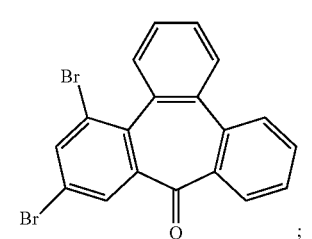

Intermediate A8

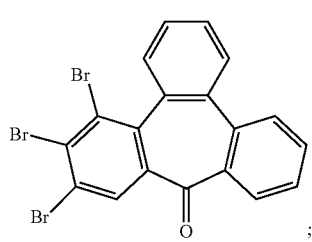

Intermediate A9

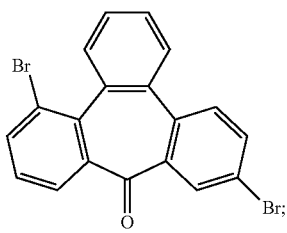 [SMILES: O=c1c2ccccc2c2ccccc2c2ccc(Br)cc12]

Intermediate A10

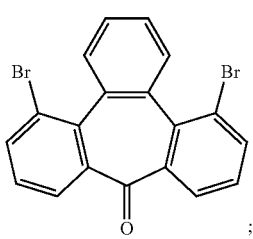

Intermediate A11

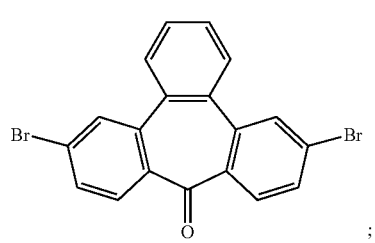

Intermediate A12

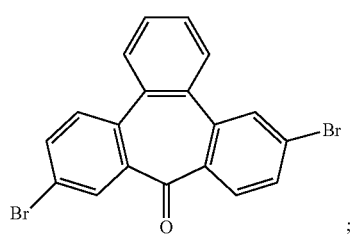

Intermediate A13

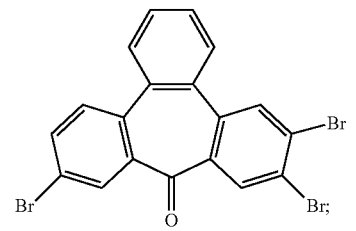

Intermediate A14

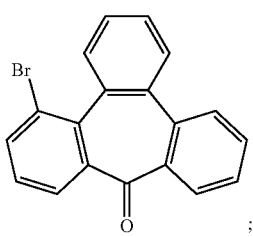

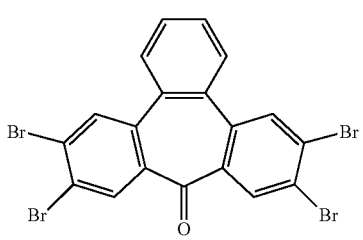

Intermediate A15

Synthesis of Intermediate B1

The foresaid Intermediate A1 was further reacted with 2-bromo-biphenyl to synthesis Intermediate B1. The synthesis pathway of the Intermediate B1 was summarized in Scheme B1.

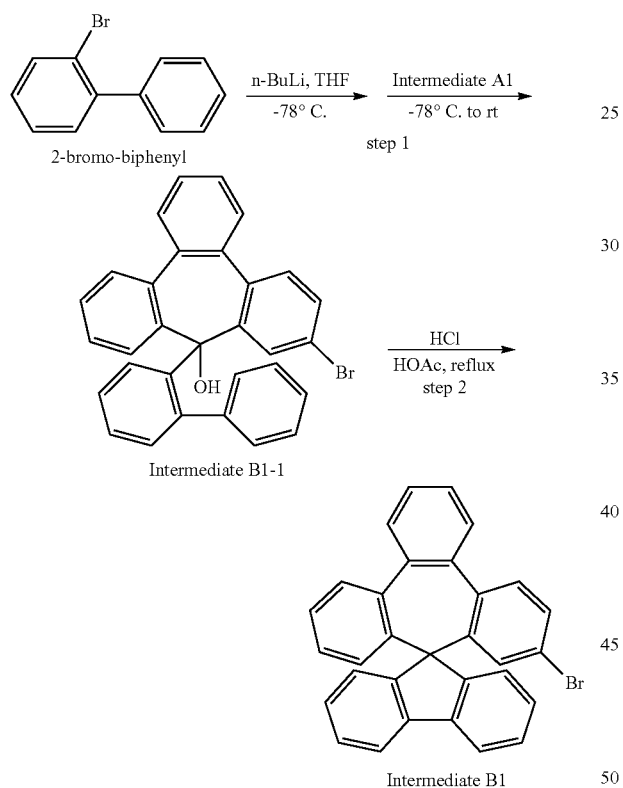

Scheme B1

Step 1: Synthesis of Intermediate B1-1

2-bromo-biphenyl (1.0 eq) was dissolved in 120 ml of anhydrous THF, and cooled to −78° C. n-Butyl lithium (n-BuLi) (2.5 M, 1.0 eq) was slowly added to the above cooled solution, and stirred for 1 hour. After 1 hour of stirring, Intermediate A1 (0.7 eq) was added to the reaction solution and then stirred for 3 hours at normal temperature. After the reaction completion, it was quenched by saturated solution of ammonium chloride, and extracted with an organic solvent. The organic layer was separated, concentrated, and recrystallized with petroleum ether to obtain a white solid product in 83.1% yield.

The solid product was identified as Intermediate B1-1 by FD-MS analysis. FD-MS analysis: $C_{31}H_{21}BrO$: theoretical value of 489.40 and observed value of 489.40.

Step 2: Synthesis of Intermediate B1

Intermediate B1-1 (1.0 eq), acetic acid (w/v=⅓ to the reactant) and $H_2SO_4$ (5 drops) were mixed, and the mixture was stirred at 110° C. for 6 hours. The solvent was then removed under reduced pressure, and the residue was purified with column chromatography. The residual mass was recrystallized with toluene to obtain a white solid product in a yield of 93.0%. The solid product was identified as Intermediate B1 by FD-MS analysis. FD-MS analysis: $C_{31}H_{19}Br$: theoretical value of 471.39 and observed value of 471.39.

Synthesis of Intermediate B2

Intermediate B2 was synthesized in a similar manner as Intermediate B1 through steps 1 and 2, except that the Intermediate A1 was replaced by Intermediate A2. The synthesis pathway of Intermediate B2 was summarized in Scheme B2. All intermediates were analyzed according to the methods as described above, and the results were listed in Table 2.

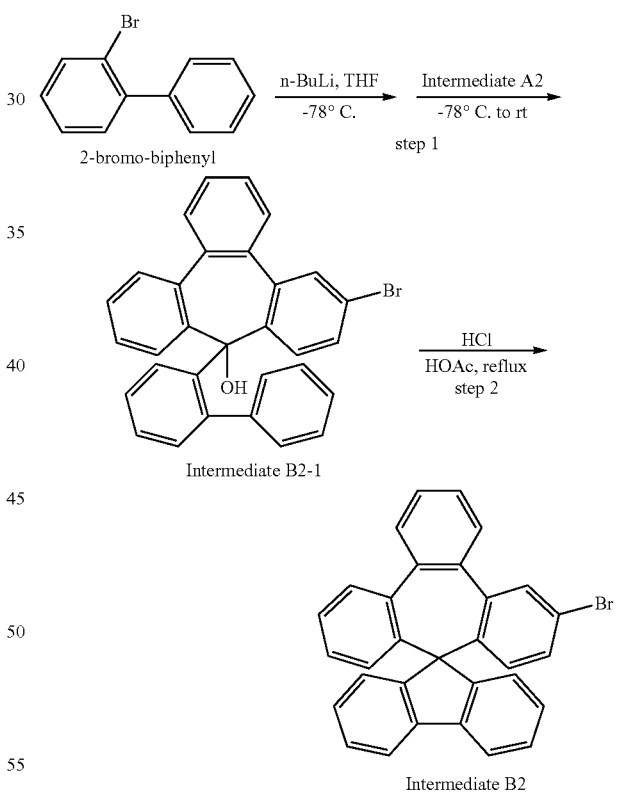

Scheme B2

Synthesis of Intermediate B3

Intermediate B3 was synthesized in a similar manner as Intermediate B1 through steps 1 and 2, except that the Intermediate A1 was replaced by Intermediate A3. The synthesis pathway of Intermediate B3 was summarized in Scheme B3. All intermediates were analyzed according to the methods as described above, and the results were listed in Table 2.

Scheme B3
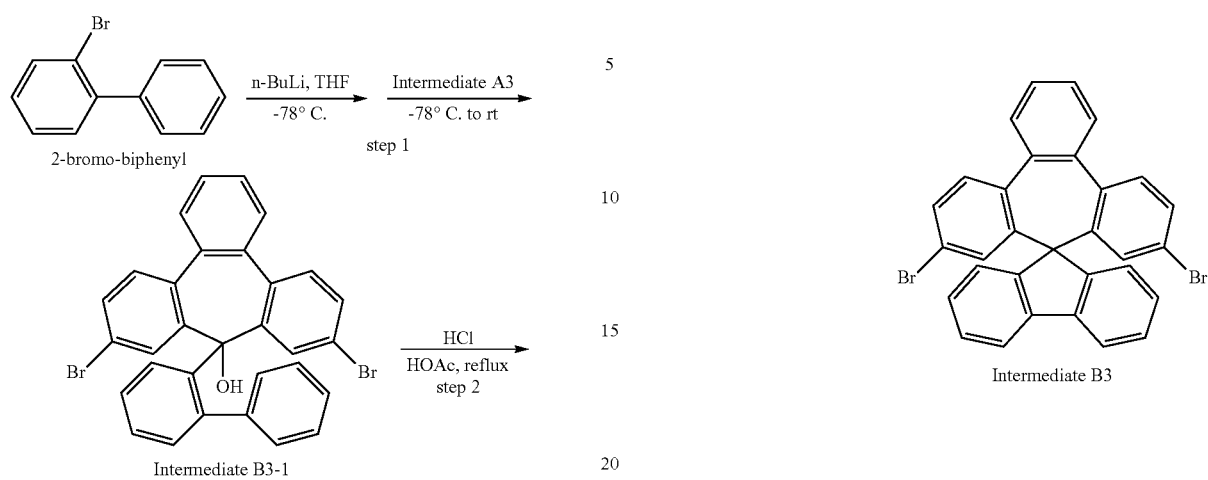
TABLE 2
chemical structures, yields, formulae, and mass analyzed by FD-MS of intermediates.
| Intermediate No. | Chemical Structure | Yield | Formula | Mass |
|---|---|---|---|---|
| B1-1 | 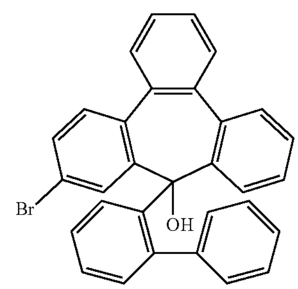 [SMILES: OC1(c2ccccc2-c2ccccc2)c2ccccc2-c2ccccc2-c2ccc(Br)cc21] | 83.1 | $C_{31}H_{21}BrO$ | 489.41 |
| B1 | 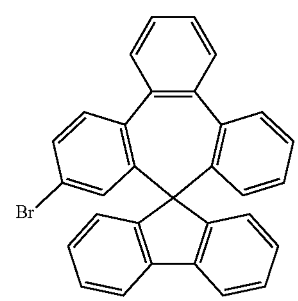 [SMILES: Brc1ccc2c(c1)C1(c3ccccc3-c3ccccc3-2)c2ccccc2-c2ccccc21] | 93.0 | $C_{31}H_{19}Br$ | 471.39 |
| B2-1 | 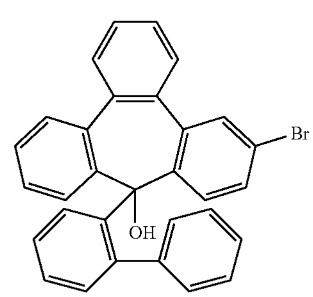 [SMILES: OC1(c2ccccc2-c2ccccc2)c2ccccc2-c2ccccc2-c2cc(Br)ccc21] | 87.6 | $C_{31}H_{21}BrO$ | 489.40 |

TABLE 2-continued chemical structures, yields, formulae, and mass analyzed by FD-MS of intermediates.

| Intermediate No. | Chemical Structure | Yield | Formula | Mass |
|---|---|---|---|---|
| B2 | 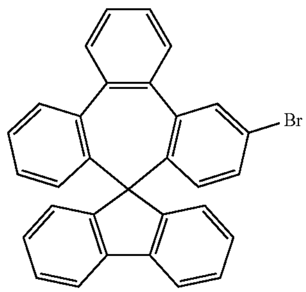 [SMILES: Brc1ccc2c(c1)-c1ccccc1-c1ccccc1C21c2ccccc2-c2ccccc21] | 91.5 | $C_{31}H_{19}Br$ | 471.39 |
| B3-1 | 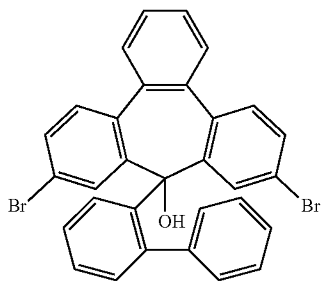 [SMILES: OC1(c2ccccc2-c2ccccc2)c2cc(Br)ccc2-c2ccccc2-c2ccc(Br)cc21] | 86.7 | $C_{13}H_{20}Br_2O$ | 568.3 |
| B3 | 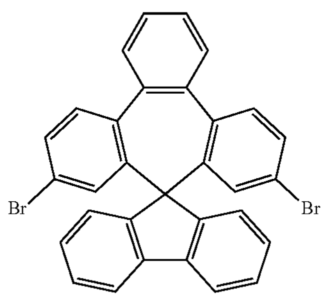 [SMILES: Brc1ccc2c(c1)C1(c3cc(Br)ccc3-c3ccccc3-2)c2ccccc2-c2ccccc21] | 91.5 | $C_{13}H_{18}Br_2$ | 550.28 |

Modifications of Intermediates B1 to B3

In addition to the Intermediates B1 to B3, one person skilled in the art can successfully synthesize other desired intermediates from Intermediates A1 to A15 through a reaction mechanism similar to Scheme B1 to B3. Applicable modifications of Intermediates B1 to B3 may be, for example, but not limited to, Intermediates B4 to B15 as follows.

Intermediate B4

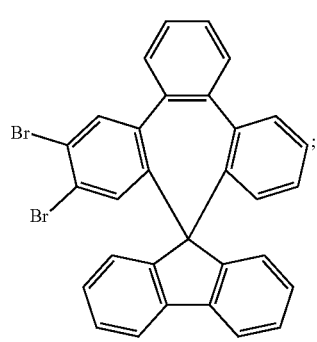

Intermediate B5

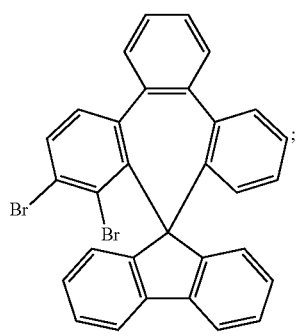

-continued
Intermediate B6
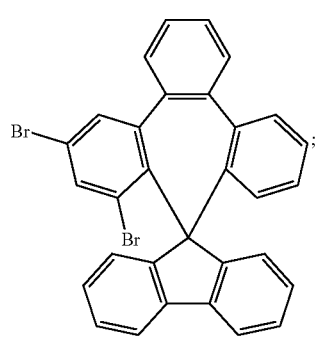
Intermediate B7
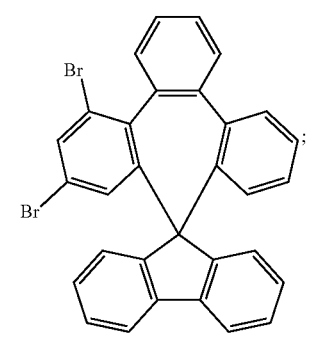
Intermediate B8
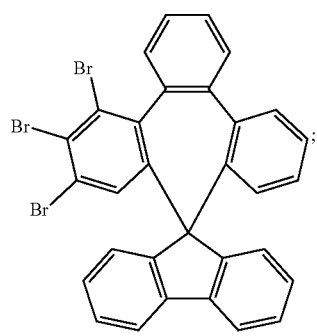
Intermediate B9
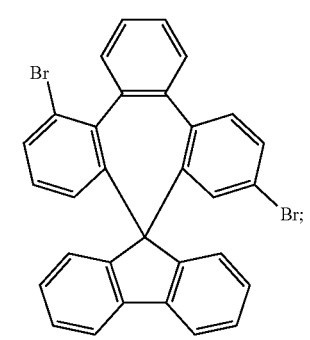
Intermediate B10
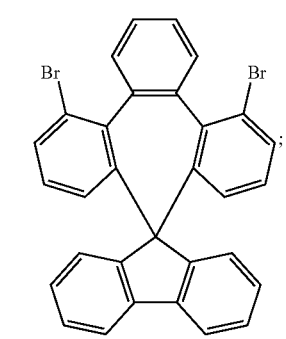
-continued
Intermediate B11
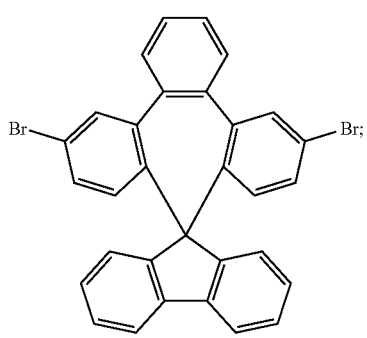
Intermediate B12
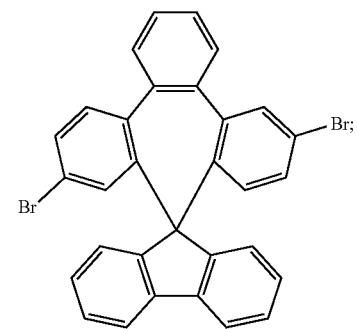
Intermediate B13
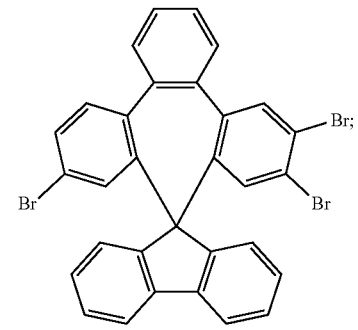
Intermediate B14
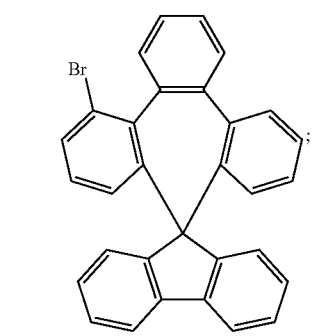

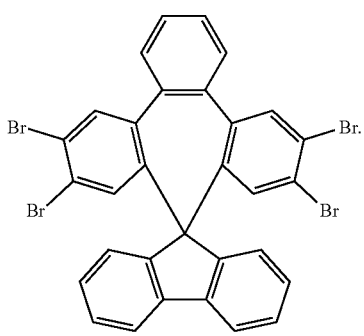

Intermediate B15

Synthesis of Intermediate C1

The foresaid intermediate B1 was further reacted with bis(pinacolato)diboron for the synthesis of Intermediate C1. The synthetic pathway of the Intermediate C1 was summarized in Scheme C1.

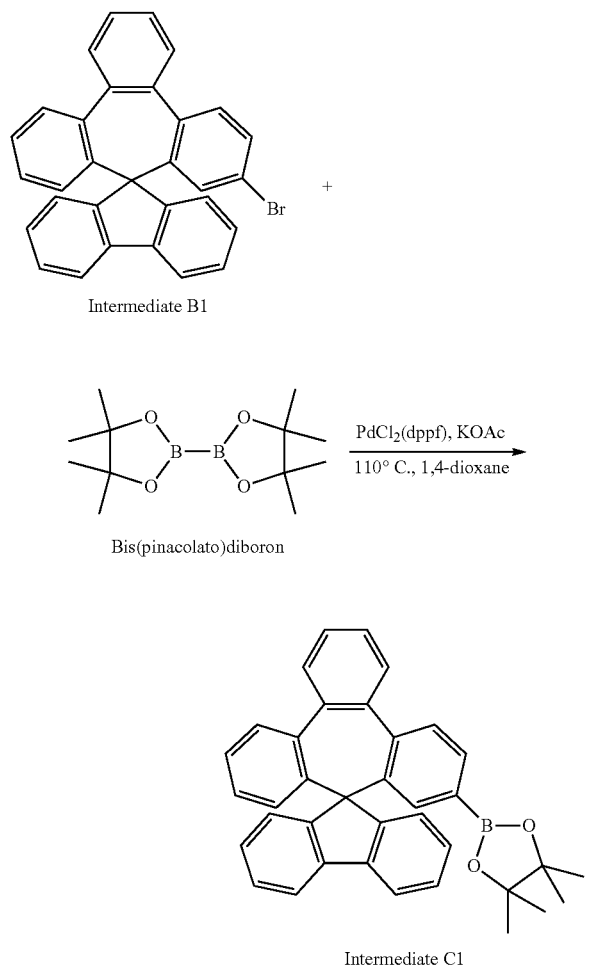

A mixture of intermediate B1 (1.0 eq), bis(pinacolato)diboron (1.2 eq), PdCl$_2$(dppf) (0.0025 eq), KOAc (3.0 eq) in 1,4-dioxane (0.3M) was heated at 100° C. for 8 hours under nitrogen atmosphere. After cooling to room temperature, the solvent was then removed under reduced pressure, and the residue was purified via column chromatography to obtain white solids in a yield of 95.7%.

The solid product was identified as intermediate C1 by FD-MS analysis. FD-MS analysis: $C_{37}H_{31}BO_2$: theoretical value of 518.45 and observed value of 518.45.

Synthesis of Intermediate C2

Intermediate C2 was synthesized in a similar manner as Intermediate C1 in a yield of 96.1%, except that the intermediate B1 was replaced by intermediate B2. The synthesis pathway of Intermediate C2 was summarized in Scheme C2.

The solid product was identified as Intermediate C2 by FD-MS analysis. FD-MS analysis: $C_{37}H_{31}BO_2$: theoretical value of 518.45 and observed value of 518.45.

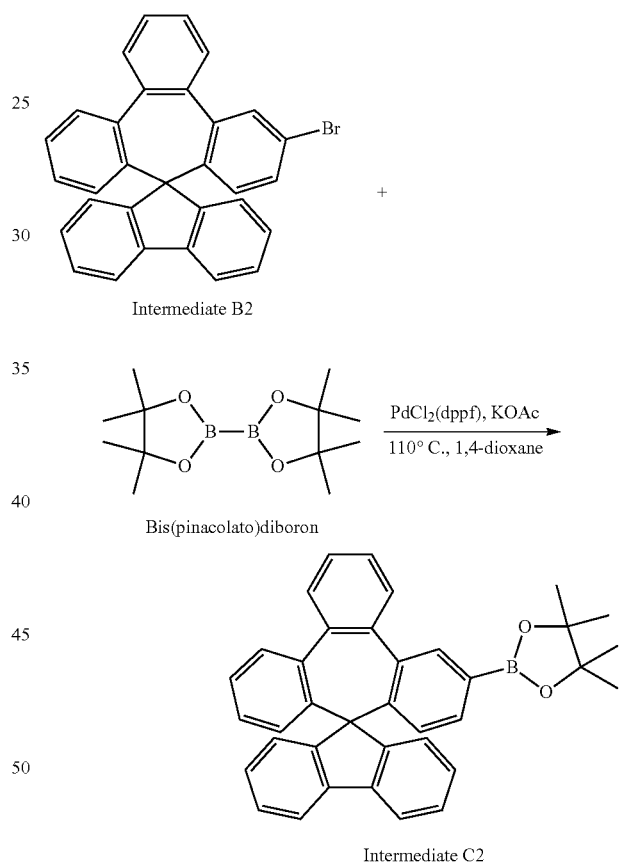

Synthesis of Intermediate C3

Intermediate C3 was synthesized in a similar manner as intermediate C1 in a yield of 84.2%, except that the Intermediate B1 was replaced by Intermediate B3 and the equivalent amount of bis(pinacolato)diboron was increased to 2.4 eq. The synthesis pathway of intermediate C3 was summarized in Scheme C3.

The solid product was identified as Intermediate C3 by FD-MS analysis. FD-MS analysis: $C_{43}H_{42}B_2O_4$: theoretical value of 644.41 and observed value of 644.40.

Scheme C3

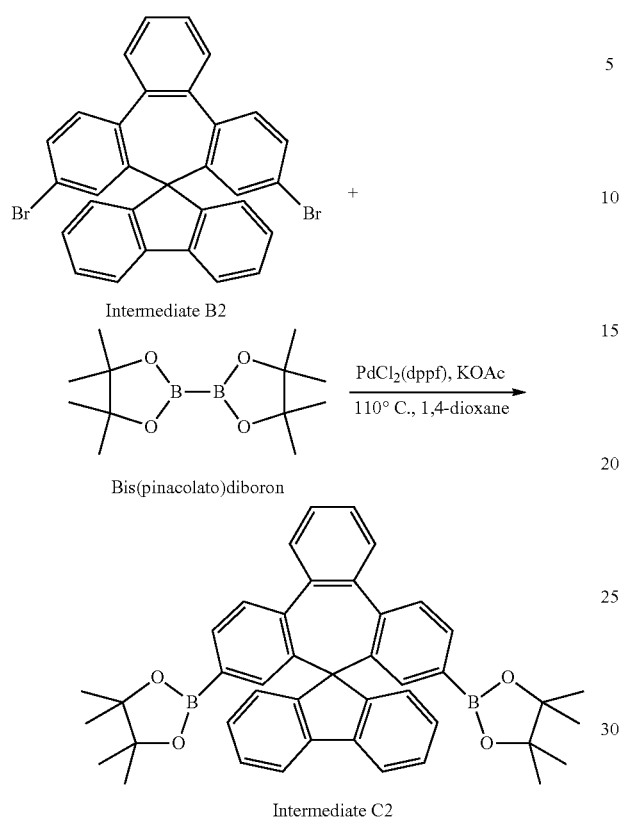

Intermediate B2

Bis(pinacolato)diboron

PdCl$_2$(dppf), KOAc
110° C., 1,4-dioxane

Intermediate C2

Synthesis of Novel Compounds I to XIV:

Approach 1:

Each of Intermediates B1 to B3 could be reacted with various reactants to synthesize various claimed novel compounds. The synthesis pathway for the claimed novel compound was summarized in Scheme I. In the following Scheme I, "Intermediate B" may be any one of foresaid Intermediates B1 to B3, and "Reactant A" may be any one of Reactants A1 to A6 as listed in Table 3-1.

Scheme I

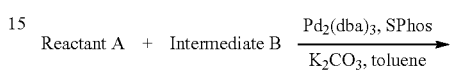

Reactant A + Intermediate B $\xrightarrow[\text{K}_2\text{CO}_3\text{, toluene}]{\text{Pd}_2(\text{dba})_3\text{, SPhos}}$

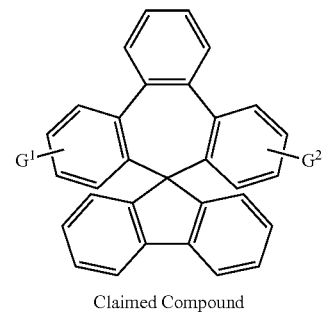

Claimed Compound

TABLE 3-1 chemical structure and CAS No. of Reactants A1 to A6.

| Reactant No. | Reactant A1 | Reactant A2 | Reactant A3 |
|---|---|---|---|
| Chemical Structure | (HO)₂B—⟨C₆H₄⟩—CN | 3,2'-bipyridine-5-Bpin | 2-phenylpyrimidine-5-Bpin |
| CAS No. | [126747-14-6] | [1260106-29-3] | [1319255-85-0] |

| Reactant No. | Reactant A4 | Reactant A5 | Reactant A6 |
|---|---|---|---|
| Chemical Structure | pyridine-4-Bpin | NC—biphenyl—Bpin | (HO)₂B—⟨C₆H₄⟩—CN (meta) |
| CAS No. | [181219-01-2] | [406482-72-7] | [150255-96-2] |

Approach 2:

Each of intermediates C1 to C3 could be reacted with various reactants to synthesize various novel compounds as claimed. The synthetic pathway for the novel compound was summarized in Scheme II. In the following Scheme II, "Intermediate C" may be any one of foresaid intermediates C1 to C3 and "Reactant B" may be any one of reactants B1 to B5 as listed in Table 3-2.

Scheme II

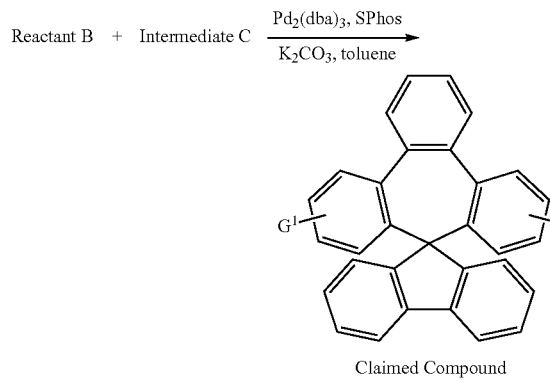

Claimed Compound

Specifically, a 500-mL recovery flask was charged with Reactant A (1.2 eq), Intermediate B or C (1.0 eq), tris(dibenzylideneacetone)dipalladium(0) ($Pd_2(dba)_3$) (0.005 eq), SPhos (0.02 eq), toluene/ethanol (0.5M, v/v=10/1), and 3.0 M of $K_2CO_3$ aqueous solution, followed by stirring at 100° C. for 12 hours under a nitrogen gas flow. Herein, mono- and bis-coupled products can be obtained regioselectively by varying the equivalent amount of Reactant A/B and catalyst. After completion of the reaction, water and toluene were added to the reaction mass. Subsequently, the organic layer was recovered by solvent extraction operation and dried over sodium sulfate. The solvent was then removed from the organic layer by distillation under reduced pressure, and the resulting residue was purified by silica gel column chromatography. The obtained residue was recrystallized with toluene to obtain white solid as the claimed novel compound.

Figure 2:
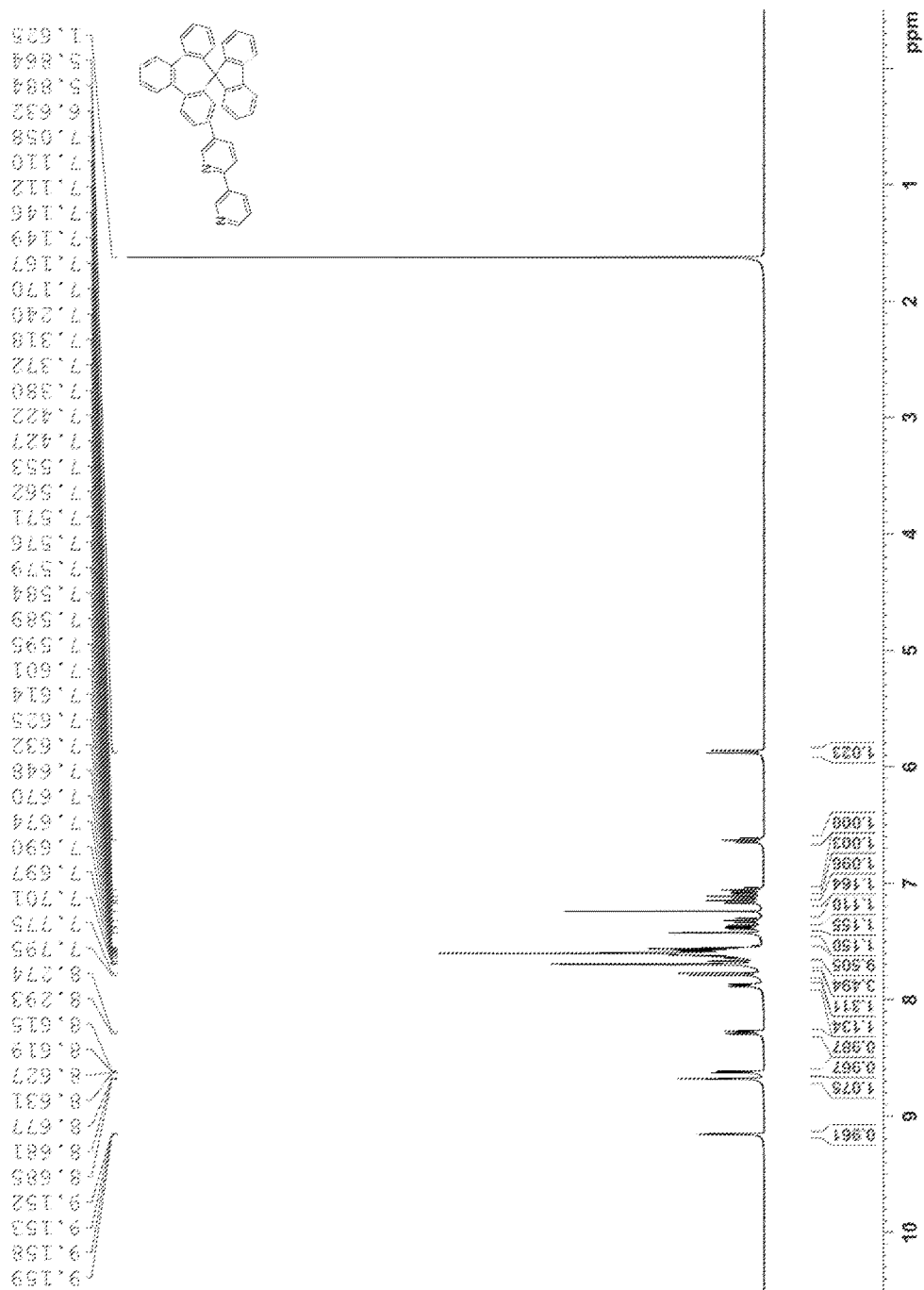
Figure 3:
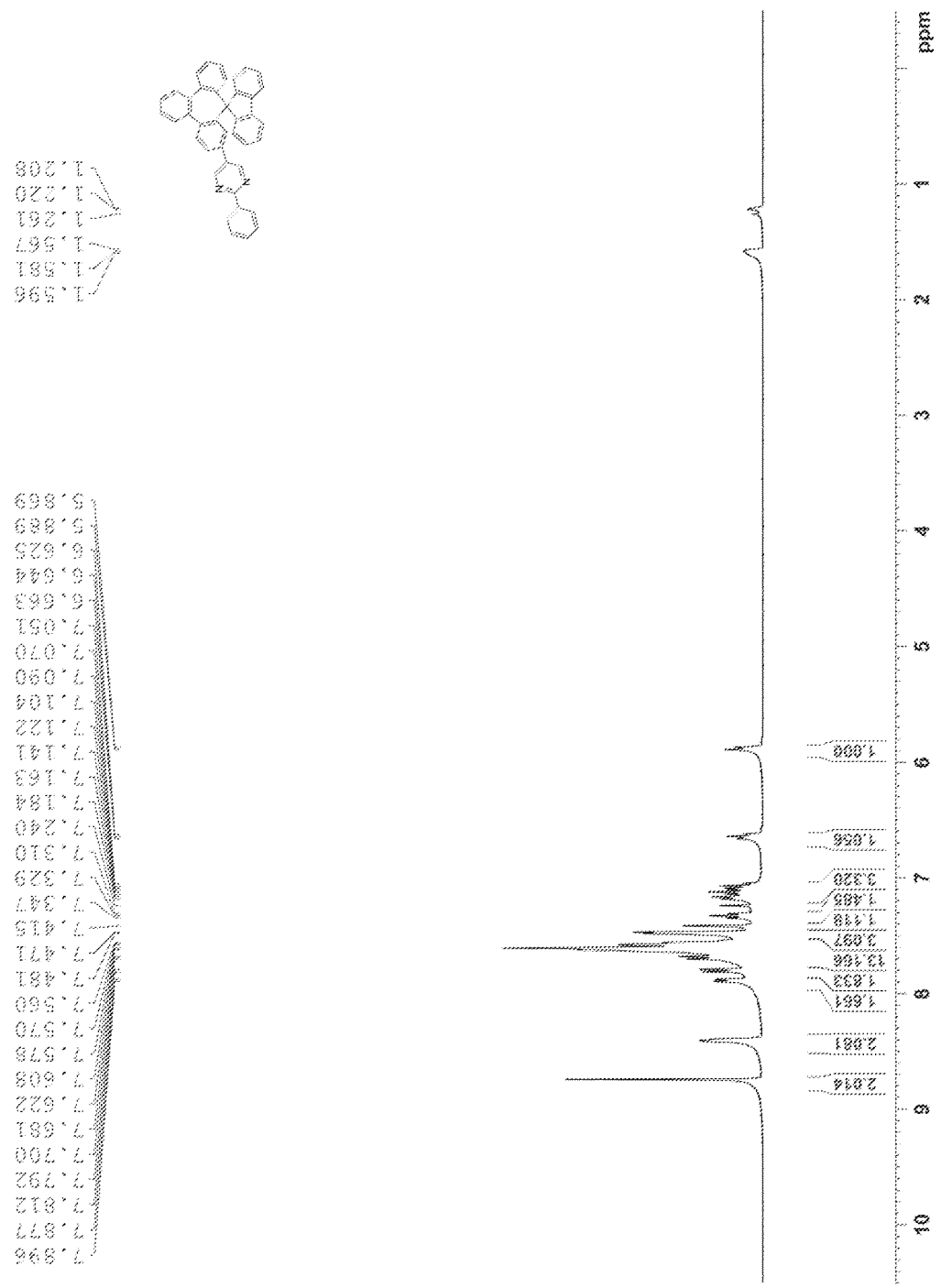
Figure 4:
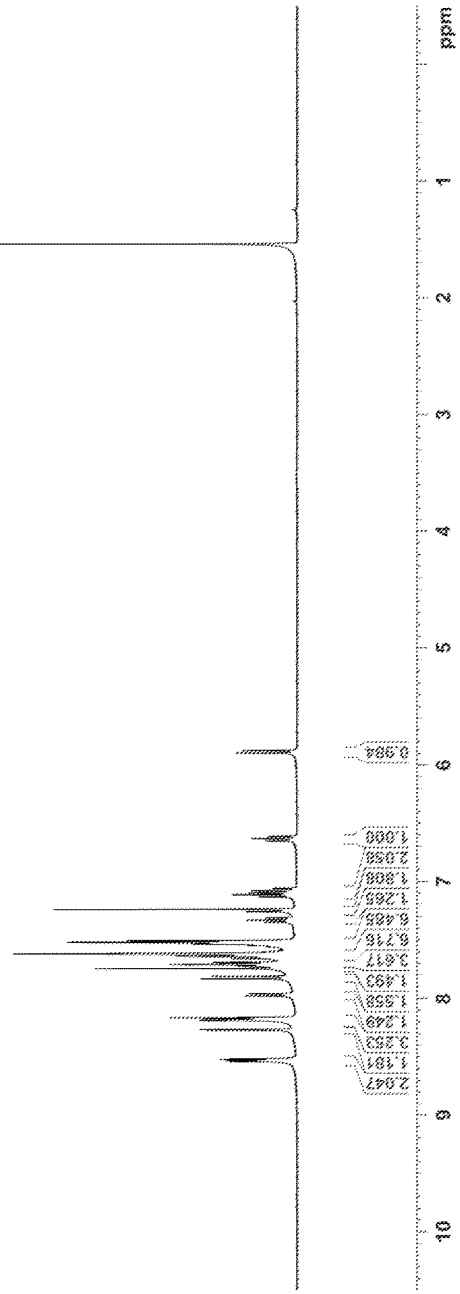
Figure 6:
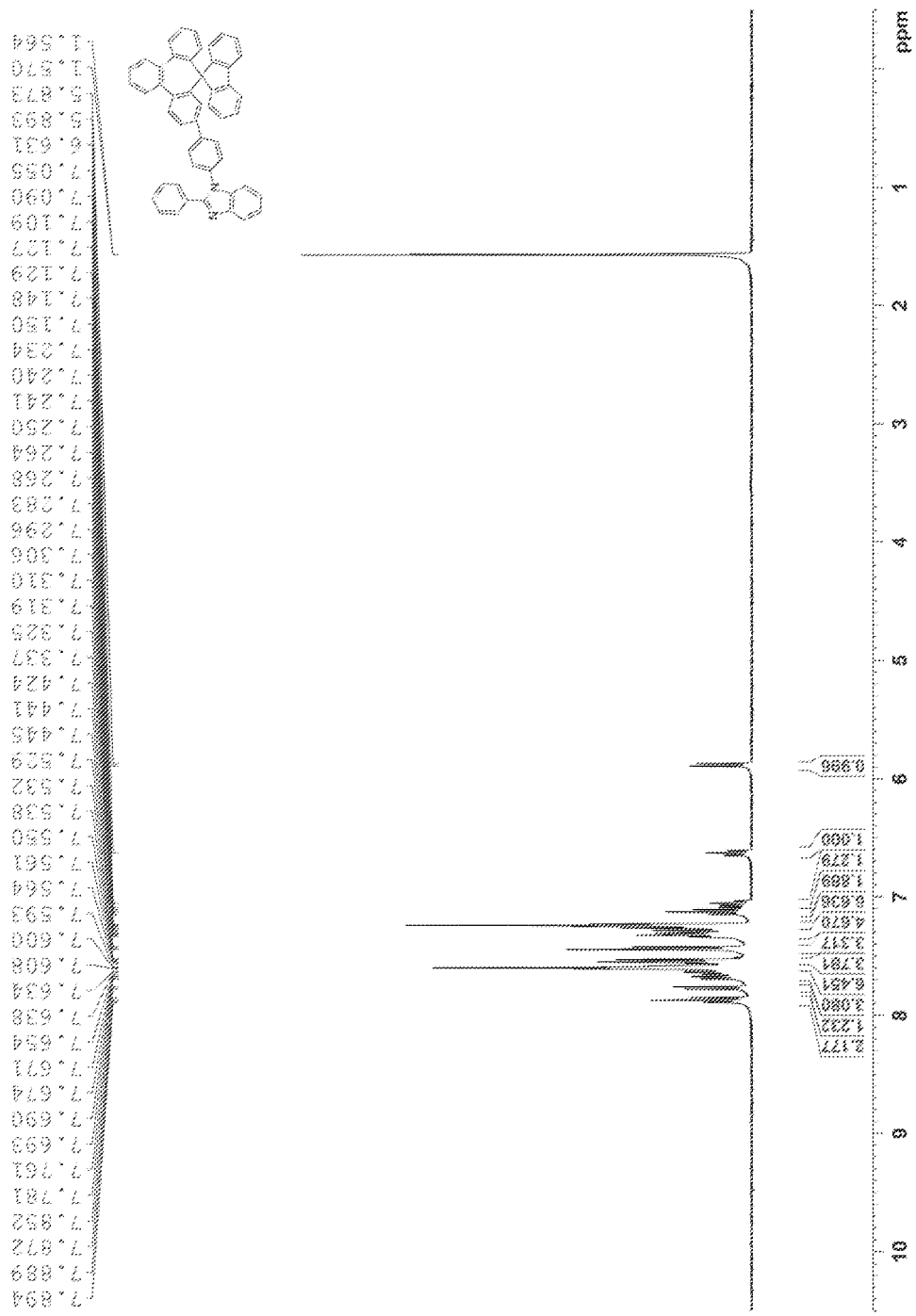
Figure 7:
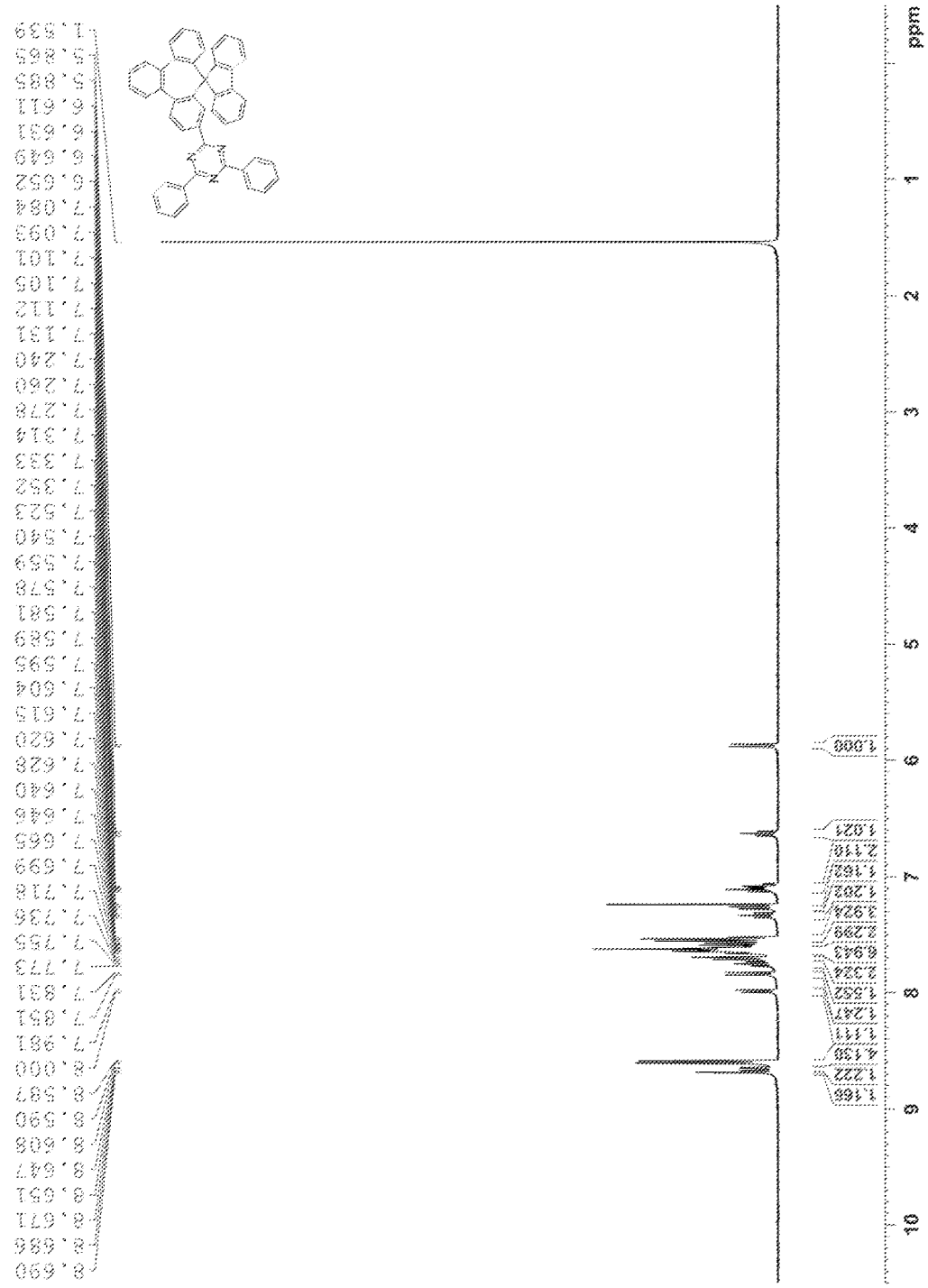
Figure 8:
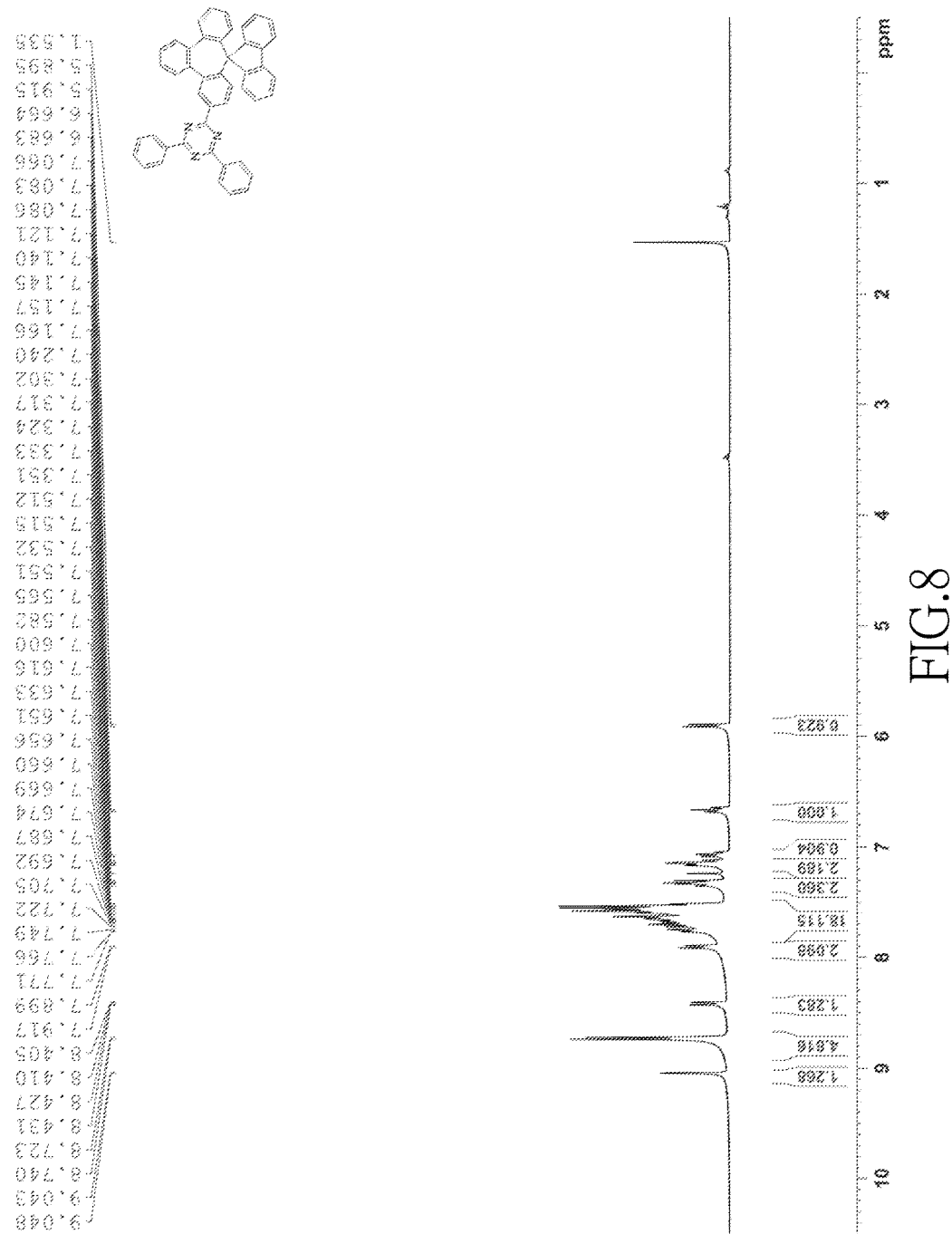
Figure 9:
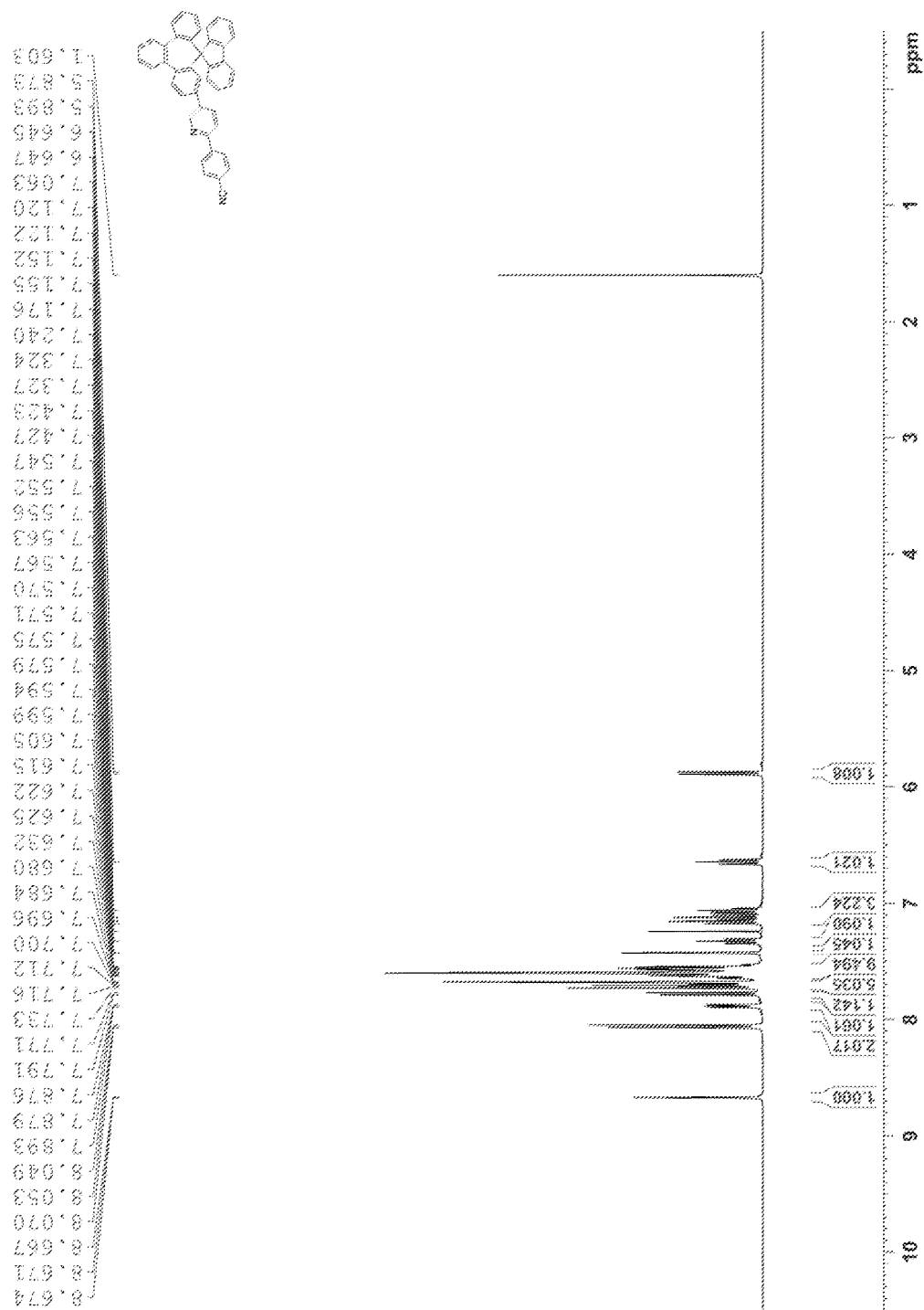
Figure 10:
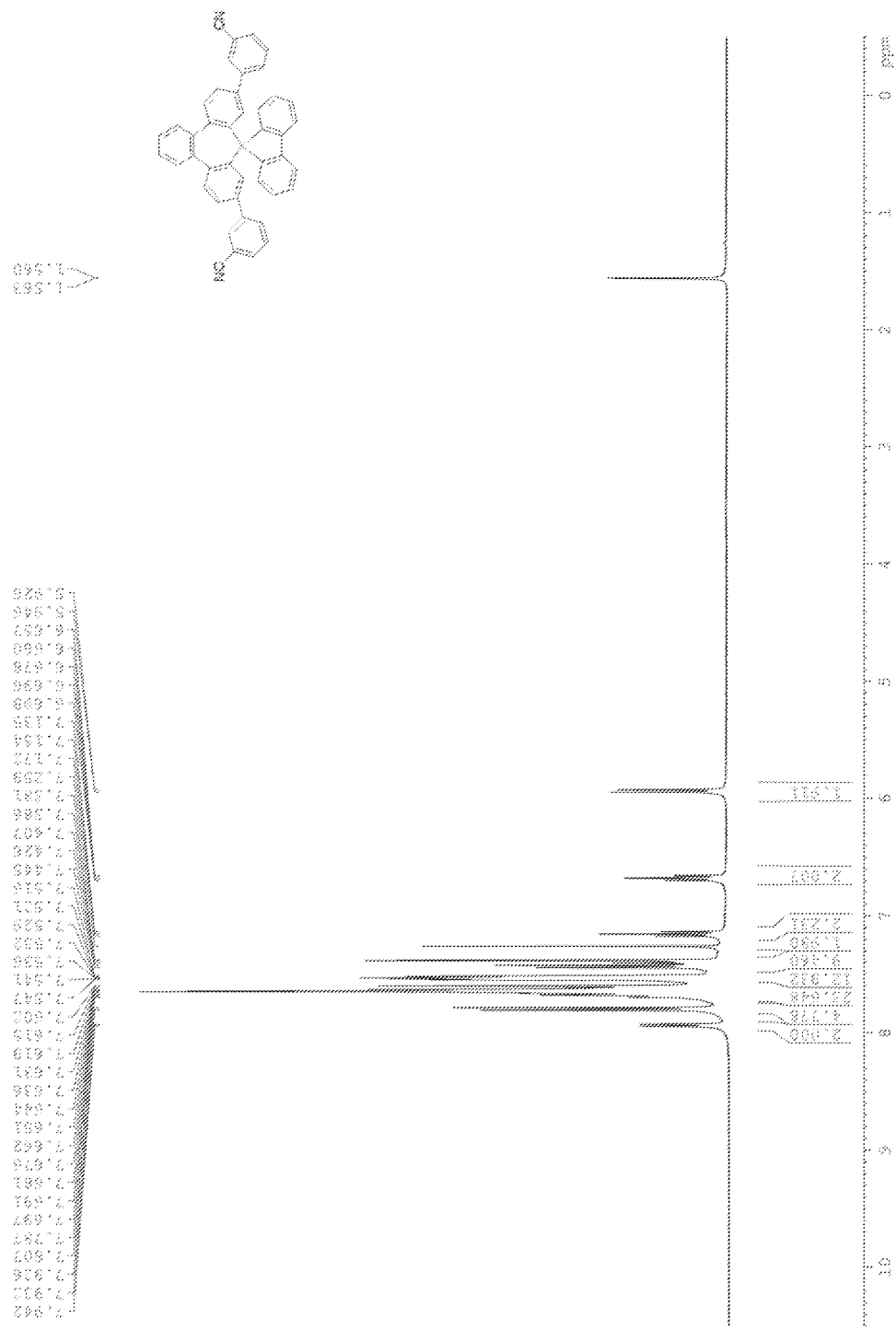
Figure 11:
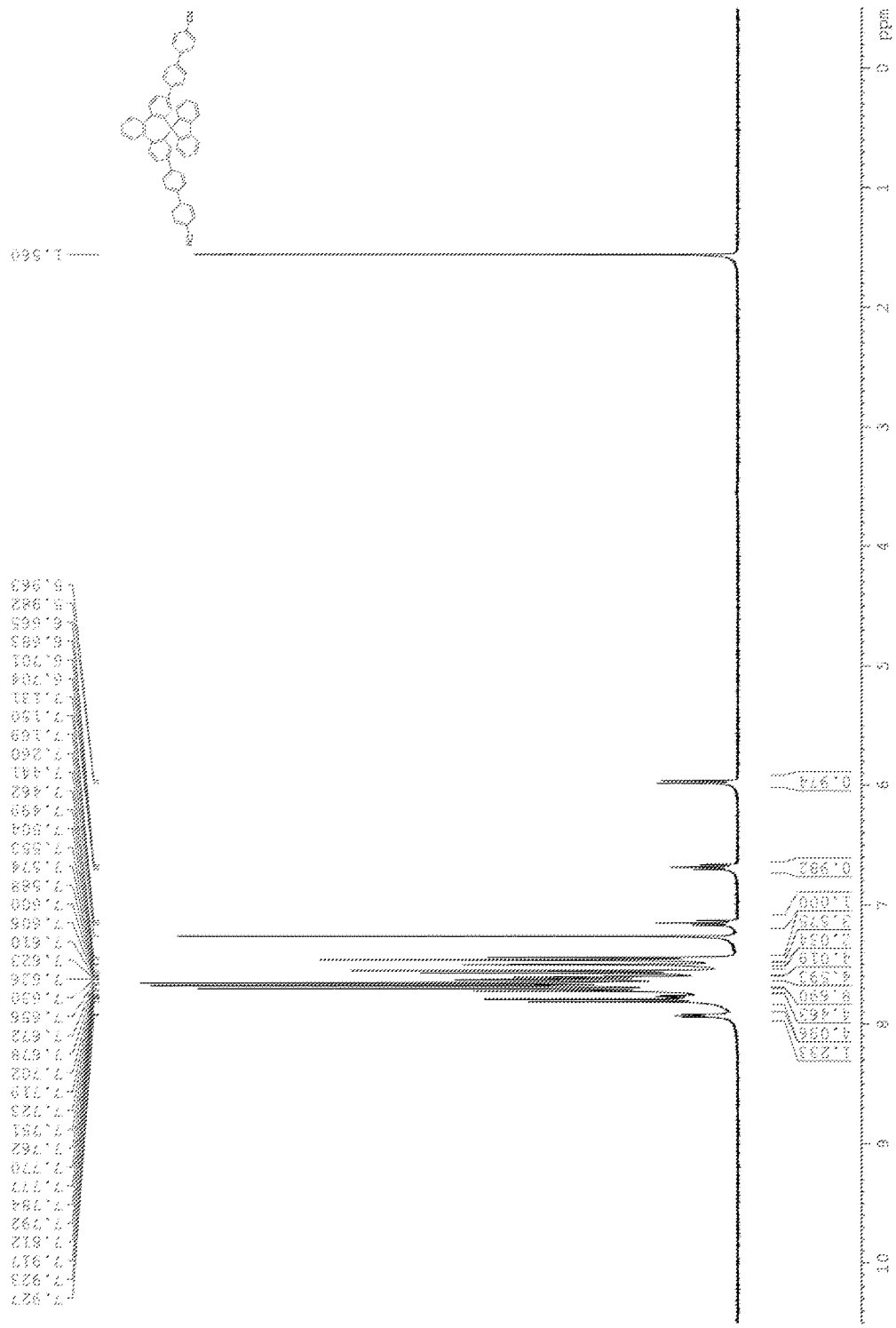
Figure 12:
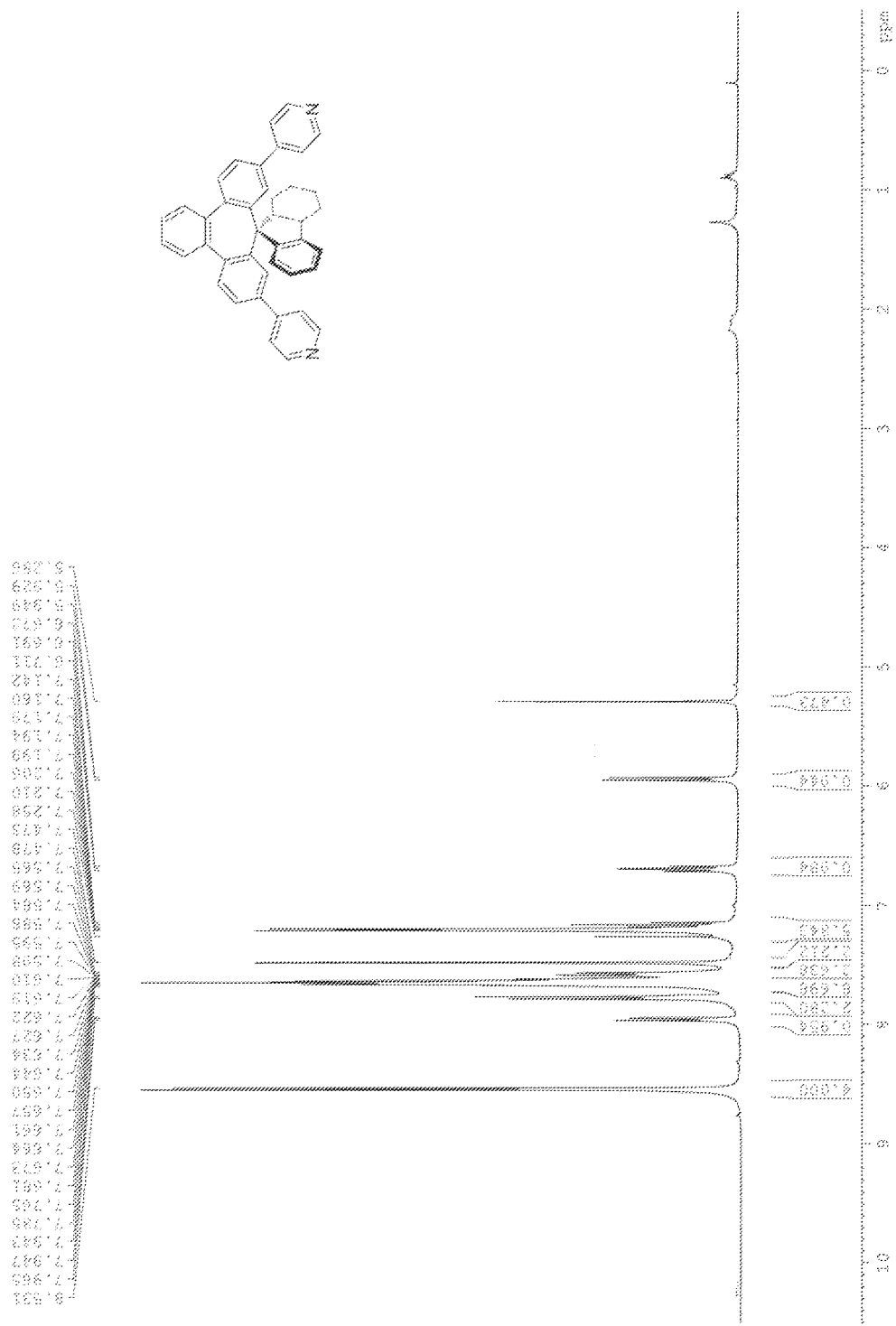
Figure 13:
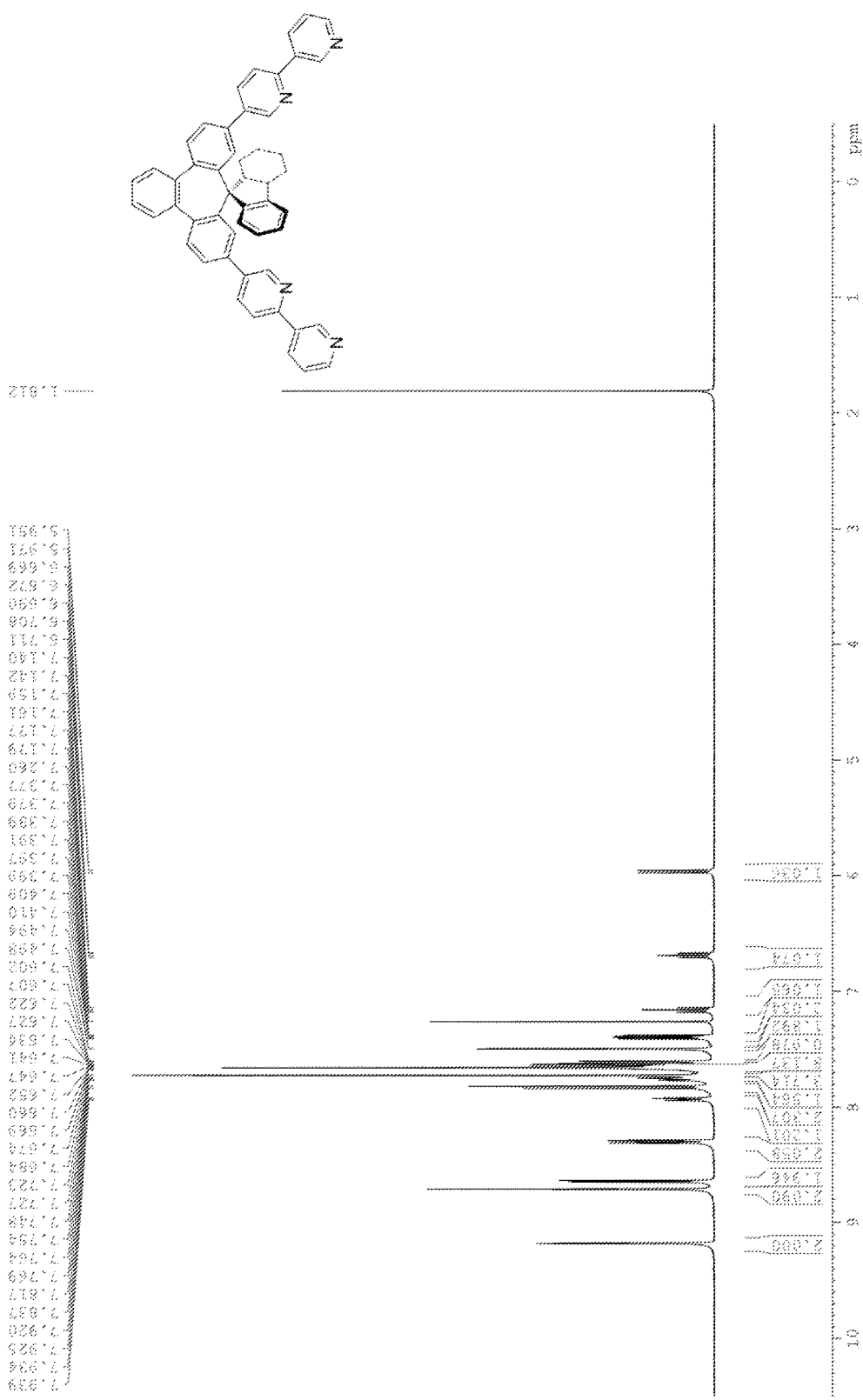
Figure 14:
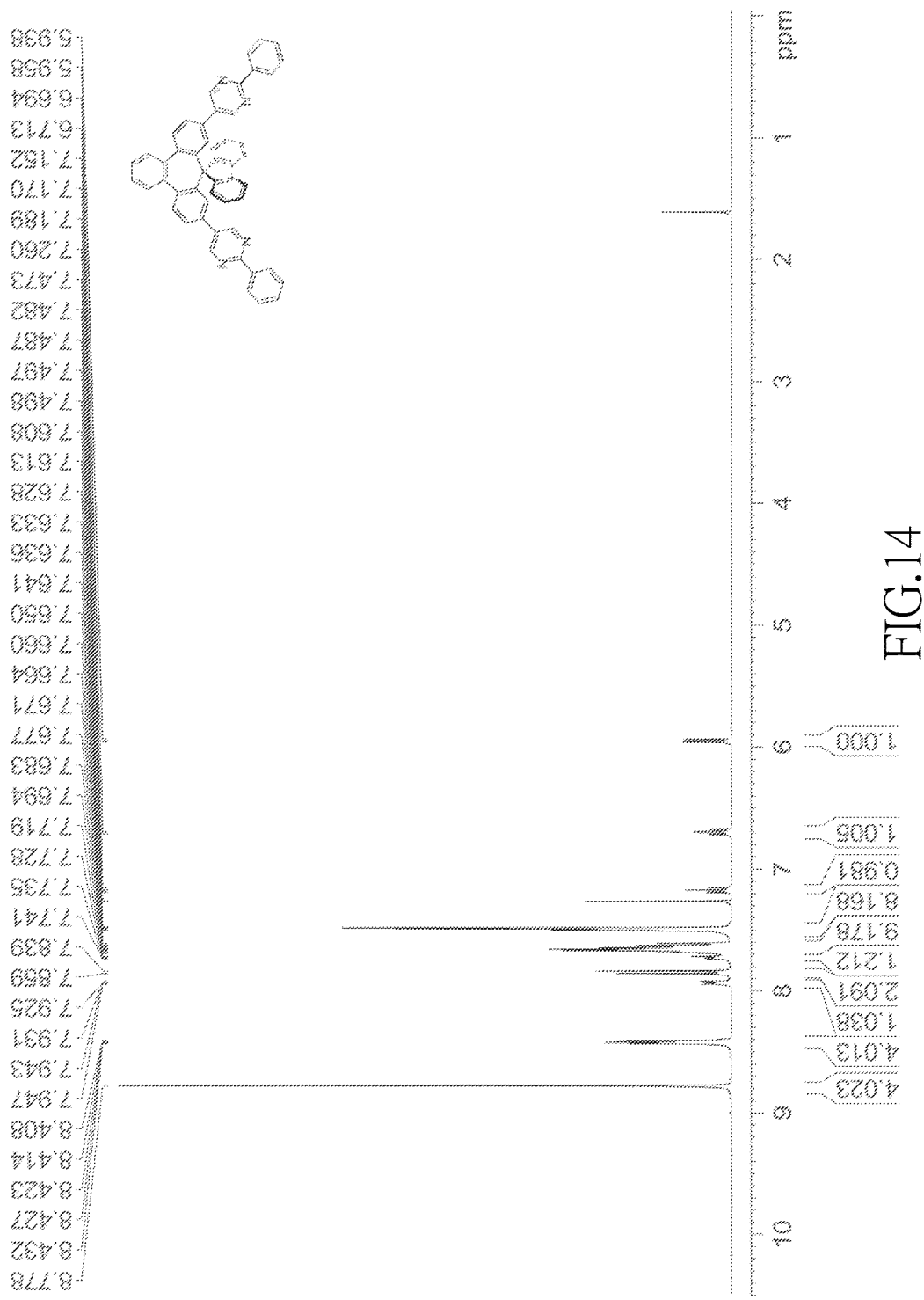
Figure 15:
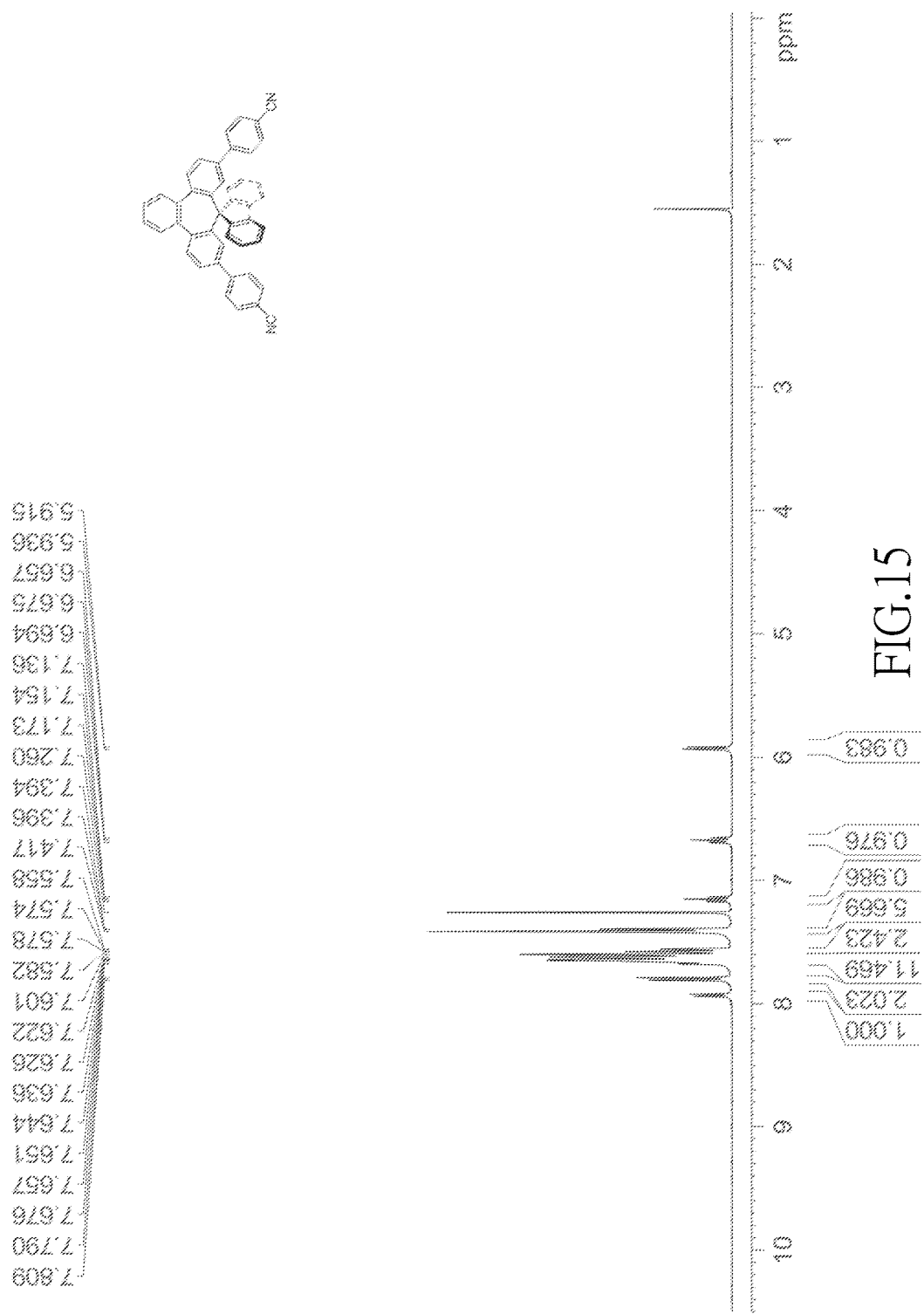

The reactants and intermediates adopted to synthesize Compounds I to XIV were listed in Table 4. Compounds I to XIV were identified by $^1$H-NMR and FD-MS, and the chemical structure, yield, formula and mass of each of Compounds I to XIV were also listed in Table 4. According to FIGS. 2 to 15 and the mass information in Table 4, the chemical structure of Compounds I to XIV were identified as follows.

TABLE 3-2 chemical structure and CAS No. of Reactants B1 to B5.

| Reactant No. | Reactant B1 | Reactant B2 | Reactant B3 |
|---|---|---|---|
| Chemical Structure | 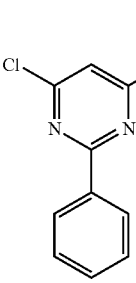 | 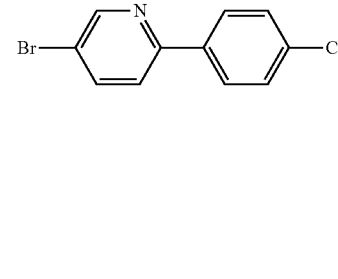 | 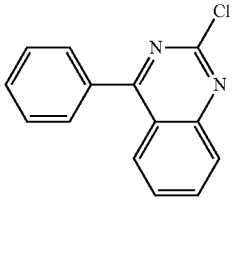 [SMILES: Clc1nc(-c2ccccc2)c2ccccc2n1] |
| CAS No. | [29509-91-9] | [916653-46-8] | [29874-83-7] |

| Reactant No. | Reactant B4 | Reactant B5 |
|---|---|---|
| Chemical Structure | 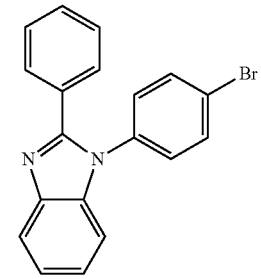 [SMILES: Brc1ccc(-n2c(-c3ccccc3)nc3ccccc32)cc1] | 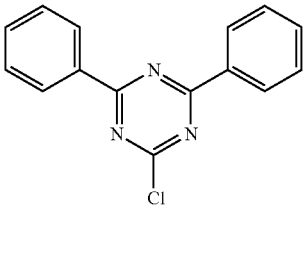 [SMILES: Clc1nc(-c2ccccc2)nc(-c2ccccc2)n1] |
| CAS No. | [867044-33-5] | [3842-55-5] |

TABLE 4
reactants and intermediates adopted to prepare Compounds I to XIV (abbreviated as Cpd. I to XIV) and their yields, formulae, and FD-MS data.
| Cpd. No. | Reactant No. | Intermediate No. | Chemical Structure of Claimed Compound | Yield | Formula/ Mass (M+) |
|---|---|---|---|---|---|
| I | A2 | B1 | 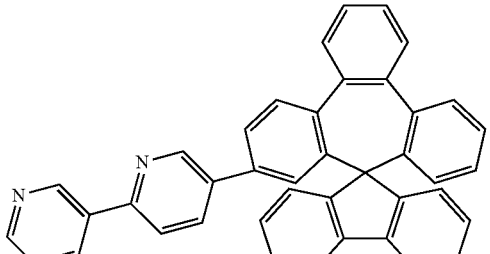 | 81.7 | $C_{41}H_{26}N_2$/ 546.66 |
| II | A3 | B1 | 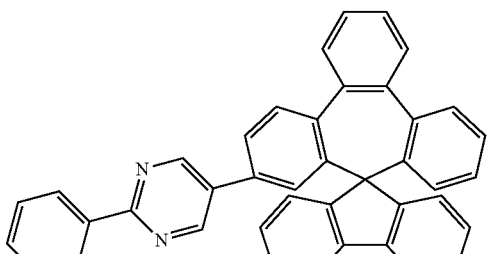 | 78.0 | $C_{41}H_{26}N_2$/ 546.66 |
| III | B1 | C1 | 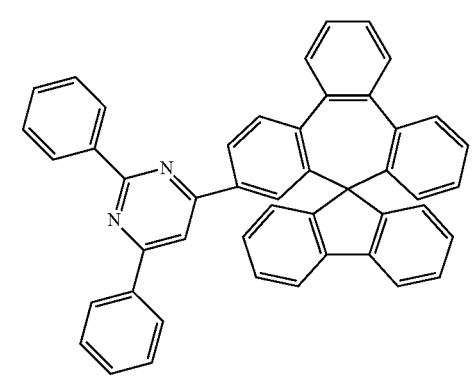 [SMILES: c1ccc(-c2cc(-c3ccc4c(c3)C3(c5ccccc5-c5ccccc5-4)c4ccccc4-c4ccccc43)nc(-c3ccccc3)n2)cc1] | 85.1 | $C_{47}H_{30}N_2$/ 622.75 |
| IV | B3 | C1 | 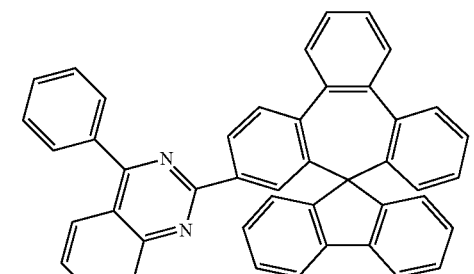 | 83.6 | $C_{45}H_{28}N_2$/ 596.72 |

TABLE 4-continued reactants and intermediates adopted to prepare Compounds I to XIV
(abbreviated as Cpd. I to XIV) and their yields, formulae, and FD-MS data.

| Cpd. No. | Reactant No. | Intermediate No. | Chemical Structure of Claimed Compound | Yield | Formula/ Mass ($M^+$) |
|---|---|---|---|---|---|
| V | B4 | C1 | | 77.8 | $C_{50}H_{32}N_2$/ 660.8 |
| VI | B5 | C1 | | 80.4 | $C_{46}H_{29}N_3$/ 623.74 |
| VII | B5 | C2 | | 82.9 | $C_{46}H_{29}N_3$/ 623.74 |
| VIII | B2 | C1 | | 82.3 | $C_{43}H_{26}N_2$/ 570.68 |

TABLE 4-continued reactants and intermediates adopted to prepare Compounds I to XIV
(abbreviated as Cpd. I to XIV) and their yields, formulae, and FD-MS data.

| Cpd. No. | Reactant No. | Intermediate No. | Chemical Structure of Claimed Compound | Yield | Formula/ Mass (M⁺) |
|---|---|---|---|---|---|
| IX | A6 | B3 | | 71.5 | $C_{45}H_{26}N_2$/ 594.71 |
| X | A5 | B3 | | 70.7 | $C_{57}H_{34}N_2$/ 746.88 |
| XI | A4 | B3 | | 68.2 | $C_{41}H_{26}N_2$/ 546.66 |
| XII | A2 | B3 | | 62.1 | $C_{51}H_{32}N_4$/ 700.83 |
| XIII | A3 | B3 | | 76.4 | $C_{51}H_{32}N_4$/ 700.83 |

TABLE 4-continued reactants and intermediates adopted to prepare Compounds I to XIV
(abbreviated as Cpd. I to XIV) and their yields, formulae, and FD-MS data.

| Cpd. No. | Reactant No. | Intermediate No. | Chemical Structure of Claimed Compound | Yield | Formula/ Mass (M+) |
|---|---|---|---|---|---|
| XIV | A1 | B3 | 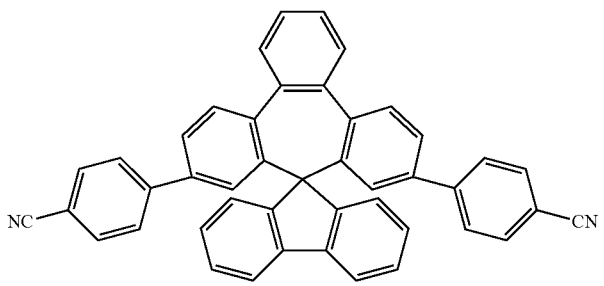 [SMILES: N#Cc1ccc(-c2ccc3c(c2)C2(c4cc(-c5ccc(C#N)cc5)ccc4-c4ccccc4-3)c3ccccc3-c3ccccc32)cc1] | 79.3 | C₄₅H₂₆N₂/ 594.70 |

Modifications of Compounds I to XIV In addition to the Compounds I to XIV, one person skilled in the art can adopt any intermediates other than Intermediates B1 to B3 or Intermediates C1 to C3 and any other reactants to successfully synthesize other desired novel compounds through a reaction mechanism similar to Scheme I or II.

Preparation of OLED Devices

A glass substrate coated with ITO layer (abbreviated in ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples and Comparative Examples as stated above. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and HID; HI-2 was a material for forming HIL-2; HT-1 and HT-2 were materials for forming HTL-1 and HTL-2; conventional ET and novel compounds of the present invention were ET materials for forming ETL; Liq was a material for forming ETD and EIL. RH/GH/BH were host materials for forming REL/GEL/BEL, and RD/GD/BD-1/BD-2 were dopants for forming REL/GEL/BEL. The main difference of the OLEDs between Example and Comparative Example was that the ETL of OLED in following comparative examples was made of BCP but the ETL of OLED in following examples was made of the novel compounds of the present invention were listed in Table 4. The detailed chemical structures of foresaid commercial materials were listed in Table 5.

TABLE 5 chemical structures of commercial materials for OLED devices.

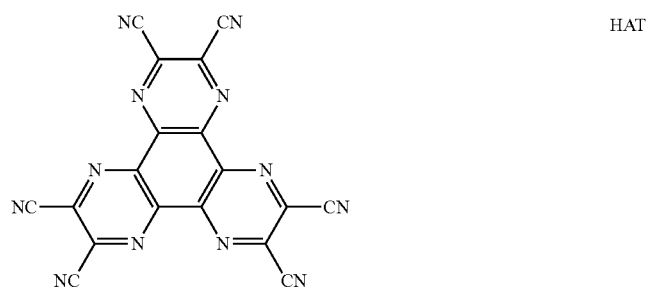

HAT

TABLE 5-continued
chemical structures of commercial materials for OLED devices.
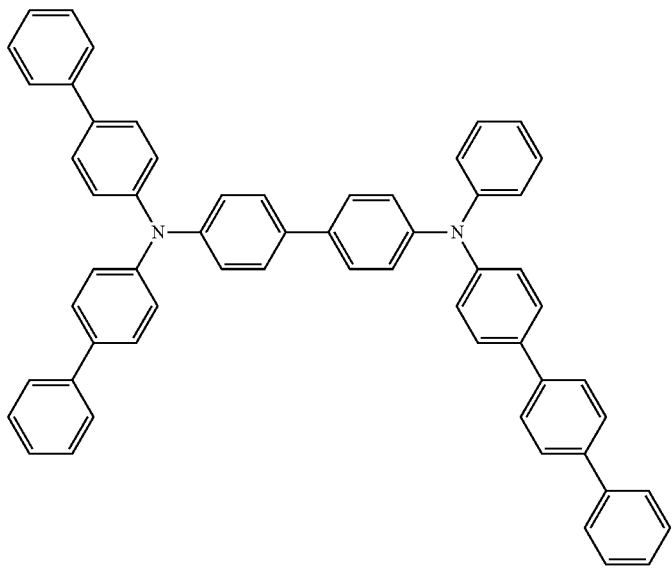 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
HI-2
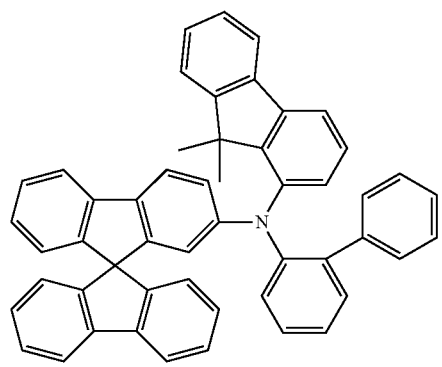 [SMILES: CC1(C)c2ccccc2-c2cccc(N(c3ccc4c(c3)C3(c5ccccc5-c5ccccc53)c3ccccc3-4)c3ccccc3-c3ccccc3)c21]
HT-1
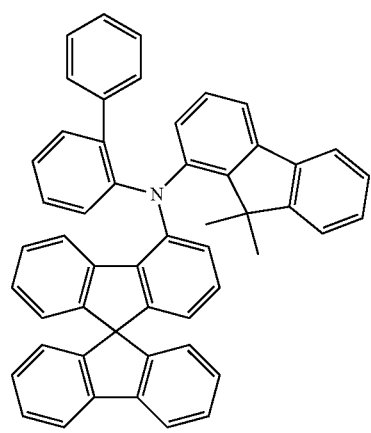 [SMILES: CC1(C)c2ccccc2-c2cccc(N(c3ccccc3-c3ccccc3)c3cccc4c3-c3ccccc3C43c4ccccc4-c4ccccc43)c21]
HT-2

TABLE 5-continued
chemical structures of commercial materials for OLED devices.
BH
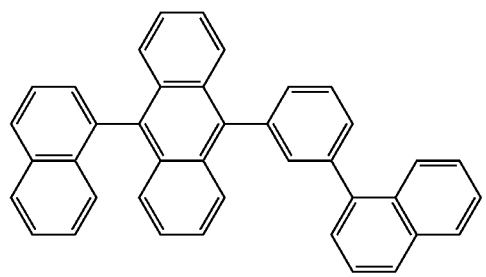 [SMILES: c1cc(-c2cccc3ccccc23)cc(-c2c3ccccc3c(-c3cccc4ccccc34)c3ccccc23)c1]
BD-1
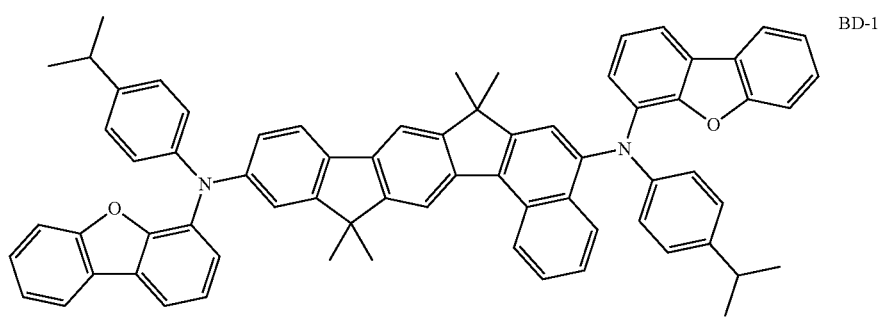
BD-2
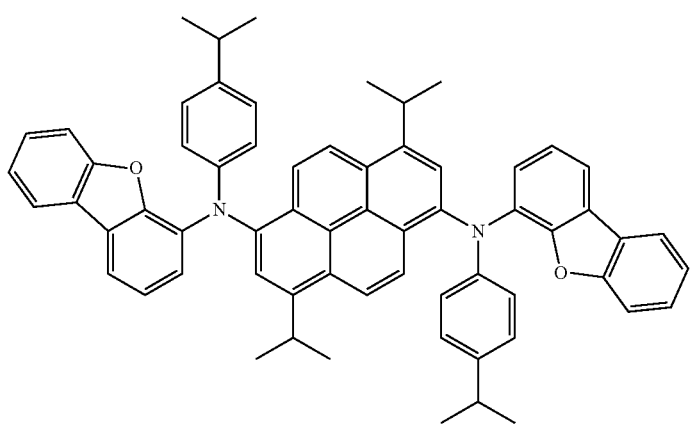 [SMILES: CC(C)c1ccc(N(c2cc(C(C)C)c3ccc4c(N(c5ccc(C(C)C)cc5)c5cccc6c5oc5ccccc56)cc(C(C)C)c5ccc2c3c54)c2cccc3c2oc2ccccc23)cc1]
GH
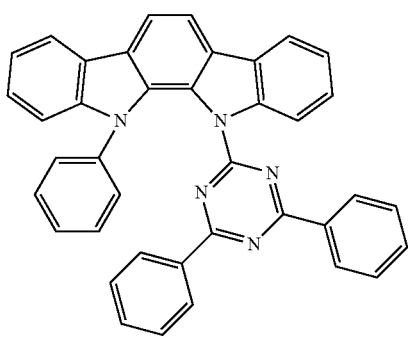 [SMILES: c1ccc(-c2nc(-c3ccccc3)nc(-n3c4ccccc4c4ccc5c6ccccc6n(-c6ccccc6)c5c43)n2)cc1]

TABLE 5-continued
chemical structures of commercial materials for OLED devices.
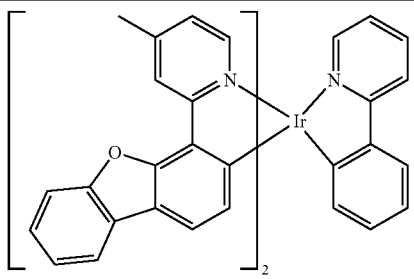
GD
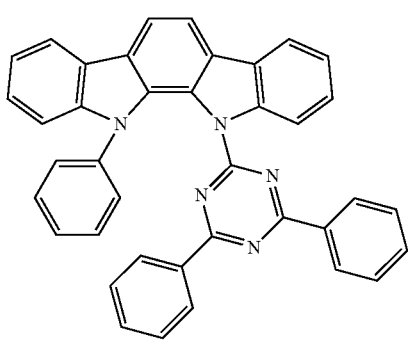 [SMILES: c1ccc(-c2nc(-c3ccccc3)nc(-n3c4ccccc4c4ccc5c6ccccc6n(-c6ccccc6)c5c43)n2)cc1]
RH
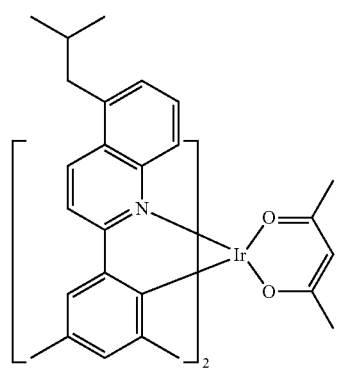
RD
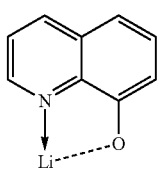
Liq
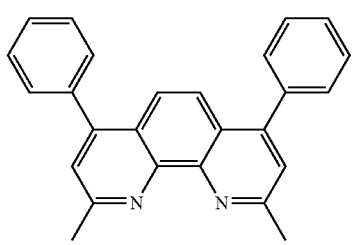 [SMILES: Cc1cc(-c2ccccc2)c2ccc3c(-c4ccccc4)cc(C)nc3c2n1]
BCP Preparation of Red OLED Devices To prepare the red OLED device, multiple organic layers were respectively deposited on the ITO substrate according to the sequence as listed in Table 6, and the materials and the thicknesses of the organic layers in red OLED devices were also listed in Table 6.

TABLE 6 coating sequence, materials and thickness of the organic layers in red OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 2100 Å |
| 3 | HTL-1 | HT-1 | 100 Å |
| 4 | HTL-2 | HT-2 | 100 Å |
| 5 | REL | RH doped with 3.5 wt % of RD and 10.0 wt % of HT-2 | 300 Å |
| 6 | ETL | ET material doped with 35.0 wt % of Liq | 350 Å |
| 7 | EIL | Liq | 15 Å |
| 8 | Cthd | Al | 1500 Å |

Preparation of Green OLED Devices

To prepare the green OLED device, multiple organic layers were respectively deposited on the ITO substrate according to the sequence as listed in Table 7, and the materials and the thicknesses of the organic layers in green OLED devices were also listed in Table 7.

TABLE 7 coating sequence, materials and thickness of the layers in green OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 1300 Å |
| 3 | HTL-1 | HT-1 | 100 Å |
| 4 | HTL-2 | HT-2 | 100 Å |
| 5 | GEL | GH doped with 10.0 wt % of GD and 15.0 wt % of HT-2 | 400 Å |
| 6 | ETL | ET material doped with 35.0 wt % of Liq | 350 Å |
| 7 | EIL | Liq | 15 Å |
| 8 | Cthd | Al | 1500 Å |

Preparation of Blue OLED Devices

To prepare the blue OLED device, multiple organic layers were respectively deposited on the ITO substrate according to the sequence as listed in Table 8, and the materials and the thicknesses of the organic layers in green OLED devices were also listed in Table 8.

For blue OLEDs, the dopant could be BD-1 or BD-2 as listed in Table 5. In the following Examples and Comparative Examples, the dopants of OLEDs of Examples B-4 to B-8 and Comparative Example B-1 were BD-1, and the dopants of OLEDs of Examples B-1 to B-3, and Comparative Example B-2 were BD-2.

TABLE 8 coating sequence, materials and thickness of the layers in blue OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 750 Å |
| 3 | HTL-1 | HT-1 | 100 Å |
| 4 | HTL-2 | HT-2 | 100 Å |
| 5 | BEL | BH doped with 3.5 wt % of BD-1 or BD-2 | 250 Å |
| 6 | ETL | ET material doped with 35.0 wt % of Liq | 250 Å |
| 7 | EIL | Liq | 15 Å |
| 8 | Cthd | Al | 1500 Å |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 9. For the blue and red OLED devices, the data were collected at 1000 nits. For the green OLED devices, the data were collected at 3000 nits.

The materials of ETL, color and data of CIE, driving voltage, and current efficiency of Examples R-1 to R-4 and Comparative Example R were listed in Table 9. The materials of ETL, color and data of CIE, driving voltage, and current efficiency of Examples G-1 to G-5 and Comparative Example G were listed in Table 10. The materials of ETL, color and data of CIE, driving voltage, and current efficiency of Examples B-1 to B-8 and Comparative Examples B-1 and B-2 were listed in Table 11.

TABLE 9 materials of ETL, colors, CIEs, voltages, and current efficiencies of red OLED devices of Examples R-1 to R-4 and Comparative Example R.

| Example | Material of ETL | Color, CIE (x, y) | Voltage (V) | Current Efficiency (cd/A) |
|---|---|---|---|---|
| Example R-1 | Compound I | R, (0.660, 0.339) | 3.77 | 24.5 |
| Example R-2 | Compound VII | R, (0.661, 0.338) | 3.99 | 25.1 |
| Example R-3 | Compound VIII | R, (0.661, 0.338) | 3.76 | 25.0 |
| Example R-4 | Compound XII | R, (0.665, 0.334) | 3.68 | 24.2 |
| Comparative Example R | BCP | R, (0.659, 0.340) | 4.16 | 24.1 |

TABLE 10 materials of ETL, colors, CIEs, voltages, and current efficiencies of green OLED devices of Examples G1 to G5 and Comparative Example G.

| Example | Material of ETL | Color, CIE (x, y) | Voltage (V) | Current Efficiency (cd/A) |
|---|---|---|---|---|
| Example G-1 | Compound III | G, (0.315, 0.639) | 3.81 | 76.1 |
| Example G-2 | Compound IV | G, (0.314, 0.638) | 3.82 | 76.2 |
| Example G-3 | Compound VI | G, (0.332, 0.635) | 3.00 | 76.6 |
| Example G-4 | Compound X | G, (0.342, 0.621) | 2.93 | 81.4 |
| Example G-5 | Compound XI | G, (0.336, 0.626) | 3.08 | 81.2 |
| Comparative Example G | BCP | G, (0.314, 0.638) | 3.86 | 73.7 |

TABLE 11 materials of ETL, colors, CIEs, voltages, and current efficiencies of blue OLED devices of Examples B-1 to B-8 and Comparative Examples B-1 and B-2.

| Example | Material of ETL | Color, CIE (x, y) | Voltage (V) | Current Efficiency (cd/A) |
|---|---|---|---|---|
| Example B-1 | Compound I | B, (0.129, 0.152) | 4.69 | 10.3 |
| Example B-2 | Compound III | B, (0.129, 0.163) | 4.92 | 11.4 |
| Example B-3 | Compound VI | B, (0.130, 0.153) | 4.08 | 11.6 |
| Example B-4 | Compound IX | B, (0.136, 0.173) | 4.34 | 9.24 |
| Example B-5 | Compound X | B, (0.135, 0.180) | 3.95 | 10.4 |
| Example B-6 | Compound XI | B, (0.135, 0.176) | 4.33 | 13.1 |
| Example B-7 | Compound XIII | B, (0.136, 0.166) | 4.19 | 9.32 |
| Example B-8 | Compound XIV | B, (0.136, 0.164) | 3.97 | 10.2 |
| Comparative Example B-1 | BCP | B, (0.136, 0.170) | 6.35 | 8.05 |
| Comparative Example B-2 | BCP | B, (0.130, 0.142) | 6.71 | 6.98 |

Based on the results, in comparison with the commercial electron transport material, BCP, adopting the novel compounds of the present invention as the electron transport material can reduce the driving voltage and improve the current efficiency of the red, green, or blue OLEDs. It demonstrated that the novel compound of the present invention is suitable as an electron transport material for any color OLEDs, and allows the OLEDs using the same to have low driving voltage and improved current efficiency.

Even though numerous characteristics and advantages of the present invention have been set forth in the foregoing description, together with details of the structure and features of the invention, the disclosure is illustrative only. Changes may be made in the details, especially in matters of quantity, position, and arrangement of substitution groups within the principles of the invention to the full extent indicated by the broad general meaning of the terms in which the appended claims are expressed.

What is claimed is:

1. A compound represented by the following Formula (I):

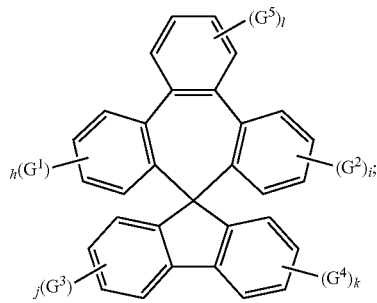

Formula (I)

wherein one of $G^1$ to $G^4$ is selected from the group consisting of: an heteroaryl group having 3 to 60 carbon atoms and containing at least one nitrogen atom, an aryl group having 6 to 60 carbon atoms and substituted with at least one functional group, and an arylboron group having 6 to 60 carbon atoms and substituted with at least one functional group, wherein said functional group is selected from the group consisting of: a cyano group, a nitro group, a trifluoromethyl group, a fluoro group, and a chloro group;

the others of $G^1$ to $G^4$ and $G^5$ are each independently selected from the group consisting of: a hydrogen atom, a deuterium atom, a halogen group, a substituted or nonsubstituted aryl group having 6 to 60 carbon atoms, a substituted or nonsubstituted heteroaryl group having 3 to 60 carbon atoms, and a substituted or nonsubstituted arylboron group having 6 to 60 carbon atoms;

wherein h, i, j, k, l are each independently an integral of 1 to 4.

2. The compound as claimed in claim 1, wherein h, i, j, k, l are each independently an integral of 1 to 2, and the total of h, i, j, k, and l is not more than 6.

3. The compound as claimed in claim 1, wherein the compound is represented by the following Formulae (I-I) to (I-XV):

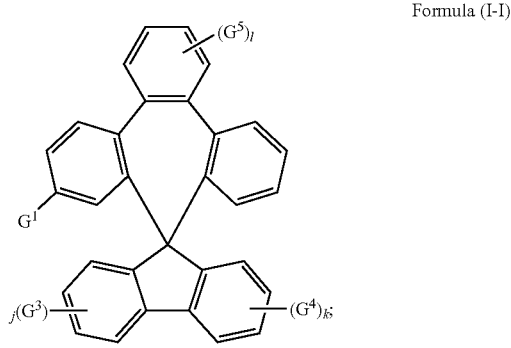

Formula (I-I)

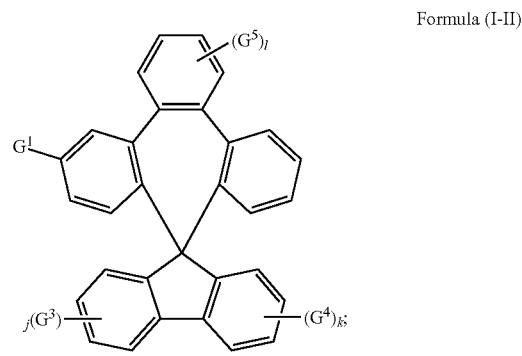

Formula (I-II)

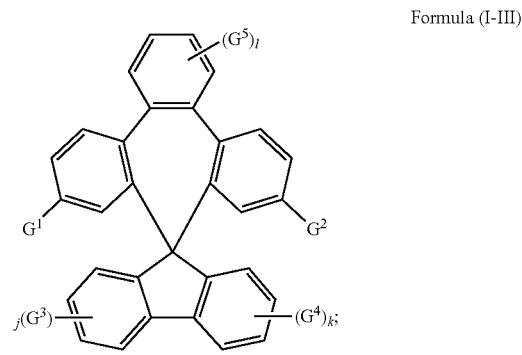

Formula (I-III)

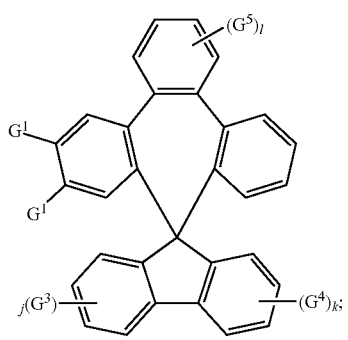
Formula (I-IV)
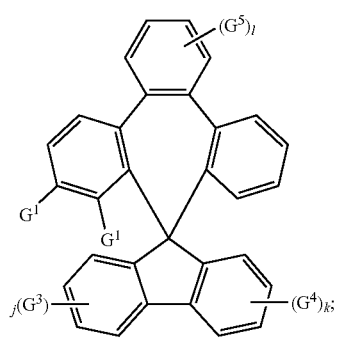
Formula (I-V)
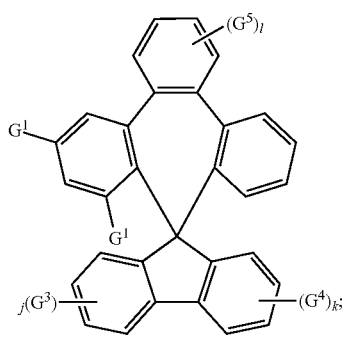
Formula (I-VI)
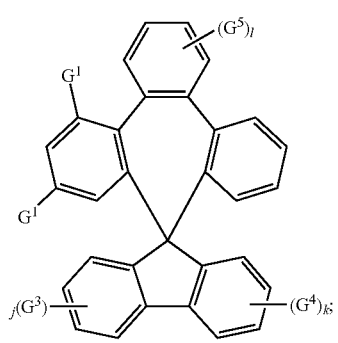
Formula (I-VII)
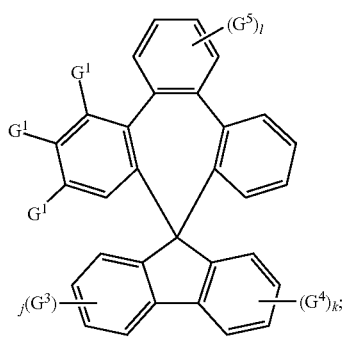
Formula (I-VIII)
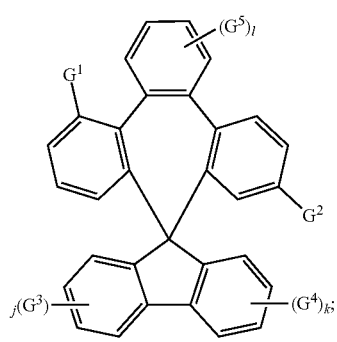
Formula (I-IX)
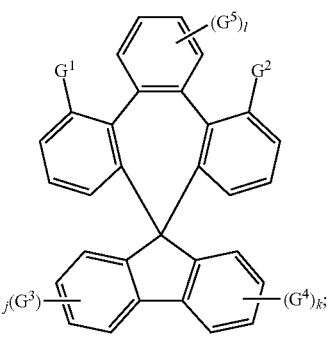
Formula (I-X)
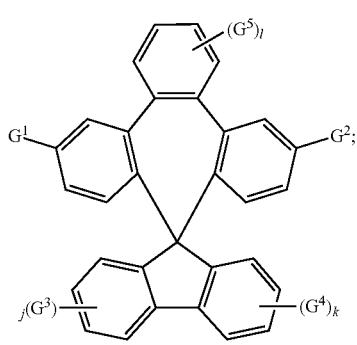
Formula (I-XI)

-continued
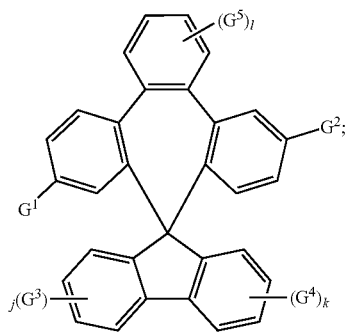
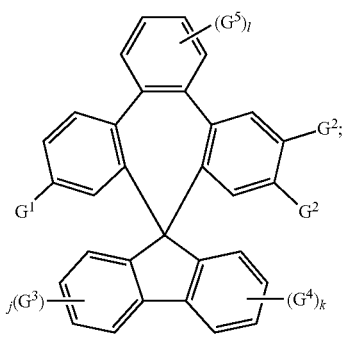
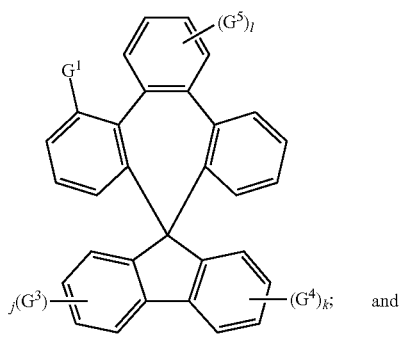
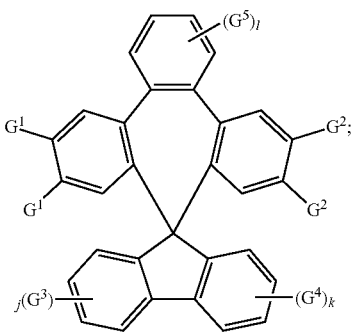
wherein j, k, l are each independently an integral of 1 to 3.
4. The compound as claimed in claim 1, wherein the heteroaryl group having 3 to 60 carbon atoms and containing the at least one nitrogen atom is selected from the group consisting of:
Formula (I-XII)
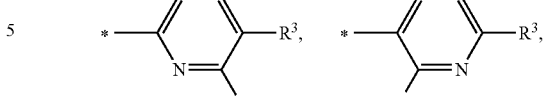
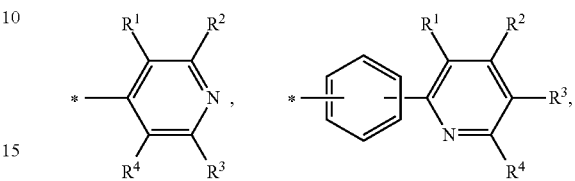
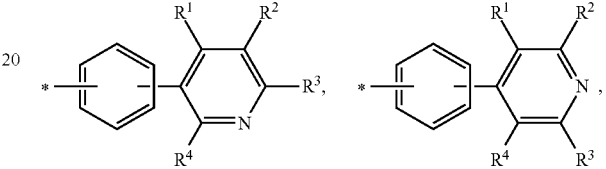
Formula (I-XIII)
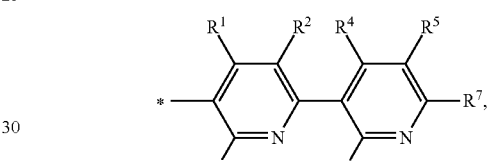
Formula (I-XIV)
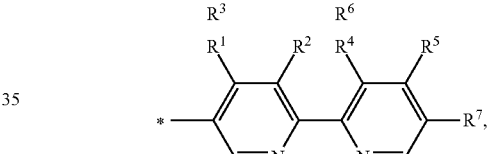
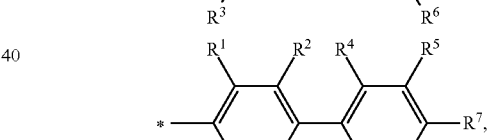
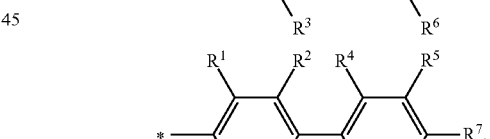
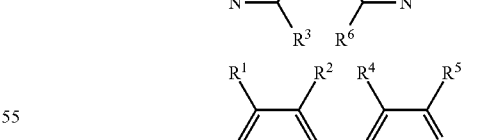
Formula (I-XV)
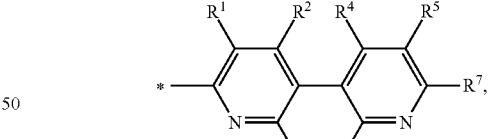
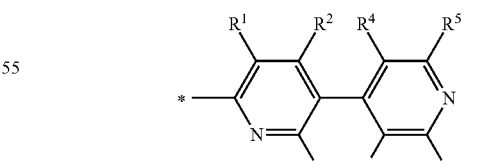
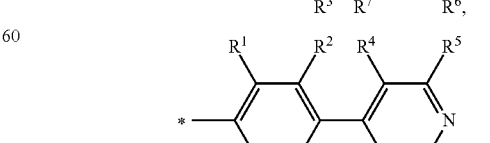
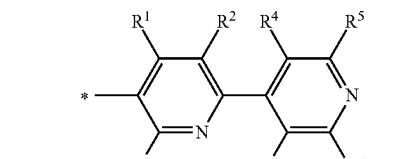

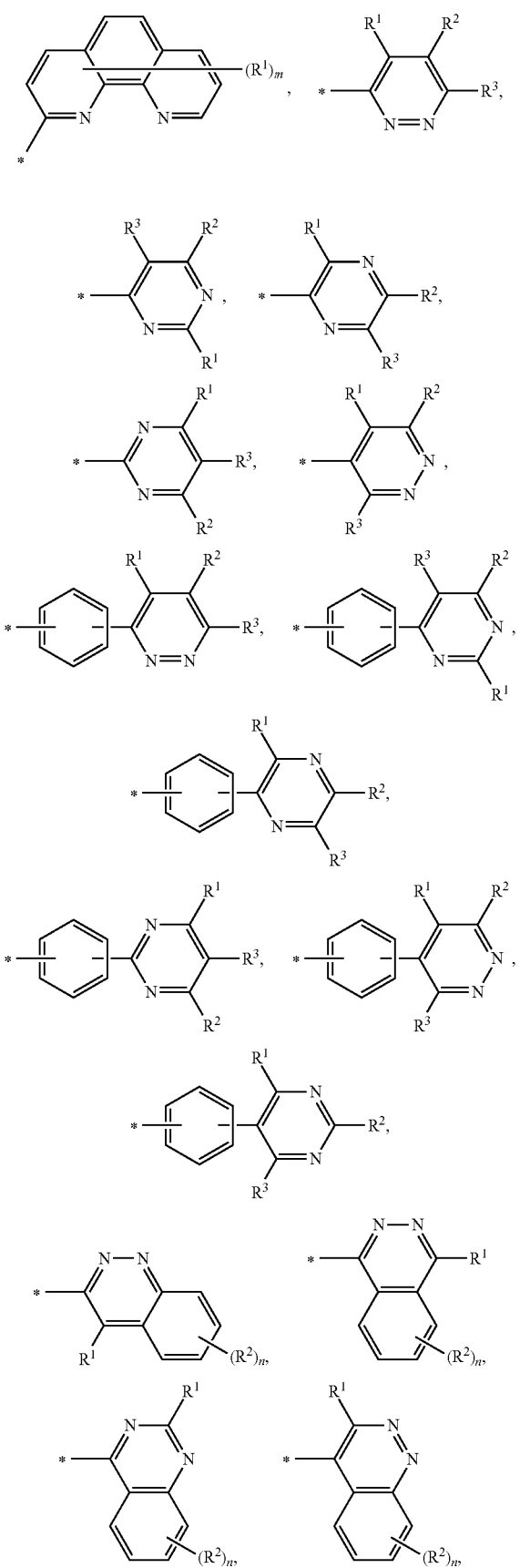
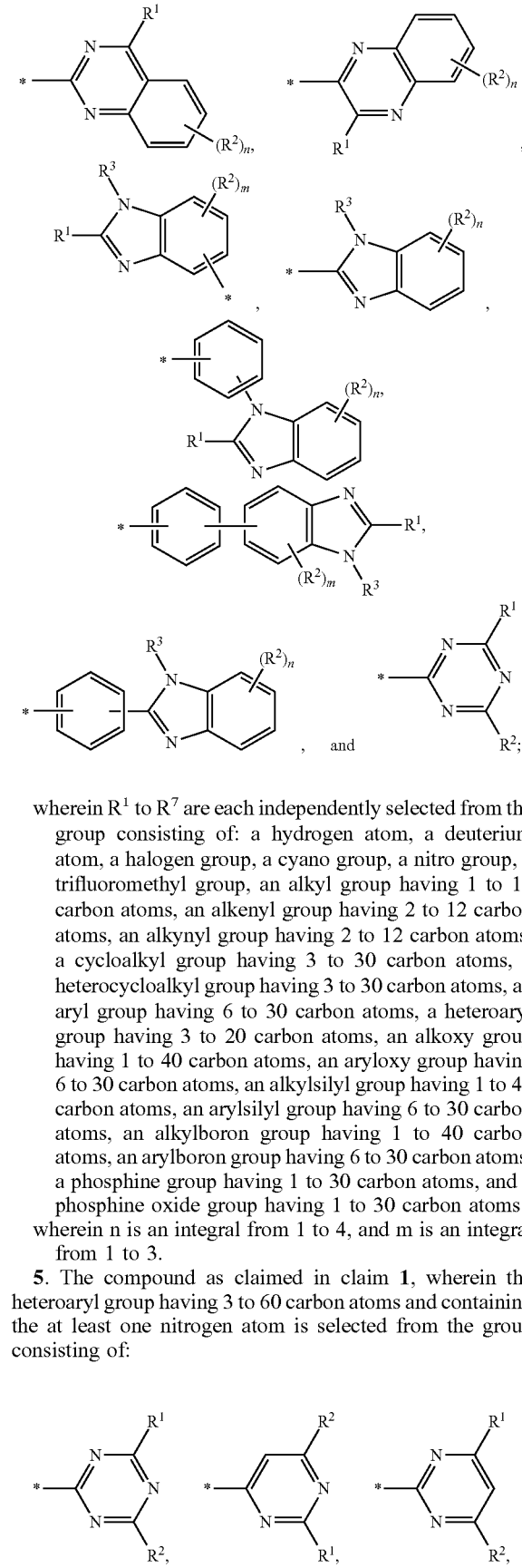

wherein $R^1$ to $R^7$ are each independently selected from the group consisting of: a hydrogen atom, a deuterium atom, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 20 carbon atoms, an alkoxy group having 1 to 40 carbon atoms, an aryloxy group having 6 to 30 carbon atoms, an alkylsilyl group having 1 to 40 carbon atoms, an arylsilyl group having 6 to 30 carbon atoms, an alkylboron group having 1 to 40 carbon atoms, an arylboron group having 6 to 30 carbon atoms, a phosphine group having 1 to 30 carbon atoms, and a phosphine oxide group having 1 to 30 carbon atoms;

wherein n is an integral from 1 to 4, and m is an integral from 1 to 3.

5. The compound as claimed in claim 1, wherein the heteroaryl group having 3 to 60 carbon atoms and containing the at least one nitrogen atom is selected from the group consisting of:

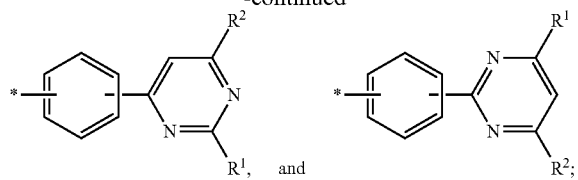

wherein $R^1$ and $R^2$ are each selected from the group consisting of: a phenyl group, a napthyl group, a pyridine group, a pyrimidine group, a pyrazine group, a pyridazine group, a cyano group, a nitro group, a trifluoromethyl group, a fluoro group, a biphenyl group, a phenylnapthyl group, a phenylpyridine group, a phenylpyrimidine group, a phenylpyrazine group, a phenylpyridazine group, a cyanophenyl group, a nitrophenyl group, and a trifluoromethylphenyl group.

6. The compound as claimed in claim 5, wherein $R^1$ and $R^2$ are each selected from the group consisting of: the pyridine group, the pyrimidine group, the pyrazine group, the pyridazine group, the cyano group, the nitro group, the trifluoromethyl group, the fluoro group, the phenylpyridine group, the phenylpyrimidine group, the phenylpyrazine group, the phenylpyridazine group, the cyanophenyl group, the nitrophenyl group, and the trifluoromethylphenyl group.

7. The compound as claimed in claim 1, wherein the heteroaryl group having 3 to 60 carbon atoms and containing the at least one nitrogen atom is selected from the group consisting of:

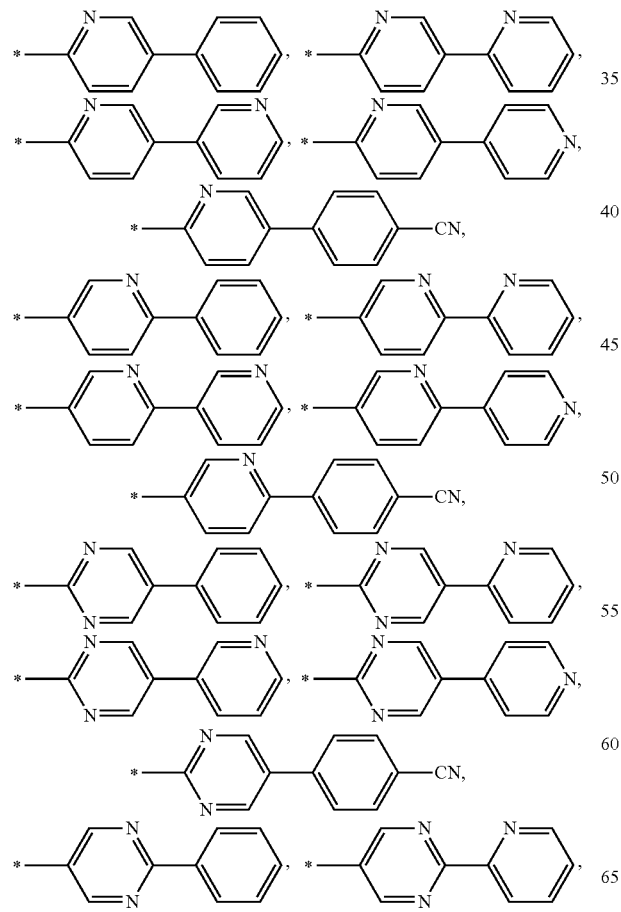

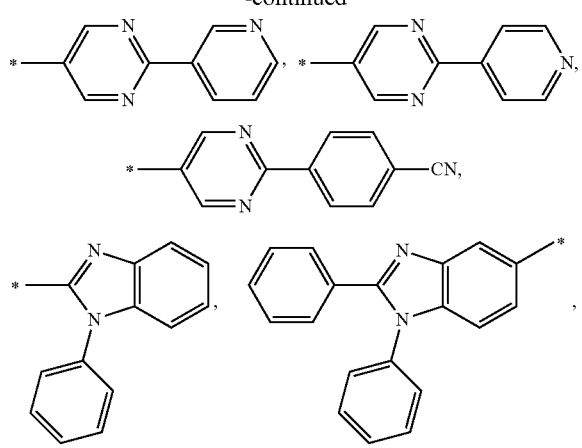

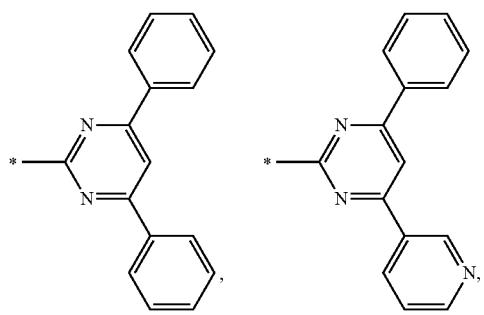

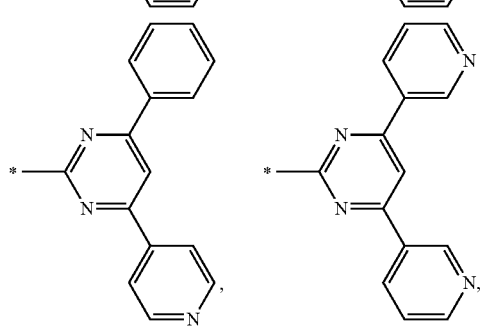

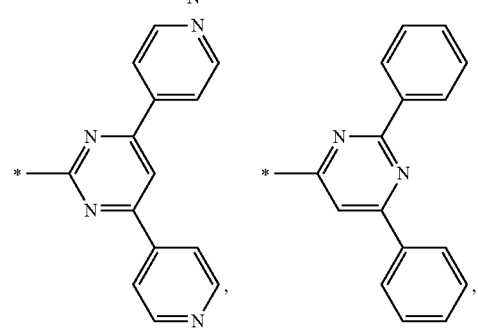

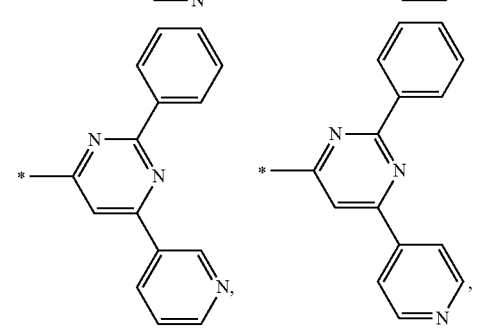

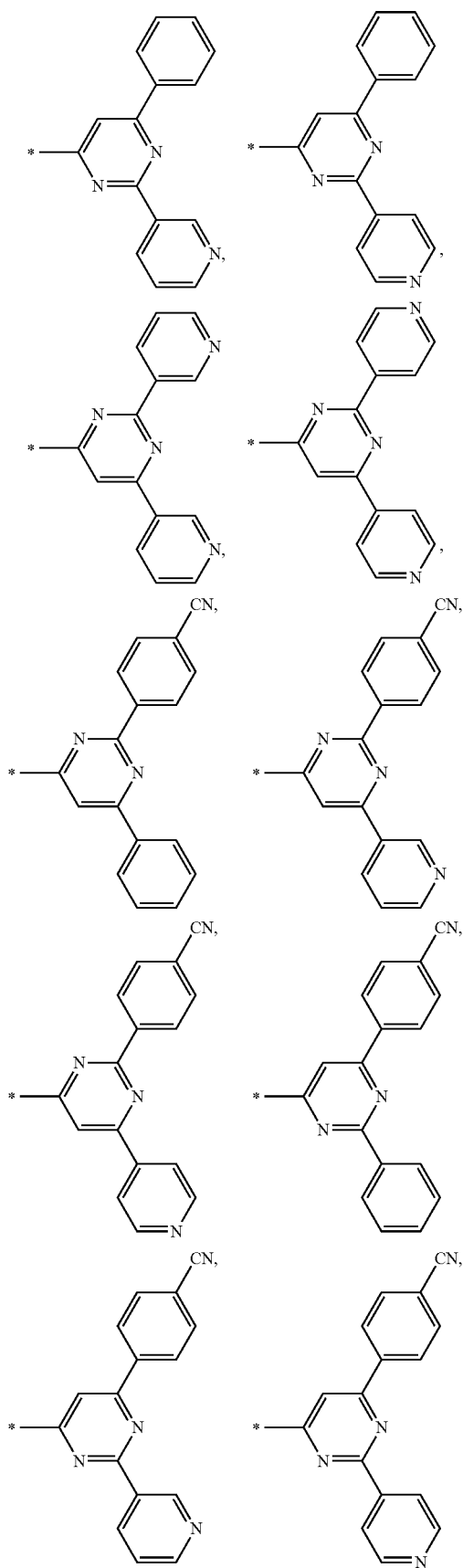
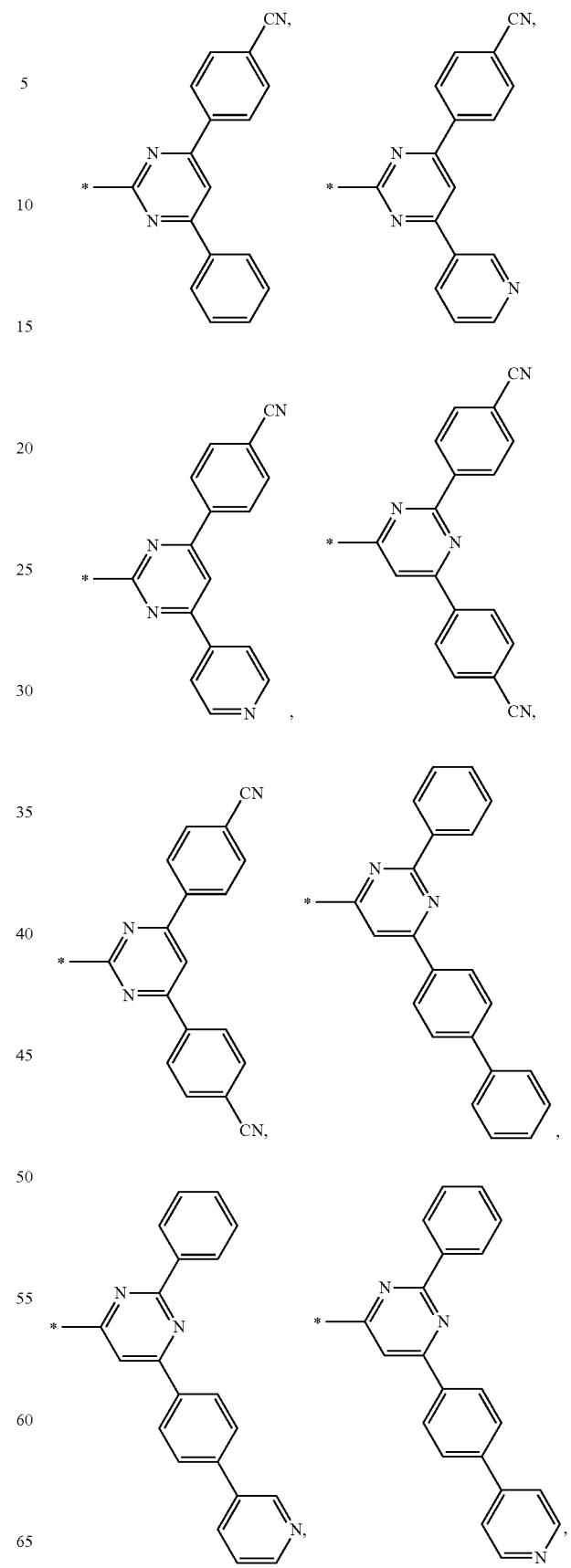

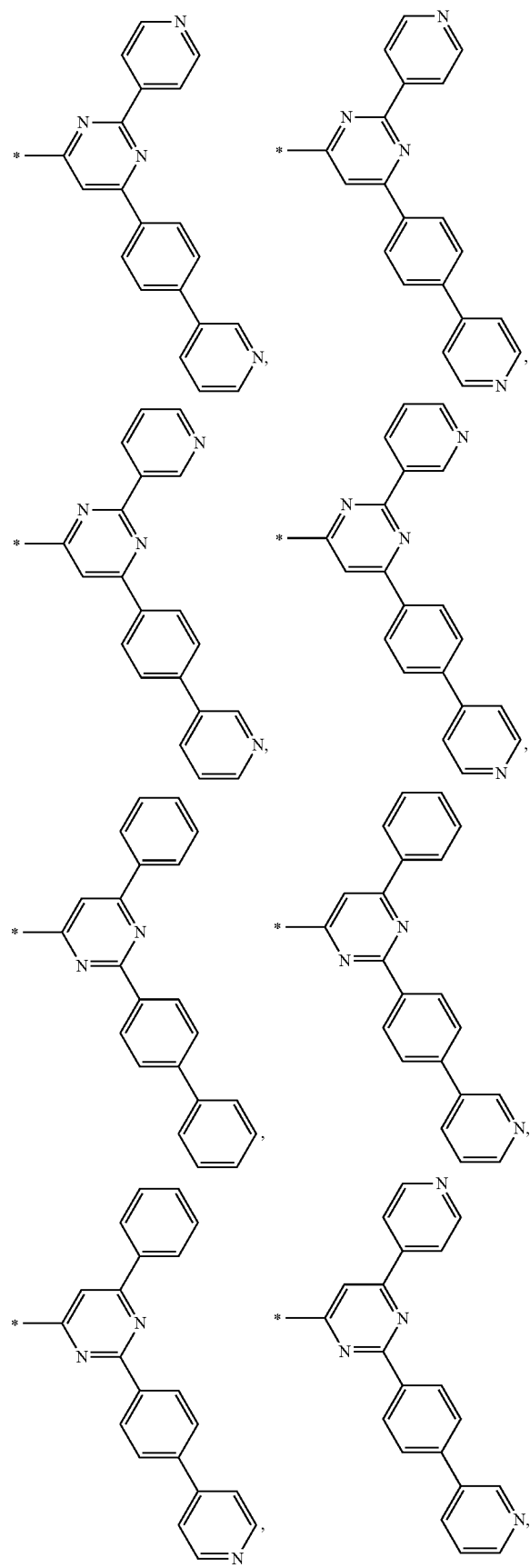
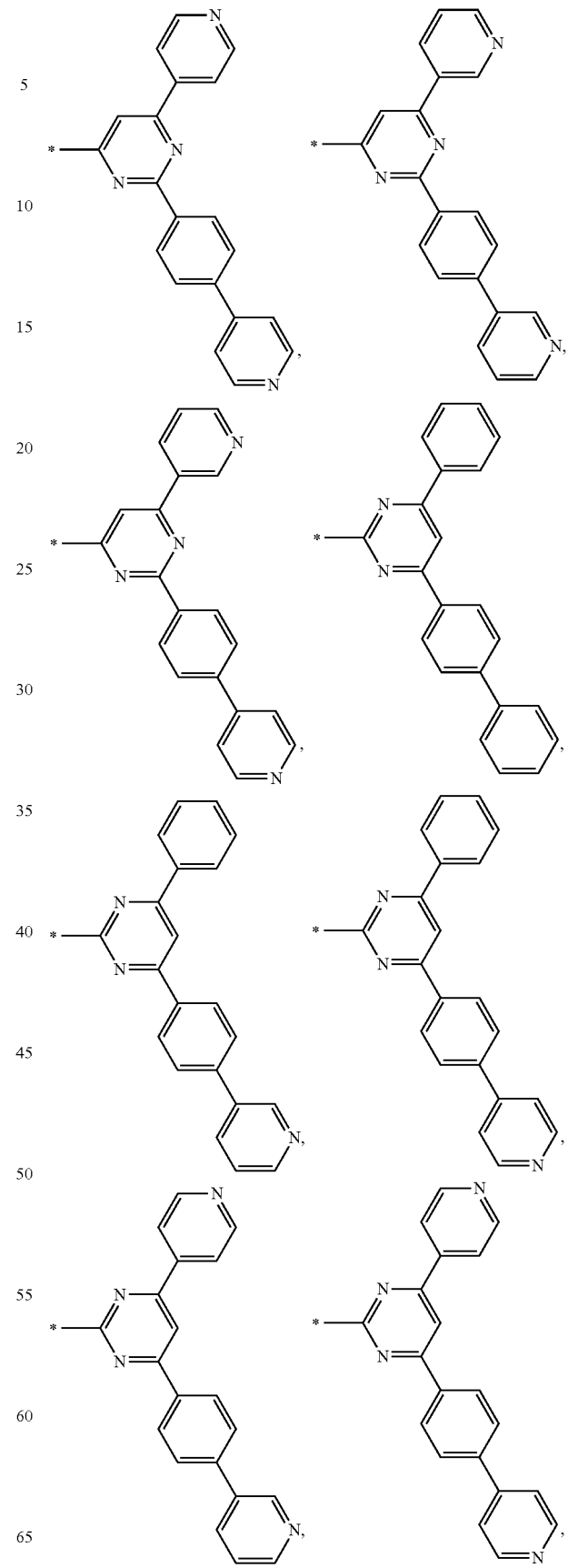

191
-continued
192
-continued
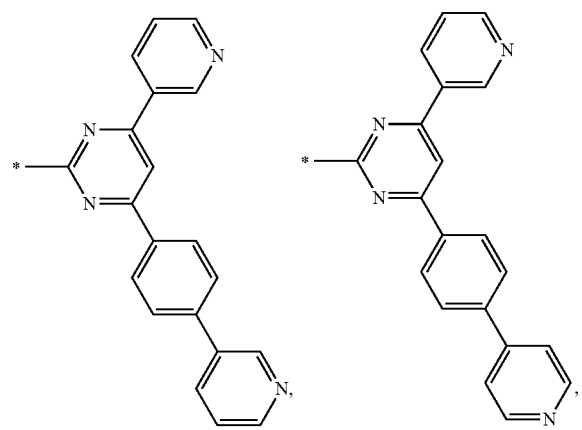
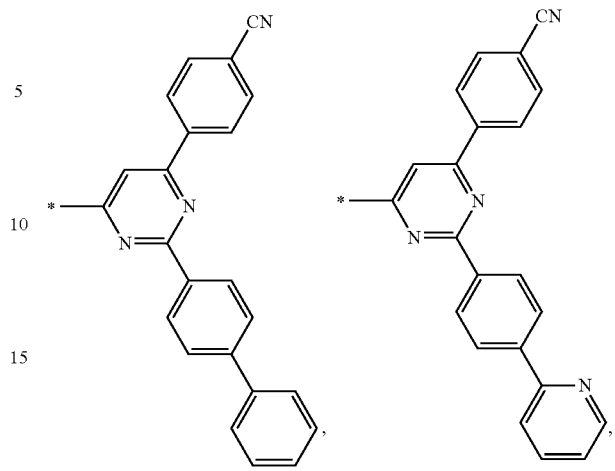
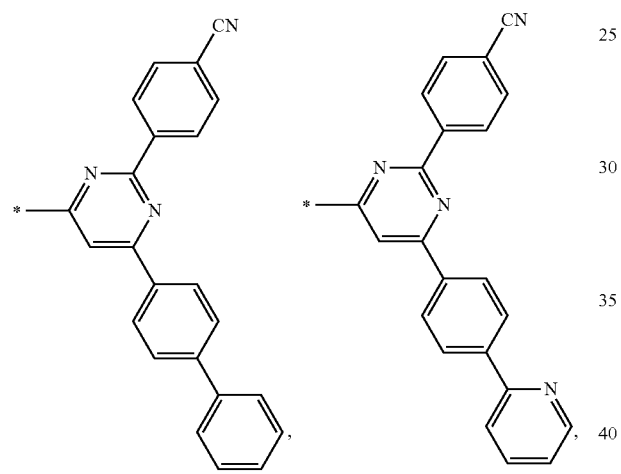
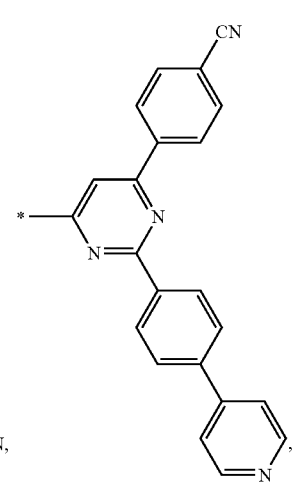
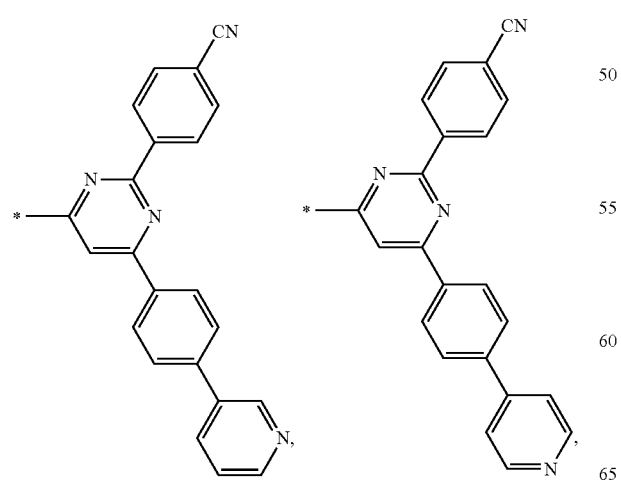
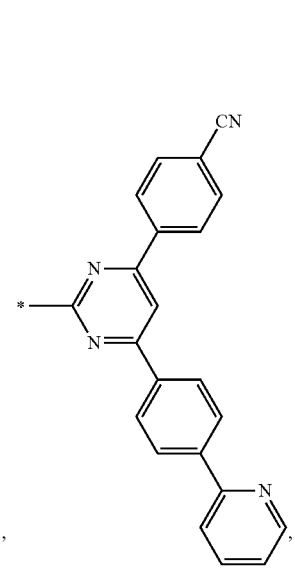

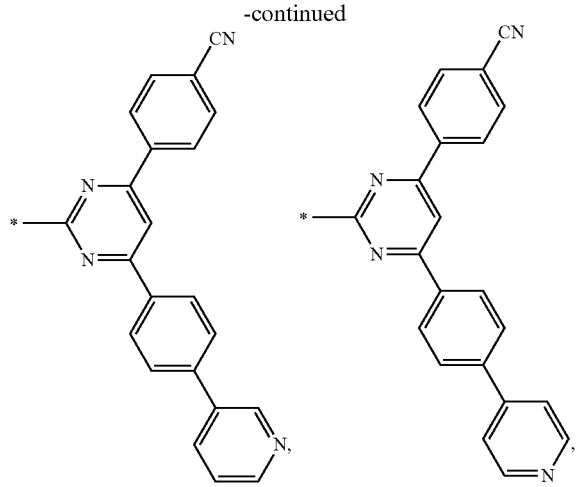
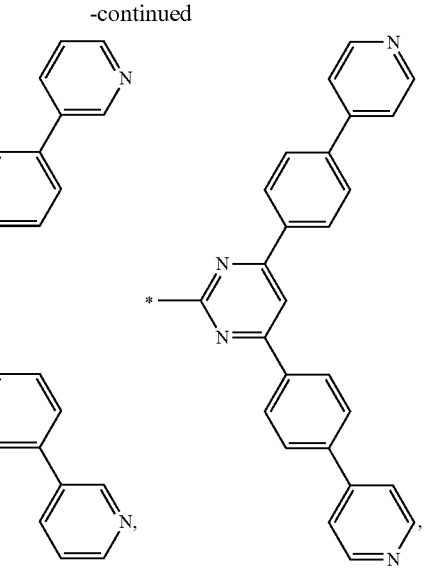
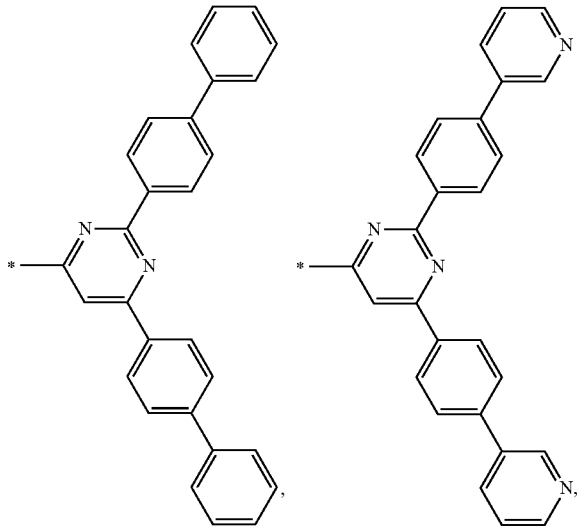
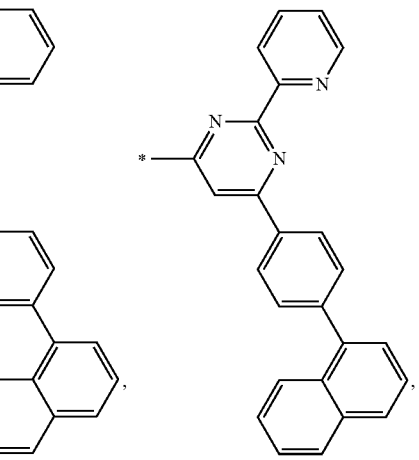
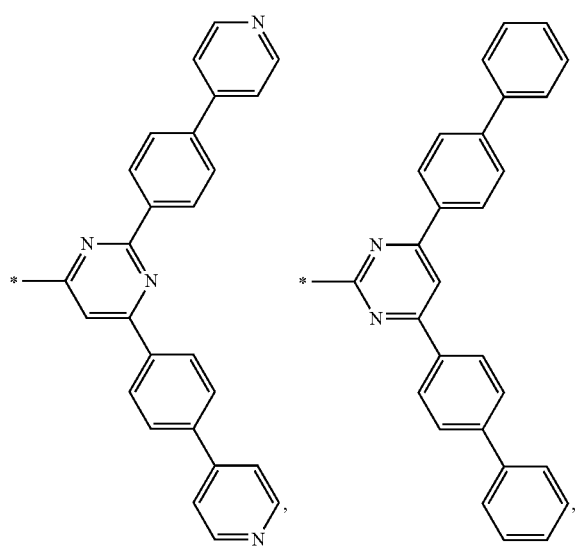

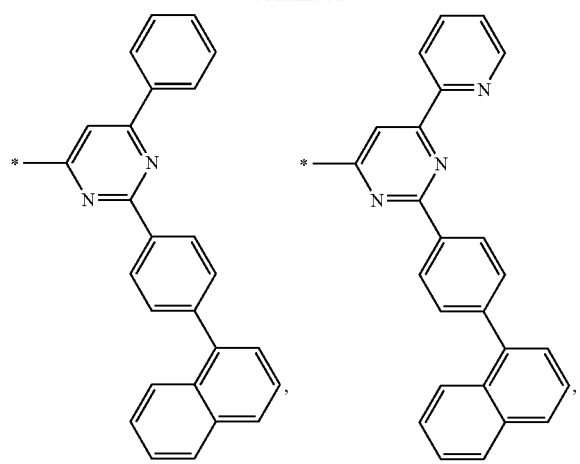
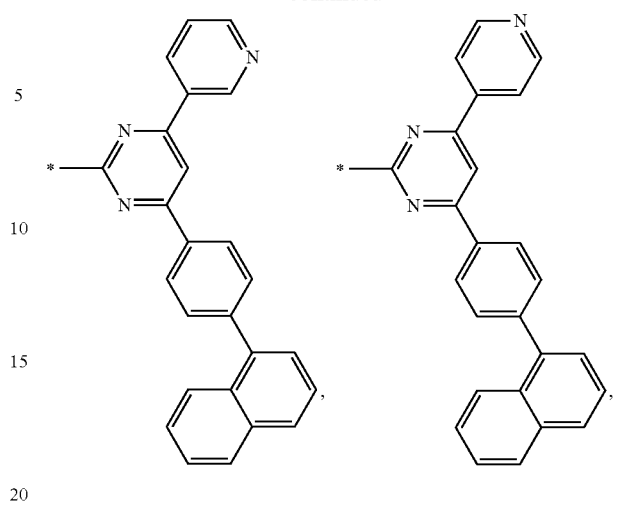
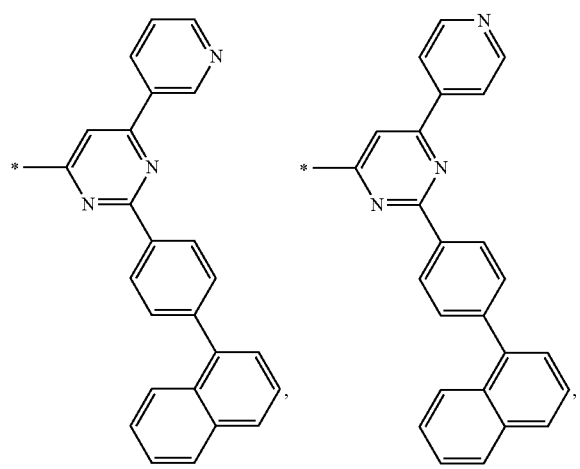
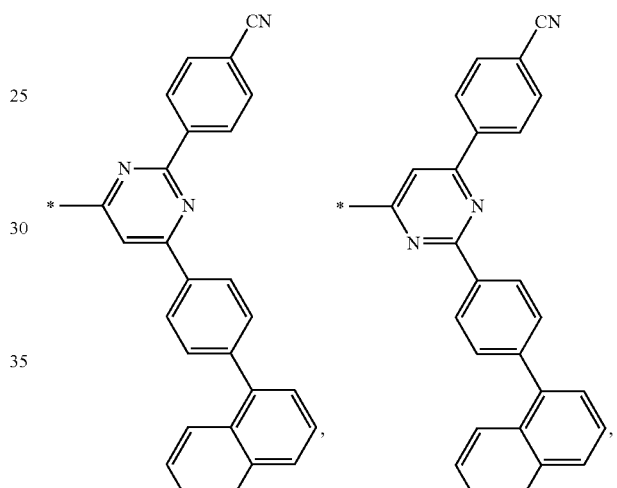
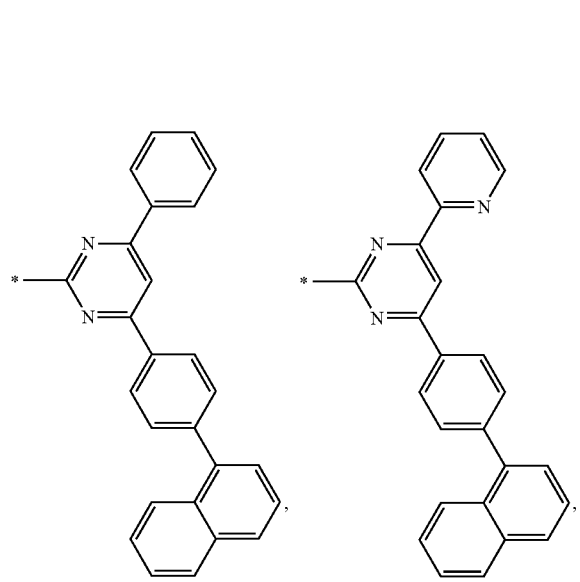
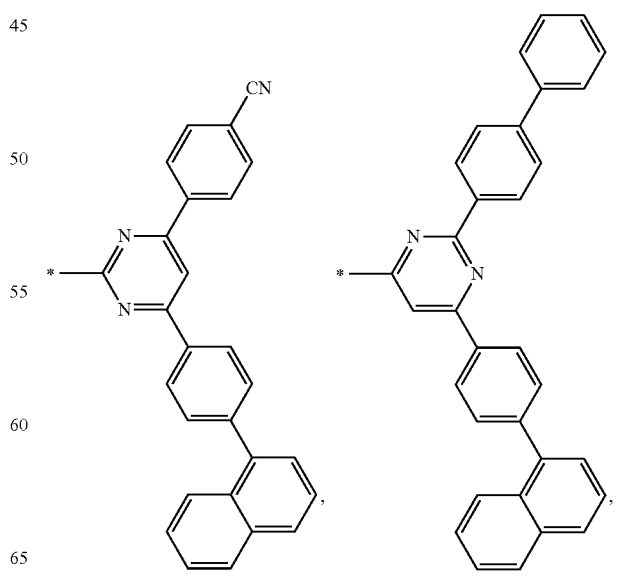

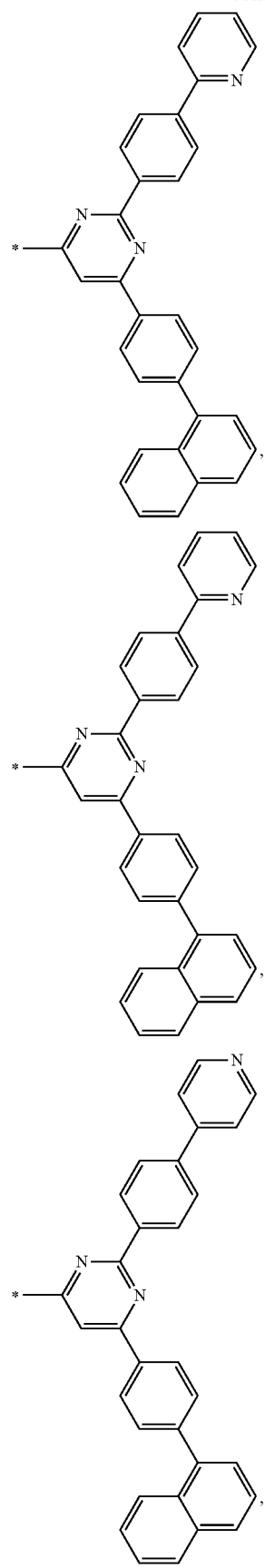
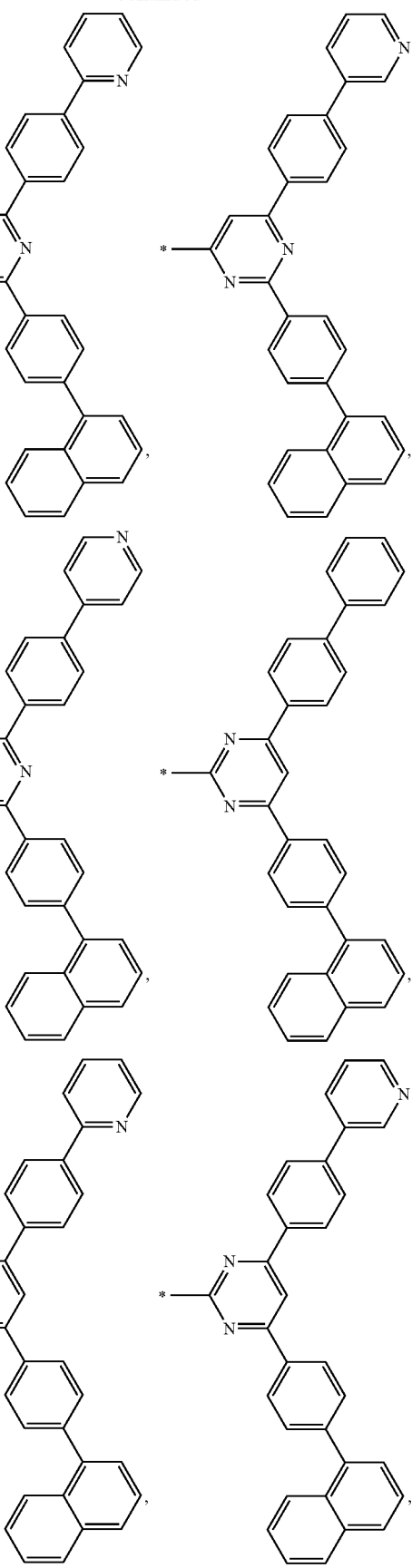

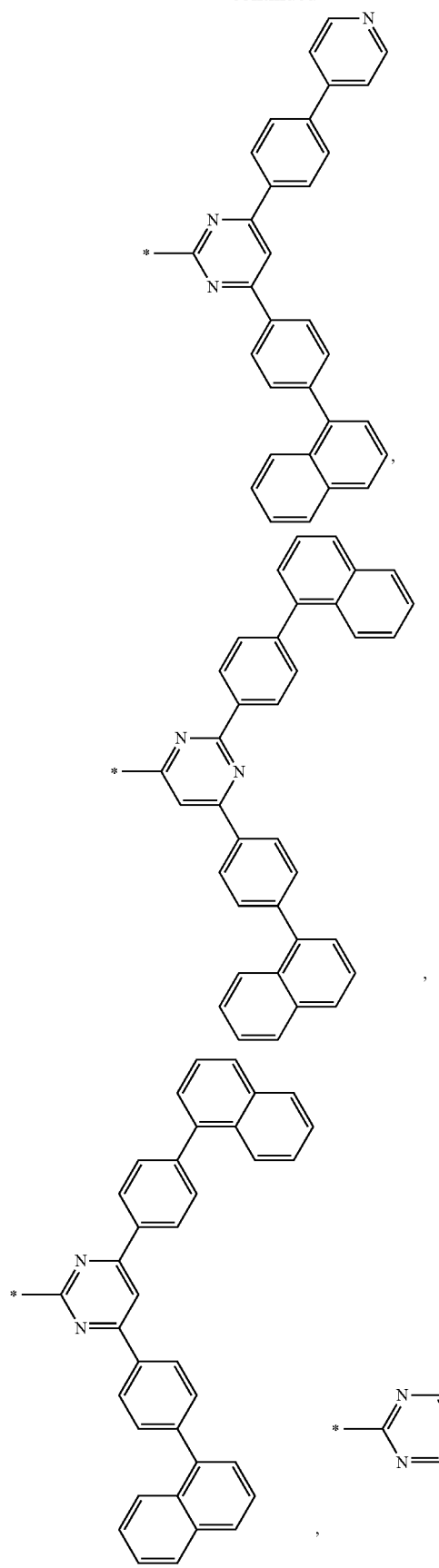
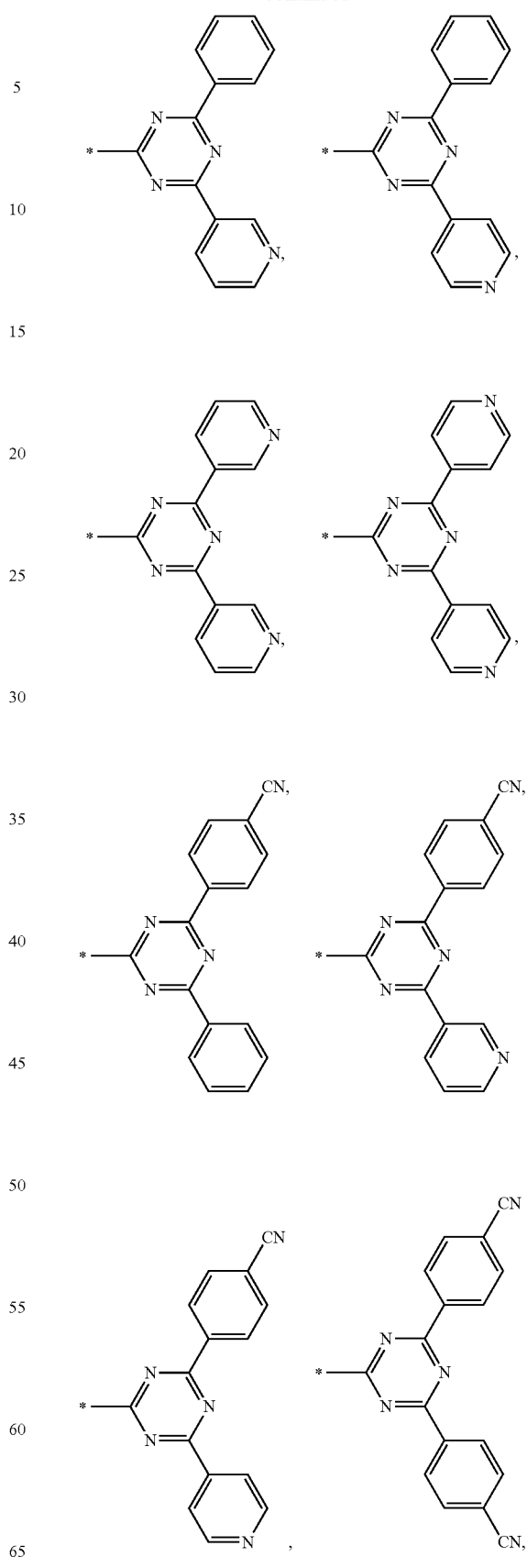

201
-continued
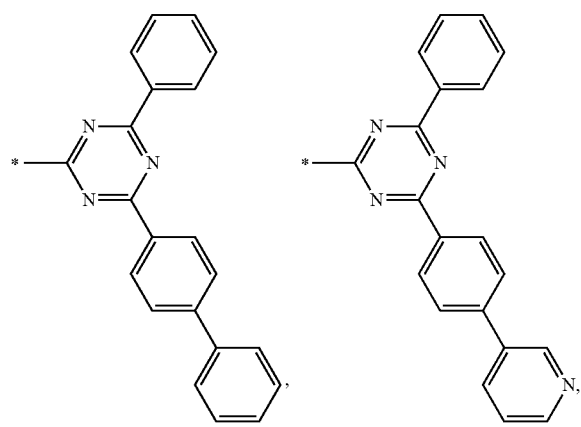
202
-continued
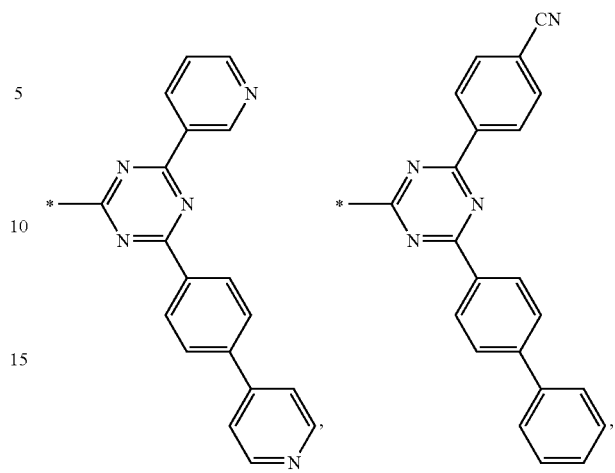
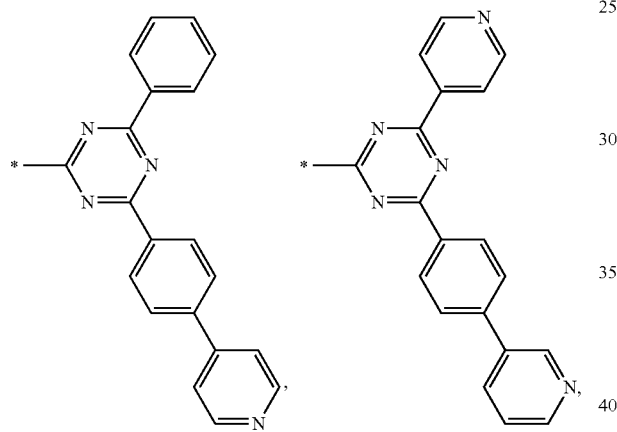
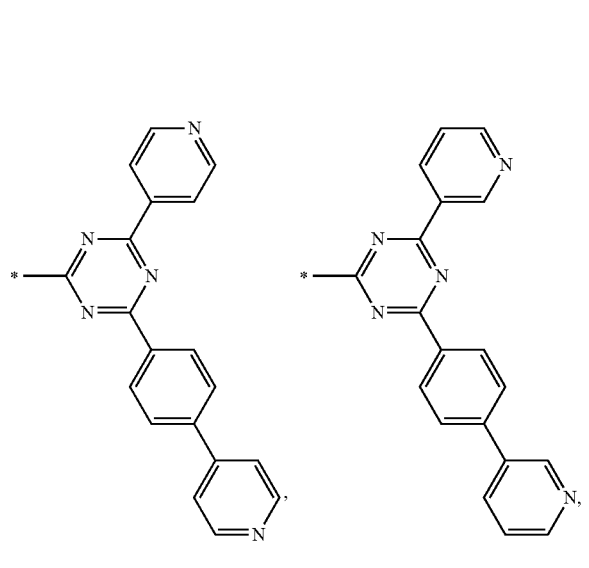
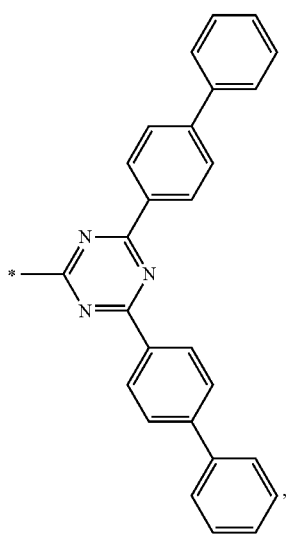

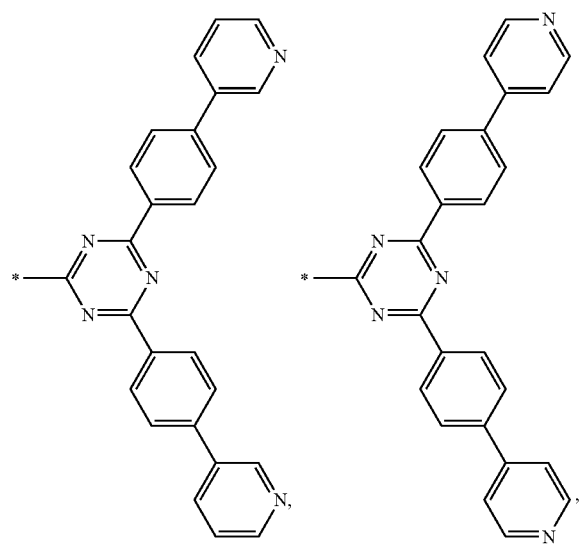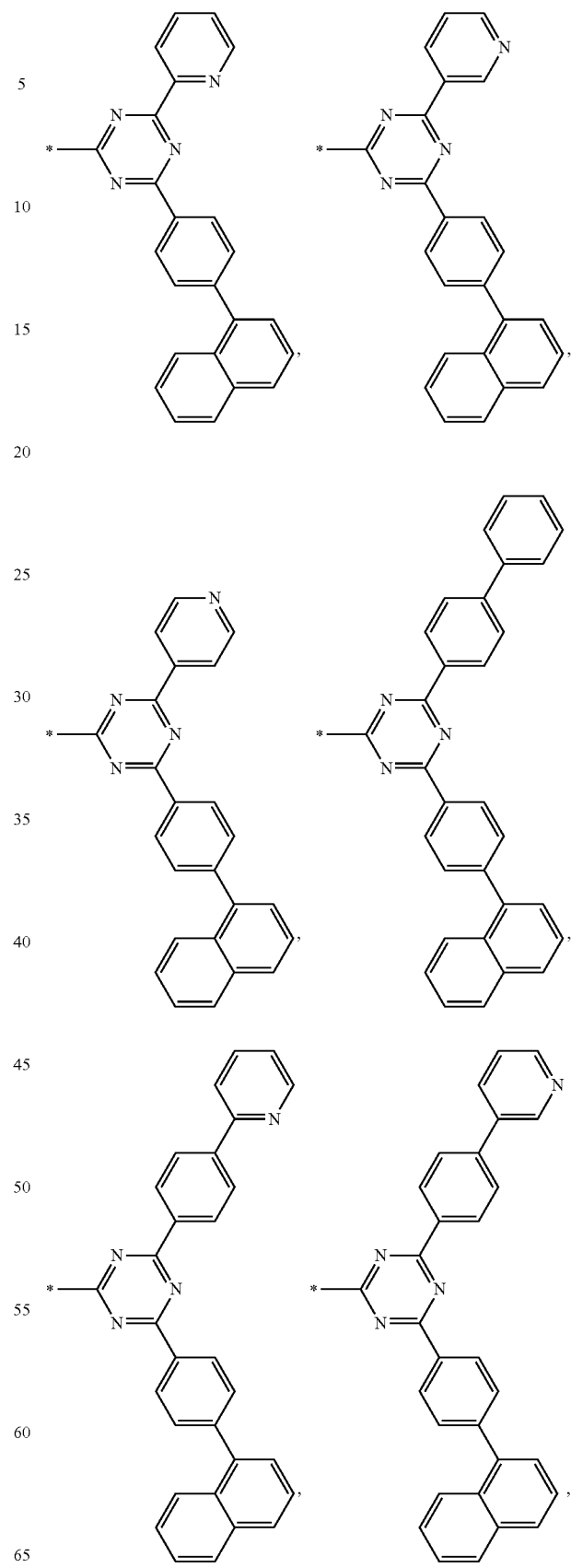

-continued

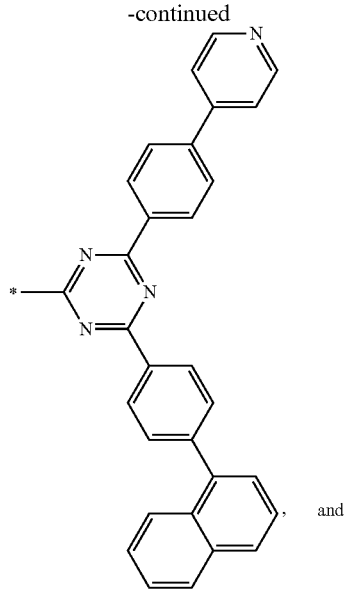, and

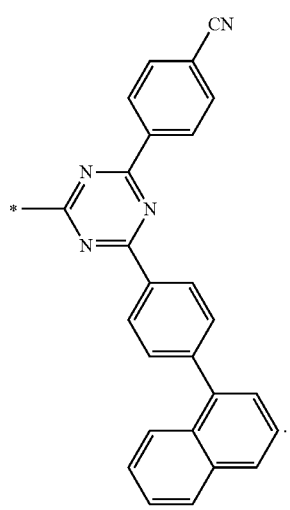.

8. The compound as claimed in claim 1, wherein the aryl group having 6 to 60 carbon atoms and substituted with the at least one functional group is selected from the group consisting of:

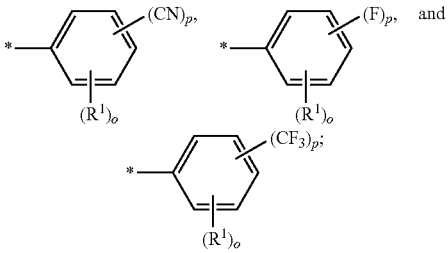

wherein $R^1$ is selected from the group consisting of: a hydrogen atom, a deuterium atom, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 20 carbon atoms, an alkoxy group having 1 to 40 carbon atoms, an aryloxy group having 6 to 30 carbon atoms, an alkylsilyl group having 1 to 40 carbon atoms, an arylsilyl group having 6 to 30 carbon atoms, an alkylboron group having 1 to 40 carbon atoms, an arylboron group having 6 to 30 carbon atoms, a phosphine group having 1 to 30 carbon atoms, and a phosphine oxide group having 1 to 30 carbon atoms;

wherein o is an integral from 0 to 4, p is an integral from 1 to 5, and the total of o and p is not more than 5.

9. The compound as claimed in claim 1, wherein $G^3$ to $G^5$ are each independently selected from the group consisting of: a hydrogen atom, a deuterium atom, and a halogen group.

10. The compound as claimed in claim 1, wherein $G^1$ and $G^2$ are the same.

11. The compound as claimed in claim 1, wherein $G^3$ and $G^4$ are the same.

12. The compound as claimed in claim 1, wherein the compound is selected from the group consisting of:

Compound I

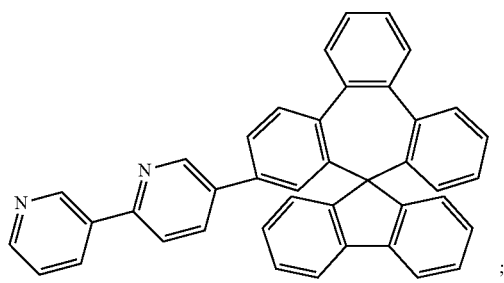;

Compound II

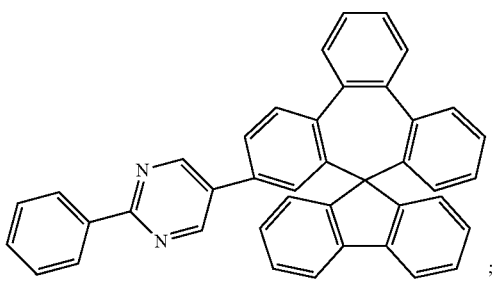;

-continued
Compound III
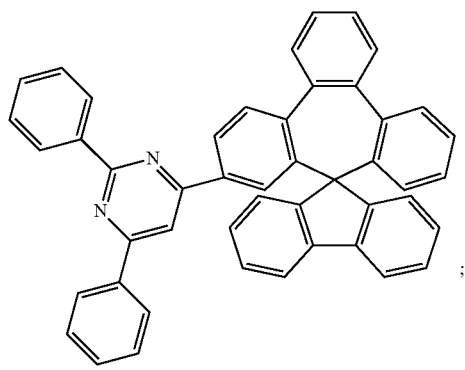
Compound IV
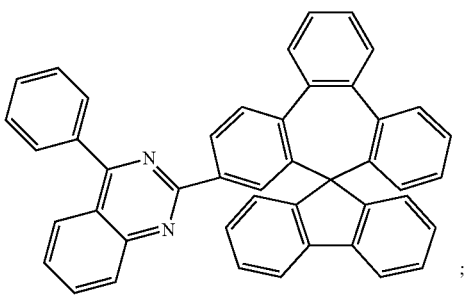
Compound V
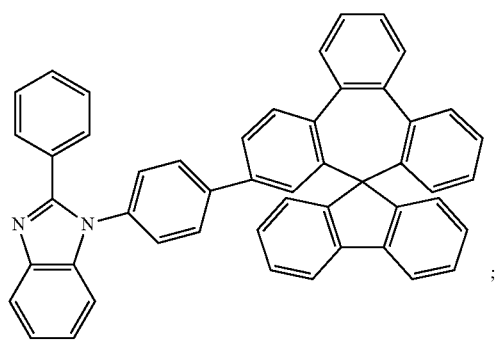
Compound VI
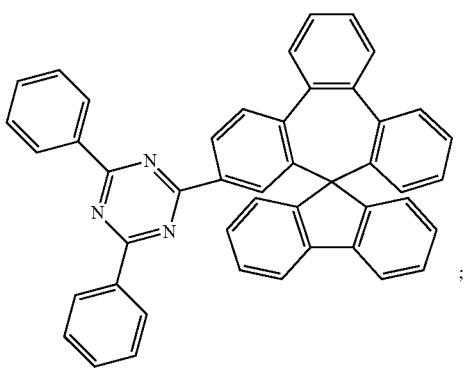
Compound VII
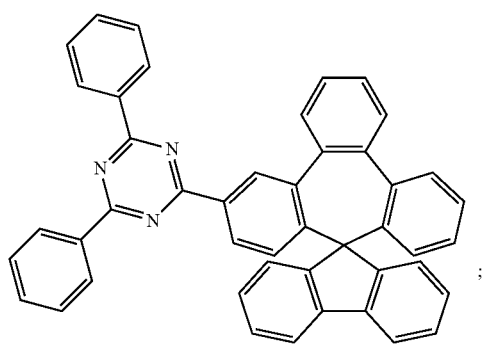
Compound VIII
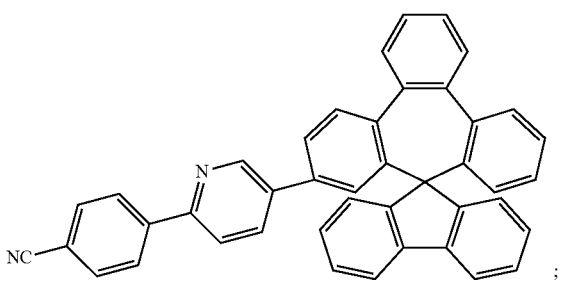
Compound IX
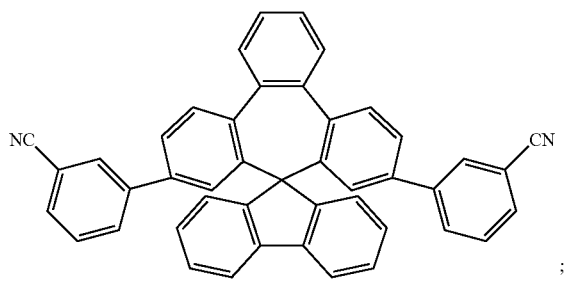

Compound X

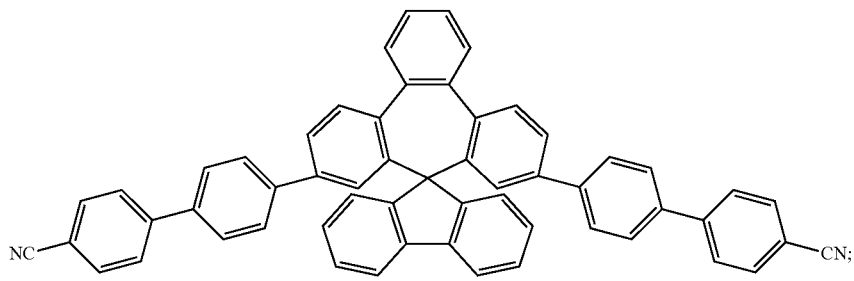

Compound XI

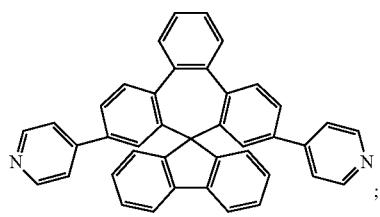

Compound XII

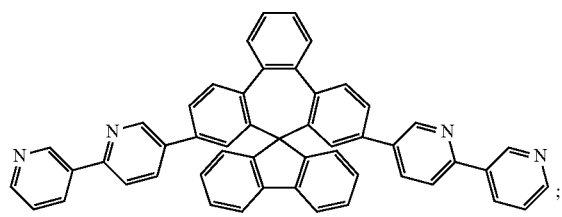

Compound XIII

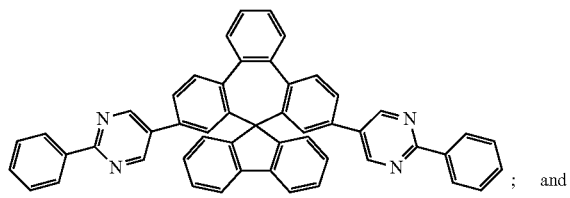
; and

Compound XIV

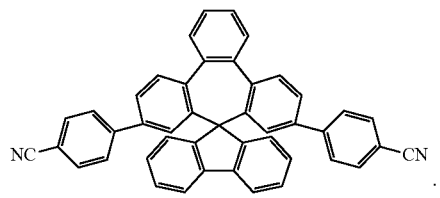
.

13. An organic electronic device, comprising a first electrode, a second electrode, and an organic layer disposed between the first electrode and the second electrode, wherein the organic layer comprises the compound as claimed in claim 1.

14. The organic electronic device as claimed in claim 13, wherein the organic electronic device is an organic light emitting device.

15. The organic electronic device as claimed in claim 14, wherein the organic light emitting device comprises:
a hole injection layer formed on the first electrode;
a hole transport layer formed on the hole injection layer;
an emission layer formed on the hole transport layer;
an electron transport layer formed on the emission layer, wherein the organic layer is the electron transport layer;
an electron injection layer formed between the electron transport layer and the second electrode.

16. The organic electronic device as claimed in claim 14, wherein the organic light emitting device comprises:
a hole injection layer formed on the first electrode;
a hole transport layer formed on the hole injection layer;
an emission layer formed on the hole transport layer;
a hole blocking layer formed on the emission layer, wherein the organic layer is the hole blocking layer;
an electron transport layer formed on the hole blocking layer;
an electron injection layer formed between the electron transport layer and the second electrode.

17. The organic electronic device as claimed in claim 13, wherein the organic layer comprises the compound as claimed in claim 3.

18. The organic electronic device as claimed in claim 13, wherein the organic layer comprises the compound as claimed in claim 4.

19. The organic electronic device as claimed in claim 13, wherein the organic layer comprises the compound as claimed in claim 5.

20. The organic electronic device as claimed in claim 13, wherein the compound is selected from the group consisting of:

211                                                          212
Compound I 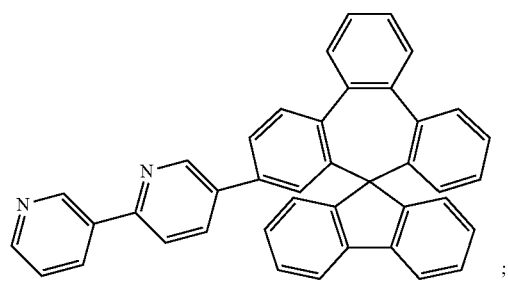                              Compound II 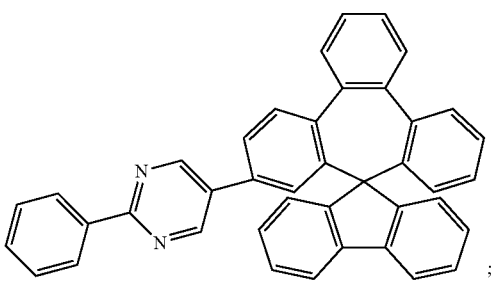
Compound III 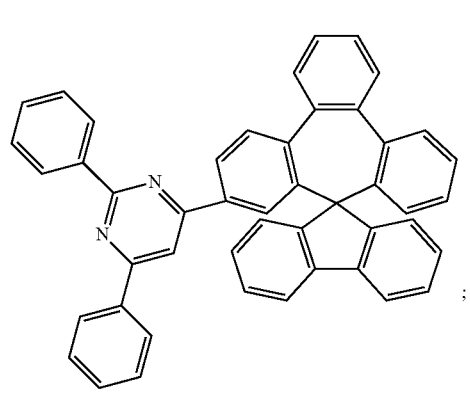                            Compound IV 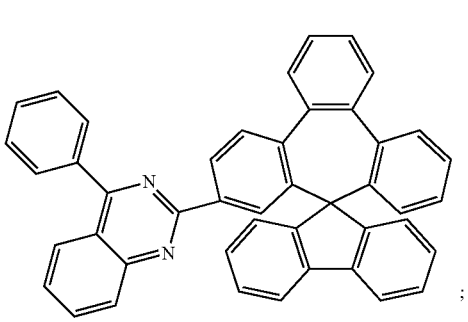
Compound V 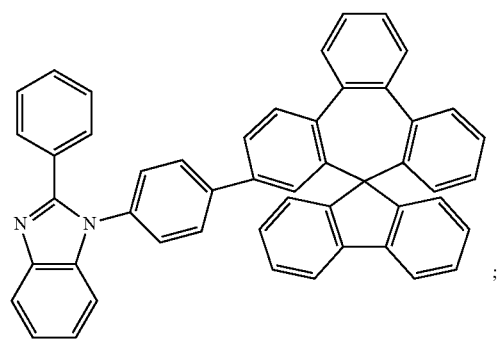                              Compound VI 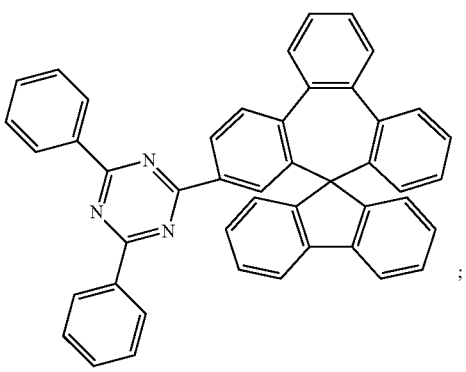
Compound VII 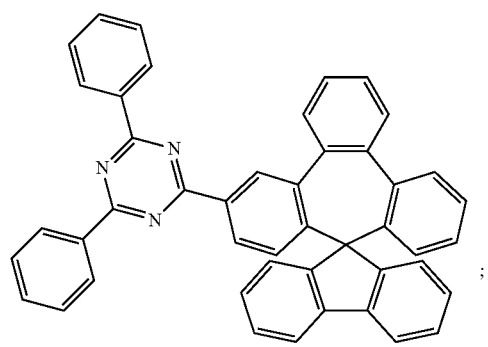                            Compound VIII 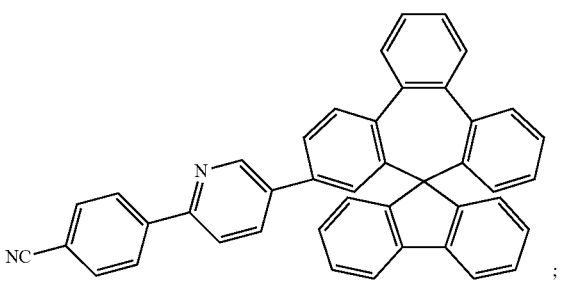

-continued
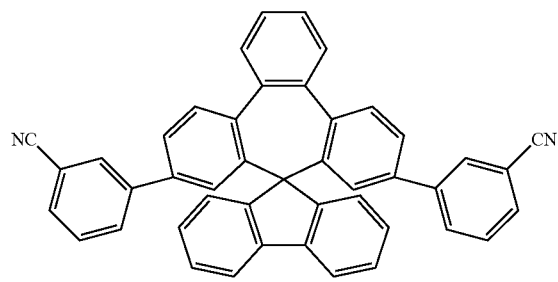
Compound IX
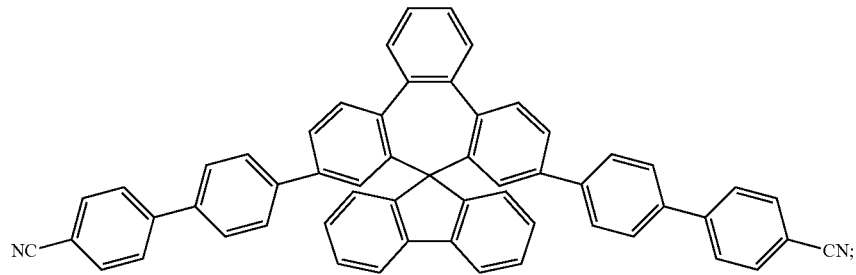
Compound X
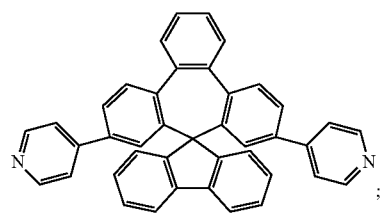
Compound XI
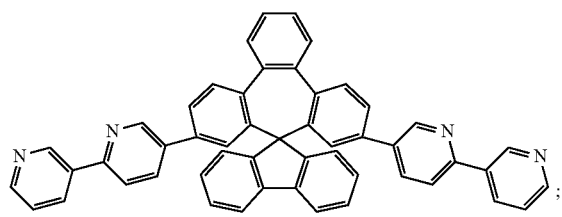
Compound XII
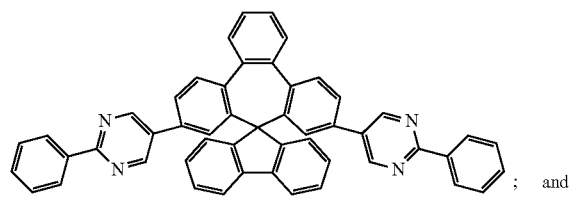  ; and
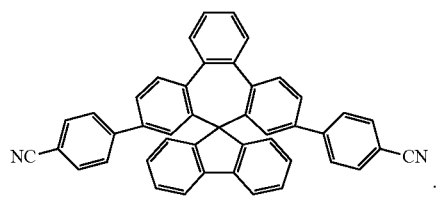 .
Compound XIII
Compound XIV
* * * * *